(12) United States Patent
Descamps et al.

(10) Patent No.: US 9,994,639 B2
(45) Date of Patent: Jun. 12, 2018

(54) BIOLOGICAL MATERIALS RELATED TO CXCR7

(71) Applicant: Ablynx N.V., Zwijnaarde (BE)

(72) Inventors: Francis Descamps, Roeselare (BE); David Andre Baptiste Maussang-Detaille, Rotterdam (NL); Maarten Van Roy, Zwijnaarde (BE); Maria Gonzalez Pajuelo, Porto (PT); Regorius Leurs, Amsterdam (NL); Pascal Gerard Merchiers, Tielen (BE); Martine Smit, Amsterdam (NL); Catelijne Stortelers, Ghent (BE); Philippe Van Rompaey, Melle (BE); Peter Vanlandschoot, Bellem (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 997 days.

(21) Appl. No.: 13/937,718

(22) Filed: Jul. 9, 2013

(65) Prior Publication Data
US 2014/0178390 A1   Jun. 26, 2014

Related U.S. Application Data

(63) Continuation-in-part of application No. PCT/EP2012/055499, filed on Mar. 28, 2012.

(60) Provisional application No. 61/600,263, filed on Feb. 17, 2012, provisional application No. 61/540,272, filed on Sep. 28, 2011, provisional application No. 61/468,250, filed on Mar. 28, 2011.

(51) Int. Cl.
*C07K 16/28* (2006.01)
*A61K 39/00* (2006.01)

(52) U.S. Cl.
CPC .... *C07K 16/2866* (2013.01); *A61K 2039/507* (2013.01); *C07K 2317/22* (2013.01); *C07K 2317/31* (2013.01); *C07K 2317/33* (2013.01); *C07K 2317/569* (2013.01); *C07K 2317/76* (2013.01); *C07K 2319/31* (2013.01)

(58) Field of Classification Search
None
See application file for complete search history.

(56) References Cited

U.S. PATENT DOCUMENTS

| 8,937,164 | B2* | 1/2015 | Descamps | C07K 16/2866 |
| | | | | 530/350 |
| 9,212,226 | B2 | 12/2015 | Blanchetot et al. | |
| 2002/0106739 | A1 | 8/2002 | Oakley et al. | |
| 2004/0170634 | A1 | 9/2004 | Burns et al. | |
| 2007/0167443 | A1 | 7/2007 | Melikian et al. | |
| 2007/0269422 | A1* | 11/2007 | Beirnaert | C07K 16/18 |
| | | | | 424/130.1 |
| 2009/0022717 | A1* | 1/2009 | Premack | C07K 16/2866 |
| | | | | 424/133.1 |
| 2010/0062004 | A1 | 3/2010 | Adams et al. | |
| 2011/0206660 | A1* | 8/2011 | Blanchetot | C07K 16/2866 |
| | | | | 424/133.1 |
| 2011/0262438 | A1 | 10/2011 | Descamps et al. | |
| 2013/0130379 | A1 | 5/2013 | Adams et al. | |
| 2014/0228223 | A1 | 8/2014 | Descamps et al. | |

FOREIGN PATENT DOCUMENTS

| EP | 0 368 684 A1 | 5/1990 |
| EP | 0 542 810 A1 | 5/1993 |
| EP | 1 316 801 A1 | 9/2002 |
| JP | 2008-539772 A | 11/2008 |
| JP | 2008-539775 A | 11/2008 |
| JP | 2010-500876 A | 1/2010 |
| JP | 2010-506912 A | 3/2010 |
| WO | WO 91/01743 A1 | 2/1991 |
| WO | WO 99/50461 A1 | 10/1999 |
| WO | WO 01/45746 A2 | 6/2001 |
| WO | WO 02/076489 A1 | 10/2002 |
| WO | WO 03/050531 A2 | 6/2003 |
| WO | WO 03/066830 A2 | 8/2003 |
| WO | WO 2004/041867 A2 | 5/2004 |
| WO | WO 2004/051268 A1 | 6/2004 |
| WO | WO 2004/064595 A2 | 8/2004 |
| WO | WO 2004/106377 A1 | 12/2004 |
| WO | WO 2005/018629 A1 | 3/2005 |
| WO | WO 2005/019824 A1 | 3/2005 |
| WO | WO 2005/044792 A2 | 5/2005 |
| WO | WO 2006/003388 A2 | 1/2006 |
| WO | WO 2006/030220 A1 | 3/2006 |
| WO | WO 2006/038027 A2 | 4/2006 |
| WO | WO 2006/047417 A2 | 5/2006 |

(Continued)

OTHER PUBLICATIONS

Rudikoff et al (Proc Natl Acad Sci USA 1982 vol. 79 p. 1979).*
MacCallum et al. J. Mol. Biol. (1996) 262, 732-745.*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Lamminmaki et al. (JBC 2001, 276:36687-36694).*
Padlan et al. (PNAS 1989, 86:5938-5942).*
PCT/EP2007/064243, Oct. 9, 2008, International Search Report and Written Opinion.
PCT/EP2007/064243, Jun. 24, 2009, International Preliminary Report on Patentability.
PCT/EP2009/056026, Sep. 17, 2009, International Search Report and Written Opinion.

(Continued)

*Primary Examiner* — Sharon X Wen
(74) *Attorney, Agent, or Firm* — Wolf, Greenfield & Sacks, P.C.

(57) ABSTRACT

The present invention relates to particular polypeptides, nucleic acids encoding such polypeptides; to methods for preparing such polypeptides; to host cells expressing or capable of expressing such polypeptides; to compositions and in particular to pharmaceutical compositions that comprise such polypeptides, for prophylactic, therapeutic or diagnostic purposes. In particular, the present invention provides immunoglobulin single variable domains inhibiting CXCR7 mediated tumor growth.

8 Claims, 6 Drawing Sheets

(56) References Cited

FOREIGN PATENT DOCUMENTS

| WO | WO 2006/089141 A2 | 8/2006 |
|---|---|---|
| WO | WO 2006/116319 A2 | 11/2006 |
| WO | WO 2007/042289 A2 | 4/2007 |
| WO | WO 2007/051063 A2 | 5/2007 |
| WO | WO 2007/118670 A1 | 10/2007 |
| WO | WO 2008/028977 A2 | 3/2008 |
| WO | WO 2008/048519 A2 | 4/2008 |
| WO | WO 2008/068280 A1 | 6/2008 |
| WO | WO 2009/138519 A1 | 11/2009 |
| WO | WO 2010/010119 A1 | 1/2010 |
| WO | WO 2010/043650 A2 | 4/2010 |
| WO | WO 2010/070145 A2 | 6/2010 |
| WO | WO 2010/141986 A1 | 12/2010 |
| WO | WO 2011/117423 A1 | 9/2011 |

OTHER PUBLICATIONS

PCT/EP2009/056026, Nov. 25, 2010, International Preliminary Report on Patentability.
PCT/EP2011/054755, Jun. 30, 2011, International Search Report and Written Opinion.
PCT/EP2012/055499, Aug. 6, 2012, International Search Report.
EP 12185862.5, Jan. 10, 2013, Partial European Search Report.
Genbank Submission; NCBI; Accession No. NM_000609.5; Bracci et al.; Mar. 21, 2010. 4 pages.
Desmyter et al., Three camelid VHH domains in complex with porcine pancreatic alpha-amylase. Inhibition and versatility of binding topology. J Biol Chem. Jun. 28, 2002;277(26):23645-50. Epub Apr. 17, 2002.
Zabel et al., Elucidation of CXCR7-mediated signaling events and inhibition of CXCR4-mediated tumor cell transendothelial migration by CXCR7 ligands. J Immunol. Sep. 1, 2009;183(5):3204-11.
Brown et al., Tolerance of single, but not multiple, amino acid replacements in antibody VH CDR 2: a means of minimizing B cell wastage from somatic hypermutation? J Immunol. May 1, 1996;156(9):3285-91.
Chen et al., Selection and analysis of an optimized anti-VEGF antibody: crystal structure of an affinity-matured Fab in complex with antigen. J Mol Biol. Nov. 5, 1999;293(4):865-81.
Hattermann et al., The chemokine receptor CXCR7 is highly expressed in human glioma cells and mediates antiapoptotic effects. Cancer Res. Apr. 15, 2010;70(8):3299-308. doi: 10.1158/0008-5472.CAN-09-3642. Epub Apr. 13, 2010.
Lamminmäki et al., Crystal structure of a recombinant anti-estradiol Fab fragment in complex with 17beta-estradiol. J Biol Chem. Sep. 28, 2001;276(39):36687-94. Epub Jul. 12, 2001.
Maussang et al., Llama-derived single variable domains (nanobodies) directed against chemokine receptor CXCR7 reduce head and neck cancer cell growth in vivo. J Biol Chem. Oct. 11, 2013;288(41):29562-72. doi: 10.1074/jbc.M113.498436. Epub Aug. 26, 2013.
Muyldermans, Single domain camel antibodies: current status. J Biotechnol. Jun. 2001;74(4):277-302.
Padlan et al., Structure of an antibody-antigen complex: crystal structure of the HyHEL-10 Fab-lysozyme complex. Proc Natl Acad Sci U S A. Aug. 1989;86(15):5938-42.
Xia et al., Expressions of CXCR7/ligands may be involved in oral carcinogenesis. J Mol Histol. Apr. 2011;42(2):175-80. doi: 10.1007/s10735-011-9322-x. Epub Mar. 26, 2011.
Zheng et al., Chemokine receptor CXCR7 regulates the invasion, angiogenesis and tumor growth of human hepatocellular carcinoma cells. J Exp Clin Cancer Res. Apr. 11, 2010;29:31. doi:10.1186/1756-9966-29-31.
[No Author Listed], The state of GPCR research in 2004. Nat Rev Drug Discov. Jul. 2004;3(7): 577-626.
[No Author Listed], Monoclonal Antibody Anti-CXCR7/RDC1; K0223-3 9C4 Mouse IgG1 [kappa] 100 [mu]g. Jan. 12, 2009.
André et al., Enhancing functional production of G protein-coupled receptors in Pichia pastoris to levels required for structural studies via a single expression screen. Protein Sci. May 2006;15(5):1115-26. Epub Apr. 5, 2006.

Balabanian et al., The chemokine SDF-1/CXCL12 binds to and signals through the orphan receptor RDC1 in T lymphocytes. J Biol Chem. Oct. 21, 2005;280(42):35760-6. Epub Aug. 17, 2005.
Baribaud et al., Antigenically distinct conformations of CXCR4. J Virol. Oct. 2001;75(19):8957-67.
Bednarek et al., Ligands of the melanocortin receptors, 2002-2003 update. Expert Opin Ther Patents. 2004;14(3):327-336.
Binz et al., Engineering novel binding proteins from nonimmunoglobulin domains. Nat Biotechnol. Oct. 2005;23(10):1257-68.
Burns et al., A novel chemokine receptor for SDF-1 and I-TAC involved in cell survival, cell adhesion, and tumor development. J Exp Med. Sep. 4, 2006;203(9):2201-13. Epub Aug. 28, 2006.
Caldas et al., Humanization of the anti-CD18 antibody 6.7: an unexpected effect of a framework residue in binding to antigen. Mol Immunol. May 2003;39(15):941-52.
Carnec et al., Anti-CXCR4 monoclonal antibodies recognizing overlapping epitopes differ significantly in their ability to inhibit entry of human immunodeficiency virus type 1. J Virol. Feb. 2005;79(3):1930-3.
Casset et al., A peptide mimetic of an anti-CD4 monoclonal antibody by rational design. Biochem Biophys Res Commun. Jul. 18, 2003;307(1):198-205.
Chien et al., Significant structural and functional change of an antigen-binding site by a distant amino acid substitution: proposal of a structural mechanism. Proc Natl Acad Sci U S A. Jul. 1989;86(14):5532-6.
Coutts et al., Localisation of cannabinoid CB (1) receptor immunoreactivity in the guinea pig and rat myenteric plexus. J. Comp. Neurol. 2002; 448(4):410-22.
Dahmen et al., Expression of olfactory receptors in Xenopus oocytes. J Neurochem. Mar. 1992;58(3):1176-9.
De Pascalis et al., Grafting of "abbreviated" complementarity-determining regions containing specificity-determining residues essential for ligand contact to engineer a less immunogenic humanized monoclonal antibody. J Immunol. Sep. 15, 2002;169(6):3076-84.
Dimitrov et al., A mechanism of resistance to HIV-1 entry: inefficient interactions of CXCR4 with CD4 and gp120 in macrophages. Virology. Jun. 20, 1999;259(1):1-6.
Dove Pettit et al., Immunohistochemical localization of the neural cannabinoid receptor in rat brain. J Neurosci Res. Feb. 1, 1998;51(3):391-402.
Gensure et al., Parathyroid hormone and parathyroid hormone-related peptide, and their receptors. Biochem Biophys Res Commun. Mar. 18, 2005;328(3):666-78.
George et al., G-protein-coupled receptor oligomerization and its potential for drug discovery. Nat Rev Drug Discov. Oct. 2002;1(10):808-20.
Getting, Targeting melanocortin receptors as potential novel therapeutics. Pharmacol Ther. Jul. 2006;111(1):1-15. Epub Feb. 20, 2006.
Giusti et al., Somatic diversification of S107 from an antiphosphocholine to an anti-DNA autoantibody is due to a single base change in its heavy chain variable region. Proc Natl Acad Sci U S A. May 1987;84(9):2926-30.
Güssow et al., Humanization of monoclonal antibodies. Methods Enzymol. 1991;203:99-121.
Hachet-Haas, et al.; Small Neutralizing Molecules to Inhibit Actions of the Chemokine CXCL12. Journal of Biological Chemistry; (2008); 283(34): 23189-23199.
Halaby et al., The immunoglobulin fold family: sequence analysis and 3D structure comparisons. Protein Eng. Jul. 1999;12(7):563-71.
Hartmann et al., A crosstalk between intracellular CXCR7 and CXCR4 involved in rapid CXCL12-triggered integrin activation but not in chemokine-triggered motility of human T lymphocytes and CD34+ cells. J. of Leukocyte Biology; (2008); 84: 1130-1140.
Hassaine et al., Semliki Forest virus vectors for overexpression of 101 G protein-coupled receptors in mammalian host cells. Protein Expr Purif. Feb. 2006;45(2):343-51. Epub Jul. 11, 2005.
Hoffman et al., A biosensor assay for studying ligand-membrane receptor interactions: binding of antibodies and HIV-1 Env to chemokine receptors. Proc Natl Acad Sci U S A. Oct. 10, 2000;97(21):11215-20.

(56) References Cited

OTHER PUBLICATIONS

Hoffmann et al., Conformational changes in G-protein-coupled receptors—the quest for functionally selective conformations is open. Br J Pharmacol. Mar. 2008;153 Suppl 1:S358-66. Epub Dec. 3, 2007.
Holliger et al., Engineered antibody fragments and the rise of single domains. Nat Biotechnol. Sep. 2005;23(9):1126-36.
Holm et al., Functional mapping and single chain construction of the anti-cytokeratin 8 monoclonal antibody TS1. Mol Immunol. Feb. 2007;44(6):1075-84. Epub Sep. 20, 2006.
Holt et al., Domain antibodies: proteins for therapy. Trends Biotechnol. Nov. 2003;21(11):484-90.
Hoogenboom et al., Selection-dominant and nonaccessible epitopes on cell-surface receptors revealed by cell-panning with a large phage antibody library. Eur J Biochem. Mar. 1999;260(3):774-84.
Hoogenboom, Selecting and screening recombinant antibody libraries. Nat Biotechnol. Sep. 2005;23(9):1105-16.
Houamed et al., Cloning, expression, and gene structure of a G protein-coupled glutamate receptor from rat brain. Science. May 31, 1991;252(5010):1318-21.
Hovius et al., Characterization of a mouse serotonin 5-HT3 receptor purified from mammalian cells. J Neurochem. Feb. 1998;70(2):824-34.
Howard et al., Orphan G-protein-coupled receptors and natural ligand discovery. Trends Pharmacol Sci. Mar. 2001;22(3):132-40.
Hutchings et al., Therapeutic antibodies directed at G protein-coupled receptors. MAbs. Nov.-Dec. 2010;2(6):594-606. Epub Nov. 1, 2010. Review.
Jacoby et al., The 7 TM G-protein-coupled receptor target family. ChemMedChem. Aug. 2006;1(8):761-82. Review.
Jähnichen et al., CXCR4 nanobodies (VHH-based single variable domains) potently inhibit chemotaxis and HIV-1 replication and mobilize stem cells. Proc Natl Acad Sci U S A. Nov. 23, 2010;107(47):20565-70. Epub Nov. 8, 2010.
Kenakin, Efficacy as a vector: the relative prevalence and paucity of inverse agonism. Mol Pharmacol. Jan. 2004;65(1):2-11.
Kenakin, Principles: receptor theory in pharmacology. Trends Pharmacol Sci. Apr. 2004;25(4):186-92.
Kiefer, In vitro folding of alpha-helical membrane proteins. Biochim Biophys Acta. Feb. 17, 2003;1610(1):57-62.
Kim et al., Efficient targeting of gastric cancer cells using radiolabeled anti-carcinoembryonic ntigen-specific T84.66 fragments in experimental radioimmunoguided surgery. Anticancer Res. Mar.-Apr. 2004;24(2B):663-70.
Kim et al., Enhancement of colorectal tumor targeting using a novel biparatopic monoclonal antibody against carcinoembryonic antigen in experimental radioimmunoguided surgery. Int J Cancer. Feb. 1, 2002;97(4):542-7.
Kollmar et al., CXCR4 and CXCR7 regulate angiogenesis and CT26.WT tumor growth independent from SDF-1. Int J Cancer. Mar. 15, 2010;126(6):1302-15.
Lagane et al., CXCR4 dimerization and beta-arrestin-mediated signaling account for the enhanced chemotaxis to CXCL12 in WHIM syndrome. Blood. Jul. 1, 2008;112(1):34-44. doi: 10.1182/blood-2007-07-102103. Epub Apr. 24, 2008.
Lieby et al., The clonal analysis of anticardiolipin antibodies in a single patient with primary antiphospholipid syndrome reveals an extreme antibody heterogeneity. Blood. Jun. 15, 2001;97(12):3820-8.
Luker, et al., Imaging chemokine receptor dimerization with firefly luciferase complementation. The FASEB Journal; (2009); 23: 823-834.
Lundstrom et al., Structural genomics on membrane proteins: comparison of more than 100 GPCRs in 3 expression systems. J Struct Funct Genomics. Jun. 2006;7(2):77-91. Epub Nov. 22, 2006.
MacCallum et al., Antibody-antigen interactions: contact analysis and binding site topography. J Mol Biol. Oct. 11, 1996;262(5):732-45.
Maksym et al., The role of stromal-derived factor-1—CXCR7 axis in development and cancer. Eur. J. of Pharmacol..; (2009); 625(1-3): 31-40.
Marinissen et al., G-protein-coupled receptors and signaling networks: emerging paradigms. Trends Pharmacol Sci. Jul. 2001;22(7):368-76.
Mariuzza et al., The structural basis of antigen-antibody recognition. Annu Rev Biophys Biophys Chem. 1987;16:139-59.
McIntosh et al., CB1 cannabinoid receptor: cellular regulation and distribution in N18TG2 neuroblastoma cells. Mol Brain Res. Jan. 1998;53(1-2):163-73.
Miao et al., CXCR7 (RDC1) promotes breast and hung tumor growth in vivo and is expressed on tumor-associated vasculature. Proc Natl Acad Sci USA. Oct. 2, 2007;104(40):15735-40. Epub Sep. 26, 2007.
Michel et al., How reliable are G-protein-coupled receptor antibodies? Naunyn Schmiedebergs Arch Pharmacol. Apr. 2009;379(4):385-8. doi: 10.1007/s00210-009-0395-y. Epub Jan. 27, 2009.
Milligan, Constitutive activity and inverse agonists of G protein-coupled receptors: a current perspective. Mol Pharmacol. Dec. 2003;64(6):1271-6.
Misumi et al., A novel cyclic peptide immunization strategy for preventing HIV-1/AIDS infection and progression. J Biol Chem. Aug. 22, 2003;278(34):32335-43. Epub May 27, 2003.
Mitrirattanakul et al., Expression of cannabinoid 1 receptors in rat dorsal root ganglia remains unchanged after spinal nerve ligation. 33rd Annual Meeting Soc Neurosci. Nov. 10, 2003;Program No. 483.9. Abstract.
Nicholson et al., Peripheral administration of a melanocortin 4-receptor inverse agonist prevents loss of lean body mass in tumor-bearing mice. J Pharmacol Exp Ther. May 2006;317(2):771-7. Epub Jan. 25, 2006.
Pacher et al., The endocannabinoid system as an emerging target of pharmacotherapy. Pharmacol Rev. Sep. 2006;58(3):389-462.
Pierce et al., Seven-transmembrane receptors. Nat Rev Mol Cell Biol. Sep. 2002;3(9):639-50.
Raman et al., Role of chemokines in tumor growth. Cancer Lett. Oct. 28, 2007;256(2):137-65. Epub Jul. 12, 2007. Review.
Rios et al., G-protein-coupled receptor dimerization: modulation of receptor function. Pharmacol Ther. Nov.-Dec. 2001;92(2-3):71-87.
Robert et al., Tumor targeting with newly designed biparatopic antibodies directed against two different epitopes of the carcinoembryonic antigen (CEA). Int J Cancer. Apr. 12, 1999;81(2):285-91.
Rosenkilde et al., Virally encoded 7TM receptors. Oncogene. Mar. 26, 2001;20(13):1582-93.
Rudikoff et al., Single amino acid substitution altering antigen-binding specificity. Proc Natl Acad Sci U S A. Mar. 1982;79(6):1979-83.
Sadee, Genetic variations in human G protein-coupled receptors: implications for drug therapy. AAPS PharmSci. 2001;3(3):E22.
Schlyer et al., I want a new drug: G-protein-coupled receptors in drug development. Drug Discov Today. Jun. 2006;11(11-12):481-93.
Sui et al., Identification of CD4 and transferrin receptor antibodies by CXCR4 antibody-guided Pathfinder selection. Eur J Biochem. Nov. 2003;270(22):4497-506.
Surgand et al., A chemogenomic analysis of the transmembrane binding cavity of human G-protein-coupled receptors. Proteins. Feb. 1, 2006;62(2):509-38.
Ulrich et al., DNA and RNA aptamers: from tools for basic research towards therapeutic applications. Comb Chem High Throughput Screen. Sep. 2006;9(8):619-32.
Vaday et al., CXCR4 and CXCL12 (SDF-1) in prostate cancer: inhibitory effects of human single chain Fv antibodies. Clin Cancer Res. Aug. 15, 2004;10(16):5630-9.
Vajdos et al., Comprehensive functional maps of the antigen-binding site of an anti-ErbB2 antibody obtained with shotgun scanning mutagenesis. J Mol Biol. Jul. 5, 2002;320(2):415-28.
Vassilatis et al., The G protein-coupled receptor repertoires of human and mouse. Proc Natl Acad Sci U S A. Apr. 15, 2003;100(8):4903-8. Epub Apr. 4, 2003.

(56) References Cited

OTHER PUBLICATIONS

Vilardaga et al., Differential conformational requirements for activation of G proteins and the regulatory proteins arrestin and G protein-coupled receptor kinase in the G protein-coupled receptor for parathyroid hormone (PTH)/PTH-related protein. J Biol Chem. Sep. 7, 2001;276(36):33435-43. Epub May 31, 2001.

Vosjan et al., Nanobodies targeting the hepatocyte growth factor: potential new drugs for molecular cancer therapy. Mol Cancer Ther. Apr. 2012;11(4):1017-25. doi: 10.1158/1535-7163.MCT-11-0891. Epub Feb. 7, 2012.

Wang et al., The role of CXCR7/RDC1 as a chemokine receptor for CXCL12/SDF-1 in prostate cancer. J Biol Chem. Feb. 15, 2008;283(7):4283-94. Epub Dec. 5, 2007.

Ward et al., Binding activities of a repertoire of single immunoglobulin variable domains secreted from *Escherichia coli*. Nature. Oct. 12, 1989;341(6242):544-6.

Winkler et al., Changing the antigen binding specificity by single point mutations of an anti-p24 (HIV-1) antibody. J Immunol. Oct. 15, 2000;165(8):4505-14.

Wu et al., Humanization of a murine monoclonal antibody by simultaneous optimization of framework and CDR residues. J Mol Biol. Nov. 19, 1999;294(1):151-62.

[No Author Listed] Ion Channel Modulating Nanobodies: two in vitro to in vivo case studies. Ablynx. Apr. 2015.

Depla, ALX-0171: safety, efficacy and therapeutic potential of an inhaled anti-RSV Nanobody. Ablynx. May 6, 2015.

Gram et al., In vitro selection and affinity maturation of antibodies from a naive combinatorial immunoglobulin library. Proc Natl Acad Sci U S A. Apr. 15, 1992;89(8):3576-80.

Kaliberov et al., Adenoviral targeting using genetically incorporated camelid single variable domains. Lab Invest. Aug. 2014;94(8):893-905. doi: 10.1038/labinvest.2014.82. Epub Jun. 16, 2014.

Kontermann, Dual targeting strategies with bispecific antibodies. MAbs. Mar.-Apr. 2012;4(2):182-97. doi: 10.4161/mabs.4.2.19000. Epub Mar. 1, 2012.

Saerens et al., Single-domain antibodies as building blocks for novel therapeutics. Curr Opin Pharmacol. Oct. 2008;8(5):600-8. doi:10.1016/j.coph.2008.07.006. Epub Aug. 22, 2008.

Schepens et al., Nanobodies® specific for respiratory syncytial virus fusion protein protect against infection by inhibition of fusion. J Infect Dis. Dec. 1, 2011;204(11):1692-701. doi: 10.1093/infdis/jir622. Epub Oct. 12, 2011.

Tijink et al., Improved tumor targeting of anti-epidermal growth factor receptor Nanobodies through albumin binding: taking advantage of modular Nanobody technology. Mol Cancer Ther. Aug. 2008;7(8):2288-97. doi:10.1158/1535-7163.MCT-7-2384.

\* cited by examiner 50 d therapy

B

SEQUENCE LISTING

```
<160> NUMBER OF SEQ ID NOS: 140

<210> SEQ ID NO 1
<211> LENGTH: 362
<212> TYPE: PRT
<213> ORGANISM: Homo sapiens

<400> SEQUENCE: 1

Met Asp Leu His Leu Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ser
        35                  40                  45
```

Phe Ile Tyr Ile Phe Ile Phe Val Ile Gly Met Ile Ala Asn Ser Val
            50                  55                  60

Val Val Trp Val Asn Ile Gln Ala Lys Thr Thr Gly Tyr Asp Thr His
65                  70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
            115                 120                 125

Phe Gly Ser Ile Phe Phe Leu Thr Cys Met Ser Val Asp Arg Tyr Leu
            130                 135                 140

Ser Ile Thr Tyr Phe Thr Asn Thr Pro Ser Ser Arg Lys Lys Met Val
145                 150                 155                 160

Arg Arg Val Val Cys Ile Leu Val Trp Leu Leu Ala Phe Cys Val Ser
                165                 170                 175

Leu Pro Asp Thr Tyr Tyr Leu Lys Thr Val Thr Ser Ala Ser Asn Asn
                180                 185                 190

Glu Thr Tyr Cys Arg Ser Phe Tyr Pro Glu His Ser Ile Lys Glu Trp
                195                 200                 205

Leu Ile Gly Met Glu Leu Val Ser Val Val Leu Gly Phe Ala Val Pro
            210                 215                 220

Phe Ser Ile Ile Ala Val Phe Tyr Phe Leu Leu Ala Arg Ala Ile Ser
225                 230                 235                 240

Ala Ser Ser Asp Gln Glu Lys His Ser Ser Arg Lys Ile Ile Phe Ser
            245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
            275                 280                 285

Leu Glu His Ala Leu Phe Thr Ala Leu His Val Thr Gln Cys Leu Ser
            290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
            355                 360

<210> SEQ ID NO 2
<211> LENGTH: 115
<212> TYPE: PRT
<213> ORGANISM: Artificial Sequence
<220> FEATURE:
<223> OTHER INFORMATION: Nanobody sequence

<400> SEQUENCE: 2

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

```
Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
               100                 105                 110

Val Ser Ser
       115

<210> SEQ ID NO 3
<211> LENGTH: 362
<212> TYPE: PRT
<213> ORGANISM: Mus musculus

<400> SEQUENCE: 3

Met Asp Val His Leu Phe Asp Tyr Ala Glu Pro Gly Asn Tyr Ser Asp
 1               5                  10                  15

Ile Asn Trp Pro Cys Asn Ser Ser Asp Cys Ile Val Val Asp Thr Val
                20                  25                  30

Gln Cys Pro Thr Met Pro Asn Lys Asn Val Leu Leu Tyr Thr Leu Ser
            35                  40                  45

Phe Ile Tyr Ile Phe Ile Phe Val Ile Gly Met Ile Ala Asn Ser Val
        50                  55                  60

Val Val Trp Val Asn Ile Gln Ala Lys Thr Thr Gly Tyr Asp Thr His
 65                  70                  75                  80

Cys Tyr Ile Leu Asn Leu Ala Ile Ala Asp Leu Trp Val Val Ile Thr
                85                  90                  95

Ile Pro Val Trp Val Val Ser Leu Val Gln His Asn Gln Trp Pro Met
               100                 105                 110

Gly Glu Leu Thr Cys Lys Ile Thr His Leu Ile Phe Ser Ile Asn Leu
           115                 120                 125

Phe Gly Ser Ile Phe Phe Leu Ala Cys Met Ser Val Asp Arg Tyr Leu
       130                 135                 140

Ser Ile Thr Tyr Phe Thr Gly Thr Ser Ser Tyr Lys Lys Lys Met Val
145                 150                 155                 160

Arg Arg Val Val Cys Ile Leu Val Trp Leu Leu Ala Phe Phe Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
        195                 200                 205

Leu Ile Gly Met Glu Leu Val Ser Val Ile Leu Gly Phe Ala Val Pro
    210                 215                 220

Phe Thr Ile Ile Ala Ile Phe Tyr Phe Leu Leu Ala Arg Ala Met Ser
225                 230                 235                 240

Ala Ser Gly Asp Gln Glu Lys His Ser Ser Arg Lys Ile Ile Phe Ser
                245                 250                 255

Tyr Val Val Val Phe Leu Val Cys Trp Leu Pro Tyr His Phe Val Val
            260                 265                 270

Leu Leu Asp Ile Phe Ser Ile Leu His Tyr Ile Pro Phe Thr Cys Gln
        275                 280                 285

Leu Glu Asn Val Leu Phe Thr Ala Leu His Val Thr Gln Cys Leu Ser
```

```
            290                 295                 300
Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
                325                 330                 335

Lys Thr Gly Leu Thr Lys Leu Ile Asp Ala Ser Arg Val Ser Glu Thr
            340                 345                 350

Glu Tyr Ser Ala Leu Glu Gln Asn Thr Lys
        355                 360

<210> SEQ ID NO 4
<211> LENGTH: 30
<212> TYPE: PRT
<213> ORGANISM: Artificial Sequence
<220> FEATURE:
<223> OTHER INFORMATION: Nanobody sequence

<400> SEQUENCE: 4

Glu Val Gln Leu Val Glu Ser Gly Gly Asn Leu Val Gln Ala Gly Gly
1               5                   10                  15

Ser Leu Gly Leu Ser Cys Ala Ala Ser Val Ser Ile Ser Ser
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Nanobody sequence

<400> SEQUENCE: 5

Glu Val Gln Leu Val Glu Ser Gly Gly Gly Leu Val Gln Ala Gly Glu
1               5                   10                  15

Ser Leu Thr Leu Ser Cys Ala Ala Ser Gly Arg Thr Leu Ser
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Nanobody sequence

<400> SEQUENCE: 6

Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Nanobody sequence

<400> SEQUENCE: 7

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser
            20                  25                  30
```

```
<210> SEQ ID NO 8
<211> LENGTH: 30
<212> TYPE: PRT
<213> ORGANISM: Artificial Sequence
<220> FEATURE:
<223> OTHER INFORMATION: Nanobody sequence

<400> SEQUENCE: 8

Glu Val Gln Leu Val Glu Ser Gly Gly Gly Leu Val Gln Pro Gly Gly
1               5                   10                  15

Ser Leu Arg Ile Ser Cys Ala Ala Ser Gly Ser Ile Tyr Leu
            20                  25                  30

<210> SEQ ID NO 9
<211> LENGTH: 5
<212> TYPE: PRT
<213> ORGANISM: Artificial Sequence
<220> FEATURE:
<223> OTHER INFORMATION: Nanobody sequence

<400> SEQUENCE: 9

Ile His Ile Met Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Nanobody sequence

<400> SEQUENCE: 10

Ala Tyr Ile Met Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Nanobody sequence

<400> SEQUENCE: 11

Asn Tyr Asp Met Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Nanobody sequence

<400> SEQUENCE: 12

Ile Ala Ala Met Gly
1               5

<210> SEQ ID NO 13
<211> LENGTH: 5
<212> TYPE: PRT
<213> ORGANISM: Artificial Sequence
<220> FEATURE:
<223> OTHER INFORMATION: Nanobody sequence

<400> SEQUENCE: 13

Ile Asn Tyr Met Gly
1               5
```

```
<210> SEQ ID NO 14
<211> LENGTH: 14
<212> TYPE: PRT
<213> ORGANISM: Artificial Sequence
<220> FEATURE:
<223> OTHER INFORMATION: Nanobody sequence

<400> SEQUENCE: 14

Trp Tyr Arg Gln Ala Pro Gly Lys Gln Arg Asp Leu Val Ala
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Nanobody sequence

<400> SEQUENCE: 15

Trp Phe Arg Gln Ala Pro Gly Lys Glu Arg Glu Phe Val Ala
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Nanobody sequence

<400> SEQUENCE: 16

Trp Phe Arg Gln Ala Pro Gly Lys Glu Arg Glu Phe Val Gly
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Nanobody sequence

<400> SEQUENCE: 17

Trp Tyr Arg Gln Ala Thr Gly Lys Gln Arg Glu Leu Val Ala
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Nanobody sequence

<400> SEQUENCE: 18

Trp Tyr Arg Gln Ala Pro Gly Lys Gln Arg Glu Leu Val Ala
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Nanobody sequence

<400> SEQUENCE: 19

Thr Ile Thr Ser Gly Gly Ser Thr Ala Tyr Ala Asp Ser Val Lys Gly
1               5                   10                  15
```

<210> SEQ ID NO 20
<211> LENGTH: 16
<212> TYPE: PRT
<213> ORGANISM: Artificial Sequence
<220> FEATURE:
<223> OTHER INFORMATION: Nanobody sequence

<400> SEQUENCE: 20

Gly Ile Trp Ser Gly Gly Tyr Thr His Leu Ala Asp Ser Ala Lys Gly
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: Nanobody sequence

<400> SEQUENCE: 21

Ala Ser Trp Trp Ser Gly Gly Ala Pro Tyr Tyr Ser Asp Ser Val Lys
1               5                   10                  15

Gly

<210> SEQ ID NO 22
<211> LENGTH: 16
<212> TYPE: PRT
<213> ORGANISM: Artificial Sequence
<220> FEATURE:
<223> OTHER INFORMATION: Nanobody sequence

<400> SEQUENCE: 22

Thr Ile Thr Asp Gly Gly Thr Thr Thr Tyr Ala Asp Ser Val Lys Gly
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Nanobody sequence

<400> SEQUENCE: 23

Thr Leu Thr Ser Gly Gly Ser Thr Asn Tyr Ala Gly Ser Val Lys Gly
1               5                   10                  15

<210> SEQ ID NO 24
<211> LENGTH: 32
<212> TYPE: PRT
<213> ORGANISM: Artificial Sequence
<220> FEATURE:
<223> OTHER INFORMATION: Nanobody sequence

<400> SEQUENCE: 24

Arg Phe Thr Val Ser Lys Asp Asn Ala Lys Asn Thr Val Tyr Leu Gln
1               5                   10                  15

Met Asp Ser Leu Lys Pro Glu Asp Thr Ser Val Tyr Tyr Cys Ala Ala
                20                  25                  30

<210> SEQ ID NO 25
<211> LENGTH: 32
<212> TYPE: PRT
<213> ORGANISM: Artificial Sequence
<220> FEATURE:
<223> OTHER INFORMATION: Nanobody sequence

<400> SEQUENCE: 25

```
Arg Phe Ser Ile Ser Arg Asp Asn Ala Lys Asn Thr Val Tyr Leu Gln
1               5                   10                  15

Met Asn Gly Leu Lys Pro Glu Asp Thr Ala Val Tyr Tyr Cys Ala Ala
            20                  25                  30
```

<210> SEQ ID NO 26
<211> LENGTH: 32
<212> TYPE: PRT
<213> ORGANISM: Artificial Sequence
<220> FEATURE:
<223> OTHER INFORMATION: Nanobody sequence

<400> SEQUENCE: 26

```
Arg Phe Thr Ile Ser Arg Asp Asn Ala Lys Asn Thr Val Tyr Leu Gln
1               5                   10                  15

Ala Asn Ser Leu Arg Pro Glu Asp Thr Ala Val Tyr Tyr Cys Ala Ala
            20                  25                  30
```

<210> SEQ ID NO 27
<211> LENGTH: 32
<212> TYPE: PRT
<213> ORGANISM: Artificial Sequence
<220> FEATURE:
<223> OTHER INFORMATION: Nanobody sequence

<400> SEQUENCE: 27

```
Arg Val Thr Ile Ser Arg Asp Arg Ser Ala Asn Thr Val Tyr Leu Ala
1               5                   10                  15

Met Asn Asn Leu Lys Pro Asp Asp Thr Ala Val Tyr Tyr Cys Tyr Ala
            20                  25                  30
```

<210> SEQ ID NO 28
<211> LENGTH: 32
<212> TYPE: PRT
<213> ORGANISM: Artificial Sequence
<220> FEATURE:
<223> OTHER INFORMATION: Nanobody sequence

<400> SEQUENCE: 28

```
Arg Phe Ala Ile Ser Arg Asp Asn Ala Lys Asn Thr Val Tyr Leu Gln
1               5                   10                  15

Met Asn Ser Leu Lys Pro Glu Asp Thr Ala Val Tyr Tyr Cys Asn Ile
            20                  25                  30
```

<210> SEQ ID NO 29
<211> LENGTH: 13
<212> TYPE: PRT
<213> ORGANISM: Artificial Sequence
<220> FEATURE:
<223> OTHER INFORMATION: Nanobody sequence

<400> SEQUENCE: 29

```
Glu Val Arg Asn Gly Val Phe Gly Lys Trp Asn His Tyr
1               5                   10
```

<210> SEQ ID NO 30
<211> LENGTH: 9
<212> TYPE: PRT
<213> ORGANISM: Artificial Sequence
<220> FEATURE:
<223> OTHER INFORMATION: Nanobody sequence

<400> SEQUENCE: 30

```
Gly Leu Arg Gly Arg Gln Tyr Ser Asn
```

```
1               5

<210> SEQ ID NO 31
<211> LENGTH: 14
<212> TYPE: PRT
<213> ORGANISM: Artificial Sequence
<220> FEATURE:
<223> OTHER INFORMATION: Nanobody sequence

<400> SEQUENCE: 31

Lys Arg Leu Arg Ser Phe Ala Ser Gly Gly Ser Tyr Asp Tyr
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Nanobody sequence

<400> SEQUENCE: 32

Tyr Leu Arg Tyr Thr Ser Arg Val Pro Gly Asp Asn Tyr
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Nanobody sequence

<400> SEQUENCE: 33

Gly Gly Thr Leu Tyr Asp Arg Arg Arg Phe Glu Ser
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Nanobody sequence

<400> SEQUENCE: 34

Trp Gly Gln Gly Thr Gln Val Thr Val Ser Ser
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Nanobody sequence

<400> SEQUENCE: 35

Trp Gly Gln Gly Thr Gln Val Thr Val Ser Ser
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Nanobody sequence

<400> SEQUENCE: 36

Trp Gly Gln Gly Thr Gln Val Thr Val Ser Ser
1               5                   10
```

<210> SEQ ID NO 37
<211> LENGTH: 11
<212> TYPE: PRT
<213> ORGANISM: Artificial Sequence
<220> FEATURE:
<223> OTHER INFORMATION: Nanobody sequence

<400> SEQUENCE: 37

```
Trp Gly Gln Gly Thr Gln Val Thr Val Ser Ser
 1               5                  10
```

<210> SEQ ID NO 38
<211> LENGTH: 11
<212> TYPE: PRT
<213> ORGANISM: Artificial Sequence
<220> FEATURE:
<223> OTHER INFORMATION: Nanobody sequence

<400> SEQUENCE: 38

```
Trp Gly Gln Gly Thr Gln Val Thr Val Ser Ser
 1               5                  10
```

<210> SEQ ID NO 39
<211> LENGTH: 121
<212> TYPE: PRT
<213> ORGANISM: Artificial Sequence
<220> FEATURE:
<223> OTHER INFORMATION: Nanobody sequence

<400> SEQUENCE: 39

```
Glu Val Gln Leu Val Glu Ser Gly Gly Asn Leu Val Gln Ala Gly Gly
 1               5                  10                  15

Ser Leu Gly Leu Ser Cys Ala Ala Ser Val Ser Ile Ser Ile His
            20                  25                  30

Ile Met Gly Trp Tyr Arg Gln Ala Pro Gly Lys Gln Arg Asp Leu Val
        35                  40                  45

Ala Thr Ile Thr Ser Gly Gly Ser Thr Ala Tyr Ala Asp Ser Val Lys
    50                  55                  60

Gly Arg Phe Thr Val Ser Lys Asp Asn Ala Lys Asn Thr Val Tyr Leu
65                  70                  75                  80

Gln Met Asp Ser Leu Lys Pro Glu Asp Thr Ser Val Tyr Tyr Cys Ala
                85                  90                  95

Ala Glu Val Arg Asn Gly Val Phe Gly Lys Trp Asn His Tyr Trp Gly
            100                 105                 110

Gln Gly Thr Gln Val Thr Val Ser Ser
        115                 120
```

<210> SEQ ID NO 40
<211> LENGTH: 117
<212> TYPE: PRT
<213> ORGANISM: Artificial Sequence
<220> FEATURE:
<223> OTHER INFORMATION: Nanobody sequence

<400> SEQUENCE: 40

```
Glu Val Gln Leu Val Glu Ser Gly Gly Gly Leu Val Gln Ala Gly Glu
 1               5                  10                  15

Ser Leu Thr Leu Ser Cys Ala Ala Ser Gly Arg Thr Leu Ser Ala Tyr
            20                  25                  30

Ile Met Gly Trp Phe Arg Gln Ala Pro Gly Lys Glu Arg Glu Phe Val
        35                  40                  45
```

```
Ala Gly Ile Trp Ser Gly Gly Tyr Thr His Leu Ala Asp Ser Ala Lys
        50                  55                  60

Gly Arg Phe Ser Ile Ser Arg Asp Asn Ala Lys Asn Thr Val Tyr Leu
 65                  70                  75                  80

Gln Met Asn Gly Leu Lys Pro Glu Asp Thr Ala Val Tyr Tyr Cys Ala
                85                  90                  95

Ala Gly Leu Arg Gly Arg Gln Tyr Ser Asn Trp Gly Gln Gly Thr Gln
               100                 105                 110

Val Thr Val Ser Ser
            115

<210> SEQ ID NO 41
<211> LENGTH: 123
<212> TYPE: PRT
<213> ORGANISM: Artificial Sequence
<220> FEATURE:
<223> OTHER INFORMATION: Nanobody sequence

<400> SEQUENCE: 41

Glu Val Gln Leu Val Glu Ser Gly Gly Gly Leu Val Gln Ala Gly Asp
 1               5                  10                  15

Ser Leu Arg Leu Ser Cys Ala Ala Ser Gly Leu Thr Phe Ser Asn Tyr
            20                  25                  30

Asp Met Gly Trp Phe Arg Gln Ala Pro Gly Lys Glu Arg Glu Phe Val
        35                  40                  45

Gly Ala Ser Trp Trp Ser Gly Ala Pro Tyr Tyr Ser Asp Ser Val
    50                  55                  60

Lys Gly Arg Phe Thr Ile Ser Arg Asp Asn Ala Lys Asn Thr Val Tyr
 65                  70                  75                  80

Leu Gln Ala Asn Ser Leu Arg Pro Glu Asp Thr Ala Val Tyr Tyr Cys
                85                  90                  95

Ala Ala Lys Arg Leu Arg Ser Phe Ala Ser Gly Gly Ser Tyr Asp Tyr
               100                 105                 110

Trp Gly Gln Gly Thr Gln Val Thr Val Ser Ser
        115                 120

<210> SEQ ID NO 42
<211> LENGTH: 121
<212> TYPE: PRT
<213> ORGANISM: Artificial Sequence
<220> FEATURE:
<223> OTHER INFORMATION: Nanobody sequence

<400> SEQUENCE: 42

Glu Val Gln Leu Val Glu Ser Gly Gly Gly Leu Val Gln Ala Gly Gly
 1               5                  10                  15

Ser Leu Arg Leu Ser Cys Ala Ala Ser Gly Ser Ile Phe Ser Ile Ala
            20                  25                  30

Ala Met Gly Trp Tyr Arg Gln Ala Thr Gly Lys Gln Arg Glu Leu Val
        35                  40                  45

Ala Thr Ile Thr Asp Gly Gly Thr Thr Tyr Ala Asp Ser Val Lys
    50                  55                  60

Gly Arg Val Thr Ile Ser Arg Asp Arg Ser Ala Asn Thr Val Tyr Leu
 65                  70                  75                  80

Ala Met Asn Asn Leu Lys Pro Asp Asp Thr Ala Val Tyr Tyr Cys Tyr
                85                  90                  95

Ala Tyr Leu Arg Tyr Thr Ser Arg Val Pro Gly Asp Asn Tyr Trp Gly
```

```
                   100                 105                 110

Gln Gly Thr Gln Val Thr Val Ser Ser
        115                 120

<210> SEQ ID NO 43
<211> LENGTH: 120
<212> TYPE: PRT
<213> ORGANISM: Artificial Sequence
<220> FEATURE:
<223> OTHER INFORMATION: Nanobody sequence

<400> SEQUENCE: 43

Glu Val Gln Leu Val Glu Ser Gly Gly Gly Leu Val Gln Pro Gly Gly
1               5                  10                  15

Ser Leu Arg Ile Ser Cys Ala Ala Ser Gly Ser Ile Tyr Leu Ile Asn
            20                  25                  30

Tyr Met Gly Trp Tyr Arg Gln Ala Pro Gly Lys Gln Arg Glu Leu Val
        35                  40                  45

Ala Thr Leu Thr Ser Gly Gly Ser Thr Asn Tyr Ala Gly Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ile Gly Gly Thr Leu Tyr Asp Arg Arg Arg Phe Glu Ser Trp Gly Gln
            100                 105                 110

Gly Thr Gln Val Thr Val Ser Ser
        115                 120

<210> SEQ ID NO 44
<211> LENGTH: 245
<212> TYPE: PRT
<213> ORGANISM: Artificial Sequence
<220> FEATURE:
<223> OTHER INFORMATION: Nanobody sequence

<400> SEQUENCE: 44

Glu Val Gln Leu Val Glu Ser Gly Gly Asn Leu Val Gln Ala Gly Gly
1               5                  10                  15

Ser Leu Gly Leu Ser Cys Ala Ala Ser Val Ser Ile Ser Ser Ile His
            20                  25                  30

Ile Met Gly Trp Tyr Arg Gln Ala Pro Gly Lys Gln Arg Asp Leu Val
        35                  40                  45

Ala Thr Ile Thr Ser Gly Gly Ser Thr Ala Tyr Ala Asp Ser Val Lys
    50                  55                  60

Gly Arg Phe Thr Val Ser Lys Asp Asn Ala Lys Asn Thr Val Tyr Leu
65                  70                  75                  80

Gln Met Asp Ser Leu Lys Pro Glu Asp Thr Ser Val Tyr Tyr Cys Ala
                85                  90                  95

Ala Glu Val Arg Asn Gly Val Phe Gly Lys Trp Asn His Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Leu Val Gln Pro
    130                 135                 140

Gly Asn Ser Leu Arg Leu Ser Cys Ala Ala Ser Gly Phe Thr Phe Ser
145                 150                 155                 160
```

```
Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser
                245

<210> SEQ ID NO 45
<211> LENGTH: 241
<212> TYPE: PRT
<213> ORGANISM: Artificial Sequence
<220> FEATURE:
<223> OTHER INFORMATION: Nanobody sequence

<400> SEQUENCE: 45

Glu Val Gln Leu Val Glu Ser Gly Gly Gly Leu Val Gln Ala Gly Glu
1               5                   10                  15

Ser Leu Thr Leu Ser Cys Ala Ala Ser Gly Arg Thr Leu Ser Ala Tyr
            20                  25                  30

Ile Met Gly Trp Phe Arg Gln Ala Pro Gly Lys Glu Arg Glu Phe Val
        35                  40                  45

Ala Gly Ile Trp Ser Gly Gly Tyr Thr His Leu Ala Asp Ser Ala Lys
    50                  55                  60

Gly Arg Phe Ser Ile Ser Arg Asp Asn Ala Lys Asn Thr Val Tyr Leu
65                  70                  75                  80

Gln Met Asn Gly Leu Lys Pro Glu Asp Thr Ala Val Tyr Tyr Cys Ala
                85                  90                  95

Ala Gly Leu Arg Gly Arg Gln Tyr Ser Asn Trp Gly Gln Gly Thr Gln
            100                 105                 110

Val Thr Val Ser Ser Gly Gly Gly Gly Ser Gly Gly Gly Ser Glu Val
        115                 120                 125

Gln Leu Val Glu Ser Gly Gly Gly Leu Val Gln Pro Gly Asn Ser Leu
    130                 135                 140

Arg Leu Ser Cys Ala Ala Ser Gly Phe Thr Phe Ser Ser Phe Gly Met
145                 150                 155                 160

Ser Trp Val Arg Gln Ala Pro Gly Lys Gly Leu Glu Trp Val Ser Ser
                165                 170                 175

Ile Ser Gly Ser Gly Ser Asp Thr Leu Tyr Ala Asp Ser Val Lys Gly
            180                 185                 190

Arg Phe Thr Ile Ser Arg Asp Asn Ala Lys Thr Thr Leu Tyr Leu Gln
        195                 200                 205

Met Asn Ser Leu Arg Pro Glu Asp Thr Ala Val Tyr Tyr Cys Thr Ile
    210                 215                 220

Gly Gly Ser Leu Ser Arg Ser Ser Gln Gly Thr Leu Val Thr Val Ser
225                 230                 235                 240

Ser

<210> SEQ ID NO 46
<211> LENGTH: 247
<212> TYPE: PRT
```

<213> ORGANISM: Artificial Sequence
<220> FEATURE:
<223> OTHER INFORMATION: Nanobody sequence

<400> SEQUENCE: 46

```
Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser Asn Tyr
            20                  25                  30

Asp Met Gly Trp Phe Arg Gln Ala Pro Gly Lys Glu Arg Glu Phe Val
        35                  40                  45

Gly Ala Ser Trp Trp Ser Gly Ala Pro Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Ala Asn Ser Leu Arg Pro Glu Asp Thr Ala Val Tyr Tyr Cys
                85                  90                  95

Ala Ala Lys Arg Leu Arg Ser Phe Ala Ser Gly Gly Ser Tyr Asp Tyr
            100                 105                 110

Trp Gly Gln Gly Thr Gln Val Thr Val Ser Ser Gly Gly Gly Gly Ser
        115                 120                 125

Gly Gly Gly Ser Glu Val Gln Leu Val Glu Ser Gly Gly Gly Leu Val
    130                 135                 140

Gln Pro Gly Asn Ser Leu Arg Leu Ser Cys Ala Ala Ser Gly Phe Thr
145                 150                 155                 160

Phe Ser Ser Phe Gly Met Ser Trp Val Arg Gln Ala Pro Gly Lys Gly
                165                 170                 175

Leu Glu Trp Val Ser Ser Ile Ser Gly Ser Gly Ser Asp Thr Leu Tyr
            180                 185                 190

Ala Asp Ser Val Lys Gly Arg Phe Thr Ile Ser Arg Asp Asn Ala Lys
        195                 200                 205

Thr Thr Leu Tyr Leu Gln Met Asn Ser Leu Arg Pro Glu Asp Thr Ala
    210                 215                 220

Val Tyr Tyr Cys Thr Ile Gly Gly Ser Leu Ser Arg Ser Ser Gln Gly
225                 230                 235                 240

Thr Leu Val Thr Val Ser Ser
                245
```

<210> SEQ ID NO 47
<211> LENGTH: 245
<212> TYPE: PRT
<213> ORGANISM: Artificial Sequence
<220> FEATURE:
<223> OTHER INFORMATION: Nanobody sequence

<400> SEQUENCE: 47

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Ala
            20                  25                  30

Ala Met Gly Trp Tyr Arg Gln Ala Thr Gly Lys Gln Arg Glu Leu Val
        35                  40                  45

Ala Thr Ile Thr Asp Gly Gly Thr Thr Tyr Ala Asp Ser Val Lys
    50                  55                  60

Gly Arg Val Thr Ile Ser Arg Asp Arg Ser Ala Asn Thr Val Tyr Leu
65                  70                  75                  80
```

```
Ala Met Asn Asn Leu Lys Pro Asp Asp Thr Ala Val Tyr Tyr Cys Tyr
                    85                  90                  95

Ala Tyr Leu Arg Tyr Thr Ser Arg Val Pro Gly Asp Asn Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Leu Val Gln Pro
    130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
                180                 185                 190

Ser Val Lys Gly Arg Phe Thr Ile Ser Arg Asp Asn Ala Lys Thr Thr
                195                 200                 205

Leu Tyr Leu Gln Met Asn Ser Leu Arg Pro Glu Asp Thr Ala Val Tyr
            210                 215                 220

Tyr Cys Thr Ile Gly Gly Ser Leu Ser Arg Ser Ser Gln Gly Thr Leu
225                 230                 235                 240

Val Thr Val Ser Ser
                245

<210> SEQ ID NO 48
<211> LENGTH: 244
<212> TYPE: PRT
<213> ORGANISM: Artificial Sequence
<220> FEATURE:
<223> OTHER INFORMATION: Nanobody sequence

<400> SEQUENCE: 48

Glu Val Gln Leu Val Glu Ser Gly Gly Gly Leu Val Gln Pro Gly Gly
1               5                   10                  15

Ser Leu Arg Ile Ser Cys Ala Ala Ser Gly Ser Ile Tyr Leu Ile Asn
            20                  25                  30

Tyr Met Gly Trp Tyr Arg Gln Ala Pro Gly Lys Gln Arg Glu Leu Val
        35                  40                  45

Ala Thr Leu Thr Ser Gly Gly Ser Thr Asn Tyr Ala Gly Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ile Gly Gly Thr Leu Tyr Asp Arg Arg Arg Phe Glu Ser Trp Gly Gln
            100                 105                 110

Gly Thr Gln Val Thr Val Ser Ser Gly Gly Gly Gly Ser Gly Gly Gly
        115                 120                 125

Ser Glu Val Gln Leu Val Glu Ser Gly Gly Gly Leu Val Gln Pro Gly
    130                 135                 140

Asn Ser Leu Arg Leu Ser Cys Ala Ala Ser Gly Phe Thr Phe Ser Ser
145                 150                 155                 160

Phe Gly Met Ser Trp Val Arg Gln Ala Pro Gly Lys Gly Leu Glu Trp
                165                 170                 175

Val Ser Ser Ile Ser Gly Ser Gly Ser Asp Thr Leu Tyr Ala Asp Ser
                180                 185                 190
```

Val Lys Gly Arg Phe Thr Ile Ser Arg Asp Asn Ala Lys Thr Thr Leu
            195                 200                 205

Tyr Leu Gln Met Asn Ser Leu Arg Pro Glu Asp Thr Ala Val Tyr Tyr
        210                 215                 220

Cys Thr Ile Gly Gly Ser Leu Ser Arg Ser Ser Gln Gly Thr Leu Val
225                 230                 235                 240

Thr Val Ser Ser

<210> SEQ ID NO 49
<211> LENGTH: 5
<212> TYPE: PRT
<213> ORGANISM: Artificial Sequence
<220> FEATURE:
<223> OTHER INFORMATION: Nanobody sequence

<400> SEQUENCE: 49

Gly Gly Gly Gly Ser
1               5

<210> SEQ ID NO 50
<211> LENGTH: 7
<212> TYPE: PRT
<213> ORGANISM: Artificial Sequence
<220> FEATURE:
<223> OTHER INFORMATION: Nanobody sequence

<400> SEQUENCE: 50

Ser Gly Gly Ser Gly Gly Ser
1               5

<210> SEQ ID NO 51
<211> LENGTH: 9
<212> TYPE: PRT
<213> ORGANISM: Artificial Sequence
<220> FEATURE:
<223> OTHER INFORMATION: Nanobody sequence

<400> SEQUENCE: 51

Gly Gly Gly Gly Ser Gly Gly Gly Ser
1               5

<210> SEQ ID NO 52
<211> LENGTH: 10
<212> TYPE: PRT
<213> ORGANISM: Artificial Sequence
<220> FEATURE:
<223> OTHER INFORMATION: Nanobody sequence

<400> SEQUENCE: 52

Gly Gly Gly Gly Ser Gly Gly Gly Gly Ser
1               5                   10

<210> SEQ ID NO 53
<211> LENGTH: 15
<212> TYPE: PRT
<213> ORGANISM: Artificial Sequence
<220> FEATURE:
<223> OTHER INFORMATION: Nanobody sequence

<400> SEQUENCE: 53

Gly Gly Gly Gly Ser Gly Gly Gly Gly Ser Gly Gly Gly Gly Ser
1               5                   10                  15

<210> SEQ ID NO 54
<211> LENGTH: 18

```
<212> TYPE: PRT
<213> ORGANISM: Artificial Sequence
<220> FEATURE:
<223> OTHER INFORMATION: Nanobody sequence

<400> SEQUENCE: 54

Gly Gly Gly Gly Ser Gly Gly Gly Ser Gly Gly Gly Gly Gly
1               5                   10                  15

Gly Ser

<210> SEQ ID NO 55
<211> LENGTH: 20
<212> TYPE: PRT
<213> ORGANISM: Artificial Sequence
<220> FEATURE:
<223> OTHER INFORMATION: Nanobody sequence

<400> SEQUENCE: 55

Gly Gly Gly Gly Ser Gly Gly Gly Gly Ser Gly Gly Gly Gly Ser Gly
1               5                   10                  15

Gly Gly Gly Ser
            20

<210> SEQ ID NO 56
<211> LENGTH: 25
<212> TYPE: PRT
<213> ORGANISM: Artificial Sequence
<220> FEATURE:
<223> OTHER INFORMATION: Nanobody sequence

<400> SEQUENCE: 56

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 57
<211> LENGTH: 30
<212> TYPE: PRT
<213> ORGANISM: Artificial Sequence
<220> FEATURE:
<223> OTHER INFORMATION: Nanobody sequence

<400> SEQUENCE: 57

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 58
<211> LENGTH: 35
<212> TYPE: PRT
<213> ORGANISM: Artificial Sequence
<220> FEATURE:
<223> OTHER INFORMATION: Nanobody sequence

<400> SEQUENCE: 58

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35
```

<210> SEQ ID NO 59
<211> LENGTH: 363
<212> TYPE: DNA
<213> ORGANISM: Artificial Sequence
<220> FEATURE:
<223> OTHER INFORMATION: Nanobody sequence

<400> SEQUENCE: 59

```
gaggtgcaat tggtggagtc tgggggaaac ttggtgcagg ctgggggtc tctgggactc      60
tcctgtgcag cctctgtaag catctccagt atccatatca tgggctggta ccggcaggct    120
ccaggcaaac agcgcgactt ggtcgctact attactagtg gtggtagcac agcatatgca    180
gactccgtga agggacgatt caccgtctcc aaagacaacg ccaagaacac ggtgtatctg    240
caaatggaca gcctgaaacc tgaggacaca tccgtctatt actgtgcagc cgaggtcaga    300
aatggggtgt ttggaaaatg gaatcactac tggggccagg ggacccaggt caccgtctcc    360
tca                                                                 363
```

<210> SEQ ID NO 60
<211> LENGTH: 351
<212> TYPE: DNA
<213> ORGANISM: Artificial Sequence
<220> FEATURE:
<223> OTHER INFORMATION: Nanobody sequence

<400> SEQUENCE: 60

```
gaggtgcaat tggtggagtc tgggggagga ttggtgcagg ctggggagtc tctgactctc      60
tcctgtgcag cctctggacg caccttaagt gcctatatca tgggctggtt ccgccaggct    120
ccagggaagg agcgggagtt tgtagccggt atctggagtg gtggttacac acaccttgca    180
gactccgcga agggccgatt cagcatctct agagacaacg ccaagaacac tgtatatctg    240
caaatgaacg gcctgaaacc tgaggacacg gccgtctatt actgtgcagc aggtctgaga    300
ggccgccagt atagtaactg gggccagggg acccaggtca ccgtctcctc a             351
```

<210> SEQ ID NO 61
<211> LENGTH: 369
<212> TYPE: DNA
<213> ORGANISM: Artificial Sequence
<220> FEATURE:
<223> OTHER INFORMATION: Nanobody sequence

<400> SEQUENCE: 61

```
gaggtgcaat tggtggagtc tgggggagga ttggtgcagg ctggggactc tctgagactc      60
tcctgtgcag cctctggact cactttcagt aactatgaca tgggctggtt ccgccaggct    120
ccagggaagg agcgtgaatt tgtagggggct agttggtgga gtggtggtgc cccatactat    180
tcagactccg tgaagggccg attcaccatc tccagagaca cgccaagaa cacggtgtat     240
ctgcaagcga acagcctgag acctgaggac acggccgttt attactgtgc agccaaaagg    300
ctgcgtagtt tcgcctccgg tggtcgtat gattactggg gtcaggggac ccaggtcacc    360
gtctcctca                                                           369
```

<210> SEQ ID NO 62
<211> LENGTH: 348
<212> TYPE: DNA
<213> ORGANISM: Artificial Sequence
<220> FEATURE:
<223> OTHER INFORMATION: Nanobody sequence

<400> SEQUENCE: 62

```
gagtctgggg gaggcttggt gcaggctgga gggtctctga gactctcctg tgcagcttct      60
ggaagcatct tcagtatcgc tgccatgggc tggtaccgcc aggctacagg gaagcagcgc     120
gagttggtcg caactatcac tgatggcggt acgacaacct atgcagactc cgtgaagggc     180
cgagtcacca tctccaggga caggtctgcg aacacggtgt atctggcaat gaacaatttg     240
aaacctgatg acacagccgt ctattattgt tatgcgtatc tgcgctatac aagcagagta     300
cctggcgata actactgggg ccaggggacc caggtcaccg tctcctca                  348
```

<210> SEQ ID NO 63
<211> LENGTH: 361
<212> TYPE: DNA
<213> ORGANISM: Artificial Sequence
<220> FEATURE:
<223> OTHER INFORMATION: Nanobody sequence

<400> SEQUENCE: 63

```
gaggtgcaat tggtggagtc tgggggaggc ttggtgcagc ctgggggtc tctgagaatt       60 tcctgtgcag cctctggaag catctacctt atcaattaca tgggctggta ccgccaggct     120
ccagggaagc agcgcgagtt ggtcgcaacg cttactagtg gtggtagtac caactatgca     180
ggctccgtga agggccgatt cgccatctcc agagacaacg ccaagaacac ggtttatctg     240
caaatgaaca gcctgaaacc tgaggacacg gccgtctatt actgtaatat aggaggaacg     300
ctatacgaca gaaggcggtt tgaatcctgg ggccagggga cccaggtcac cgtctcctca     360
g                                                                     361
```

<210> SEQ ID NO 64
<211> LENGTH: 30
<212> TYPE: PRT
<213> ORGANISM: Artificial Sequence
<220> FEATURE:
<223> OTHER INFORMATION: Nanobody sequence

<400> SEQUENCE: 64

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser
            20                  25                  30

<210> SEQ ID NO 65
<211> LENGTH: 5
<212> TYPE: PRT
<213> ORGANISM: Artificial Sequence
<220> FEATURE:
<223> OTHER INFORMATION: Nanobody sequence

<400> SEQUENCE: 65

Ser Phe Gly Met Ser
1               5

<210> SEQ ID NO 66
<211> LENGTH: 14
<212> TYPE: PRT
<213> ORGANISM: Artificial Sequence
<220> FEATURE:
<223> OTHER INFORMATION: Nanobody sequence

<400> SEQUENCE: 66

Trp Val Arg Gln Ala Pro Gly Lys Gly Leu Glu Trp Val Ser
1               5                   10

-continued

<210> SEQ ID NO 67
<211> LENGTH: 17
<212> TYPE: PRT
<213> ORGANISM: Artificial Sequence
<220> FEATURE:
<223> OTHER INFORMATION: Nanobody sequence

<400> SEQUENCE: 67

Ser Ile Ser Gly Ser Gly Ser Asp Thr Leu Tyr Ala Asp Ser Val Lys
1               5                   10                  15

Gly

<210> SEQ ID NO 68
<211> LENGTH: 32
<212> TYPE: PRT
<213> ORGANISM: Artificial Sequence
<220> FEATURE:
<223> OTHER INFORMATION: Nanobody sequence

<400> SEQUENCE: 68

Arg Phe Thr Ile Ser Arg Asp Asn Ala Lys Thr Thr Leu Tyr Leu Gln
1               5                   10                  15

Met Asn Ser Leu Arg Pro Glu Asp Thr Ala Val Tyr Tyr Cys Thr Ile
            20                  25                  30

<210> SEQ ID NO 69
<211> LENGTH: 6
<212> TYPE: PRT
<213> ORGANISM: Artificial Sequence
<220> FEATURE:
<223> OTHER INFORMATION: Nanobody sequence

<400> SEQUENCE: 69

Gly Gly Ser Leu Ser Arg
1               5

<210> SEQ ID NO 70
<211> LENGTH: 11
<212> TYPE: PRT
<213> ORGANISM: Artificial Sequence
<220> FEATURE:
<223> OTHER INFORMATION: Nanobody sequence

<400> SEQUENCE: 70

Ser Ser Gln Gly Thr Leu Val Thr Val Ser Ser
1               5                   10

<210> SEQ ID NO 71
<211> LENGTH: 26
<212> TYPE: PRT
<213> ORGANISM: Artificial Sequence
<220> FEATURE:
<223> OTHER INFORMATION: Nanobody sequence

<400> SEQUENCE: 71

Ala Ala Ala His His His His His His Gly Ala Ala Glu Gln Lys Leu
1               5                   10                  15

Ile Ser Glu Glu Asp Leu Asn Gly Ala Ala
            20                  25

<210> SEQ ID NO 72
<211> LENGTH: 23
<212> TYPE: PRT
<213> ORGANISM: Artificial Sequence
<220> FEATURE:

<223> OTHER INFORMATION: Nanobody sequence

<400> SEQUENCE: 72

Ala Ala Ala Glu Gln Lys Leu Ile Ser Glu Glu Asp Leu Asn Gly Ala
1               5                   10                  15
Ala His His His His His His
            20

<210> SEQ ID NO 73
<211> LENGTH: 735
<212> TYPE: DNA
<213> ORGANISM: Artificial Sequence
<220> FEATURE:
<223> OTHER INFORMATION: Nanobody sequence

<400> SEQUENCE: 73

| gaggtgcaat tggtggagtc tgggggaaac ttggtgcagg ctgggggtc tctgggactc | 60 |
| tcctgtgcag cctctgtaag catctccagt atccatatca tgggctggta ccggcaggct | 120 |
| ccaggcaaac agcgcgactt ggtcgctact attactagtg gtggtagcac agcatatgca | 180 |
| gactccgtga agggacgatt caccgtctcc aaagacaacg ccaagaacac ggtgtatctg | 240 |
| caaatggaca gcctgaaacc tgaggacaca tccgtctatt actgtgcagc cgaggtcaga | 300 |
| aatggggtgt ttggaaaatg gaatcactac tggggccagg ggacccaggt cacggtctcc | 360 |
| tcaggaggtg gcgggtccgg aggcggatcc gaggtacagc tggtggagtc tggggtggc | 420 |
| ttggtgcaac cggtaacag tctgcgcctt agctgcgcag cgtctggctt accttcagc | 480 |
| tcctttggca tgagctgggt tcgccaggct ccgggaaaag gactggaatg ggtttcgtct | 540 |
| attagcggca gtggtagcga tacgctctac gcggactccg tgaagggccg tttcaccatc | 600 |
| tcccgcgata acgccaaaac tacactgtat ctgcaaatga atagcctgcg tcctgaagac | 660 |
| acggccgttt attactgtac tattggtggc tcgttaagcc gttcttcaca gggtaccctg | 720 |
| gtcaccgtct cctca | 735 |

<210> SEQ ID NO 74
<211> LENGTH: 723
<212> TYPE: DNA
<213> ORGANISM: Artificial Sequence
<220> FEATURE:
<223> OTHER INFORMATION: Nanobody sequence

<400> SEQUENCE: 74

| gaggtgcaat tggtggagtc tgggggagga ttggtgcagg ctggggagtc tctgactctc | 60 |
| tcctgtgcag cctctggacg caccttaagt gcctatatca tgggctggtt ccgccaggct | 120 |
| ccagggaagg agcgggagtt tgtagccggt atctggagtg gtggttacac acaccttgca | 180 |
| gactccgcga agggccgatt cagcatctct agagacaacg ccaagaacac tgtatatctg | 240 |
| caaatgaacg gcctgaaacc tgaggacacg gccgtctatt actgtgcagc aggtctgaga | 300 |
| ggccgccagt atagtaactg gggccagggg acccaggtca cggtctcctc aggaggtggc | 360 |
| gggtccggag gcggatccga ggtacagctg gtggagtctg gggtggctt ggtgcaaccg | 420 |
| gtaacagtc tgcgccttag ctgcgcagcg tctggcttta ccttcagctc ctttggcatg | 480 |
| agctgggttc gccaggctcc gggaaaagga ctggaatggg tttcgtctat tagcggcagt | 540 |
| ggtagcgata cgctctacgc ggactccgtg aagggccgtt tcaccatctc ccgcgataac | 600 |
| gccaaaacta cactgtatct gcaaatgaat agcctgcgtc ctgaagacac ggccgtttat | 660 |
| tactgtacta ttggtggctc gttaagccgt tcttcacagg gtaccctggt caccgtctcc | 720 |

<210> SEQ ID NO 75
<211> LENGTH: 741
<212> TYPE: DNA
<213> ORGANISM: Artificial Sequence
<220> FEATURE:
<223> OTHER INFORMATION: Nanobody sequence

<400> SEQUENCE: 75

| | |
|---|---|
| gaggtgcaat tggtggagtc tgggggagga ttggtgcagg ctggggactc tctgagactc | 60 |
| tcctgtgcag cctctggact cactttcagt aactatgaca tgggctggtt ccgccaggct | 120 |
| ccagggaagg agcgtgaatt tgtaggggct agttggtgga gtggtggtgc cccatactat | 180 |
| tcagactccg tgaagggccg attcaccatc tccagagaca cgccaagaa cacggtgtat | 240 |
| ctgcaagcga acagcctgag acctgaggac acggccgttt attactgtgc agccaaaagg | 300 |
| ctgcgtagtt tcgcctccgg tgggtcgtat gattactggg gtcaggggac ccaggtcacg | 360 |
| gtctcctcag gaggtggcgg gtccggaggc ggatccgagg tacagctggt ggagtctggg | 420 |
| ggtggcttgg tgcaaccggg taacagtctg cgccttagct gcgcagcgtc tggctttacc | 480 |
| ttcagctcct ttggcatgag ctgggttcgc caggctccgg aaaaggact ggaatgggtt | 540 |
| tcgtctatta gcggcagtgg tagcgatacg ctctacgcgg actccgtgaa gggccgtttc | 600 |
| accatctccc gcgataacgc caaaactaca ctgtatctgc aaatgaatag cctgcgtcct | 660 |
| gaagacacgg ccgtttatta ctgtactatt ggtggctcgt taagccgttc ttcacagggt | 720 |
| accctggtca ccgtctcctc a | 741 |

<210> SEQ ID NO 76
<211> LENGTH: 735
<212> TYPE: DNA
<213> ORGANISM: Artificial Sequence
<220> FEATURE:
<223> OTHER INFORMATION: Nanobody sequence

<400> SEQUENCE: 76

| | |
|---|---|
| gaggtgcaat tggtggagtc tgggggaggc ttggtgcagg ctggagggtc tctgagactc | 60 |
| tcctgtgcag cttctggaag catcttcagt atcgctgcca tgggctggta ccgccaggct | 120 |
| acagggaagc agcgcgagtt ggtcgcaact atcactgatg gcggtacgac aacctatgca | 180 |
| gactccgtga agggccgagt caccatctcc agggacaggt ctgcgaacac ggtgtatctg | 240 |
| gcaatgaaca atttgaaacc tgatgacaca gccgtctatt attgttatgc gtatctgcgc | 300 |
| tatacaagca gagtacctgg cgataactac tggggccagg ggacccaggt cacggtctcc | 360 |
| tcaggaggtg gcgggtccgg aggcggatcc gaggtacagc tggtggagtc tgggggtggc | 420 |
| ttggtgcaac cgggtaacag tctgcgcctt agctgcgcag cgtctggctt taccttcagc | 480 |
| tcctttggca tgagctgggt tcgccaggct ccggaaaag gactggaatg ggtttcgtct | 540 |
| attagcggca gtggtagcga tacgctctac gcggactccg tgaagggccg tttcaccatc | 600 |
| tcccgcgata acgccaaaac tacactgtat ctgcaaatga atagcctgcg tcctgaagac | 660 |
| acggccgttt attactgtac tattggtggc tcgttaagcc gttcttcaca gggtaccctg | 720 |
| gtcaccgtct cctca | 735 |

<210> SEQ ID NO 77
<211> LENGTH: 732
<212> TYPE: DNA

```
<213> ORGANISM: Artificial Sequence
<220> FEATURE:
<223> OTHER INFORMATION: Nanobody sequence

<400> SEQUENCE: 77
gaggtgcaat tggtggagtc tgggggaggc ttggtgcagc ctgggggtc tctgagaatt      60
tcctgtgcag cctctggaag catctacctt atcaattaca tgggctggta ccgccaggct    120
ccagggaagc agcgcgagtt ggtcgcaacg cttactagtg gtggtagtac caactatgca    180
ggctccgtga agggccgatt cgccatctcc agagacaacg ccaagaacac ggtttatctg    240
caaatgaaca gcctgaaacc tgaggacacg gccgtctatt actgtaatat aggaggaacg    300
ctatacgaca gaaggcggtt tgaatcctgg ggccagggga cccaggtcac ggtctcctca    360
ggaggtggcg gtccggagg cggatccgag gtacagctgg tggagtctgg gggtggcttg    420
gtgcaaccgg gtaacagtct cgccttagc tgcgcagcgt ctggctttac cttcagctcc    480
tttggcatga ctgggttcg ccaggctccg gaaaaggac tggaatgggt ttcgtctatt    540
agcggcagtg gtagcgatac gctctacgcg gactccgtga agggccgttt caccatctcc    600
cgcgataacg ccaaaactac actgtatctg caaatgaata gcctgcgtcc tgaagacacg    660
gccgtttatt actgtactat tggtggctcg ttaagccgtt cttcacaggg taccctggtc    720
accgtctcct ca                                                        732

<210> SEQ ID NO 78
<211> LENGTH: 247
<212> TYPE: PRT
<213> ORGANISM: Artificial Sequence
<220> FEATURE:
<223> OTHER INFORMATION: Nanobody sequence

<400> SEQUENCE: 78

Glu Val Gln Leu Val Glu Ser Gly Gly Asn Leu Val Gln Ala Gly Gly
1               5                   10                  15
Ser Leu Gly Leu Ser Cys Ala Ala Ser Val Ser Ile Ser Ser Ile His
            20                  25                  30
Ile Met Gly Trp Tyr Arg Gln Ala Pro Gly Lys Gln Arg Asp Leu Val
        35                  40                  45
Ala Thr Ile Thr Ser Gly Gly Ser Thr Ala Tyr Ala Asp Ser Val Lys
    50                  55                  60
Gly Arg Phe Thr Val Ser Lys Asp Asn Ala Lys Asn Thr Val Tyr Leu
65                  70                  75                  80
Gln Met Asp Ser Leu Lys Pro Glu Asp Thr Ser Val Tyr Tyr Cys Ala
                85                  90                  95
Ala Glu Val Arg Asn Gly Val Phe Gly Lys Trp Asn His Tyr Trp Gly
            100                 105                 110
Gln Gly Thr Gln Val Thr Val Ser Ser Gly Gly Gly Ser Gly Gly
        115                 120                 125
Gly Ser Glu Val Gln Leu Val Glu Ser Gly Gly Gly Leu Val Gln Ala
    130                 135                 140
Gly Glu Ser Leu Thr Leu Ser Cys Ala Ala Ser Gly Arg Thr Leu Ser
145                 150                 155                 160
Ala Tyr Ile Met Gly Trp Phe Arg Gln Ala Pro Gly Lys Glu Arg Glu
                165                 170                 175
Phe Val Ala Gly Ile Trp Ser Gly Gly Tyr Thr His Leu Ala Asp Ser
            180                 185                 190
Ala Lys Gly Arg Phe Ser Ile Ser Arg Asp Asn Ala Lys Asn Thr Val
```

```
            195                 200                 205

Tyr Leu Gln Met Asn Gly Leu Lys Pro Glu Asp Thr Ala Val Tyr Tyr
    210                 215                 220

Cys Ala Ala Gly Leu Arg Gly Arg Gln Tyr Ser Asn Trp Gly Gln Gly
225                 230                 235                 240

Thr Gln Val Thr Val Ser Ser
                245

<210> SEQ ID NO 79
<211> LENGTH: 247
<212> TYPE: PRT
<213> ORGANISM: Artificial Sequence
<220> FEATURE:
<223> OTHER INFORMATION: Nanobody sequence

<400> SEQUENCE: 79

Glu Val Gln Leu Val Glu Ser Gly Gly Gly Leu Val Gln Ala Gly Glu
1               5                   10                  15

Ser Leu Thr Leu Ser Cys Ala Ala Ser Gly Arg Thr Leu Ser Ala Tyr
            20                  25                  30

Ile Met Gly Trp Phe Arg Gln Ala Pro Gly Lys Glu Arg Glu Phe Val
        35                  40                  45

Ala Gly Ile Trp Ser Gly Gly Tyr Thr His Leu Ala Asp Ser Ala Lys
    50                  55                  60

Gly Arg Phe Ser Ile Ser Arg Asp Asn Ala Lys Asn Thr Val Tyr Leu
65                  70                  75                  80

Gln Met Asn Gly Leu Lys Pro Glu Asp Thr Ala Val Tyr Tyr Cys Ala
                85                  90                  95

Ala Gly Leu Arg Gly Arg Gln Tyr Ser Asn Trp Gly Gln Gly Thr Gln
            100                 105                 110

Val Thr Val Ser Ser Gly Gly Gly Ser Gly Gly Gly Ser Glu Val
        115                 120                 125

Gln Leu Val Glu Ser Gly Gly Asn Leu Val Gln Ala Gly Gly Ser Leu
    130                 135                 140

Gly Leu Ser Cys Ala Ala Ser Val Ser Ile Ser Ser Ile His Ile Met
145                 150                 155                 160

Gly Trp Tyr Arg Gln Ala Pro Gly Lys Gln Arg Asp Leu Val Ala Thr
                165                 170                 175

Ile Thr Ser Gly Gly Ser Thr Ala Tyr Ala Asp Ser Val Lys Gly Arg
            180                 185                 190

Phe Thr Val Ser Lys Asp Asn Ala Lys Asn Thr Val Tyr Leu Gln Met
        195                 200                 205

Asp Ser Leu Lys Pro Glu Asp Thr Ser Val Tyr Tyr Cys Ala Ala Glu
    210                 215                 220

Val Arg Asn Gly Val Phe Gly Lys Trp Asn His Tyr Trp Gly Gln Gly
225                 230                 235                 240

Thr Gln Val Thr Val Ser Ser
                245

<210> SEQ ID NO 80
<211> LENGTH: 371
<212> TYPE: PRT
<213> ORGANISM: Artificial Sequence
<220> FEATURE:
<223> OTHER INFORMATION: Nanobody sequence

<400> SEQUENCE: 80
```

-continued

```
Glu Val Gln Leu Val Glu Ser Gly Gly Asn Leu Val Gln Ala Gly Gly
  1               5                  10                  15

Ser Leu Gly Leu Ser Cys Ala Ala Ser Val Ser Ile Ser Ile Ser Ile His
             20                  25                  30

Ile Met Gly Trp Tyr Arg Gln Ala Pro Gly Lys Gln Arg Asp Leu Val
             35                  40                  45

Ala Thr Ile Thr Ser Gly Gly Ser Thr Ala Tyr Ala Asp Ser Val Lys
         50                  55                  60

Gly Arg Phe Thr Val Ser Lys Asp Asn Ala Lys Asn Thr Val Tyr Leu
 65                  70                  75                  80

Gln Met Asp Ser Leu Lys Pro Glu Asp Thr Ser Val Tyr Tyr Cys Ala
                 85                  90                  95

Ala Glu Val Arg Asn Gly Val Phe Gly Lys Trp Asn His Tyr Trp Gly
                100                 105                 110

Gln Gly Thr Gln Val Thr Val Ser Gly Gly Gly Ser Gly Gly
                115                 120                 125

Gly Ser Glu Val Gln Leu Val Glu Ser Gly Gly Gly Leu Val Gln Pro
        130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
                180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Arg Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Ala Gly Glu Ser Leu
        260                 265                 270

Thr Leu Ser Cys Ala Ala Ser Gly Arg Thr Leu Ser Ala Tyr Ile Met
    275                 280                 285

Gly Trp Phe Arg Gln Ala Pro Gly Lys Glu Arg Glu Phe Val Ala Gly
    290                 295                 300

Ile Trp Ser Gly Gly Tyr Thr His Leu Ala Asp Ser Ala Lys Gly Arg
305                 310                 315                 320

Phe Ser Ile Ser Arg Asp Asn Ala Lys Asn Thr Val Tyr Leu Gln Met
                325                 330                 335

Asn Gly Leu Lys Pro Glu Asp Thr Ala Val Tyr Tyr Cys Ala Ala Gly
                340                 345                 350

Leu Arg Gly Arg Gln Tyr Ser Asn Trp Gly Gln Gly Thr Gln Val Thr
        355                 360                 365

Val Ser Ser
    370

<210> SEQ ID NO 81
<211> LENGTH: 371
<212> TYPE: PRT
<213> ORGANISM: Artificial Sequence
<220> FEATURE:
<223> OTHER INFORMATION: Nanobody sequence
```

<400> SEQUENCE: 81

```
Glu Val Gln Leu Val Glu Ser Gly Gly Asn Leu Val Gln Ala Gly Gly
1               5                   10                  15

Ser Leu Gly Leu Ser Cys Ala Ala Ser Val Ser Ile Ser Ser Ile His
            20                  25                  30

Ile Met Gly Trp Tyr Arg Gln Ala Pro Gly Lys Gln Arg Asp Leu Val
        35                  40                  45

Ala Thr Ile Thr Ser Gly Gly Ser Thr Ala Tyr Ala Asp Ser Val Lys
    50                  55                  60

Gly Arg Phe Thr Val Ser Lys Asp Asn Ala Lys Asn Thr Val Tyr Leu
65                  70                  75                  80

Gln Met Asp Ser Leu Lys Pro Glu Asp Thr Ser Val Tyr Tyr Cys Ala
                85                  90                  95

Ala Glu Val Arg Asn Gly Val Phe Gly Lys Trp Asn His Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Leu Val Gln Ala
130                 135                 140

Gly Glu Ser Leu Thr Leu Ser Cys Ala Ala Ser Gly Arg Thr Leu Ser
145                 150                 155                 160

Ala Tyr Ile Met Gly Trp Phe Arg Gln Ala Pro Gly Lys Glu Arg Glu
                165                 170                 175

Phe Val Ala Gly Ile Trp Ser Gly Gly Tyr Thr His Leu Ala Asp Ser
            180                 185                 190

Ala Lys Gly Arg Phe Ser Ile Ser Arg Asp Asn Ala Lys Asn Thr Val
        195                 200                 205

Tyr Leu Gln Met Asn Gly Leu Lys Pro Glu Asp Thr Ala Val Tyr Tyr
    210                 215                 220

Cys Ala Ala Gly Leu Arg Gly Arg Gln Tyr Ser Asn Trp Gly Gln Gly
225                 230                 235                 240

Thr Gln Val Thr Val Ser Ser Gly Gly Gly Ser Gly Gly Gly Ser
                245                 250                 255

Glu Val Gln Leu Val Glu Ser Gly Gly Leu Val Gln Pro Gly Asn
            260                 265                 270

Ser Leu Arg Leu Ser Cys Ala Ala Ser Gly Phe Thr Phe Ser Ser Phe
        275                 280                 285

Gly Met Ser Trp Val Arg Gln Ala Pro Gly Lys Gly Leu Glu Trp Val
    290                 295                 300

Ser Ser Ile Ser Gly Ser Gly Ser Asp Thr Leu Tyr Ala Asp Ser Val
305                 310                 315                 320

Lys Gly Arg Phe Thr Ile Ser Arg Asp Asn Ala Lys Thr Thr Leu Tyr
                325                 330                 335

Leu Gln Met Asn Ser Leu Arg Pro Glu Asp Thr Ala Val Tyr Tyr Cys
            340                 345                 350

Thr Ile Gly Gly Ser Leu Ser Arg Ser Ser Gln Gly Thr Leu Val Thr
        355                 360                 365

Val Ser Ser
    370

<210> SEQ ID NO 82
<211> LENGTH: 253
<212> TYPE: PRT
```

<213> ORGANISM: Artificial Sequence
<220> FEATURE:
<223> OTHER INFORMATION: Nanobody sequence

<400> SEQUENCE: 82

Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser Asn Tyr
            20                  25                  30

Asp Met Gly Trp Phe Arg Gln Ala Pro Gly Lys Glu Arg Glu Phe Val
        35                  40                  45

Gly Ala Ser Trp Trp Ser Gly Gly Ala Pro Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Ala Asn Ser Leu Arg Pro Glu Asp Thr Ala Val Tyr Tyr Cys
                85                  90                  95

Ala Ala Lys Arg Leu Arg Ser Phe Ala Ser Gly Gly Ser Tyr Asp Tyr
            100                 105                 110

Trp Gly Gln Gly Thr Gln Val Thr Val Ser Ser Gly Gly Gly Gly Ser
        115                 120                 125

Gly Gly Gly Ser Glu Val Gln Leu Val Glu Ser Gly Gly Gly Leu Val
    130                 135                 140

Gln Ala Gly Gly Ser Leu Arg Leu Ser Cys Ala Ala Ser Gly Ser Ile
145                 150                 155                 160

Phe Ser Ile Ala Ala Met Gly Trp Tyr Arg Gln Ala Thr Gly Lys Gln
                165                 170                 175

Arg Glu Leu Val Ala Thr Ile Thr Asp Gly Gly Thr Thr Thr Tyr Ala
            180                 185                 190

Asp Ser Val Lys Gly Arg Val Thr Ile Ser Arg Asp Arg Ser Ala Asn
        195                 200                 205

Thr Val Tyr Leu Ala Met Asn Asn Leu Lys Pro Asp Asp Thr Ala Val
    210                 215                 220

Tyr Tyr Cys Tyr Ala Tyr Leu Arg Tyr Thr Ser Arg Val Pro Gly Asp
225                 230                 235                 240

Asn Tyr Trp Gly Gln Gly Thr Gln Val Thr Val Ser Ser
                245                 250

<210> SEQ ID NO 83
<211> LENGTH: 375
<212> TYPE: PRT
<213> ORGANISM: Artificial Sequence
<220> FEATURE:
<223> OTHER INFORMATION: Nanobody sequence

<400> SEQUENCE: 83

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Ala
            20                  25                  30

Ala Met Gly Trp Tyr Arg Gln Ala Thr Gly Lys Gln Arg Glu Leu Val
        35                  40                  45

Ala Thr Ile Thr Asp Gly Gly Thr Thr Thr Tyr Ala Asp Ser Val Lys
    50                  55                  60

Gly Arg Val Thr Ile Ser Arg Asp Arg Ser Ala Asn Thr Val Tyr Leu
65                  70                  75                  80

```
Ala Met Asn Asn Leu Lys Pro Asp Asp Thr Ala Val Tyr Tyr Cys Tyr
                85                  90                  95

Ala Tyr Leu Arg Tyr Thr Ser Arg Val Pro Gly Asp Asn Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Leu Val Gln Pro
130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
                165                 170                 175

Trp Val Ser Ser Ile Ser Gly Ser Gly Ser Asp Thr Leu Tyr Ala Asp
                180                 185                 190

Ser Val Lys Gly Arg Phe Thr Ile Ser Arg Asp Asn Ala Lys Thr Thr
                195                 200                 205

Leu Tyr Leu Gln Met Asn Ser Leu Arg Pro Glu Asp Thr Ala Val Tyr
        210                 215                 220

Tyr Cys Thr Ile Gly Gly Ser Leu Ser Arg Ser Ser Gln Gly Thr Leu
225                 230                 235                 240

Val Thr Val Ser Ser Gly Gly Gly Ser Gly Gly Gly Ser Glu Val
                245                 250                 255

Gln Leu Val Glu Ser Gly Gly Gly Leu Val Gln Ala Gly Gly Ser Leu
        260                 265                 270

Arg Leu Ser Cys Ala Ala Ser Gly Ser Ile Phe Ser Ile Ala Ala Met
        275                 280                 285

Gly Trp Tyr Arg Gln Ala Thr Gly Lys Gln Arg Glu Leu Val Ala Thr
        290                 295                 300

Ile Thr Asp Gly Gly Thr Thr Thr Tyr Ala Asp Ser Val Lys Gly Arg
305                 310                 315                 320

Val Thr Ile Ser Arg Asp Arg Ser Ala Asn Thr Val Tyr Leu Ala Met
                325                 330                 335

Asn Asn Leu Lys Pro Asp Asp Thr Ala Val Tyr Tyr Cys Tyr Ala Tyr
                340                 345                 350

Leu Arg Tyr Thr Ser Arg Val Pro Gly Asp Asn Tyr Trp Gly Gln Gly
            355                 360                 365

Thr Gln Val Thr Val Ser Ser
    370                 375

<210> SEQ ID NO 84
<211> LENGTH: 375
<212> TYPE: PRT
<213> ORGANISM: Artificial Sequence
<220> FEATURE:
<223> OTHER INFORMATION: Nanobody sequence

<400> SEQUENCE: 84

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Ala
                20                  25                  30

Ala Met Gly Trp Tyr Arg Gln Ala Thr Gly Lys Gln Arg Glu Leu Val
            35                  40                  45

Ala Thr Ile Thr Asp Gly Gly Thr Thr Thr Tyr Ala Asp Ser Val Lys
        50                  55                  60
```

```
Gly Arg Val Thr Ile Ser Arg Asp Arg Ser Ala Asn Thr Val Tyr Leu
 65                  70                  75                  80

Ala Met Asn Asn Leu Lys Pro Asp Asp Thr Ala Val Tyr Tyr Cys Tyr
                 85                  90                  95

Ala Tyr Leu Arg Tyr Thr Ser Arg Val Pro Gly Asp Asn Tyr Trp Gly
            100                 105                 110

Gln Gly Thr Gln Val Thr Val Ser Gly Gly Gly Ser Gly Gly
        115                 120                 125

Gly Ser Glu Val Gln Leu Val Glu Ser Gly Gly Leu Val Gln Ala
        130                 135                 140

Gly Gly Ser Leu Arg Leu Ser Cys Ala Ala Ser Gly Ser Ile Phe Ser
145                 150                 155                 160

Ile Ala Ala Met Gly Trp Tyr Arg Gln Ala Thr Gly Lys Gln Arg Glu
                165                 170                 175

Leu Val Ala Thr Ile Thr Asp Gly Gly Thr Thr Tyr Ala Asp Ser
            180                 185                 190

Val Lys Gly Arg Val Thr Ile Ser Arg Asp Arg Ser Ala Asn Thr Val
        195                 200                 205

Tyr Leu Ala Met Asn Asn Leu Lys Pro Asp Asp Thr Ala Val Tyr Tyr
    210                 215                 220

Cys Tyr Ala Tyr Leu Arg Tyr Thr Ser Arg Val Pro Gly Asp Asn Tyr
225                 230                 235                 240

Trp Gly Gln Gly Thr Gln Val Thr Val Ser Ser Gly Gly Gly Gly Ser
                245                 250                 255

Gly Gly Gly Ser Glu Val Gln Leu Val Glu Ser Gly Gly Leu Val
        260                 265                 270

Gln Pro Gly Asn Ser Leu Arg Leu Ser Cys Ala Ala Ser Gly Phe Thr
    275                 280                 285

Phe Ser Ser Phe Gly Met Ser Trp Val Arg Gln Ala Pro Gly Lys Gly
290                 295                 300

Leu Glu Trp Val Ser Ser Ile Ser Gly Ser Gly Ser Asp Thr Leu Tyr
305                 310                 315                 320

Ala Asp Ser Val Lys Gly Arg Phe Thr Ile Ser Arg Asp Asn Ala Lys
                325                 330                 335

Thr Thr Leu Tyr Leu Gln Met Asn Ser Leu Arg Pro Glu Asp Thr Ala
            340                 345                 350

Val Tyr Tyr Cys Thr Ile Gly Gly Ser Leu Ser Arg Ser Ser Gln Gly
        355                 360                 365

Thr Leu Val Thr Val Ser Ser
    370                 375

<210> SEQ ID NO 85
<211> LENGTH: 377
<212> TYPE: PRT
<213> ORGANISM: Artificial Sequence
<220> FEATURE:
<223> OTHER INFORMATION: Nanobody sequence

<400> SEQUENCE: 85

Glu Val Gln Leu Val Glu Ser Gly Gly Gly Leu Val Gln Ala Gly Asp
 1               5                  10                  15

Ser Leu Arg Leu Ser Cys Ala Ala Ser Gly Leu Thr Phe Ser Asn Tyr
                 20                  25                  30

Asp Met Gly Trp Phe Arg Gln Ala Pro Gly Lys Glu Arg Glu Phe Val
            35                  40                  45
```

```
Gly Ala Ser Trp Trp Ser Gly Gly Ala Pro Tyr Tyr Ser Asp Ser Val
    50                  55                  60
Lys Gly Arg Phe Thr Ile Ser Arg Asp Asn Ala Lys Asn Thr Val Tyr
 65                  70                  75                  80
Leu Gln Ala Asn Ser Leu Arg Pro Glu Asp Thr Ala Val Tyr Tyr Cys
                 85                  90                  95
Ala Ala Lys Arg Leu Arg Ser Phe Ala Ser Gly Gly Ser Tyr Asp Tyr
            100                 105                 110
Trp Gly Gln Gly Thr Gln Val Thr Val Ser Ser Gly Gly Gly Gly Ser
        115                 120                 125
Gly Gly Gly Ser Glu Val Gln Leu Val Glu Ser Gly Gly Gly Leu Val
    130                 135                 140
Gln Ala Gly Gly Ser Leu Arg Leu Ser Cys Ala Ala Ser Gly Ser Ile
145                 150                 155                 160
Phe Ser Ile Ala Ala Met Gly Trp Tyr Arg Gln Ala Thr Gly Lys Gln
                165                 170                 175
Arg Glu Leu Val Ala Thr Ile Thr Asp Gly Gly Thr Thr Thr Tyr Ala
            180                 185                 190
Asp Ser Val Lys Gly Arg Val Thr Ile Ser Arg Asp Arg Ser Ala Asn
        195                 200                 205
Thr Val Tyr Leu Ala Met Asn Asn Leu Lys Pro Asp Asp Thr Ala Val
    210                 215                 220
Tyr Tyr Cys Tyr Ala Tyr Leu Arg Tyr Thr Ser Arg Val Pro Gly Asp
225                 230                 235                 240
Asn Tyr Trp Gly Gln Gly Thr Gln Val Thr Val Ser Ser Gly Gly Gly
                245                 250                 255
Gly Ser Gly Gly Gly Ser Glu Val Gln Leu Val Glu Ser Gly Gly Gly
            260                 265                 270
Leu Val Gln Pro Gly Asn Ser Leu Arg Leu Ser Cys Ala Ala Ser Gly
        275                 280                 285
Phe Thr Phe Ser Ser Phe Gly Met Ser Trp Val Arg Gln Ala Pro Gly
    290                 295                 300
Lys Gly Leu Glu Trp Val Ser Ser Ile Ser Gly Ser Gly Ser Asp Thr
305                 310                 315                 320
Leu Tyr Ala Asp Ser Val Lys Gly Arg Phe Thr Ile Ser Arg Asp Asn
                325                 330                 335
Ala Lys Thr Thr Leu Tyr Leu Gln Met Asn Ser Leu Arg Pro Glu Asp
            340                 345                 350
Thr Ala Val Tyr Tyr Cys Thr Ile Gly Gly Ser Leu Ser Arg Ser Ser
        355                 360                 365
Gln Gly Thr Leu Val Thr Val Ser Ser
    370                 375

<210> SEQ ID NO 86
<211> LENGTH: 252
<212> TYPE: PRT
<213> ORGANISM: Artificial Sequence
<220> FEATURE:
<223> OTHER INFORMATION: Nanobody sequence

<400> SEQUENCE: 86

Glu Val Gln Leu Val Glu Ser Gly Gly Asn Leu Val Gln Ala Gly Gly
  1               5                  10                  15
Ser Leu Gly Leu Ser Cys Ala Ala Ser Val Ser Ile Ser Ile His
             20                  25                  30
```

Ile Met Gly Trp Tyr Arg Gln Ala Pro Gly Lys Gln Arg Asp Leu Val
            35                  40                  45

Ala Thr Ile Thr Ser Gly Gly Ser Thr Ala Tyr Ala Asp Ser Val Lys
 50                      55                  60

Gly Arg Phe Thr Val Ser Lys Asp Asn Ala Lys Asn Thr Val Tyr Leu
 65                  70                  75                  80

Gln Met Asp Ser Leu Lys Pro Glu Asp Thr Ser Val Tyr Tyr Cys Ala
                 85                  90                  95

Ala Glu Val Arg Asn Gly Val Phe Gly Lys Trp Asn His Tyr Trp Gly
            100                 105                 110

Gln Gly Thr Gln Val Thr Val Ser Ser Gly Gly Gly Ser Gly Gly
            115                 120                 125

Gly Ser Glu Val Gln Leu Val Glu Ser Gly Gly Gly Leu Val Gln Thr
130                     135                 140

Gly Gly Ser Leu Arg Leu Ser Cys Ala Ala Ser Gly Phe Thr Phe Ser
145                 150                 155                 160

Ser Tyr Ala Met Ser Trp Val Arg Gln Ala Pro Gly Lys Gly Leu Glu
                165                 170                 175

Trp Val Ser Gly Ile Lys Ser Ser Gly Asp Ser Thr Arg Tyr Ala Gly
                180                 185                 190

Ser Val Lys Gly Arg Phe Thr Ile Ser Arg Asp Asn Ala Lys Asn Met
            195                 200                 205

Leu Tyr Leu Gln Met Tyr Ser Leu Lys Pro Glu Asp Thr Ala Val Tyr
        210                 215                 220

Tyr Cys Ala Lys Ser Arg Val Ser Arg Thr Gly Leu Tyr Thr Tyr Asp
225                 230                 235                 240

Asn Arg Gly Gln Gly Thr Gln Val Thr Val Ser Ser
                245                 250

<210> SEQ ID NO 87
<211> LENGTH: 254
<212> TYPE: PRT
<213> ORGANISM: Artificial Sequence
<220> FEATURE:
<223> OTHER INFORMATION: Nanobody sequence

<400> SEQUENCE: 87

Glu Val Gln Leu Val Glu Ser Gly Gly Gly Leu Val Gln Ala Gly Glu
 1               5                  10                  15

Ser Leu Thr Leu Ser Cys Ala Ala Ser Gly Arg Thr Leu Ser Ala Tyr
             20                  25                  30

Ile Met Gly Trp Phe Arg Gln Ala Pro Gly Lys Glu Arg Glu Phe Val
            35                  40                  45

Ala Gly Ile Trp Ser Gly Gly Tyr Thr His Leu Ala Asp Ser Ala Lys
 50                      55                  60

Gly Arg Phe Ser Ile Ser Arg Asp Asn Ala Lys Asn Thr Val Tyr Leu
 65                  70                  75                  80

Gln Met Asn Gly Leu Lys Pro Glu Asp Thr Ala Val Tyr Tyr Cys Ala
                 85                  90                  95

Ala Gly Leu Arg Gly Arg Gln Tyr Ser Asn Trp Gly Gln Gly Thr Gln
            100                 105                 110

Val Thr Val Ser Ser Gly Gly Gly Ser Gly Gly Gly Ser Glu Val
            115                 120                 125

Gln Leu Met Glu Ser Gly Gly Gly Leu Val Gln Ala Gly Gly Ser Leu
        130                 135                 140

Arg Leu Ser Cys Ala Ala Ser Gly Arg Thr Phe Asn Asn Tyr Ala Met
145                 150                 155                 160

Gly Trp Phe Arg Arg Ala Pro Gly Lys Glu Arg Glu Phe Val Ala Ala
            165                 170                 175

Ile Thr Arg Ser Gly Val Arg Ser Gly Val Ser Ala Ile Tyr Gly Asp
            180                 185                 190

Ser Val Lys Asp Arg Phe Thr Ile Ser Arg Asp Asn Ala Lys Asn Thr
            195                 200                 205

Leu Tyr Leu Gln Met Asn Ser Leu Lys Pro Glu Asp Thr Ala Val Tyr
            210                 215                 220

Thr Cys Ala Ala Ser Ala Ile Gly Ser Gly Ala Leu Arg Arg Phe Glu
225                 230                 235                 240

Tyr Asp Tyr Ser Gly Gln Gly Thr Gln Val Thr Val Ser Ser
                245                 250

<210> SEQ ID NO 88
<211> LENGTH: 376
<212> TYPE: PRT
<213> ORGANISM: Artificial Sequence
<220> FEATURE:
<223> OTHER INFORMATION: Nanobody sequence

<400> SEQUENCE: 88

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Ala
            20                  25                  30

Ala Met Gly Trp Tyr Arg Gln Ala Thr Gly Lys Gln Arg Glu Leu Val
        35                  40                  45

Ala Thr Ile Thr Asp Gly Gly Thr Thr Thr Tyr Ala Asp Ser Val Lys
    50                  55                  60

Gly Arg Val Thr Ile Ser Arg Asp Arg Ser Ala Asn Thr Val Tyr Leu
65                  70                  75                  80

Ala Met Asn Asn Leu Lys Pro Asp Asp Thr Ala Val Tyr Tyr Cys Tyr
                85                  90                  95

Ala Tyr Leu Arg Tyr Thr Ser Arg Val Pro Gly Asp Asn Tyr Trp Gly
            100                 105                 110

Gln Gly Thr Gln Val Thr Val Ser Ser Gly Gly Gly Ser Gly Gly
            115                 120                 125

Gly Ser Glu Val Gln Leu Val Glu Ser Gly Gly Gly Leu Val Gln Pro
130                 135                 140

Gly Asn Ser Leu Arg Leu Ser Cys Ala Ala Ser Gly Phe Thr Phe Ser
145                 150                 155                 160

Ser Phe Gly Met Ser Trp Val Arg Gln Ala Pro Gly Lys Gly Leu Glu
            165                 170                 175

Trp Val Ser Ser Ile Ser Gly Ser Gly Ser Asp Thr Leu Tyr Ala Asp
            180                 185                 190

Ser Val Lys Gly Arg Phe Thr Ile Ser Arg Asp Asn Ala Lys Thr Thr
            195                 200                 205

Leu Tyr Leu Gln Met Asn Ser Leu Arg Pro Glu Asp Thr Ala Val Tyr
            210                 215                 220

Tyr Cys Thr Ile Gly Gly Ser Leu Ser Arg Ser Ser Gln Gly Thr Leu
225                 230                 235                 240

Val Thr Val Ser Ser Gly Gly Gly Gly Ser Gly Gly Gly Ser Glu Val
                245                 250                 255

```
Gln Leu Val Glu Ser Gly Gly Gly Leu Val Gln Thr Gly Gly Ser Leu
                260                 265                 270

Arg Leu Ser Cys Ala Ala Ser Gly Phe Thr Phe Ser Ser Tyr Ala Met
            275                 280                 285

Ser Trp Val Arg Gln Ala Pro Gly Lys Gly Leu Glu Trp Val Ser Gly
        290                 295                 300

Ile Lys Ser Ser Gly Asp Ser Thr Arg Tyr Ala Gly Ser Val Lys Gly
305                 310                 315                 320

Arg Phe Thr Ile Ser Arg Asp Asn Ala Lys Asn Met Leu Tyr Leu Gln
                325                 330                 335

Met Tyr Ser Leu Lys Pro Glu Asp Thr Ala Val Tyr Tyr Cys Ala Lys
            340                 345                 350

Ser Arg Val Ser Arg Thr Gly Leu Tyr Thr Tyr Asp Asn Arg Gly Gln
        355                 360                 365

Gly Thr Gln Val Thr Val Ser Ser
    370                 375

<210> SEQ ID NO 89
<211> LENGTH: 384
<212> TYPE: PRT
<213> ORGANISM: Artificial Sequence
<220> FEATURE:
<223> OTHER INFORMATION: Nanobody sequence

<400> SEQUENCE: 89

Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser Asn Tyr
            20                  25                  30

Asp Met Gly Trp Phe Arg Gln Ala Pro Gly Lys Glu Arg Glu Phe Val
        35                  40                  45

Gly Ala Ser Trp Trp Ser Gly Ala Pro Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Ala Asn Ser Leu Arg Pro Glu Asp Thr Ala Val Tyr Tyr Cys
                85                  90                  95

Ala Ala Lys Arg Leu Arg Ser Phe Ala Ser Gly Gly Ser Tyr Asp Tyr
            100                 105                 110

Trp Gly Gln Gly Thr Gln Val Thr Val Ser Ser Gly Gly Gly Gly Ser
        115                 120                 125

Gly Gly Gly Ser Glu Val Gln Leu Met Glu Ser Gly Gly Gly Leu Val
130                 135                 140

Gln Ala Gly Gly Ser Leu Arg Leu Ser Cys Ala Ala Ser Gly Arg Thr
145                 150                 155                 160

Phe Asn Asn Tyr Ala Met Gly Trp Phe Arg Arg Ala Pro Gly Lys Glu
                165                 170                 175

Arg Glu Phe Val Ala Ala Ile Thr Arg Ser Gly Val Arg Ser Gly Val
            180                 185                 190

Ser Ala Ile Tyr Gly Asp Ser Val Lys Asp Arg Phe Thr Ile Ser Arg
        195                 200                 205

Asp Asn Ala Lys Asn Thr Leu Tyr Leu Gln Met Asn Ser Leu Lys Pro
210                 215                 220

Glu Asp Thr Ala Val Tyr Thr Cys Ala Ala Ser Ala Ile Gly Ser Gly
225                 230                 235                 240
```

```
Ala Leu Arg Arg Phe Glu Tyr Asp Tyr Ser Gly Gln Gly Thr Gln Val
                    245                 250                 255

Thr Val Ser Ser Gly Gly Gly Ser Gly Gly Gly Ser Glu Val Gln
            260                 265                 270

Leu Val Glu Ser Gly Gly Gly Leu Val Gln Pro Gly Asn Ser Leu Arg
            275                 280                 285

Leu Ser Cys Ala Ala Ser Gly Phe Thr Phe Ser Ser Phe Gly Met Ser
            290                 295                 300

Trp Val Arg Gln Ala Pro Gly Lys Gly Leu Glu Trp Val Ser Ser Ile
305                 310                 315                 320

Ser Gly Ser Gly Ser Asp Thr Leu Tyr Ala Asp Ser Val Lys Gly Arg
                325                 330                 335

Phe Thr Ile Ser Arg Asp Asn Ala Lys Thr Thr Leu Tyr Leu Gln Met
                340                 345                 350

Asn Ser Leu Arg Pro Glu Asp Thr Ala Val Tyr Tyr Cys Thr Ile Gly
                355                 360                 365

Gly Ser Leu Ser Arg Ser Ser Gln Gly Thr Leu Val Thr Val Ser Ser
                370                 375                 380

<210> SEQ ID NO 90
<211> LENGTH: 362
<212> TYPE: PRT
<213> ORGANISM: Macaca fascicularis

<400> SEQUENCE: 90

Met Asp Leu His Val Phe Asp Tyr Ser Glu Pro Gly Asn Phe Ser Asp
1               5                   10                  15

Ile Ser Trp Pro Cys Asn Ser Ser Asp Cys Ile Val Val Asp Thr Val
            20                  25                  30

Met Cys Pro Asn Met Pro Asn Lys Ser Val Leu Leu Tyr Thr Leu Ala
            35                  40                  45

Phe Ile Tyr Ile Phe Ile Phe Val Ile Gly Met Ile Ala Asn Ser Val
        50                  55                  60

Val Val Trp Val Asn Ile Gln Ala Lys Thr Thr Gly Tyr Asp Thr His
65              70                  75                  80

Cys Tyr Ile Leu Asn Leu Ala Ile Ala Asp Leu Trp Val Val Leu Thr
                85                  90                  95

Ile Pro Val Trp Val Val Ser Leu Val Gln His Asn Gln Trp Pro Met
            100                 105                 110

Gly Glu Leu Thr Cys Lys Val Thr His Leu Ile Phe Ser Ile Asn Leu
            115                 120                 125

Phe Gly Ser Ile Phe Phe Leu Thr Cys Met Ser Val Asp Arg Tyr Leu
        130                 135                 140

Ser Ile Thr Tyr Phe Thr Asn Thr Ser Ser Arg Lys Lys Met Val
145                 150                 155                 160

Arg Arg Val Val Cys Val Leu Val Trp Leu Leu Ala Phe Cys Val Ser
                165                 170                 175

Leu Pro Asp Thr Tyr Tyr Leu Lys Thr Val Thr Ser Ala Ser Asn Asn
            180                 185                 190

Glu Thr Tyr Cys Arg Ser Phe Tyr Pro Glu His Ser Ile Lys Glu Trp
            195                 200                 205

Leu Ile Gly Met Glu Leu Val Ser Val Leu Gly Phe Ala Val Pro
        210                 215                 220

Phe Ser Val Ile Ala Val Phe Tyr Phe Leu Leu Ala Arg Ala Ile Ser
225                 230                 235                 240
```

```
Ala Ser Gly Asp Gln Glu Lys His Ser Ser Arg Lys Ile Ile Phe Ser
            245                 250                 255

Tyr Val Val Val Phe Leu Val Cys Trp Leu Pro Tyr His Val Ala Val
            260                 265                 270

Leu Leu Asp Ile Phe Ser Ile Leu His Tyr Ile Pro Phe Thr Cys Arg
            275                 280                 285

Leu Glu His Ala Leu Phe Thr Ala Leu His Val Thr Gln Cys Leu Ser
            290                 295                 300

Leu Val His Cys Cys Val Asn Pro Val Leu Tyr Ser Phe Ile Asn Arg
305                 310                 315                 320

Asn Tyr Arg Tyr Glu Leu Met Lys Ala Phe Ile Phe Lys Tyr Ser Ala
            325                 330                 335

Lys Thr Gly Leu Thr Lys Leu Ile Asp Ala Ser Arg Val Ser Glu Thr
            340                 345                 350

Glu Tyr Ser Ala Leu Glu Gln Ser Thr Lys
            355                 360

<210> SEQ ID NO 91
<211> LENGTH: 126
<212> TYPE: PRT
<213> ORGANISM: Artificial Sequence
<220> FEATURE:
<223> OTHER INFORMATION: Nanobody sequence

<400> SEQUENCE: 91

Glu Val Gln Leu Val Glu Ser Gly Gly Gly Leu Val Gln Thr Gly Ala
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Arg Val
            35                  40                  45

Ala Ala Ile Thr Pro Arg Ala Phe Thr Thr Tyr Tyr Ala Asp Ser Val
            50                  55                  60

Lys Gly Arg Phe Thr Ile Ser Arg Asp Asn Ala Lys Asn Thr Ala Tyr
65                  70                  75                  80

Leu Gln Met Val Ser Leu Lys Pro Glu Asp Thr Ala Val Tyr Tyr Cys
            85                  90                  95

Ala Ala Gln Leu Val Gly Ser Gly Ser Asn Leu Gly Arg Gln Glu Ser
            100                 105                 110

Tyr Ala Tyr Trp Gly Gln Gly Thr Gln Val Thr Val Ser Ser
            115                 120                 125

<210> SEQ ID NO 92
<211> LENGTH: 30
<212> TYPE: PRT
<213> ORGANISM: Artificial Sequence
<220> FEATURE:
<223> OTHER INFORMATION: Nanobody sequence

<400> SEQUENCE: 92

Glu Val Gln Leu Val Glu Ser Gly Gly Gly Leu Val Gln Thr Gly Ala
1               5                   10                  15

Ser Leu Arg Leu Ser Cys Ala Ala Ser Gly Arg Thr Phe Ser
            20                  25                  30

<210> SEQ ID NO 93
<211> LENGTH: 5
<212> TYPE: PRT
```

```
<213> ORGANISM: Artificial Sequence
<220> FEATURE:
<223> OTHER INFORMATION: Nanobody sequence

<400> SEQUENCE: 93

Asn Tyr Ala Met Gly
1               5

<210> SEQ ID NO 94
<211> LENGTH: 14
<212> TYPE: PRT
<213> ORGANISM: Artificial Sequence
<220> FEATURE:
<223> OTHER INFORMATION: Nanobody sequence

<400> SEQUENCE: 94

Trp Phe Arg Gln Ala Pro Gly Lys Glu Arg Glu Arg Val Ala
1               5                   10

<210> SEQ ID NO 95
<211> LENGTH: 17
<212> TYPE: PRT
<213> ORGANISM: Artificial Sequence
<220> FEATURE:
<223> OTHER INFORMATION: Nanobody sequence

<400> SEQUENCE: 95

Ala Ile Thr Pro Arg Ala Phe Thr Thr Tyr Tyr Ala Asp Ser Val Lys
1               5                   10                  15

Gly

<210> SEQ ID NO 96
<211> LENGTH: 32
<212> TYPE: PRT
<213> ORGANISM: Artificial Sequence
<220> FEATURE:
<223> OTHER INFORMATION: Nanobody sequence

<400> SEQUENCE: 96

Arg Phe Thr Ile Ser Arg Asp Asn Ala Lys Asn Thr Ala Tyr Leu Gln
1               5                   10                  15

Met Val Ser Leu Lys Pro Glu Asp Thr Ala Val Tyr Tyr Cys Ala Ala
                20                  25                  30

<210> SEQ ID NO 97
<211> LENGTH: 17
<212> TYPE: PRT
<213> ORGANISM: Artificial Sequence
<220> FEATURE:
<223> OTHER INFORMATION: Nanobody sequence

<400> SEQUENCE: 97

Gln Leu Val Gly Ser Gly Ser Asn Leu Gly Arg Gln Glu Ser Tyr Ala
1               5                   10                  15

Tyr

<210> SEQ ID NO 98
<211> LENGTH: 11
<212> TYPE: PRT
<213> ORGANISM: Artificial Sequence
<220> FEATURE:
<223> OTHER INFORMATION: Nanobody sequence

<400> SEQUENCE: 98

Trp Gly Gln Gly Thr Gln Val Thr Val Ser Ser
```

<210> SEQ ID NO 99
<211> LENGTH: 126
<212> TYPE: PRT
<213> ORGANISM: Artificial Sequence
<220> FEATURE:
<223> OTHER INFORMATION: Nanobody sequence

<400> SEQUENCE: 99

```
Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Arg Val
        35                  40                  45

Ala Ala Ile Ser Pro Ser Ala Val Thr Thr Tyr Tyr Ala Asp Ser Val
    50                  55                  60

Lys Gly Arg Phe Thr Ile Ser Arg Asp Asn Ala Lys Asn Thr Ala Tyr
65                  70                  75                  80

Leu Gln Met Val Ser Leu Lys Pro Glu Asp Thr Ala Val Tyr Tyr Cys
                85                  90                  95

Ala Ala Gln Leu Pro Gly Arg Gly Ser Asn Leu Gly Arg Gln Ala Ser
            100                 105                 110

Tyr Ala Tyr Trp Gly Gln Gly Thr Gln Val Thr Val Ser Ser
        115                 120                 125
```

<210> SEQ ID NO 100
<211> LENGTH: 126
<212> TYPE: PRT
<213> ORGANISM: Artificial Sequence
<220> FEATURE:
<223> OTHER INFORMATION: Nanobody sequence

<400> SEQUENCE: 100

```
Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Pro Val
        35                  40                  45

Ala Ala Ile Ser Pro Ala Ala Leu Thr Thr Tyr Tyr Ala Asp Phe Val
    50                  55                  60

Lys Gly Arg Phe Thr Ile Ser Arg Asp Asn Ala Lys Asn Thr Ala Tyr
65                  70                  75                  80

Leu Gln Met Val Ser Leu Lys Pro Glu Asp Thr Ala Val Tyr Tyr Cys
                85                  90                  95

Ala Ala Gln Leu Val Gly Ser Gly Ser Asn Leu Gly Arg Gln Gln Ser
            100                 105                 110

Tyr Ala Tyr Trp Gly Gln Gly Thr Gln Val Thr Val Ser Ser
        115                 120                 125
```

<210> SEQ ID NO 101
<211> LENGTH: 126
<212> TYPE: PRT
<213> ORGANISM: Artificial Sequence
<220> FEATURE:
<223> OTHER INFORMATION: Nanobody sequence

<400> SEQUENCE: 101

```
Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Pro Val
        35                  40                  45

Ala Ala Ile Ser Pro Ala Ala Leu Thr Thr Tyr Tyr Ala Asp Phe Val
        50                  55                  60

Lys Gly Arg Phe Thr Ile Ser Arg Asp Asn Ala Lys Asn Thr Ala Tyr
65                  70                  75                  80

Leu Gln Met Val Ser Leu Lys Pro Glu Asp Thr Ala Val Tyr Tyr Cys
                85                  90                  95

Ala Ala Gln Leu Val Gly Ser Gly Ser Asn Leu Gly Arg Gln Gln Ser
            100                 105                 110

Tyr Ala Tyr Trp Gly Gln Gly Thr Gln Val Thr Val Ser Ser
            115                 120                 125
```

```
<210> SEQ ID NO 102
<211> LENGTH: 126
<212> TYPE: PRT
<213> ORGANISM: Artificial Sequence
<220> FEATURE:
<223> OTHER INFORMATION: Nanobody sequence

<400> SEQUENCE: 102
```

```
Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Gly Asn Tyr
            20                  25                  30

Ala Met Gly Trp Phe Arg Gln Ala Pro Gly Lys Glu Arg Glu Pro Val
        35                  40                  45

Ala Ala Ile Ser Pro Ala Ala Val Thr Thr Tyr Tyr Ala Asp Phe Val
        50                  55                  60

Lys Gly Arg Phe Thr Ile Ser Arg Asp Asn Ala Lys Asn Thr Ala Tyr
65                  70                  75                  80

Leu Gln Met Val Ser Leu Lys Pro Glu Asp Thr Ala Val Tyr Tyr Cys
                85                  90                  95

Ala Ala Gln Leu Val Gly Ser Gly Ser Asn Leu Gly Arg Gln Gln Ser
            100                 105                 110

Tyr Ala Tyr Trp Gly Gln Gly Thr Gln Val Thr Val Ser Ser
            115                 120                 125
```

```
<210> SEQ ID NO 103
<211> LENGTH: 30
<212> TYPE: PRT
<213> ORGANISM: Artificial Sequence
<220> FEATURE:
<223> OTHER INFORMATION: Nanobody sequence

<400> SEQUENCE: 103
```

```
Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Ser
            20                  25                  30
```

```
<210> SEQ ID NO 104
<211> LENGTH: 30
<212> TYPE: PRT
```

-continued

```
<213> ORGANISM: Artificial Sequence
<220> FEATURE:
<223> OTHER INFORMATION: Nanobody sequence

<400> SEQUENCE: 104

Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Ser
            20                  25                  30

<210> SEQ ID NO 105
<211> LENGTH: 30
<212> TYPE: PRT
<213> ORGANISM: Artificial Sequence
<220> FEATURE:
<223> OTHER INFORMATION: Nanobody sequence

<400> SEQUENCE: 105

Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Ser
            20                  25                  30

<210> SEQ ID NO 106
<211> LENGTH: 30
<212> TYPE: PRT
<213> ORGANISM: Artificial Sequence
<220> FEATURE:
<223> OTHER INFORMATION: Nanobody sequence

<400> SEQUENCE: 106

Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Gly
            20                  25                  30

<210> SEQ ID NO 107
<211> LENGTH: 5
<212> TYPE: PRT
<213> ORGANISM: Artificial Sequence
<220> FEATURE:
<223> OTHER INFORMATION: Nanobody sequence

<400> SEQUENCE: 107

Asn Tyr Ala Met Gly
1               5

<210> SEQ ID NO 108
<211> LENGTH: 5
<212> TYPE: PRT
<213> ORGANISM: Artificial Sequence
<220> FEATURE:
<223> OTHER INFORMATION: Nanobody sequence

<400> SEQUENCE: 108

Asn Tyr Ala Met Gly
1               5

<210> SEQ ID NO 109
<211> LENGTH: 5
<212> TYPE: PRT
<213> ORGANISM: Artificial Sequence
<220> FEATURE:
<223> OTHER INFORMATION: Nanobody sequence

<400> SEQUENCE: 109
```

```
Asn Tyr Ala Met Gly
1               5

<210> SEQ ID NO 110
<211> LENGTH: 5
<212> TYPE: PRT
<213> ORGANISM: Artificial Sequence
<220> FEATURE:
<223> OTHER INFORMATION: Nanobody sequence

<400> SEQUENCE: 110

Asn Tyr Ala Met Gly
1               5

<210> SEQ ID NO 111
<211> LENGTH: 14
<212> TYPE: PRT
<213> ORGANISM: Artificial Sequence
<220> FEATURE:
<223> OTHER INFORMATION: Nanobody sequence

<400> SEQUENCE: 111

Trp Phe Arg Gln Ala Pro Gly Lys Glu Arg Glu Arg Val Ala
1               5                   10

<210> SEQ ID NO 112
<211> LENGTH: 14
<212> TYPE: PRT
<213> ORGANISM: Artificial Sequence
<220> FEATURE:
<223> OTHER INFORMATION: Nanobody sequence

<400> SEQUENCE: 112

Trp Phe Arg Gln Ala Pro Gly Lys Glu Arg Glu Pro Val Ala
1               5                   10

<210> SEQ ID NO 113
<211> LENGTH: 14
<212> TYPE: PRT
<213> ORGANISM: Artificial Sequence
<220> FEATURE:
<223> OTHER INFORMATION: Nanobody sequence

<400> SEQUENCE: 113

Trp Phe Arg Gln Ala Pro Gly Lys Glu Arg Glu Pro Val Ala
1               5                   10

<210> SEQ ID NO 114
<211> LENGTH: 14
<212> TYPE: PRT
<213> ORGANISM: Artificial Sequence
<220> FEATURE:
<223> OTHER INFORMATION: Nanobody sequence

<400> SEQUENCE: 114

Trp Phe Arg Gln Ala Pro Gly Lys Glu Arg Glu Pro Val Ala
1               5                   10

<210> SEQ ID NO 115
<211> LENGTH: 17
<212> TYPE: PRT
<213> ORGANISM: Artificial Sequence
<220> FEATURE:
<223> OTHER INFORMATION: Nanobody sequence

<400> SEQUENCE: 115
```

```
Ala Ile Ser Pro Ser Ala Val Thr Thr Tyr Tyr Ala Asp Ser Val Lys
1               5                   10                  15

Gly

<210> SEQ ID NO 116
<211> LENGTH: 17
<212> TYPE: PRT
<213> ORGANISM: Artificial Sequence
<220> FEATURE:
<223> OTHER INFORMATION: Nanobody sequence

<400> SEQUENCE: 116

Ala Ile Ser Pro Ala Ala Leu Thr Thr Tyr Tyr Ala Asp Phe Val Lys
1               5                   10                  15

Gly

<210> SEQ ID NO 117
<211> LENGTH: 17
<212> TYPE: PRT
<213> ORGANISM: Artificial Sequence
<220> FEATURE:
<223> OTHER INFORMATION: Nanobody sequence

<400> SEQUENCE: 117

Ala Ile Ser Pro Ala Ala Leu Thr Thr Tyr Tyr Ala Asp Phe Val Lys
1               5                   10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: Nanobody sequence

<400> SEQUENCE: 118

Ala Ile Ser Pro Ala Ala Val Thr Thr Tyr Tyr Ala Asp Phe Val Lys
1               5                   10                  15

Gly

<210> SEQ ID NO 119
<211> LENGTH: 32
<212> TYPE: PRT
<213> ORGANISM: Artificial Sequence
<220> FEATURE:
<223> OTHER INFORMATION: Nanobody sequence

<400> SEQUENCE: 119

Arg Phe Thr Ile Ser Arg Asp Asn Ala Lys Asn Thr Ala Tyr Leu Gln
1               5                   10                  15

Met Val Ser Leu Lys Pro Glu Asp Thr Ala Val Tyr Tyr Cys Ala Ala
                20                  25                  30

<210> SEQ ID NO 120
<211> LENGTH: 32
<212> TYPE: PRT
<213> ORGANISM: Artificial Sequence
<220> FEATURE:
<223> OTHER INFORMATION: Nanobody sequence

<400> SEQUENCE: 120

Arg Phe Thr Ile Ser Arg Asp Asn Ala Lys Asn Thr Ala Tyr Leu Gln
1               5                   10                  15
```

Met Val Ser Leu Lys Pro Glu Asp Thr Ala Val Tyr Tyr Cys Ala Ala
            20                  25                  30

<210> SEQ ID NO 121
<211> LENGTH: 32
<212> TYPE: PRT
<213> ORGANISM: Artificial Sequence
<220> FEATURE:
<223> OTHER INFORMATION: Nanobody sequence

<400> SEQUENCE: 121

Arg Phe Thr Ile Ser Arg Asp Asn Ala Lys Asn Thr Ala Tyr Leu Gln
1               5                   10                  15

Met Val Ser Leu Lys Pro Glu Asp Thr Ala Val Tyr Tyr Cys Ala Ala
            20                  25                  30

<210> SEQ ID NO 122
<211> LENGTH: 32
<212> TYPE: PRT
<213> ORGANISM: Artificial Sequence
<220> FEATURE:
<223> OTHER INFORMATION: Nanobody sequence

<400> SEQUENCE: 122

Arg Phe Thr Ile Ser Arg Asp Asn Ala Lys Asn Thr Ala Tyr Leu Gln
1               5                   10                  15

Met Val Ser Leu Lys Pro Glu Asp Thr Ala Val Tyr Tyr Cys Ala Ala
            20                  25                  30

<210> SEQ ID NO 123
<211> LENGTH: 17
<212> TYPE: PRT
<213> ORGANISM: Artificial Sequence
<220> FEATURE:
<223> OTHER INFORMATION: Nanobody sequence

<400> SEQUENCE: 123

Gln Leu Pro Gly Arg Gly Ser Asn Leu Gly Arg Gln Ala Ser Tyr Ala
1               5                   10                  15

Tyr

<210> SEQ ID NO 124
<211> LENGTH: 17
<212> TYPE: PRT
<213> ORGANISM: Artificial Sequence
<220> FEATURE:
<223> OTHER INFORMATION: Nanobody sequence

<400> SEQUENCE: 124

Gln Leu Val Gly Ser Gly Ser Asn Leu Gly Arg Gln Gln Ser Tyr Ala
1               5                   10                  15

Tyr

<210> SEQ ID NO 125
<211> LENGTH: 17
<212> TYPE: PRT
<213> ORGANISM: Artificial Sequence
<220> FEATURE:
<223> OTHER INFORMATION: Nanobody sequence

<400> SEQUENCE: 125

Gln Leu Val Gly Ser Gly Ser Asn Leu Gly Arg Gln Gln Ser Tyr Ala
1               5                   10                  15

Tyr

<210> SEQ ID NO 126
<211> LENGTH: 17
<212> TYPE: PRT
<213> ORGANISM: Artificial Sequence
<220> FEATURE:
<223> OTHER INFORMATION: Nanobody sequence

<400> SEQUENCE: 126

Gln Leu Val Gly Ser Gly Ser Asn Leu Gly Arg Gln Gln Ser Tyr Ala
1               5                   10                  15

Tyr

<210> SEQ ID NO 127
<211> LENGTH: 11
<212> TYPE: PRT
<213> ORGANISM: Artificial Sequence
<220> FEATURE:
<223> OTHER INFORMATION: Nanobody sequence

<400> SEQUENCE: 127

Trp Gly Gln Gly Thr Gln Val Thr Val Ser Ser
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Nanobody sequence

<400> SEQUENCE: 128

Trp Gly Gln Gly Thr Gln Val Thr Val Ser Ser
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Nanobody sequence

<400> SEQUENCE: 129

Trp Gly Gln Gly Thr Gln Val Thr Val Ser Ser
1               5                   10

<210> SEQ ID NO 130
<211> LENGTH: 11
<212> TYPE: PRT
<213> ORGANISM: Artificial Sequence
<220> FEATURE:
<223> OTHER INFORMATION: Nanobody sequence

<400> SEQUENCE: 130

Trp Gly Gln Gly Thr Gln Val Thr Val Ser Ser
1               5                   10

<210> SEQ ID NO 131
<211> LENGTH: 405
<212> TYPE: PRT
<213> ORGANISM: Artificial Sequence
<220> FEATURE:
<223> OTHER INFORMATION: Nanobody sequence

<400> SEQUENCE: 131

Glu Val Gln Leu Val Glu Ser Gly Gly Gly Leu Val Gln Ala Gly Asp

```
1               5                   10                  15
Ser Leu Arg Leu Ser Cys Ala Ala Ser Gly Leu Thr Phe Ser Asn Tyr
            20                  25                  30

Asp Met Gly Trp Phe Arg Gln Ala Pro Gly Lys Glu Arg Glu Phe Val
        35                  40                  45

Gly Ala Ser Trp Trp Ser Gly Ala Pro Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Ala Asn Ser Leu Arg Pro Glu Asp Thr Ala Val Tyr Tyr Cys
                85                  90                  95

Ala Ala Lys Arg Leu Arg Ser Phe Ala Ser Gly Gly Ser Tyr Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Ser Gly Gly Gly Gly Ser Gly
130                 135                 140

Gly Gly Ser Gly Gly Gly Ser Gly Gly Gly Ser Glu Val
145                 150                 155                 160

Gln Leu Val Glu Ser Gly Gly Leu Val Gln Ala Gly Asp Ser Leu
                165                 170                 175

Arg Leu Ser Cys Ala Ala Ser Gly Leu Thr Phe Ser Asn Tyr Asp Met
            180                 185                 190

Gly Trp Phe Arg Gln Ala Pro Gly Lys Glu Arg Glu Phe Val Gly Ala
            195                 200                 205

Ser Trp Trp Ser Gly Gly Ala Pro Tyr Tyr Ser Asp Ser Val Lys Gly
        210                 215                 220

Arg Phe Thr Ile Ser Arg Asp Asn Ala Lys Asn Thr Val Tyr Leu Gln
225                 230                 235                 240

Ala Asn Ser Leu Arg Pro Glu Asp Thr Ala Val Tyr Tyr Cys Ala Ala
                245                 250                 255

Lys Arg Leu Arg Ser Phe Ala Ser Gly Gly Ser Tyr Asp Tyr Trp Gly
            260                 265                 270

Gln Gly Thr Leu Val Thr Val Ser Ser Gly Gly Gly Gly Ser Gly Gly
            275                 280                 285

Gly Ser Glu Val Gln Leu Val Glu Ser Gly Gly Leu Val Gln Pro
290                 295                 300

Gly Asn Ser Leu Arg Leu Ser Cys Ala Ala Ser Gly Phe Thr Phe Ser
305                 310                 315                 320

Ser Phe Gly Met Ser Trp Val Arg Gln Ala Pro Gly Lys Gly Leu Glu
            325                 330                 335

Trp Val Ser Ser Ile Ser Gly Ser Gly Ser Asp Thr Leu Tyr Ala Asp
            340                 345                 350

Ser Val Lys Gly Arg Phe Thr Ile Ser Arg Asp Asn Ala Lys Thr Thr
            355                 360                 365

Leu Tyr Leu Gln Met Asn Ser Leu Arg Pro Glu Asp Thr Ala Val Tyr
        370                 375                 380

Tyr Cys Thr Ile Gly Gly Ser Leu Ser Arg Ser Ser Gln Gly Thr Leu
385                 390                 395                 400

Val Thr Val Ser Ser
            405

<210> SEQ ID NO 132
```

<211> LENGTH: 268
<212> TYPE: PRT
<213> ORGANISM: Artificial Sequence
<220> FEATURE:
<223> OTHER INFORMATION: Nanobody sequence

<400> SEQUENCE: 132

Glu Val Gln Leu Val Glu Ser Gly Gly Gly Leu Val Gln Ala Gly Asp
1               5                   10                  15
Ser Leu Arg Leu Ser Cys Ala Ala Ser Gly Leu Thr Phe Ser Asn Tyr
            20                  25                  30
Asp Met Gly Trp Phe Arg Gln Ala Pro Gly Lys Glu Arg Glu Phe Val
        35                  40                  45
Gly Ala Ser Trp Trp Ser Gly Ala Pro Tyr Tyr Ser Asp Ser Val
    50                  55                  60
Lys Gly Arg Phe Thr Ile Ser Arg Asp Asn Ala Lys Asn Thr Val Tyr
65                  70                  75                  80
Leu Gln Ala Asn Ser Leu Arg Pro Glu Asp Thr Ala Val Tyr Tyr Cys
                85                  90                  95
Ala Ala Lys Arg Leu Arg Ser Phe Ala Ser Gly Gly Ser Tyr Asp Tyr
            100                 105                 110
Trp Gly Gln Gly Thr Leu Val Thr Val Ser Ser Gly Gly Gly Gly Ser
        115                 120                 125
Gly Gly Gly Gly Ser Gly Gly Gly Ser Gly Gly Gly Gly Ser Gly
    130                 135                 140
Gly Gly Gly Ser Gly Gly Gly Gly Ser Glu Val Gln Leu Val Glu Ser
145                 150                 155                 160
Gly Gly Gly Leu Val Gln Pro Gly Asn Ser Leu Arg Leu Ser Cys Ala
                165                 170                 175
Ala Ser Gly Phe Thr Phe Ser Ser Phe Gly Met Ser Trp Val Arg Gln
            180                 185                 190
Ala Pro Gly Lys Gly Leu Glu Trp Val Ser Ser Ile Ser Gly Ser Gly
        195                 200                 205
Ser Asp Thr Leu Tyr Ala Asp Ser Val Lys Gly Arg Phe Thr Ile Ser
    210                 215                 220
Arg Asp Asn Ala Lys Thr Thr Leu Tyr Leu Gln Met Asn Ser Leu Arg
225                 230                 235                 240
Pro Glu Asp Thr Ala Val Tyr Tyr Cys Thr Ile Gly Gly Ser Leu Ser
                245                 250                 255
Arg Ser Ser Gln Gly Thr Leu Val Thr Val Ser Ser
            260                 265

<210> SEQ ID NO 133
<211> LENGTH: 431
<212> TYPE: PRT
<213> ORGANISM: Artificial Sequence
<220> FEATURE:
<223> OTHER INFORMATION: Nanobody sequence

<400> SEQUENCE: 133

Glu Val Gln Leu Val Glu Ser Gly Gly Gly Leu Val Gln Pro Gly Gly
1               5                   10                  15
Ser Leu Arg Ile Ser Cys Ala Ala Ser Gly Ser Ile Tyr Leu Ile Asn
            20                  25                  30
Tyr Met Gly Trp Tyr Arg Gln Ala Pro Gly Lys Gln Arg Glu Leu Val
        35                  40                  45
Ala Thr Leu Thr Ser Gly Gly Ser Thr Asn Tyr Ala Gly Ser Val Lys

```
                50                  55                  60
Gly Arg Phe Ala Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ile Gly Gly Thr Leu Tyr Asp Arg Arg Phe Glu Ser Trp Gly Gln
            100                 105                 110

Gly Thr Leu Val Thr Val Ser Gly Gly Gly Ser Gly Gly Gly
            115                 120                 125

Gly Ser Gly Gly Gly Ser Gly Gly Gly Ser Gly Gly Gly
            130                 135                 140

Ser Gly Gly Gly Ser Gly Gly Gly Ser Glu Val Gln Leu Val
145                 150                 155                 160

Glu Ser Gly Gly Gly Leu Val Gln Thr Gly Ala Ser Leu Arg Leu Ser
                165                 170                 175

Cys Ala Ala Ser Gly Arg Thr Phe Ser Asn Tyr Ala Met Gly Trp Phe
                180                 185                 190

Arg Gln Ala Pro Gly Lys Glu Arg Glu Arg Val Ala Ala Ile Thr Pro
                195                 200                 205

Arg Ala Phe Thr Thr Tyr Tyr Ala Asp Ser Val Lys Gly Arg Phe Thr
210                 215                 220

Ile Ser Arg Asp Asn Ala Lys Asn Thr Ala Tyr Leu Gln Met Val Ser
225                 230                 235                 240

Leu Lys Pro Glu Asp Thr Ala Val Tyr Tyr Cys Ala Ala Gln Leu Val
                245                 250                 255

Gly Ser Gly Ser Asn Leu Gly Arg Gln Glu Ser Tyr Ala Tyr Trp Gly
                260                 265                 270

Gln Gly Thr Leu Val Thr Val Ser Ser Gly Gly Gly Ser Gly Gly
            275                 280                 285

Gly Gly Ser Gly Gly Gly Ser Gly Gly Gly Ser Gly Gly Gly
            290                 295                 300

Gly Ser Gly Gly Gly Ser Gly Gly Gly Ser Glu Val Gln Leu
305                 310                 315                 320

Val Glu Ser Gly Gly Leu Val Gln Pro Gly Asn Ser Leu Arg Leu
                325                 330                 335

Ser Cys Ala Ala Ser Gly Phe Thr Phe Ser Ser Phe Gly Met Ser Trp
                340                 345                 350

Val Arg Gln Ala Pro Gly Lys Gly Leu Glu Trp Val Ser Ser Ile Ser
                355                 360                 365

Gly Ser Gly Ser Asp Thr Leu Tyr Ala Asp Ser Val Lys Gly Arg Phe
370                 375                 380

Thr Ile Ser Arg Asp Asn Ala Lys Thr Thr Leu Tyr Leu Gln Met Asn
385                 390                 395                 400

Ser Leu Arg Pro Glu Asp Thr Ala Val Tyr Tyr Cys Thr Ile Gly Gly
                405                 410                 415

Ser Leu Ser Arg Ser Ser Gln Gly Thr Leu Val Thr Val Ser Ser
                420                 425                 430

<210> SEQ ID NO 134
<211> LENGTH: 437
<212> TYPE: PRT
<213> ORGANISM: Artificial Sequence
<220> FEATURE:
<223> OTHER INFORMATION: Nanobody sequence
```

<400> SEQUENCE: 134

```
Glu Val Gln Leu Val Glu Ser Gly Gly Gly Leu Val Gln Thr Gly Ala
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Arg Val
        35                  40                  45

Ala Ala Ile Thr Pro Arg Ala Phe Thr Thr Tyr Tyr Ala Asp Ser Val
    50                  55                  60

Lys Gly Arg Phe Thr Ile Ser Arg Asp Asn Ala Lys Asn Thr Ala Tyr
65                  70                  75                  80

Leu Gln Met Val Ser Leu Lys Pro Glu Asp Thr Ala Val Tyr Tyr Cys
                85                  90                  95

Ala Ala Gln Leu Val Gly Ser Gly Ser Asn Leu Gly Arg Gln Glu Ser
            100                 105                 110

Tyr Ala Tyr Trp Gly Gln Gly Thr Leu Val Thr Val Ser Ser Gly Gly
        115                 120                 125

Gly Gly Ser Gly Gly Gly Gly Ser Gly Gly Gly Gly Ser Gly Gly Gly
    130                 135                 140

Gly Ser Gly Gly Gly Gly Ser Gly Gly Gly Gly Ser Gly Gly Gly Gly
145                 150                 155                 160

Ser Glu Val Gln Leu Val Glu Ser Gly Gly Gly Leu Val Gln Thr Gly
                165                 170                 175

Ala Ser Leu Arg Leu Ser Cys Ala Ala Ser Gly Arg Thr Phe Ser Asn
            180                 185                 190

Tyr Ala Met Gly Trp Phe Arg Gln Ala Pro Gly Lys Glu Arg Glu Arg
        195                 200                 205

Val Ala Ala Ile Thr Pro Arg Ala Phe Thr Thr Tyr Tyr Ala Asp Ser
    210                 215                 220

Val Lys Gly Arg Phe Thr Ile Ser Arg Asp Asn Ala Lys Asn Thr Ala
225                 230                 235                 240

Tyr Leu Gln Met Val Ser Leu Lys Pro Glu Asp Thr Ala Val Tyr Tyr
                245                 250                 255

Cys Ala Ala Gln Leu Val Gly Ser Gly Ser Asn Leu Gly Arg Gln Glu
            260                 265                 270

Ser Tyr Ala Tyr Trp Gly Gln Gly Thr Leu Val Thr Val Ser Ser Gly
        275                 280                 285

Gly Gly Gly Ser Gly Gly Gly Gly Ser Gly Gly Gly Gly Ser Gly Gly
    290                 295                 300

Gly Gly Ser Gly Gly Gly Gly Ser Gly Gly Gly Gly Ser Gly Gly Gly
305                 310                 315                 320

Gly Ser Glu Val Gln Leu Val Glu Ser Gly Gly Gly Leu Val Gln Pro
                325                 330                 335

Gly Asn Ser Leu Arg Leu Ser Cys Ala Ala Ser Gly Phe Thr Phe Ser
            340                 345                 350

Ser Phe Gly Met Ser Trp Val Arg Gln Ala Pro Gly Lys Gly Leu Glu
        355                 360                 365

Trp Val Ser Ser Ile Ser Gly Ser Gly Ser Asp Thr Leu Tyr Ala Asp
    370                 375                 380

Ser Val Lys Gly Arg Phe Thr Ile Ser Arg Asp Asn Ala Lys Thr Thr
385                 390                 395                 400

Leu Tyr Leu Gln Met Asn Ser Leu Arg Pro Glu Asp Thr Ala Val Tyr
                405                 410                 415
```

```
Tyr Cys Thr Ile Gly Gly Ser Leu Ser Arg Ser Ser Gln Gly Thr Leu
            420                 425                 430

Val Thr Val Ser Ser
            435

<210> SEQ ID NO 135
<211> LENGTH: 406
<212> TYPE: PRT
<213> ORGANISM: Artificial Sequence
<220> FEATURE:
<223> OTHER INFORMATION: Nanobody sequence

<400> SEQUENCE: 135

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Ile Phe Ser Ile Ala
            20                  25                  30

Ala Met Gly Trp Tyr Arg Gln Ala Thr Gly Lys Gln Arg Glu Leu Val
        35                  40                  45

Ala Thr Ile Thr Asp Gly Gly Thr Thr Tyr Ala Asp Ser Val Lys
    50                  55                  60

Gly Arg Val Thr Ile Ser Arg Asp Arg Ser Ala Asn Thr Val Tyr Leu
65                  70                  75                  80

Ala Met Asn Asn Leu Lys Pro Asp Asp Thr Ala Val Tyr Tyr Cys Tyr
                85                  90                  95

Ala Tyr Leu Arg Tyr Thr Ser Arg Val Pro Gly Asp Asn Tyr Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gly Gly Gly Ser Gly Gly Gly
    130                 135                 140

Gly Ser Gly Gly Gly Ser Gly Gly Gly Ser Glu Val Gln Leu
145                 150                 155                 160

Val Glu Ser Gly Gly Gly Leu Val Gln Thr Gly Ala Ser Leu Arg Leu
                165                 170                 175

Ser Cys Ala Ala Ser Gly Arg Thr Phe Ser Asn Tyr Ala Met Gly Trp
            180                 185                 190

Phe Arg Gln Ala Pro Gly Lys Glu Arg Glu Arg Val Ala Ala Ile Thr
        195                 200                 205

Pro Arg Ala Phe Thr Thr Tyr Tyr Ala Asp Ser Val Lys Gly Arg Phe
    210                 215                 220

Thr Ile Ser Arg Asp Asn Ala Lys Asn Thr Ala Tyr Leu Gln Met Val
225                 230                 235                 240

Ser Leu Lys Pro Glu Asp Thr Ala Val Tyr Tyr Cys Ala Ala Gln Leu
                245                 250                 255

Val Gly Ser Gly Ser Asn Leu Gly Arg Gln Glu Ser Tyr Ala Tyr Trp
            260                 265                 270

Gly Gln Gly Thr Leu Val Thr Val Ser Ser Gly Gly Gly Gly Ser Gly
        275                 280                 285

Gly Gly Ser Glu Val Gln Leu Val Glu Ser Gly Gly Gly Leu Val Gln
    290                 295                 300

Pro Gly Asn Ser Leu Arg Leu Ser Cys Ala Ala Ser Gly Phe Thr Phe
305                 310                 315                 320

Ser Ser Phe Gly Met Ser Trp Val Arg Gln Ala Pro Gly Lys Gly Leu
                325                 330                 335
```

```
Glu Trp Val Ser Ser Ile Ser Gly Ser Gly Ser Asp Thr Leu Tyr Ala
                340             345                 350

Asp Ser Val Lys Gly Arg Phe Thr Ile Ser Arg Asp Asn Ala Lys Thr
            355                 360                 365

Thr Leu Tyr Leu Gln Met Asn Ser Leu Arg Pro Glu Asp Thr Ala Val
        370                 375                 380

Tyr Tyr Cys Thr Ile Gly Gly Ser Leu Ser Arg Ser Gln Gly Thr
385             390                 395                 400

Leu Val Thr Val Ser Ser
                405

<210> SEQ ID NO 136
<211> LENGTH: 408
<212> TYPE: PRT
<213> ORGANISM: Artificial Sequence
<220> FEATURE:
<223> OTHER INFORMATION: Nanobody sequence

<400> SEQUENCE: 136

Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser Asn Tyr
            20                  25                  30

Asp Met Gly Trp Phe Arg Gln Ala Pro Gly Lys Glu Arg Glu Phe Val
        35                  40                  45

Gly Ala Ser Trp Trp Ser Gly Gly Ala Pro Tyr Tyr Ser Asp Ser Val
    50                  55                  60

Lys Gly Arg Phe Thr Ile Ser Arg Asp Asn Ala Lys Asn Thr Val Tyr
65                  70                  75                  80

Leu Gln Ala Asn Ser Leu Arg Pro Glu Asp Thr Ala Val Tyr Tyr Cys
                85                  90                  95

Ala Ala Lys Arg Leu Arg Ser Phe Ala Ser Gly Gly Ser Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Gly Gly Gly Gly Ser Gly
    130                 135                 140

Gly Gly Ser Gly Gly Gly Ser Gly Gly Gly Ser Glu Val
145                 150                 155                 160

Gln Leu Val Glu Ser Gly Gly Gly Leu Val Gln Thr Gly Ala Ser Leu
                165                 170                 175

Arg Leu Ser Cys Ala Ala Ser Gly Arg Thr Phe Ser Asn Tyr Ala Met
            180                 185                 190

Gly Trp Phe Arg Gln Ala Pro Gly Lys Glu Arg Glu Arg Val Ala Ala
        195                 200                 205

Ile Thr Pro Arg Ala Phe Thr Thr Tyr Ala Asp Ser Val Lys Gly
    210                 215                 220

Arg Phe Thr Ile Ser Arg Asp Asn Ala Lys Asn Thr Ala Tyr Leu Gln
225                 230                 235                 240

Met Val Ser Leu Lys Pro Glu Asp Thr Ala Val Tyr Tyr Cys Ala Ala
                245                 250                 255

Gln Leu Val Gly Ser Gly Ser Asn Leu Gly Arg Gln Glu Ser Tyr Ala
            260                 265                 270

Tyr Trp Gly Gln Gly Thr Leu Val Thr Val Ser Ser Gly Gly Gly Gly
        275                 280                 285
```

-continued

```
Ser Gly Gly Gly Ser Glu Val Gln Leu Val Glu Ser Gly Gly Gly Leu
        290                 295                 300

Val Gln Pro Gly Asn Ser Leu Arg Leu Ser Cys Ala Ala Ser Gly Phe
305                 310                 315                 320

Thr Phe Ser Ser Phe Gly Met Ser Trp Val Arg Gln Ala Pro Gly Lys
                325                 330                 335

Gly Leu Glu Trp Val Ser Ser Ile Ser Gly Ser Gly Ser Asp Thr Leu
            340                 345                 350

Tyr Ala Asp Ser Val Lys Gly Arg Phe Thr Ile Ser Arg Asp Asn Ala
        355                 360                 365

Lys Thr Thr Leu Tyr Leu Gln Met Asn Ser Leu Arg Pro Glu Asp Thr
370                 375                 380

Ala Val Tyr Tyr Cys Thr Ile Gly Gly Ser Leu Ser Arg Ser Ser Gln
385                 390                 395                 400

Gly Thr Leu Val Thr Val Ser Ser
                405

<210> SEQ ID NO 137
<211> LENGTH: 405
<212> TYPE: PRT
<213> ORGANISM: Artificial Sequence
<220> FEATURE:
<223> OTHER INFORMATION: Nanobody sequence

<400> SEQUENCE: 137

Glu Val Gln Leu Val Glu Ser Gly Gly Gly Leu Val Gln Pro Gly Gly
1               5                   10                  15

Ser Leu Arg Ile Ser Cys Ala Ala Ser Gly Ser Ile Tyr Leu Ile Asn
            20                  25                  30

Tyr Met Gly Trp Tyr Arg Gln Ala Pro Gly Lys Gln Arg Glu Leu Val
        35                  40                  45

Ala Thr Leu Thr Ser Gly Gly Ser Thr Asn Tyr Ala Gly Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ile Gly Gly Thr Leu Tyr Asp Arg Arg Arg Phe Glu Ser Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Ser Glu Val Gln Leu Val
145                 150                 155                 160

Glu Ser Gly Gly Gly Leu Val Gln Thr Gly Ala Ser Leu Arg Leu Ser
                165                 170                 175

Cys Ala Ala Ser Gly Arg Thr Phe Ser Asn Tyr Ala Met Gly Trp Phe
            180                 185                 190

Arg Gln Ala Pro Gly Lys Glu Arg Glu Arg Val Ala Ala Ile Thr Pro
        195                 200                 205

Arg Ala Phe Thr Thr Tyr Tyr Ala Asp Ser Val Lys Gly Arg Phe Thr
    210                 215                 220

Ile Ser Arg Asp Asn Ala Lys Asn Thr Ala Tyr Leu Gln Met Val Ser
225                 230                 235                 240
```

```
Leu Lys Pro Glu Asp Thr Ala Val Tyr Tyr Cys Ala Ala Gln Leu Val
                245                 250                 255

Gly Ser Gly Ser Asn Leu Gly Arg Gln Glu Ser Tyr Ala Tyr Trp Gly
            260                 265                 270

Gln Gly Thr Leu Val Thr Val Ser Ser Gly Gly Gly Ser Gly Gly
        275                 280                 285

Gly Ser Glu Val Gln Leu Val Glu Ser Gly Gly Leu Val Gln Pro
290                 295                 300

Gly Asn Ser Leu Arg Leu Ser Cys Ala Ala Ser Gly Phe Thr Phe Ser
305                 310                 315                 320

Ser Phe Gly Met Ser Trp Val Arg Gln Ala Pro Gly Lys Gly Leu Glu
                325                 330                 335

Trp Val Ser Ser Ile Ser Gly Ser Gly Ser Asp Thr Leu Tyr Ala Asp
                340                 345                 350

Ser Val Lys Gly Arg Phe Thr Ile Ser Arg Asp Asn Ala Lys Thr Thr
                355                 360                 365

Leu Tyr Leu Gln Met Asn Ser Leu Arg Pro Glu Asp Thr Ala Val Tyr
        370                 375                 380

Tyr Cys Thr Ile Gly Gly Ser Leu Ser Arg Ser Ser Gln Gly Thr Leu
385                 390                 395                 400

Val Thr Val Ser Ser
                405

<210> SEQ ID NO 138
<211> LENGTH: 408
<212> TYPE: PRT
<213> ORGANISM: Artificial Sequence
<220> FEATURE:
<223> OTHER INFORMATION: Nanobody sequence

<400> SEQUENCE: 138

Glu Val Gln Leu Val Glu Ser Gly Gly Gly Leu Val Gln Thr Gly Ala
1               5                   10                  15

Ser Leu Arg Leu Ser Cys Ala Ala Ser Gly Arg Thr Phe Ser Asn Tyr
                20                  25                  30

Ala Met Gly Trp Phe Arg Gln Ala Pro Gly Lys Glu Arg Glu Arg Val
            35                  40                  45

Ala Ala Ile Thr Pro Arg Ala Phe Thr Thr Tyr Tyr Ala Asp Ser Val
        50                  55                  60

Lys Gly Arg Phe Thr Ile Ser Arg Asp Asn Ala Lys Asn Thr Ala Tyr
65                  70                  75                  80

Leu Gln Met Val Ser Leu Lys Pro Glu Asp Thr Ala Val Tyr Tyr Cys
                85                  90                  95

Ala Ala Gln Leu Val Gly Ser Gly Ser Asn Leu Gly Arg Gln Glu Ser
                100                 105                 110

Tyr Ala Tyr Trp Gly Gln Gly Thr Leu Val Thr Val Ser Ser Gly Gly
            115                 120                 125

Gly Gly Ser Gly Gly Gly Gly Ser Gly Gly Gly Gly Ser Gly Gly Gly
        130                 135                 140

Gly Ser Gly Gly Gly Gly Ser Gly Gly Gly Gly Ser Gly Gly Gly Gly
145                 150                 155                 160

Ser Glu Val Gln Leu Val Glu Ser Gly Gly Gly Leu Val Gln Ala Gly
                165                 170                 175

Asp Ser Leu Arg Leu Ser Cys Ala Ala Ser Gly Leu Thr Phe Ser Asn
            180                 185                 190
```

Tyr Asp Met Gly Trp Phe Arg Gln Ala Pro Gly Lys Glu Arg Glu Phe
            195                 200                 205

Val Gly Ala Ser Trp Trp Ser Gly Gly Ala Pro Tyr Tyr Ser Asp Ser
210                 215                 220

Val Lys Gly Arg Phe Thr Ile Ser Arg Asp Asn Ala Lys Asn Thr Val
225                 230                 235                 240

Tyr Leu Gln Ala Asn Ser Leu Arg Pro Glu Asp Thr Ala Val Tyr Tyr
            245                 250                 255

Cys Ala Ala Lys Arg Leu Arg Ser Phe Ala Ser Gly Gly Ser Tyr Asp
            260                 265                 270

Tyr Trp Gly Gln Gly Thr Leu Val Thr Val Ser Gly Gly Gly Gly
            275                 280                 285

Ser Gly Gly Gly Ser Glu Val Gln Leu Val Glu Ser Gly Gly Gly Leu
290                 295                 300

Val Gln Pro Gly Asn Ser Leu Arg Leu Ser Cys Ala Ala Ser Gly Phe
305                 310                 315                 320

Thr Phe Ser Ser Phe Gly Met Ser Trp Val Arg Gln Ala Pro Gly Lys
            325                 330                 335

Gly Leu Glu Trp Val Ser Ser Ile Ser Gly Ser Gly Ser Asp Thr Leu
            340                 345                 350

Tyr Ala Asp Ser Val Lys Gly Arg Phe Thr Ile Ser Arg Asp Asn Ala
            355                 360                 365

Lys Thr Thr Leu Tyr Leu Gln Met Asn Ser Leu Arg Pro Glu Asp Thr
370                 375                 380

Ala Val Tyr Tyr Cys Thr Ile Gly Gly Ser Leu Ser Arg Ser Ser Gln
385                 390                 395                 400

Gly Thr Leu Val Thr Val Ser Ser
            405

<210> SEQ ID NO 139
<211> LENGTH: 405
<212> TYPE: PRT
<213> ORGANISM: Artificial Sequence
<220> FEATURE:
<223> OTHER INFORMATION: Nanobody sequence

<400> SEQUENCE: 139

Glu Val Gln Leu Val Glu Ser Gly Gly Gly Leu Val Gln Thr Gly Ala
1               5                   10                  15

Ser Leu Arg Leu Ser Cys Ala Ala Ser Gly Arg Thr Phe Ser Asn Tyr
            20                  25                  30

Ala Met Gly Trp Phe Arg Gln Ala Pro Gly Lys Glu Arg Glu Arg Val
            35                  40                  45

Ala Ala Ile Thr Pro Arg Ala Phe Thr Thr Tyr Tyr Ala Asp Ser Val
            50                  55                  60

Lys Gly Arg Phe Thr Ile Ser Arg Asp Asn Ala Lys Asn Thr Ala Tyr
65                  70                  75                  80

Leu Gln Met Val Ser Leu Lys Pro Glu Asp Thr Ala Val Tyr Tyr Cys
                85                  90                  95

Ala Ala Gln Leu Val Gly Ser Gly Asn Leu Gly Arg Gln Glu Ser
            100                 105                 110

Tyr Ala Tyr Trp Gly Gln Gly Thr Leu Val Thr Val Ser Ser Gly Gly
            115                 120                 125

Gly Gly Ser Gly Gly Gly Gly Ser Gly Gly Gly Gly Ser Gly Gly Gly
            130                 135                 140

Gly Ser Gly Gly Gly Ser Gly Gly Gly Ser Gly Gly Gly
145                 150                 155                 160

Ser Glu Val Gln Leu Val Glu Ser Gly Gly Gly Leu Val Gln Pro Gly
                165                 170                 175

Gly Ser Leu Arg Ile Ser Cys Ala Ala Ser Gly Ser Ile Tyr Leu Ile
            180                 185                 190

Asn Tyr Met Gly Trp Tyr Arg Gln Ala Pro Gly Lys Gln Arg Glu Leu
        195                 200                 205

Val Ala Thr Leu Thr Ser Gly Gly Ser Thr Asn Tyr Ala Gly Ser Val
    210                 215                 220

Lys Gly Arg Phe Ala Ile Ser Arg Asp Asn Ala Lys Asn Thr Val Tyr
225                 230                 235                 240

Leu Gln Met Asn Ser Leu Lys Pro Glu Asp Thr Ala Val Tyr Tyr Cys
                245                 250                 255

Asn Ile Gly Gly Thr Leu Tyr Asp Arg Arg Phe Glu Ser Trp Gly
            260                 265                 270

Gln Gly Thr Leu Val Thr Val Ser Ser Gly Gly Gly Ser Gly Gly
        275                 280                 285

Gly Ser Glu Val Gln Leu Val Glu Ser Gly Gly Gly Leu Val Gln Pro
290                 295                 300

Gly Asn Ser Leu Arg Leu Ser Cys Ala Ala Ser Gly Phe Thr Phe Ser
305                 310                 315                 320

Ser Phe Gly Met Ser Trp Val Arg Gln Ala Pro Gly Lys Gly Leu Glu
                325                 330                 335

Trp Val Ser Ser Ile Ser Gly Ser Gly Ser Asp Thr Leu Tyr Ala Asp
            340                 345                 350

Ser Val Lys Gly Arg Phe Thr Ile Ser Arg Asp Asn Ala Lys Thr Thr
        355                 360                 365

Leu Tyr Leu Gln Met Asn Ser Leu Arg Pro Glu Asp Thr Ala Val Tyr
    370                 375                 380

Tyr Cys Thr Ile Gly Gly Ser Leu Ser Arg Ser Ser Gln Gly Thr Leu
385                 390                 395                 400

Val Thr Val Ser Ser
                405

<210> SEQ ID NO 140
<211> LENGTH: 396
<212> TYPE: PRT
<213> ORGANISM: Artificial Sequence
<220> FEATURE:
<223> OTHER INFORMATION: Nanobody sequence

<400> SEQUENCE: 140

Glu Val Gln Leu Val Glu Ser Gly Gly Gly Leu Val Gln Pro Gly Gly
1               5                   10                  15

Ser Leu Arg Ile Ser Cys Ala Ala Ser Gly Ser Ile Tyr Leu Ile Asn
            20                  25                  30

Tyr Met Gly Trp Tyr Arg Gln Ala Pro Gly Lys Gln Arg Glu Leu Val
        35                  40                  45

Ala Thr Leu Thr Ser Gly Gly Ser Thr Asn Tyr Ala Gly Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

```
Ile Gly Gly Thr Leu Tyr Asp Arg Arg Phe Glu Ser Trp Gly Gln
            100                 105                 110

Gly Thr Leu Val Thr Val Ser Ser Gly Gly Gly Gly Ser Gly Gly Gly
            115                 120                 125

Gly Ser Gly Gly Gly Gly Ser Gly Gly Gly Gly Ser Gly Gly Gly Gly
        130                 135                 140

Ser Gly Gly Gly Gly Ser Gly Gly Gly Ser Glu Val Gln Leu Val
145                 150                 155                 160

Glu Ser Gly Gly Gly Leu Val Gln Ala Gly Glu Ser Leu Thr Leu Ser
                165                 170                 175

Cys Ala Ala Ser Gly Arg Thr Leu Ser Ala Tyr Ile Met Gly Trp Phe
                180                 185                 190

Arg Gln Ala Pro Gly Lys Glu Arg Glu Phe Val Ala Gly Ile Trp Ser
                195                 200                 205

Gly Gly Tyr Thr His Leu Ala Asp Ser Ala Lys Gly Arg Phe Ser Ile
                210                 215                 220

Ser Arg Asp Asn Ala Lys Asn Thr Val Tyr Leu Gln Met Asn Gly Leu
225                 230                 235                 240

Lys Pro Glu Asp Thr Ala Val Tyr Tyr Cys Ala Ala Gly Leu Arg Gly
                245                 250                 255

Arg Gln Tyr Ser Asn Trp Gly Gln Gly Thr Leu Val Thr Val Ser Ser
                260                 265                 270

Gly Gly Gly Gly Ser Gly Gly Gly Ser Glu Val Gln Leu Val Glu Ser
            275                 280                 285

Gly Gly Gly Leu Val Gln Pro Gly Asn Ser Leu Arg Leu Ser Cys Ala
            290                 295                 300

Ala Ser Gly Phe Thr Phe Ser Ser Phe Gly Met Ser Trp Val Arg Gln
305                 310                 315                 320

Ala Pro Gly Lys Gly Leu Glu Trp Val Ser Ser Ile Ser Gly Ser Gly
                325                 330                 335

Ser Asp Thr Leu Tyr Ala Asp Ser Val Lys Gly Arg Phe Thr Ile Ser
                340                 345                 350

Arg Asp Asn Ala Lys Thr Thr Leu Tyr Leu Gln Met Asn Ser Leu Arg
                355                 360                 365

Pro Glu Asp Thr Ala Val Tyr Tyr Cys Thr Ile Gly Gly Ser Leu Ser
                370                 375                 380

Arg Ser Ser Gln Gly Thr Leu Val Thr Val Ser Ser
385                 390                 395
```

BIOLOGICAL MATERIALS RELATED TO CXCR7

RELATED APPLICATIONS

This application is a continuation-in-part of international application PCT/EP2012/055499, filed Mar. 28, 2012, which was published under PCT Article 21(2) in English, and claims the benefit under 35 U.S.C. § 119(e) of U.S. provisional application Ser. No. 61/600,263 filed Feb. 17, 2012, U.S. provisional application Ser. No. 61/540,272 filed Sep. 28, 2011, and U.S. provisional application Ser. No. 61/468,250 filed Mar. 28, 2011;

FIELD OF THE INVENTION

The present invention relates to biological materials and methods related to CXCR7 including polypeptides, nucleic acids encoding such polypeptides; methods for preparing such polypeptides; host cells expressing or capable of expressing such polypeptides; compositions including pharmaceutical compositions that comprise such polypeptides, such as for prophylactic, therapeutic or diagnostic purposes.

BACKGROUND OF THE INVENTION

Although it is suggested in the art i) that the blockage of CXCR7 employed along with CXCR4 blockage may be useful for the treatment of SDF-1-dependent tumor progression and metastasis (R B Maksym et al., 2009, The role of stromal-derived factor-1-CXCR7 axis in development of cancer, European Journal of Pharmacology, 625 (1-3), pages 31-40) and ii) that some small molecular inhibitors, such as CCX733 or CCX266, siRNA and blocking antibodies (clones Mab 11G8, Mab 9C4 see e.g., US20070167443; clone 358426 (R&D Systems); Mab 8F11 (Biolegend)), may be useful for therapeutic interference with CXCR4-mediated activation of integrins (T N Hartmann et al., 2008, A crosstalk between intracellular CXCR7 and CXCR4 involved in rapid CXCL12-triggered integrin activation but not in chemokine-triggered motility of human T lymphocytes and CD34+ cells, Journal of Leukocyte Biology, 84, pages 11301140), the biology of CXCR7 is still poorly understood as the mechanism(s) of action through which CXCR7 acts is unclear because i) it may act as a kind of decoy or signalling receptor depending on cell type—R M Maksym et al., supra and since ii) the interplay between I-TAC and SDF-1 binding to CXCR7 is unclear.

The identification of selective therapeutically effective anti-CXCR7 agents is not only challenging because of its poorly understood biology (such as e.g., mechanism of action, e.g., of the potential agonists CCX733 or CCX266 versus antagonists, interplay with CXCR4, recognition of important epitopes, cross-reactivity of the compounds CCX733 or CCX266 and associated toxicity), it is also acknowledged in the art (see e.g., Nauynn-Schmied Archives Pharmacology 379: 385-388) that the generation of an anti-GPCR therapeutic agent such as an anti-CXCR7 agent is difficult since i) the native conformation of active CXCR7 in cancer cells is not exactly known, and ii) it is expected that CXCR7 shows low immunogenicity (due to a limited number of extracellular surface exposed amino acid residues that are in addition very conserved, e.g., mouse-human CXCR7 is 96% homologous).

Furthermore, compounds (CCX733, CCX754), which can selectively block binding of CXCL11 and CXCL12 to CXCR7, function like chemokine ligands with respect to homodimerization, i.e., they enhance CXCR7 homodimerization by 2.5 to 3.5 fold with significant increases (P<0.05) first detected at 10 and 100 nM (K E Luker et al., 2009, Imaging chemokine receptor dimerization with firefly luciferase complementation, FASEB journal, 23, pages 823-834).

CXCR7 has been attributed a potential role in tumour development because its expression provides cells with a growth and survival advantage. It was recently demonstrated that CXCR7 promotes the growth of breast and lung tumours and enhances lung metastases (Proc. Natl. Acad. Sci. USA 2007 104:15735-15740). Moreover, CXCR7 expression is correlated with tumour aggressiveness in prostate cancer (J. Biol. Chem. 2008 283:4283-4294). Administration of a small molecule antagonist to CXCR7 resulted in impediment of tumour growth in animal models, validating CXCR7 as target for development of novel cancer therapeutics (J. Exp. Med. 2006 203:2201-2213).

Head and neck cancers are among the most prevalent tumors in the world. Despite advances in the treatment of head and neck tumors, the survival of patients with these cancers has not markedly improved over the past several decades because of the inability to control and poor understanding of the regional and distant spread of this disease. Head and neck cancers consistently rank among the six most frequently diagnosed cancers in the world. Cancers of the oral cavity and pharynx alone account for some 300,000 new cases worldwide and little under 200,000 deaths annually. Over 90% of head and neck cancers are squamous cell carcinomas of the upper aerodigestive tract, including the oral cavity, pharynx, larynx, and paranasal sinuses. In addition, epithelial head and neck tumors can arise in the salivary and thyroid glands. Despite advances in our understanding and advances in the prevention and treatment of head and neck cancers, the survival of patients with head and neck cancers has not significantly improved over the past several decades.

SUMMARY OF THE INVENTION

WO2006/116319 and WO2008/048519 both note that the production of antibodies to G-protein coupled receptors (GPCRs) has been notoriously difficult. Indeed, the generation of a conventional anti-CXCR7 antibody has been described only in a limited number of cases, e.g., in WO2006/116319 for conventional antibodies 11G8, 6E10 and in Zabel et al. for conventional antibody 8F11 (Zabel et al., 2009, Elucidation of CXCR7 mediated signalling events and inhibition of CXCR4 mediated tumor cell transendothelial migration by CXCR7 ligands. Journal of Immunology 183 (5):3204-11). However, despite extensive research, it is unclear at present whether these or similar antibodies are suitable for a medical application.

Zheng et al. reports increased CXCR7 expression in hepatocellular carcinoma tissues. Down-regulation of CXCR7 expression leads to a reduction of tumour growth in a xenograft model of HCC. However, the authors used SMMC-7721 cells, which were previously transfected in vitro by CXCR7 shRNA (Zheng et al. 2010 "Chemokine receptor CXCR7 regulates the invasion, angiogenesis and tumour growth of human hepatocellular carcinoma cells" *J. Exp. Clin. Cancer Res.* 29:31).

Small molecules are known for side effects and unwanted effects. The small molecule CCX771 blocks CXCL12 binding (cf. Carbajal et al; 2010 "Migration of engrafted neural stem cells is mediated by CXCL12 signaling through CXCR4 in a viral model of multiple sclerosis Proc Natl Acad Sci USA. 107:11068-11073), on the other hand it is described as a synthetic CXCR7 ligand CCX771, which also potently stimulates β-arresting recruitment to CXCR7, with greater potency and efficacy than the endogenous chemokine ligands (Zabel et al. 2009 "Elucidation of CXCR7-Mediated Signaling Events and Inhibition of CXCR4-Mediated Tumor Cell Transendothelial Migration by CXCR7 Ligands" *J. Immun.* 183: 0000-0000). Similarly, the small compound VUF11403 (VU Amsterdam) behaves as an agonist in the β-arrestin assay.

Currently, there is no anti-CXCR7 drug on the market or in the clinic.

There is a need therefore for potent anti-CXCR7 agents that can explore and establish the medical potential of this target. Furthermore, there is a need for diagnostically, preventatively, and/or therapeutically suitable anti-CXCR7 agents, such as those provided herein.

CXCR7 is expressed on many human tumour cells but not on most healthy cells. In our tumour model systems we found that reduction or inhibition of CXCR7 by immunoglobulin single variable domains reduces or abolishes tumour formation in vivo.

Immunoglobulin sequences, such as antibodies and antigen binding fragments derived there from (e.g., immunoglobulin single variable domains) are used to specifically target their respective antigens in research and therapeutic applications. The generation of immunoglobulin single variable domains such as e.g., VHHs may involve the immunization of an experimental animal such as a Llama, construction of phage libraries from immune tissue, selection of phage displaying antigen binding immunoglobulin single variable domains and screening of said domains and engineered constructs thereof for the desired specificities (WO 94/04678). Alternatively, immunoglobulin single variable domains such as e.g., dAbs can be generated by selecting phage displaying antigen binding immunoglobulin single variable domains directly from naïve or synthetic libraries and subsequent screening of said domains and engineered constructs thereof for the desired specificities (Ward et al, Binding activities of a repertoire of single immunoglobulin variable domains secreted from *Escherichia coli*, Nature, 1989, Oct. 12; 341 (6242): 544-6); Holt et al., Trends Biotechnol., 2003, 21(11):484-490; as well as for example WO 06/030220, WO 06/003388 and other published patent applications of Domantis Ltd.).

Targeting serum albumin to extend the half-life of biological molecules such as e.g., immunoglobulin single variable domains has been described e.g. in WO2008/028977.

In one aspect, the present invention relates to polypeptides that comprise or essentially consist of i) a first building block consisting essentially of one or more immunoglobulin single variable domain(s), wherein said immunoglobulin single variable domain(s) is (are) directed against CXCR7 and in particular against human CXCR7; and ii) a second building block consisting essentially of one or more (preferably one) immunoglobulin single variable domain(s), wherein said immunoglobulin single variable domain(s) is (are) directed against serum albumin and in particular against human serum albumin (and even more preferably wherein said immunoglobulin single variable domain is Alb8 (as herein defined)). Furthermore, the invention also relates to nucleic acids encoding such polypeptides; to methods for preparing such polypeptides; to host cells expressing or capable of expressing such polypeptides; to compositions, and in particular to pharmaceutical compositions that comprise such polypeptides, nucleic acids and/or host cells; and to uses of such polypeptides, nucleic acids, host cells and/or compositions for prophylactic, therapeutic or diagnostic purposes. Other aspects, embodiments, advantages and applications of the invention will become clear from the further description herein.

DESCRIPTION OF THE INVENTION

Figure 1:
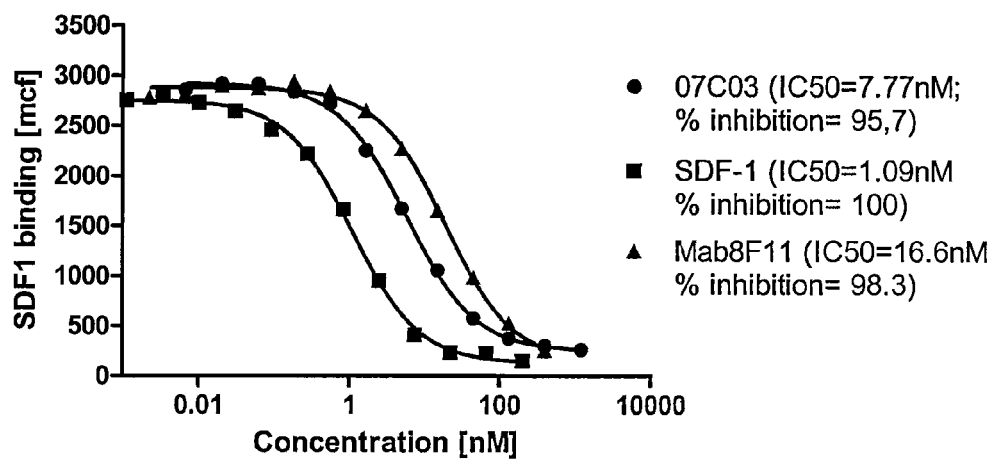
FIG. 1 shows an SDF-1 competition experiment using FACS.

Definitions a) Unless indicated or defined otherwise, all terms used have their usual meaning in the art, which will be clear to the skilled person. Reference is for example made to the standard handbooks mentioned in paragraph a) on page 46 of WO 08/020,079.

b) Unless indicated otherwise, the term "immunoglobulin single variable domain" (ISVD) is used as a general term to include but not limited to antigen-binding domains or fragments such as $V_{HH}$ domains or $V_H$ or $V_L$ domains, respectively. The terms antigen-binding molecules or antigen-binding protein are used interchangeably and include also the term Nanobodies. The immunoglobulin single variable domains further are light chain variable domain sequences (e.g., a $V_L$-sequence), or heavy chain variable domain sequences (e.g., a $V_H$-sequence); more specifically, they can be heavy chain variable domain sequences that are derived from a conventional four-chain antibody or heavy chain variable domain sequences that are derived from a heavy chain antibody. Accordingly, the immunoglobulin single variable domains can be domain antibodies, or immunoglobulin sequences that are suitable for use as domain antibodies, single domain antibodies, or immunoglobulin sequences that are suitable for use as single domain antibodies, "dAbs", or immunoglobulin sequences that are suitable for use as dAbs, or Nanobodies, including but not limited to $V_{HH}$ sequences. The invention includes immunoglobulin sequences of different origin, comprising mouse, rat, rabbit, donkey, human and camelid immunoglobulin sequences. The immunoglobulin single variable domain includes fully human, humanized, otherwise sequence optimized or chimeric immunoglobulin sequences. The immunoglobulin single variable domain and structure of an immunoglobulin single variable domain can be considered—without however being limited thereto—to be comprised of four framework regions or "FR's", which are referred to in the art and herein as "Framework region 1" or "FR1"; as "Framework region 2" or "FR2"; as "Framework region 3" or "FR3"; and as "Framework region 4" or "FR4", respectively; which framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. It is noted that the terms Nanobody or Nanobodies are registered trademarks of Ablynx N.V. and thus may also be referred to as Nanobody® and/or Nanobodies®).

c) Unless indicated otherwise, the terms "immunoglobulin sequence", "sequence", "nucleotide sequence" and "nucleic acid" are as described in paragraph b) on page 46 of WO 08/020,079. The term Nanobody is also as defined in WO 08/020,079, and as described therein generally refers to an immunoglobulin heavy chain variable domain that has the functional and/or structural characteristics of a $V_{HH}$ domain (e.g., a $V_H$ domain from the "heavy-chain only" antibodies that occur in Camelids), and as such may in particular be a (native) $V_{HH}$, a humanized $V_{HH}$ or a camelized $V_H$, such as a camelized human $V_H$.

d) Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta, Adv. Drug Deliv. Rev. 2006, 58 (5-6): 640-56; Levin and Weiss, Mol. Biosyst. 2006, 2(1): 49-57; Irving et al., J. Immunol. Methods, 2001, 248(1-2), 31-45; Schmitz et al., Placenta, 2000, 21 Suppl. A, S106-12, Gonzales et al., Tumour Biol., 2005, 26(1), 31-43, which describe techniques for protein engineering, such as affinity maturation and other techniques for improving the specificity and other desired properties of proteins such as immunoglobulins.

e) Amino acid residues will be indicated according to the standard three-letter or one-letter amino acid code. Reference is made to Table A-2 on page 48 of the International application WO 08/020,079 of Ablynx N.V. entitled "Immunoglobulin single variable domains directed against IL-6R and polypeptides comprising the same for the treatment of diseases and disorders associated with 11-6 mediated signalling".

f) For the purposes of comparing two or more nucleotide sequences, the percentage of "sequence identity" between a first nucleotide sequence and a second nucleotide sequence may be calculated or determined as described in paragraph e) on page 49 of WO 08/020,079 (incorporated herein by reference), such as by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position); or using a suitable computer algorithm or technique, again as described in paragraph e) on pages 49 of WO 08/020,079 (incorporated herein by reference).

g) For the purposes of comparing two or more immunoglobulin single variable domains or other amino acid sequences such e.g., the polypeptides of the invention etc., the percentage of "sequence identity" between a first amino acid sequence and a second amino acid sequence (also referred to herein as "amino acid identity") may be calculated or determined as described in paragraph f) on pages 49 and 50 of WO 08/020,079 (incorporated herein by reference), such as by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein; or using a suitable computer algorithm or technique, again as described in paragraph f) on pages 49 and 50 of WO 08/020,079 (incorporated herein by reference).

Also, in determining the degree of sequence identity between two immunoglobulin single variable domains, the skilled person may take into account so-called "conservative" amino acid substitutions, as described on page 50 of WO 08/020,079.

Any amino acid substitutions applied to the polypeptides described herein may also be based on the analysis of the frequencies of amino acid variations between homologous proteins of different species developed by Schulz et al., Principles of Protein Structure, Springer-Verlag, 1978, on the analyses of structure forming potentials developed by Chou and Fasman, Biochemistry 13: 211, 1974 and Adv. Enzymol., 47: 45-149, 1978, and on the analysis of hydrophobicity patterns in proteins developed by Eisenberg et al., Proc. Natl. Acad. Sci. USA 81: 140-144, 1984; Kyte & Doolittle; J. Molec. Biol. 157: 105-132, 1981, and Goldman et al., Ann. Rev. Biophys. Chem. 15: 321-353, 1986, all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al., Nature Structural Biology, Vol. 3, 9, 803 (1996); Spinelli et al., Natural Structural Biology (1996); 3, 752-757; and Decanniere et al., Structure, Vol. 7, 4, 361 (1999). Further information about some of the amino acid residues that in conventional $V_H$ domains form the $V_H/V_L$ interface and potential camelizing substitutions on these positions can be found in the prior art cited above.

h) Immunoglobulin single variable domains and nucleic acid sequences are said to be "exactly the same" if they have 100% sequence identity (as defined herein) over their entire length.

i) When comparing two immunoglobulin single variable domains, the term "amino acid difference" refers to an insertion, deletion or substitution of a single amino acid residue on a position of the first sequence, compared to the second sequence; it being understood that two immunoglobulin single variable domains can contain one, two or more such amino acid differences.

j) When a nucleotide sequence or amino acid sequence is said to "comprise" another nucleotide sequence or amino acid sequence, respectively, or to "essentially consist of" another nucleotide sequence or amino acid sequence, this has the meaning given in paragraph i) on pages 51-52 of WO 08/020,079.

k) The term "in essentially isolated form" has the meaning given to it in paragraph j) on pages 52 and 53 of WO 08/020,079.

l) The terms "domain" and "binding domain" have the meanings given to it in paragraph k) on page 53 of WO 08/020,079.

m) The terms "antigenic determinant" and "epitope", which may also be used interchangeably herein, have the meanings given to it in paragraph l) on page 53 of WO 08/020,079.

n) As further described in paragraph m) on page 53 of WO 08/020,079, an amino acid sequence (such as an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

o) The term "specificity" has the meaning given to it in paragraph n) on pages 53-56 of WO 08/020,079; and as mentioned therein refers to the number of different types of antigens or antigenic determinants to which a particular antigen-binding molecule or antigen-binding protein (such as a polypeptide of the invention) molecule can bind. The specificity of an antigen-binding protein can be determined based on affinity and/or avidity, as described on pages 53-56 of WO 08/020,079 (incorporated herein by reference), which also describes some preferred techniques for measuring binding between an antigen-binding molecule (such as a polypeptide of the invention) and the pertinent antigen. Typically, antigen-binding proteins (such as the immunoglobulin single variable domains, and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ $M^{-1}$) liters/mol is generally considered to indicate non-specific binding. Preferably, a monovalent immunoglobulin single variable domain of the invention will bind to the desired antigen with an affinity less than 500 nM, preferably less than 200 nM, more preferably less than 10 nM, such as less than 500 µM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020,079, the dissociation constant may be the actual or apparent dissociation constant. Methods for determining the dissociation constant will be clear to the skilled person, and for example include the techniques mentioned on pages 53-56 of WO 08/020,079.

p) The half-life of an amino acid sequence, compound or polypeptide of the invention can generally be defined as described in paragraph o) on page 57 of WO 08/020,079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 08/020,079. As also mentioned in paragraph o) on page 57 of WO 08/020,079, the half-life can be expressed using parameters such as the t1/2-alpha, t1/2-beta and the area under the curve (AUC). Reference is for example made to the Experimental Part below, as well as to the standard handbooks, such as Kenneth, A et al: Chemical Stability of Pharmaceuticals: A Handbook for Pharmacists and Peters et al, Pharmacokinetic analysis: A Practical Approach (1996). Reference is also made to "Pharmacokinetics", M Gibaldi & D Perron, published by Marcel Dekker, 2nd Rev. edition (1982). The terms "increase in half-life" or "increased half-life" as also as defined in paragraph o) on page 57 of WO 08/020,079 and in particular refer to an increase in the t1/2-beta, either with or without an increase in the t1/2-alpha and/or the AUC or both.

q) In respect of a target or antigen, the term "interaction site" on the target or antigen means a site, epitope, antigenic determinant, part, domain or stretch of amino acid residues on the target or antigen that is a site for binding to a ligand, receptor or other binding partner, a catalytic site, a cleavage site, a site for allosteric interaction, a site involved in multimerization (such as homomerization or heterodimerization) of the target or antigen; or any other site, epitope, antigenic determinant, part, domain or stretch of amino acid residues on the target or antigen that is involved in a biological action or mechanism of the target or antigen. More generally, an "interaction site" can be any site, epitope, antigenic determinant, part, domain or stretch of amino acid residues on the target or antigen to which an amino acid sequence or polypeptide of the invention can bind such that the target or antigen (and/or any pathway, interaction, signalling, biological mechanism or biological effect in which the target or antigen is involved) is modulated (as defined herein).

r) An immunoglobulin single variable domain or polypeptide is said to be "specific for" a first target or antigen compared to a second target or antigen when is binds to the first antigen with an affinity/avidity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10.000 times or more better than the affinity with which said amino acid sequence or polypeptide binds to the second target or polypeptide. For example, the first antigen may bind to the target or antigen with a $K_D$ value that is at least 10 times less, such as at least 100 times less, and preferably at least 1000 times less, such as 10.000 times less or even less than that, than the $K_D$ with which said amino acid sequence or polypeptide binds to the second target or polypeptide. Preferably, when an immunoglobulin single variable domain or polypeptide is "specific for" a first target or antigen compared to a second target or antigen, it is directed against (as defined herein) said first target or antigen, but not directed against said second target or antigen.

s) The terms "cross-block", "cross-blocked" and "cross-blocking" are used interchangeably herein to mean the ability of an immunoglobulin single variable domain or polypeptide to interfere with the binding directly or indirectly through allosteric modulation of other immunoglobulin single variable domains or polypeptides of the invention to a given target. The extent to which an immunoglobulin single variable domain or polypeptide of the invention is able to interfere with the binding of another to target, and therefore whether it can be said to cross-block according to the invention, can be determined using competition binding assays. One particularly suitable quantitative cross-blocking assay uses a FACS- or an ELISA-based approach to measure competition between the labelled (e.g., His tagged or radioactive labelled) immunoglobulin single variable domain or polypeptide according to the invention and the other binding agent in terms of their binding to the target. The experimental part generally describes suitable FACS-, ELISA- or radioligand-displacement-based assays for determining whether a binding molecule cross-blocks or is capable of cross-blocking an immunoglobulin single variable domain or polypeptide according to the invention. It will be appreciated that the assay can be used with any of the immunoglobulin single variable domains or other binding agents described herein. Thus, in general, a cross-blocking amino acid sequence or other binding agent according to the invention is for example one which will bind to the target in the above cross-blocking assay such that, during the assay and in the presence of a second amino acid sequence or other binding agent of the invention, the recorded displacement of the immunoglobulin single variable domain or polypeptide according to the invention is between 60% and 100% (e.g., in ELISA/radioligand based competition assay) or between 80% to 100% (e.g., in FACS based competition assay) of the maximum theoretical displacement (e.g., displacement by cold (e.g., unlabeled) immunoglobulin single variable domain or polypeptide that needs to be cross-blocked) by the to be tested potentially cross-blocking agent that is present in an amount of 0.01 mM or less (cross-blocking agent may be another conventional monoclonal antibody such as IgG, classic monovalent antibody fragments (Fab, scFv)) and engineered variants (diabodies, triabodies, minibodies, VHHs, dAbs, VHs, VLs).

t) An amino acid sequence such as e.g. an immunoglobulin single variable domain or polypeptide according to the invention is said to be "cross-reactive" for two different antigens or antigenic determinants (such as serum albumin from two different species of mammal, such as human serum albumin and cyno serum albumin) if it is specific for (as defined herein) both these different antigens or antigenic determinants.

u) As further described in paragraph q) on pages 58 and 59 of WO 08/020,079 (incorporated herein by reference), the amino acid residues of an immunoglobulin single variable domain are numbered according to the general numbering for $V_H$ domains given by Kabat et al. ("Sequence of proteins of immunological interest", US Public Health Services, NIH Bethesda, Md., Publication No. 91), as applied to $V_{HH}$ domains from Camelids in the article of Riechmann and Muyldermans, J. Immunol. Methods 2000 Jun. 23; 240 (1-2): 185-195 (see for example FIG. 2 of this publication), and accordingly FR1 of an immunoglobulin single variable domain comprises the amino acid residues at positions 1-30, CDR1 of an immunoglobulin single variable domain comprises the amino acid residues at positions 31-35, FR2 of an immunoglobulin single variable domain comprises the amino acids at positions 36-49, CDR2 of an immunoglobulin single variable domain comprises the amino acid residues at positions 50-65, FR3 of an immunoglobulin single variable domain comprises the amino acid residues at positions 66-94, CDR3 of an immunoglobulin single variable domain comprises the amino acid residues at positions 95-102, and FR4 of an immunoglobulin single variable domain comprises the amino acid residues at positions 103-113.

v) The Figures, Sequence Listing and the Experimental Part/Examples are only given to further illustrate the invention and should not be interpreted or construed as limiting the scope of the invention and/or of the appended claims in any way, unless explicitly indicated otherwise herein.

1. Polypeptides of the Invention and Uses Thereof 1.1. Anti-CXCR7 Building Blocks The polypeptides of the present invention can generally be used to modulate, and in particular inhibit and/or prevent, binding of CXCR7 and in particular human CXCR7 (SEQ ID NO: 1) to CXCL12 (and/or CXCL11) and in particular human CXCL12 (NM_000609) and/or in particular human CXCL11 (U66096), and thus to modulate, and in particular inhibit or prevent, the signalling that is mediated by CXCR7 and in particular human CXCR7 (SEQ ID NO: 1) and/or CXCL12 (and/or CXCL11) and in particular human CXCL12 (NM_000609) and/or in particular human CXCL11 (U66096), to modulate the biological pathways in which CXCR7 and in particular human CXCR7 (SEQ ID NO: 1) and/or CXCL12 (and/or CXCL11) and in particular human CXCL12 (NM_000609) and/or in particular human CXCL11 (U66096) are involved, and/or to modulate the biological mechanisms, responses and effects associated with such signalling or these pathways.

As such, the polypeptides and compositions of the present invention can be used for the diagnosis, prevention and treatment of diseases and disorders of the present invention (herein also "diseases and disorders of the present invention") and include, but are not limited to cancer, e.g., carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small Cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, Hodgkin's lymphoma, non-Hodgkin's lymphoma, Kaposi's sarcoma, multicentric Castleman's disease or AIDS-associated primary effusion lymphoma, neuroectodermal tumors, rhabdomyosarcoma (see, Cancer, Principles and practice (DeVita, V. T. et al. eds 1997) for additional cancers); preferably head and neck cancer, as well as brain and neuronal dysfunction, such as Alzheimer's disease and multiple sclerosis; kidney dysfunction, renal allograft rejection; nasal polyposis; rheumatoid arthritis; cardiac allograft rejection; cardiac dysfunction; atherosclerosis; asthma; glomerulonephritis; contact dermatitis; inflammatory bowel disease; colitis; psoriasis; reperfusion injury, blood vessel formation in cancers, such as head and neck cancers; as well as other disorders and diseases described herein. In particular, the polypeptides and compositions of the present invention can be used for the diagnosis, prevention and treatment of diseases involving CXCR7 mediated metastasis, chemotaxis, cell adhesion, trans endothelial migration, cell proliferation, angiogenesis and/or survival.

Generally, said "diseases and disorders of the present invention" can be defined as diseases and disorders that can be diagnosed, prevented and/or treated, respectively, by suitably administering to a subject in need thereof (i.e., having the disease or disorder or at least one symptom thereof and/or at risk of attracting or developing the disease or disorder) of either a polypeptide or composition of the invention (and in particular, of a pharmaceutically active amount thereof) and/or of a known active principle active against CXCR7 and in particular human CXCR7 (SEQ ID NO: 1) or a biological pathway or mechanism in which CXCR7 and in particular human CXCR7 (SEQ ID NO: 1) is involved, such as angiogenesis in cancer (and in particular, of a pharmaceutically active amount thereof).

In particular, the polypeptides of the present invention can be used for the diagnosis, prevention and treatment of diseases and disorders of the present invention, such as for instance angiogenesis, and in particular in head and neck cancers, which are characterized by excessive and/or unwanted CXCL12 and in particular human CXCL12 signalling mediated by CXCR7 and in particular human CXCR7 (SEQ ID NO: 1) or by the pathway(s) in which CXCR7 and in particular human CXCR7 (SEQ ID NO: 1) is involved (e.g., CXCL11/1-TAC-CXCR7 axis). Examples of such diseases and disorders of the present invention will again be clear to the skilled person based on the disclosure herein.

Thus, without being limited thereto, the immunoglobulin single variable domains and polypeptides of the invention can for example be used to diagnose, prevent and/or to treat all diseases and disorders that are currently being diagnosed, prevented or treated with active principles that can modulate CXCR7 and in particular human CXCR7 (SEQ ID NO: 1)-mediated signalling, such as those mentioned in the prior art cited herein. It is also envisaged that the polypeptides of the invention can be used to diagnose, prevent and/or to treat all diseases and disorders for which treatment with such active principles is currently being developed, has been proposed, or will be proposed or developed in future. In addition, it is envisaged that, because of their favourable properties as further described herein, the polypeptides of the present invention may be used for the diagnosis, prevention and treatment of other diseases and disorders than those for which these known active principles are being used or will be proposed or developed; and/or that the polypeptides of the present invention may provide new methods and regimens for treating the diseases and disorders described herein.

Other applications and uses of the immunoglobulin single variable domains and polypeptides of the invention will become clear to the skilled person from the further disclosure herein.

Generally, it is an object of the invention to provide pharmacologically active agents, as well as compositions comprising the same, that can be used in the diagnosis, prevention and/or treatment of diseases and/or disorders of the invention; and to provide methods for the diagnosis, prevention and/or treatment of such diseases and disorders that involve the administration and/or use of such agents and compositions.

In particular, it is an object of the invention to provide such pharmacologically active agents, compositions and/or methods that have certain advantages compared to the agents, compositions and/or methods that are currently used and/or known in the art. These advantages will become clear from the further description below.

More in particular, it is an object of the invention to provide therapeutic proteins that can be used as pharmacologically active agents, as well as compositions comprising the same, for the diagnosis, prevention and/or treatment of diseases and/or disorders of the invention and of the further diseases and disorders mentioned herein; and to provide methods for the diagnosis, prevention and/or treatment of such diseases and disorders that involve the administration and/or the use of such therapeutic proteins and compositions.

Accordingly, it is a specific object of the present invention to provide immunoglobulin single variable domains that are directed against CXCR7, in particular against CXCR7 from a warm-blooded animal, more in particular against CXCR7 from a mammal such as e.g., mouse, and especially against human CXCR7 (SEQ ID NO: 1); and to provide proteins and polypeptides comprising or essentially consisting of at least one such immunoglobulin single variable domain.

In particular, it is a specific object of the present invention to provide such immunoglobulin single variable domains and such proteins and/or polypeptides that are suitable for prophylactic, therapeutic and/or diagnostic use in a warm-blooded animal, and in particular in a mammal, and more in particular in a human being.

More in particular, it is a specific object of the present invention to provide such immunoglobulin single variable domains and such proteins and/or polypeptides that can be used for the prevention, treatment, alleviation and/or diagnosis of one or more diseases, disorders or conditions associated with CXCR7 and/or mediated by CXCR7 (such as the diseases, disorders and conditions mentioned herein) in a warm-blooded animal, in particular in a mammal, and more in particular in a human being.

It is also a specific object of the invention to provide such immunoglobulin single variable domains and such proteins and/or polypeptides that can be used in the preparation of pharmaceutical or veterinary compositions for the prevention and/or treatment of one or more diseases, disorders or conditions associated with and/or mediated by CXCR7 (such as the diseases, disorders and conditions mentioned herein) in a warm-blooded animal, in particular in a mammal, and more in particular in a human being.

In the invention, generally, these objects are achieved by the use of the immunoglobulin single variable domains, proteins, polypeptides and compositions that are described herein.

In general, the invention provides immunoglobulin single variable domains that are directed against (as defined herein) and/or can specifically bind (as defined herein) to CXCR7 and in particular human CXCR7 (SEQ ID NO: 1); as well as compounds and constructs, and in particular proteins and polypeptides, that comprise at least one such amino acid sequence.

More in particular, the invention provides immunoglobulin single variable domains and polypeptides that can bind to CXCR7 and in particular human CXCR7 (SEQ ID NO: 1) with an affinity (suitably measured and/or expressed as a $K_D$-value (actual or apparent), a $K_A$-value (actual or apparent), a $k_{on}$ rate and/or a $k_{off}$-rate, or alternatively as an $IC_{50}$ value, as further described herein) that is as defined herein; as well as compounds and constructs, and in particular proteins and polypeptides, that comprise at least one such amino acid sequence.

In a particular aspect, the immunoglobulin single variable domains and/or polypeptides of the invention are such that they:
bind to human CXCR7 (SEQ ID NO: 1) with an EC50 of 100 nM or lower, more preferably of 50 nM or lower, even more preferably of 20 nM or lower, most preferably of 10 nM or lower in a binding FACS assay as e.g. described in the experimental part (see Example 8), and wherein the polypeptides comprise only one human CXCR7 binding immunoglobulin single variable domain unit;
and/or such that they:
fully displace human CXCL12 (SDF-1) from human CXCR7 (SEQ ID NO: 1) at an average Ki value of 100 nM or less, more preferably at an average Ki value of 20 nM or less, even more preferably at an average Ki value of 10 nM or less in an assay as e.g., described in the experimental part (Examples 9 and 10), and wherein the polypeptides comprise only one human CXCR7 binding immunoglobulin single variable domain unit, and wherein full displacement means an average CXCL12 displacement of about 60% to 80% and more (e.g., when measured according to the ligand displacement assay of Example 9) or wherein full displacement means an average CXCL12 displacement of about 80% to 100% and more (when measured according to the FACS based competition assay of Example 10);
and/or such that they:
fully displace human CXCL11 (I-TAC) from human CXCR7 (SEQ ID NO: 1) at an average Ki value of 1000 nM or less, more preferably at an average Ki value 500 nM or less, even more preferably at an average Ki value 100 nM or less, even more preferably at an average Ki value of 20 nM or less, even more preferably at an average Ki value of 10 nM or less in an assay as e.g. described in the experimental part (Examples 9 and 10), and wherein the polypeptides comprise only one human CXCR7 binding immunoglobulin single variable domain unit, and wherein full displacement means an average CXCL11 displacement of about 60% to 80% and more (e.g., when measured according to the ligand displacement assay of Example 9) or wherein full displacement means an average CXCL12 displacement of about 80% to 100% and more (when measured according to the FACS based competition assay of Example 10)
and/or such that they:
partially displace human CXCL12 (SDF-1) from human CXCR7 (SEQ ID NO: 1) at an average Ki value of 100 nM or less, more preferably at an average Ki value of 20 nM or less, even more preferably at an average Ki value of 10 nM or less in an assay as e.g. described in the experimental part (Examples 9 and 10), and wherein the polypeptides comprise only one human CXCR7 binding immunoglobulin single variable domain unit, and wherein partial displacement means an average CXCL12 displacement of about 40% to 60% (e.g. when measured according to the ligand displacement assay of Example 9) or wherein partial displacement means an average CXCL12 displacement of about 50% to 80% (when measured according to the FACS based competition assay of Example 10);
and/or such that they:
partially displace human CXCL11 (I-TAC) from human CXCR7 (SEQ ID NO: 1) at an average Ki value of 1000 nM or less, more preferably at an average Ki value 500 nM or less, even more preferably at an average Ki value 100 nM or less, even more preferably at an average Ki value of 20 nM or less, even more preferably at an average Ki value of 10 nM or less in an assay as e.g. described in the experimental part (Examples 9 and 10), and wherein the polypeptides comprise only one human CXCR7 binding immunoglobulin single variable domain unit, and wherein partial displacement means an average CXCL11 displacement of about 40% to 60% (e.g., when measured according to the ligand displacement assay of Example 9) or wherein partial displacement means an average CXCL12 displacement of about 50% to 80% (when measured according to the FACS based competition assay of Example 10),
and/or such that they:
bind human CXCR7 (SEQ ID NO: 1) with an average Kd value of 100 nM or less, more preferably at an average Kd value of 50 nM or less, even more preferably at an average Kd value of 40 nM or less, such as less than 30, 25, 20, 15, 10, 9, 8, 7, 6, 5, 4, 3, 3 nM or even less, such as less than 1 nM, or most preferably even less than 0.1 nM.

It should be appreciated that binding of the immunoglobulin single variable domains and/or polypeptides of the invention to (human) CXCR7 may result in displacing (human) CXCL11 and/or CXCL12 from (human) CXCR7 as described herein. It should further be appreciated that binding of the immunoglobulin single variable domains and/or polypeptides of the invention to (human) CXCR7 may result in inhibiting binding of (human) CXCL11 and/or CXCL12 to its cognate receptor, such as, (human) CXCR7 as described herein.

As already mentioned, in some specific, but non-limiting aspects (described in more detail herein), the invention provides:

amino acid sequences that are directed against (as defined herein) CXCR7 and that are capable of inhibiting or blocking (fully or partially, as further described herein) ligand binding, and in particular of inhibiting or blocking (fully or partially, as further described herein) the binding of SDF-1 to CXCR7 (as further described herein). These amino acid sequences are also referred to herein as "CXCR-7 binding amino acid sequences" or "CXCR7 binding blocks". Preferably, these CXCR7-binding amino acid sequences are ISVD's (as described herein), in which case they are also referred to as "CXCR7-binding ISVD's". Preferably, any CXCR7-binding amino acid sequences, CXCR7-binding building blocks or CXCR7-binding ISVD's are such that they have blocking activity, i.e. block SDF-1 binding to CXCR7 partially or completely, which can be determined by any suitable assay known to the person skilled in the art, such as, for instance, by an Alphascreen assay or by a FACS competition assay (e.g. as described herein). Preferably, the blocking activity is determined by a FACS competition assay as described in Example 9. Preferably, the ISVD has a blocking activity or competition capacity in NIH3T3-hCXCR7 cells of blocking or competing SDF-1 binding to CXCR7 with an average Ki of less than 600 nMs, but preferably, 500 nMs, 400 nMs, 300 nMs, 200 nMs, 100 nMs or even less.

For instance, the 01C10-like ISVD has a blocking activity or competition capacity in this assay with an average Ki of less than 100 nMs, more preferably, less than 75 nMs, 50 nMs or even less, such as less than 40 nMs or 30 nMs, 25 nMs or 24 nMs or even more preferably of less than 22 nMs.

For instance, the 14G03-like ISVD has a blocking activity or competition capacity in this assay with an average Ki of less than 150 nMs, more preferably, less than 100 nMs, 90 nMs, 80 nMs or even less, such as less than 70 nMs or 60 nMs, 50 nMs or 40 nMs, 30 nMs, 20 nMs, 15 nMs or 10 nMs, 5 nMs or even more preferably of less than 4 nMs.

In one specific, but non-limiting aspect, (some of the) "CXCR-7 binding amino acid sequences" or "CXCR7 binding blocks" may (and preferably also are) be such that they are capable of inhibiting or blocking β-arrestin recruitment (see Example 15). Preferably, any CXCR7-binding amino acid sequences, CXCR7-binding building blocks or CXCR7-binding ISVD's are such that they have blocking activity, i.e. block or inhibit SDF-1 mediated CXCR7 signalling partially or completely, which can be determined by any suitable assay known to the person skilled in the art, such as, for instance, by any suitable β-arrestin recruitment assay, as described herein.

Preferably, the blocking activity or inhibiting capacity is determined by a β-arrestin assay as described in Example 15. Preferably, the ISVD has a blocking activity or an inhibition capacity of ligand (e.g. SDF-1) induced β-arrestin in the PathHunter eXpress β-arrestin assay (DiscoverX) with a % inhibition of β-arrestin recruitment of more than 25%, more than 30%, but preferably, 40%, 50%, 60%, 70%, 80% or even more.

For instance, the 14G03-like ISVD has a blocking activity or inhibition capacity in this assay with a % inhibition of more than 50%, more preferably, more than 60%, 70% or even more, such as more than 75% or 80%, 85%, or even more preferably of more than 90%.

Some preferred technical values for binding, displacing, migration or other in vivo and/or in vitro potency of the immunoglobulin single variable domains or polypeptides of the invention to CXCR7 and in particular human CXCR7 (SEQ ID NO: 1) will become clear from the further description and examples herein.

Also, in the present description and claims, the following terms are defined as follows:

A) 01C10-like sequences: a "01C10-like sequence", "01C10-like ISVD", "01C10-like building block" or "Group 1 ISVDs" is defined as an ISVD (as described herein) that comprises:
  a) a CDR1 which comprises or essentially consists of either (i) the amino acid sequence NYAMG (SEQ ID NO: 93) or (ii) an amino acid sequence that has only 3, 2 or 1 amino acid difference(s) (as defined herein) with the amino acid sequence NYAMG (SEQ ID NO: 93); and/or
  b) a CDR2 which comprises or essentially consists of either (i) the amino acid sequence AITPRAFTTYYADSVKG (SEQ ID NO: 95) or (ii) an amino acid sequence that has at least 80%, such as at least 85%, for example at least 90% or more than 95% sequence identity with the amino acid sequence AITPRAFTTYYADSVKG (SEQ ID NO: 95); or (iii) an amino acid sequence that has only 7, 6, 5, 4, 3, 2 or 1 amino acid difference(s) (as defined herein) with the amino acid sequence AITPRAFTTYYADSVKG (SEQ ID NO: 95); and/or
  c) a CDR3 which comprises or essentially consists of either (i) the amino acid sequence QLVGSGSNLGRQESYAY (SEQ ID NO: 97) or (ii) an amino acid sequence that has at least 80%, such as at least 85%, for example at least 90% or more than 95% sequence identity with the amino acid sequence QLVGSGSNLGRQESYAY (SEQ ID NO: 97); or (iii) an amino acid sequence that has only 7, 6, 5, 4, 3, 2 or 1 amino acid difference(s) (as defined herein) with the amino acid sequence QLVGSGSNLGRQESYAY (SEQ ID NO: 97);

in which the framework sequences present in such an ISVD are as further described herein, and in which CDR1, CDR2 and CDR3 are preferably such that the 01C10-like ISVD has blocking activity, e.g. block CXCL11 and/or CXCL12 binding to CXCR7 partially or completely as described above, and/or reducing and/or inhibiting tumorigenesis in a xenograph model, and/or binds and/or recognizes amino acid residue W19, and optionally amino acid residue S23 and/or amino acid residue D25 in CXCR7 (SEQ ID NO: 1), all as described herein.

As also mentioned herein, (some of the) 01C10-like sequences may (and preferably also are) be such that they are capable of inhibiting, blocking or displacing SDF-1 binding (see Examples 9 and 10), for example in the displacement assay used in Example 10. Preferably, in such a 01C10-like sequence, CDR1 and CDR2 are as defined under a) and b), respectively; or CDR1 and CDR3 are as defined under a) and c), respectively; or CDR2 and CDR3 are as defined under b) and c), respectively. More preferably, in such a 01C10-like sequence, CDR1, CDR2 and CDR3 are all as defined under a), b) and c), respectively. Again, in such an 01C10-like sequence, CDR1, CDR2 and CDR3 are preferably such that the 01C10-like ISVD has blocking activity, e.g. block SDF-1 binding to CXCR7 partially or completely as described herein, and/or reducing and/or inhibiting tumorigenesis in a xenograph model, and/or binds and/or recognizes amino acid residue W19, and optionally amino acid residue S23 and/or amino acid residue D25 in CXCR7 (SEQ ID NO: 1), all as described herein.

For example, in such an 01C10-like sequence: CDR1 may comprise or essentially consist of the amino acid sequence NYAMG (SEQ ID NO: 93) (with CDR2 and CDR3 being as defined under b) and c), respectively); and/or CDR2 may comprise or essentially consist of the amino acid sequence AITPRAFTTYYADSVKG (SEQ ID NO: 95) (with CDR1 and CDR3 being as defined under a) and c), respectively); and/or CDR3 may comprise or essentially consist of the amino acid sequence QLVGSGSNLGRQESYAY (SEQ ID NO: 97) (with CDR1 and CDR2 being as defined under a) and b), respectively). Particularly, when an 01C10-like sequence is according to this aspect: CDR1 may comprise or essentially consist of the amino acid sequence NYAMG (SEQ ID NO: 93) and CDR2 may comprise or essentially consist of the amino acid sequence AITPRAFTTYYADS-VKG (SEQ ID NO: 95) (with CDR3 being as defined under c) above); and/or CDR1 may comprise or essentially consist of the amino acid sequence NYAMG (SEQ ID NO: 93) and CDR3 may comprise or essentially consist of the amino acid sequence QLVGSGSNLGRQESYAY (SEQ ID NO: 97) (with CDR2 being as defined under b) above); and/or CDR2 may comprise or essentially consist of the amino acid sequence AITPRAFTTYYADSVKG (SEQ ID NO: 95) and CDR3 may comprise or essentially consist of the amino acid sequence QLVGSGSNLGRQESYAY (SEQ ID NO: 97) (with CDR1 being as defined under a) above). Again, in such 01C10-like sequences, CDR1, CDR2 and CDR3 are preferably such that the 01C10-like ISVD has blocking activity, e.g. block SDF-1 binding to CXCR7 partially or completely as described herein and/or reducing and/or inhibiting tumorigenesis in a xenograph model, and/or binds and/or recognizes amino acid residue W19, and optionally amino acid residue S23 and/or amino acid residue D25 in CXCR7 (SEQ ID NO: 1), all as described herein. In a specifically preferred aspect, a "01C10-like sequence", "01C10-like ISVD", "01C10-like building block" or "Group 1 ISVD" is an ISVD that comprises:

d) a CDR1 which is either (i) the amino acid sequence NYAMG (SEQ ID NO: 93) or (ii) an amino acid sequence that has only 3, 2 or 1 amino acid difference(s) (as defined herein) with the amino acid sequence NYAMG (SEQ ID NO: 93); and/or e) a CDR2 which is either (i) the amino acid sequence AITPRAFTTYYADSVKG (SEQ ID NO: 95) or (ii) an amino acid sequence that has at least 80%, such as at least 85%, for example at least 90% or more than 95% sequence identity with the amino acid sequence AITPRAFTTYYADSVKG (SEQ ID NO: 95); or (iii) an amino acid sequence that has only 7, 6, 5, 4, 3, 2 or 1 amino acid difference(s) (as defined herein) with the amino acid sequence AITPRAFTTYYADSVKG (SEQ ID NO: 95); and/or f) a CDR3 which is either (i) the amino acid sequence QLVGSGSNLGRQESYAY (SEQ ID NO: 97) or (ii) an amino acid sequence that has at least 80%, such as at least 85%, for example at least 90% or more than 95% sequence identity with the amino acid sequence QLVGSGSNLGRQESYAY (SEQ ID NO: 97); or (iii) an amino acid sequence that has only 7, 6, 5, 4, 3, 2 or 1 amino acid difference(s) (as defined herein) with the amino acid sequence QLVGSGSNLGRQESYAY (SEQ ID NO: 97);

in which the framework sequences present in such an ISVD are as further described herein, and in which CDR1, CDR2 and CDR3 are preferably such that the 01C10-like ISVD has blocking activity, e.g., block SDF-1 binding to CXCR7 partially or completely as described herein and/or reducing and/or inhibiting tumorigenesis in a xenograph model, and/or binds and/or recognizes amino acid residue W19, and optionally amino acid residue S23 and/or amino acid residue D25 in CXCR7 (SEQ ID NO: 1), all as described herein. Preferably, in a 01C10-like sequence according to this specifically preferred aspect, CDR1 and CDR2 are as defined under d) and e), respectively; or CDR1 and CDR3 are as defined under d) and f), respectively; or CDR2 and CDR3 are as defined under e) and f), respectively. More preferably, in such a 01C10-like sequence, CDR1, CDR2 and CDR3 are all as defined under d), e) and f), respectively. Again, in such an 01C10-like sequence, CDR1, CDR2 and CDR3 are preferably such that the 01C10-like ISVD has blocking activity, e.g. block SDF-1 binding to CXCR7 partially or completely as described herein, and/or reducing and/or inhibiting tumorigenesis in a xenograph model, and/or binds and/or recognizes amino acid residue W19, and optionally amino acid residue S23 and/or amino acid residue D25 in CXCR7 (SEQ ID NO: 1), all as described herein.

For example, in a 01C10-like sequence according to this specifically preferred aspect: CDR1 is the amino acid sequence NYAMG (SEQ ID NO: 93) (with CDR2 and CDR3 being as defined under e) and f), respectively); and/or CDR2 is the amino acid sequence AITPRAFTTYYADS-VKG (SEQ ID NO: 95) (with CDR1 and CDR3 being as defined under d) and f), respectively); and/or CDR3 is the amino acid sequence QLVGSGSNLGRQESYAY (SEQ ID NO: 97) (with CDR1 and CDR2 being as defined under d) and e), respectively). Particularly, when an 01C10-like sequence is according to this aspect: CDR1 is the amino acid sequence NYAMG (SEQ ID NO: 93) and CDR2 is the amino acid sequence AITPRAFTTYYADSVKG (SEQ ID NO: 95) (with CDR3 being as defined under f) above); and/or CDR1 is the amino acid sequence NYAMG (SEQ ID NO: 93) and CDR3 is the amino acid sequence QLVGSGSNLGRQESYAY (SEQ ID NO: 97) (with CDR2 being as defined under e) above); and/or CDR2 is the amino acid sequence AITPRAFTTYYADSVKG (SEQ ID NO: 95) and CDR3 is QLVGSGSNLGRQESYAY (SEQ ID NO: 97) (with CDR1 being as defined under d) above). Again, in such 01C10-like sequences, CDR1, CDR2 and CDR3 are preferably such that the 01C10-like ISVD has blocking activity, e.g., block SDF-1 binding to CXCR7 partially or completely as described herein, and/or reducing and/or inhibiting tumorigenesis in a xenograph model, and/or binds and/or recognizes amino acid residue W19, and optionally amino acid residue S23 and/or amino acid residue D25 in CXCR7 (SEQ ID NO: 1), all as described herein.

In a particularly preferred 01C10-like sequence: CDR1 is the amino acid sequence NYAMG (SEQ ID NO: 93), CDR2 is the amino acid sequence AITPRAFTTYYADSVKG (SEQ ID NO: 95); and CDR3 is the amino acid sequence QLVGSGSNLGRQESYAY (SEQ ID NO: 97).

In all the 01C10-like sequence described in this paragraph A), the framework sequences may be as further described herein. Preferably, the framework sequences are such that the framework sequences have at least 80%, such as at least 85%, for example at least 90%, such as at least 95% sequence identity with the framework sequences of 01C10 (which, for example, can be determined by determining the overall degree of sequence identity of a given sequence with the sequence of 01C10 while disregarding the CDR's in the calculation). Again, the combination of CDR's and frameworks present in a given sequence are preferably such that the resulting 01C10-like ISVD has blocking activity, e.g., block SDF-1 binding to CXCR7 partially or completely as described herein and/or reducing and/or inhibiting tumorigenesis in a xenograft model, and/or binds and/or recognizes amino acid residue W19, and optionally amino acid residue S23 and/or amino acid residue D25 in CXCR7 (SEQ ID NO: 1), all as described herein.

In one specific aspect, a 01C10-like sequence is an ISVD that has at least 70%, such at least 80%, for example at least 85%, such as at least 90% or more than 95% sequence identity with the amino acid sequence 01C10 (SEQ ID NO: 91). For example, in an 01C10-like sequence according to this aspect, the CDR's may be according to the specifically preferred aspect described above, and may in particularly (but without limitation) be NYAMG (SEQ ID NO: 93) (CDR1); AITPRAFTTYYADSVKG (SEQ ID NO: 95) (CDR2); and QLVGSGSNLGRQESYAY (SEQ ID NO: 97) (CDR3). Again, preferably, the combination of CDR's and frameworks present in such a 01C10-like ISVD are preferably such that the resulting 01C10-like ISVD has blocking activity, e.g. block SDF-1 binding to CXCR7 partially or completely as described herein and/or reducing and/or inhibiting tumorigenesis in a xenograft model, and/or binds and/or recognizes amino acid residue W19, and optionally amino acid residue S23 and/or amino acid residue D25 in CXCR7 (SEQ ID NO: 1), all as described herein. In one particular aspect, any 01C10-like sequence may be a humanized and/or sequence optimized sequence, as further described herein.

B) 14G03-like sequences: a "14G03-like sequence", "14G03-like ISVD", "14G03-like building block" or "Group 2 ISVDs" is defined as an ISVD (as described herein) that comprises:
  a) a CDR1 which comprises or essentially consists of either (i) the amino acid sequence INYMG (SEQ ID NO: 13) or (ii) an amino acid sequence that has only 3, 2 or 1 amino acid difference(s) (as defined herein) with the amino acid sequence INYMG (SEQ ID NO: 13); and/or
  b) a CDR2 which comprises or essentially consists of either (i) the amino acid sequence TLTSGGSTNYAGSVKG (SEQ ID NO: 23) or (ii) an amino acid sequence that has at least 80%, such as at least 85%, for example at least 90% or more than 95% sequence identity with the amino acid sequence TLTSGGSTNYAGSVKG (SEQ ID NO: 23); or (iii) an amino acid sequence that has only 7, 6, 5, 4, 3, 2 or 1 amino acid difference(s) (as defined herein) with the amino acid sequence TLTSGGSTNYAGSVKG (SEQ ID NO: 23); and/or
  c) a CDR3 which comprises or essentially consists of either (i) the amino acid sequence GGTLYDRRRFES (SEQ ID NO: 33) or (ii) an amino acid sequence that has at least 80%, such as at least 85%, for example at least 90% or more than 95% sequence identity with the amino acid sequence GGTLYDRRRFES (SEQ ID NO: 33); or (iii) an amino acid sequence that has only 7, 6, 5, 4, 3, 2 or 1 amino acid difference(s) (as defined herein) with the amino acid sequence GGTLYDRRRFES (SEQ ID NO: 33);

in which the framework sequences present in such an ISVD are as further described herein, and in which CDR1, CDR2 and CDR3 are preferably such that the 14G03-like ISVD has blocking activity, e.g. block CXCL11 and/or CXCL12 binding to CXCR7 partially or completely as described above, and/or reducing and/or inhibiting tumorigenesis in a xenograft model, and/or inhibits β-arrestin recruitment, and/or binds and/or recognizes amino acid residue M33, and optionally amino acid residue V32 and/or amino acid residue M37 in CXCR7 (SEQ ID NO: 1), all as described herein.

As also mentioned herein, (some of the) 14G03-like sequences may (and preferably also are) be such that they are capable of inhibiting, blocking or displacing SDF-1 binding (see Examples 9 and 10), for example in the displacement assay used in Example 10. Preferably, in such a 14G03-like sequence, CDR1 and CDR2 are as defined under a) and b), respectively; or CDR1 and CDR3 are as defined under a) and c), respectively; or CDR2 and CDR3 are as defined under b) and c), respectively. More preferably, in such a 14G03-like sequence, CDR1, CDR2 and CDR3 are all as defined under a), b) and c), respectively. Again, in such an 14G03-like sequence, CDR1, CDR2 and CDR3 are preferably such that the 14G03-like ISVD has blocking activity, e.g. block SDF-1 binding to CXCR7 partially or completely as described herein, and/or reducing and/or inhibiting tumorigenesis in a xenograft model, and/or inhibits β-arrestin recruitment, and/or binds and/or recognizes amino acid residue M33, and optionally amino acid residue V32 and/or amino acid residue M37 in CXCR7 (SEQ ID NO: 1), all as described herein.

For example, in such an 14G03-like sequence: CDR1 may comprise or essentially consist of the amino acid sequence INYMG (SEQ ID NO: 13) (with CDR2 and CDR3 being as defined under b) and c), respectively); and/or CDR2 may comprise or essentially consist of the amino acid sequence TLTSGGSTNYAGSVKG (SEQ ID NO: 23) (with CDR1 and CDR3 being as defined under a) and c), respectively); and/or CDR3 may comprise or essentially consist of the amino acid sequence GGTLYDRRRFES (SEQ ID NO: 33) (with CDR1 and CDR2 being as defined under a) and b), respectively). Particularly, when an 14G03-like sequence is according to this aspect: CDR1 may comprise or essentially consist of the amino acid sequence INYMG (SEQ ID NO: 13) and CDR2 may comprise or essentially consist of the amino acid sequence TLTSGGSTNYAGSVKG (SEQ ID NO: 23) (with CDR3 being as defined under c) above); and/or CDR1 may comprise or essentially consist of the amino acid sequence INYMG (SEQ ID NO: 13) and CDR3 may comprise or essentially consist of the amino acid sequence GGTLYDRRRFES (SEQ ID NO: 33) (with CDR2 being as defined under b) above); and/or CDR2 may comprise or essentially consist of the amino acid sequence TLTSGGSTNYAGSVKG (SEQ ID NO: 23) and CDR3 may comprise or essentially consist of the amino acid sequence GGTLYDRRRFES (SEQ ID NO: 33) (with CDR1 being as defined under a) above). Again, in such 14G03-like sequences, CDR1, CDR2 and CDR3 are preferably such that the 14G03-like ISVD has blocking activity, e.g. block SDF-1 binding to CXCR7 partially or completely as described herein and/or reducing and/or inhibiting tumorigenesis in a xenograft model, and/or inhibits β-arrestin recruitment, and/or binds and/or recognizes amino acid residue M33, and optionally amino acid residue V32 and/or amino acid residue M37 in CXCR7 (SEQ ID NO: 1), all as described herein.

In a specifically preferred aspect, a "14G03-like sequence", "14G03-like ISVD", "14G03-like building block" or "Group 2 ISVD" is an ISVD that comprises:

d) a CDR1 which is either (i) the amino acid sequence INYMG (SEQ ID NO: 13) or (ii) an amino acid sequence that has only 3, 2 or 1 amino acid difference(s) (as defined herein) with the amino acid sequence INYMG (SEQ ID NO: 13); and/or e) a CDR2 which is either (i) the amino acid sequence TLTSGGSTNYAGSVKG (SEQ ID NO: 23) or (ii) an amino acid sequence that has at least 80%, such as at least 85%, for example at least 90% or more than 95% sequence identity with the amino acid sequence TLTSGGSTNYAGSVKG (SEQ ID NO: 23); or (iii) an amino acid sequence that has only 7, 6, 5, 4, 3, 2 or 1 amino acid difference(s) (as defined herein) with the amino acid sequence TLTSGGSTNYAGSVKG (SEQ ID NO: 23); and/or f) a CDR3 which is either (i) the amino acid sequence GGTLYDRRRFES (SEQ ID NO: 33) or (ii) an amino acid sequence that has at least 80%, such as at least 85%, for example at least 90% or more than 95% sequence identity with the amino acid sequence GGTLYDRRRFES (SEQ ID NO: 33); or (iii) an amino acid sequence that has only 7, 6, 5, 4, 3, 2 or 1 amino acid difference(s) (as defined herein) with the amino acid sequence GGTLYDRRRFES (SEQ ID NO: 33);

in which the framework sequences present in such an ISVD are as further described herein, and in which CDR1, CDR2 and CDR3 are preferably such that the 14G03-like ISVD has blocking activity, e.g. block SDF-1 binding to CXCR7 partially or completely as described herein and/or reducing and/or inhibiting tumorigenesis in a xenograft model, and/or inhibits β-arrestin recruitment, and/or binds and/or recognizes amino acid residue M33, and optionally amino acid residue V32 and/or amino acid residue M37 in CXCR7 (SEQ ID NO: 1), all as described herein. Preferably, in a 14G03-like sequence according to this specifically preferred aspect, CDR1 and CDR2 are as defined under d) and e), respectively; or CDR1 and CDR3 are as defined under d) and f), respectively; or CDR2 and CDR3 are as defined under e) and f), respectively. More preferably, in such a 14G03-like sequence, CDR1, CDR2 and CDR3 are all as defined under d), e) and f), respectively. Again, in such an 14G03-like sequence, CDR1, CDR2 and CDR3 are preferably such that the 14G03-like ISVD has blocking activity, e.g. block SDF-1 binding to CXCR7 partially or completely as described herein, and/or reducing and/or inhibiting tumorigenesis in a xenograft model, and/or inhibits β-arrestin recruitment, and/or binds and/or recognizes amino acid residue M33, and optionally amino acid residue V32 and/or amino acid residue M37 in CXCR7 (SEQ ID NO: 1), all as described herein.

For example, in a 14G03-like sequence according to this specifically preferred aspect: CDR1 is the amino acid sequence INYMG (SEQ ID NO: 13) (with CDR2 and CDR3 being as defined under e) and f), respectively); and/or CDR2 is the amino acid sequence TLTSGGSTNYAGSVKG (SEQ ID NO: 23) (with CDR1 and CDR3 being as defined under d) and f), respectively); and/or CDR3 is the amino acid sequence GGTLYDRRRFES (SEQ ID NO: 33) (with CDR1 and CDR2 being as defined under d) and e), respectively). Particularly, when an 14G03-like sequence is according to this aspect: CDR1 is the amino acid sequence INYMG (SEQ ID NO: 13) and CDR2 is the amino acid sequence TLTSGGSTNYAGSVKG (SEQ ID NO: 23) (with CDR3 being as defined under f) above); and/or CDR1 is the amino acid sequence INYMG (SEQ ID NO: 13) and CDR3 is the amino acid sequence GGTLYDRRRFES (SEQ ID NO: 33) (with CDR2 being as defined under e) above); and/or CDR2 is the amino acid sequence TLTSGGSTNYAGSVKG (SEQ ID NO: 23) and CDR3 is GGTLYDRRRFES (SEQ ID NO: 33) (with CDR1 being as defined under d) above). Again, in such 14G03-like sequences, CDR1, CDR2 and CDR3 are preferably such that the 14G03-like ISVD has blocking activity, e.g. block SDF-1 binding to CXCR7 partially or completely as described herein, and/or reducing and/or inhibiting tumorigenesis in a xenograft model, and/or inhibits β-arrestin recruitment, and/or binds and/or recognizes amino acid residue M33, and optionally amino acid residue V32 and/or amino acid residue M37 in CXCR7 (SEQ ID NO: 1), all as described herein.

In a particularly preferred 14G03-like sequence: CDR1 is the amino acid sequence INYMG (SEQ ID NO: 13), CDR2 is the amino acid sequence TLTSGGSTNYAGSVKG (SEQ ID NO: 23); and CDR3 is the amino acid sequence GGTLYDRRRFES (SEQ ID NO: 33).

In all the 14G03-like sequence described in this paragraph A), the framework sequences may be as further described herein. Preferably, the framework sequences are such that the framework sequences have at least 80%, such as at least 85%, for example at least 90%, such as at least 95% sequence identity with the framework sequences of 14G03 (which, for example, can be determined by determining the overall degree of sequence identity of a given sequence with the sequence of 14G03 while disregarding the CDR's in the calculation). Again, the combination of CDR's and frameworks present in a given sequence are preferably such that the resulting 14G03-like ISVD has blocking activity, e.g. block SDF-1 binding to CXCR7 partially or completely as described herein and/or reducing and/or inhibiting tumorigenesis in a xenograft model, and/or inhibits β-arrestin recruitment, and/or binds and/or recognizes amino acid residue M33, and optionally amino acid residue V32 and/or amino acid residue M37 in CXCR7 (SEQ ID NO: 1), all as described herein.

In one specific aspect, a 14G03-like sequence is an ISVD that has at least 70%, such at least 80%, for example at least 85%, such as at least 90% or more than 95% sequence identity with the amino acid sequence 14G03 (SEQ ID NO: 43). For example, in an 14G03-like sequence according to this aspect, the CDR's may be according to the specifically preferred aspect described above, and may in particularly (but without limitation) be INYMG (SEQ ID NO: 13) (CDR1); TLTSGGSTNYAGSVKG (SEQ ID NO: 23) (CDR2); and GGTLYDRRRFES (SEQ ID NO: 33) (CDR3). Again, preferably, the combination of CDR's and frameworks present in such a 14G03-like ISVD are preferably such that the resulting 14G03-like ISVD has blocking activity, e.g., block SDF-1 binding to CXCR7 partially or completely as described herein and/or reducing and/or inhibiting tumorigenesis in a xenograft model, and/or inhibits β-arrestin recruitment, and/or binds and/or recognizes amino acid residue M33, and optionally amino acid residue V32 and/or amino acid residue M37 in CXCR7 (SEQ ID NO: 1), all as described herein. In one particular aspect, any 14G03-like sequence may be a humanized and/or sequence optimized sequence, as further described herein.

For binding to CXCR7 and in particular human CXCR7 (SEQ ID NO: 1), an amino acid sequence or polypeptide of the invention will usually contain within its amino acid sequence one or more amino acid residues or one or more stretches of amino acid residues (i.e., with each "stretch" comprising two or amino acid residues that are adjacent to each other or in close proximity to each other, i.e., in the primary or tertiary structure of the amino acid sequence) via which the amino acid sequence of the invention can bind to CXCR7 and in particular human CXCR7 (SEQ ID NO: 1), which amino acid residues or stretches of amino acid residues thus form the "site" for binding to CXCR7 and in particular human CXCR7 (SEQ ID NO: 1) (also referred to herein as the "antigen binding site").

The immunoglobulin single variable domains provided by the invention are preferably in essentially isolated form (as defined herein), or form part of a protein or polypeptide of the invention (as defined herein), which may comprise or essentially consist of one or more immunoglobulin single variable domains of the invention and which may optionally further comprise one or more further immunoglobulin single variable domains (all optionally linked via one or more suitable linkers), and/or one or more further binding domains, binding units, amino acid sequences or other (functional) groups or moieties, that preferably also confer one or more desired properties to the constructs (some non-limiting examples of the same will become clear from the further description herein).

The polypeptides or immunoglobulin single variable domains provided by the invention preferentially reduce tumorigenesis in vivo.

In a further preferred embodiment, the invention provides constructs comprising at least two immunoglobulin single variable domains against CXCR7. More preferably, said immunoglobulin single variable domains against CXCR7 are selected from variants of polypeptides and immunoglobulin single variable domains against CXCR7 as defined in section 1.5 in respect of Table B-2 infra (e.g., Group 2 immunoglobulin single variable domains), wherein said immunoglobulin single variable domains against CXCR7 may be the same or different. Preferably, said two immunoglobulin single variable domains against CXCR7 are chosen from 14G03-like ISVDs, such as 14G03, 08A05, 08A10, 07C03 and 07B11. In another further preferred embodiment, the invention provides constructs comprising at least two immunoglobulin single variable domains against CXCR7 are selected from variants of polypeptides and immunoglobulin single variable domains against CXCR7 which as defined in section 1.5 in respect of Table B-2 infra (e.g., Group 1 immunoglobulin single variable domains), wherein said immunoglobulin single variable domains against CXCR7 may be the same or different. Preferably, said two immunoglobulin single variable domains against CXCR7 are chosen from 01C10 (SEQ ID NO: 91), 01B12 (SEQ ID NO: 100), 01F11 (SEQ ID NO: 101) or 01B10 (SEQ ID NO: 102).

It has unexpectedly been demonstrated that bispecific constructs comprising at least one Group 1 immunoglobulin single variable domain and at least one Group 2 ISVD are especially suitable for reducing tumour growth in vivo. In particular, it has been shown that these constructs inhibit SDF-1 binding to CXCR7, inhibit tumour growth in vivo, as well as inhibit β-arrestin recruitment. Moreover, in view of the binding efficacy of the Group 2 ISVDs, for instance as characterized by SDF-1 displacement, these constructs comprising at least one Group 1 ISVD and at least one Group 2 ISVD bind better to the target (see e.g., Example 17). This would result in a lower dose for inhibiting tumour growth. In addition, the simultaneous inhibition of β-arrestin recruitment would result in a prolonged anti-tumorigenic effect.

Accordingly, in a further preferred embodiment, the invention provides constructs comprising at least two immunoglobulin single variable domains against CXCR7, wherein at least one of said immunoglobulin single variable domains against CXCR7 (i.e., a "first" immunoglobulin single variable domains against CXCR7) is 01C10-like, such as for instance 01C10 (SEQ ID NO: 91), 01B12 (SEQ ID NO: 100), 01F11 (SEQ ID NO: 101) or 01B10 (SEQ ID NO: 102), or variants thereof as defined in section 1.5 in respect of Table B-2 infra (e.g., Group 1 immunoglobulin single variable domains), and wherein at least one immunoglobulin single variable domains against CXCR7 (i.e., a "second" immunoglobulin single variable domain against CXCR7) is selected from variants of polypeptides and immunoglobulin single variable domains against CXCR7 as defined in section 1.5 infra in respect of Table B-2 different from the "first" immunoglobulin single variable domains against CXCR7 or variants thereof. Preferably, said "first" immunoglobulin single variable domains against CXCR7 is 01C10 and said "second" immunoglobulin single variable domains against CXCR7 is chosen from the group consisting of 14G03-like, such as for instance, 14G03, 08A05, 08A10, 07C03 and 07B11.

As described in Example 11, binding to CXCR7 by the Group 1 immunoglobulin single variable domains as represented by 01C10 was influenced by mutating W19. In contrast, binding of all tested immunoglobulin single variable domains was affected by a M33 mutation, while Group 1 ISVDs were not. It was further shown that Group 1 ISVDs preferably recognize and/or bind also S23 and D25 (data not shown).

Group 1 ISVDs or polypeptides can be characterized by binding/recognizing "Group 1 epitope". Group 1 ISVDs or polypeptides bind and/or recognize amino acid residue W19, and optionally amino acid residue S23 and/or amino acid residue D25 in CXCR7 (SEQ ID NO: 1). Group 1 epitope comprises amino acid residue W19, and optionally amino acid residue S23 and/or amino acid residue D25 in CXCR7 (SEQ ID NO: 1). Group 1 ISVDs is represented by inter alia 01C10 (SEQ ID NO: 91), 01B12 (SEQ ID NO: 100), 01F11 (SEQ ID NO: 101) or 01B10 (SEQ ID NO: 102), apparently hitting an epitope distinct from Group 2 epitope;

Group 2 ISVDs or polypeptides can be characterized by binding/recognizing "Group 2 epitope". Group 2 ISVDs or polypeptides do not bind and/or recognize amino acid residue W19, amino acid residue S23 and/or amino acid residue D25 in CXCR7 (SEQ ID NO: 1). Group 2 ISVDs or polypeptides bind and/or recognize amino acid residue M33, and optionally amino acid residue V32 and/or amino acid residue M37 in CXCR7 (SEQ ID NO: 1). Group 2 epitope comprises amino acid residue M33, and optionally amino acid residue V32 and/or amino acid residue M37 in CXCR7 (SEQ ID NO: 1). Group 2 ISVDs are represented by 14G03-like ISVDs, such as for instance, 14G03 (09A04), 08A05, 08A10 and 07C03, apparently hitting an epitope distinct from Group 1. Preferably, Group 2 ISVDs inhibit β-arrestin recruitment, as defined herein; and Group 3 ISVDs or polypeptides can be characterized by binding/recognizing (part of) "Group 1" epitope as well as (part of) "Group 2" epitope. Group 3 ISVDs or polypeptides are represented by 07B11, apparently intermediary to Group 1 and Group 2.

The person skilled in the art is familiar with methods common in the art for determining epitopes, such as for instance provided in Example 11: "epitope mapping" of the present invention.

Accordingly, the present invention relates to polypeptides ISVDs, as well as (conventional) antibodies, or parts thereof, such as Fc, Fab, minibodies, etc., recognizing and/or binding W19, and optionally S23 and/or D25 in CXCR7.

The above described anti-CXCR7/CXCR7 bispecific constructs may be suitably half-life extended (e.g., by pegylation, fusion to serum albumin, or fusion to a peptide or binding unit that can bind to a serum protein such as serum albumin, as further described herein), and thus may for example further comprise a serum-albumin binding peptide or binding domain (such as those described herein), optionally linked via one or more suitable spacers or linkers.

Again, such further binding domains, binding units, amino acid sequences or other (functional) groups or moieties include one or more other immunoglobulin single variable domains, such as one or more (single) domain antibodies, dAb's or Nanobodies (e.g., a $V_{HH}$, humanized $V_{HH}$ or camelized $V_H$, such as a camelized human $V_H$), so as to provide a "bispecific" protein or polypeptide of the invention (i.e., a polypeptide of the invention that contains at least one—such as one or two—immunoglobulin single variable domain that is directed against CXCR7 and at least one—such as one or two-immunoglobulin single variable domain that is directed against another target).

For example, according to a specific but non-limiting aspect, the constructs, proteins or polypeptides of the invention may have been provided with an increased half-life, for example by functionalisation and/or by including in the construct a moiety or binding unit that increases the half-life of the construct. Examples of such functionalisation, moieties or binding units will be clear to the skilled person and may for example include pegylation, fusion to serum albumin, or fusion to a peptide or binding unit that can bind to a serum protein such as serum albumin.

In the latter constructs (i.e., fusion constructs comprising at least one—such as one or two—amino acid sequence of the invention and at least one—such as one or two—peptide or binding unit that can bind to a serum protein such as serum albumin), the serum-albumin binding peptide or binding domain may be any suitable serum-albumin binding peptide or binding domain capable of increasing the half-life of the construct (compared to the same construct without the serum-albumin binding peptide or binding domain), and may in particular be serum albumin binding peptides as described in WO 2008/068280 by applicant (and in particular WO 2009/127691 and WO 2011/095545, both by applicant), or a serum—albumin binding immunoglobulin single variable domain (such as a serum-albumin binding Nanobody; for example Alb-1 or a humanized version of Alb-1 such as Alb-8, for which reference is for example made to WO 06/122787).

With respect to half-life, it should be noted that in the invention, and by using the various half-life extending techniques described herein (for example, by suitably choosing a serum-albumin binding peptide according to WO 2008/068280, WO 2009/127691 and/or WO 2011/095545, the half-life of a construct or polypeptide of the invention can (and preferably is) suitably "tailored" for the intended (therapeutic and/or diagnostic) application and/or to obtain the best balance between the desired therapeutic and/or pharmacological effect and possible undesired side-effects.

Thus, for example, and without limitation, a preferred aspect of the invention provides a "bispecific" polypeptide consisting essentially of one immunoglobulin single variable domain directed against human CXCR7 (or, alternatively, of two immunoglobulin single variable domains directed against human CXCR7, which may be the same or different, so as to provide—when they are the same or different—a "bivalent" polypeptide of the invention, or—when they are different—"biparatopic" polypeptide of the invention) and one immunoglobulin single variable domain directed against human serum albumin linked by a peptide linker (as defined herein), so as to provide a bispecific polypeptide of the invention, respectively, all as described herein. Such a protein or polypeptide may also be in essentially isolated form (as defined herein).

In another specific, but non-limiting aspect, an amino acid sequence (such as a Nanobody) of the invention or a polypeptide of the invention (such as a bivalent, biparatopic or bispecific polypeptide of the invention) may be suitably linked (again, chemically or via one or more suitable linkers or spacers) to a toxin or to a (cyto)toxic residue, moiety or payload. Examples of suitable (cyto)toxic moieties, compounds, payloads or residues which can be linked to amino acids sequences or polypeptides of the invention to provide—for example—a cytotoxic compound (i.e., an antibody-drug conjugate or "ADC" based upon an amino acid sequence or polypeptide of the invention) will be clear to the skilled person. Reference is for example made to the review by Ducry and Stump, Bioconjugate Chem., 2010, 21 (1), pp. 5-13. Such cytotoxic amino acid sequences or polypeptides of the invention may in particular be useful/suitable for those applications in which it is intended to kill a cell that expresses the target against which the amino acid sequences or polypeptides of the invention are directed (e.g. in the treatment of cancer), or to reduce or slow the growth and/or proliferation such a cell. Usually, but without limitation, (cyto)toxic polypeptides of the invention will either not be half-life extended or will have only a limited and/or tightly controlled half-life extension.

In another aspect, at least one amino acid sequence of the invention (i.e., immunoglobulin single variable domain against CXCR7) may be suitably linked to at least one immunoglobulin single variable domain that is directed against CXCR4, so as to provide a bispecific polypeptide of the invention that is directed against both CXCR7 and CXCR4.

For example, in this aspect, at least one—such as one or two—amino acid sequences of the invention may be suitably linked to at least one—such as one or two—immunoglobulin single variable domains against CXCR4.

Some preferred but non-limiting examples of immunoglobulin single variable domains against CXCR4 that can be used in such constructs are (or may be suitably chosen from)

- the immunoglobulin single variable domains (and in particular one of the Nanobodies) against CXCR4 from the international application WO 09/138,519 by Ablynx N.V. (for example and without limitation, 238D2/SEQ ID NO: 238 and 238D4/SEQ ID NO: 239 in Table B-1.1 of WO 09/138,519); and/or
- the sequence-optimized/improved variants of the amino acid sequences 238D2 and 238D4 described in the non-prepublished U.S. application 61/358,495 by Ablynx N.V. filed on Jun. 25, 2010; and/or
- the immunoglobulin single variable domains that are capable of binding to the same epitope as 238D2 and/or 238D4 as described in the PCT application PCT/EP2010/064766 by Ablynx N.V. filed on Oct. 4, 2010; and/or
- the 10E9-type sequences, 281E10-type sequences, 10E12-type sequences, 10A10-type sequences, 10G10-type sequences, 14A2-type sequences, 15A1-type sequences, 15H3-type sequences and/or 283B6-type sequences described on pages 7-13 of the PCT application PCT/EP2011/050156 by Ablynx N.V. filed on Jan. 7, 2011; and/or
- the 10E9-type sequences, 281E10-type sequences, 10E12-type sequences, 10A10-type sequences, 10G10- type sequences, 14A2-type sequences, 15A1-type sequences, 15H3-type sequences and/or 283B6-type sequences described on pages 15-47 of the PCT application PCT/EP2011/050156 by Ablynx N.V. filed on Jan. 7, 2011.

The above described anti-CXCR7/CXCR4 bispecific constructs (as well as other bispecific constructs comprising at least one amino acid sequence of the invention) may be suitably half-life extended (e.g., by pegylation, fusion to serum albumin, or fusion to a peptide or binding unit that can bind to a serum protein such as serum albumin, as further described herein), and thus may for example further comprise a serum-albumin binding peptide or binding domain (such as those described herein), optionally linked via one or more suitable spacers or linkers.

Thus, one specific but non-limiting aspect of the invention is a polypeptide that comprises one or two (and preferably one) immunoglobulin single variable domains (as defined herein, and preferably one or two Nanobodies) against CXCR7, one or two (and preferably one) immunoglobulin single variable domains (as defined herein, and preferably one or two Nanobodies) against CXCR4, and a peptide or immunoglobulin single variable domain against (human) serum albumin, optionally suitably linked via one or more spacers or linkers.

The above anti-CXCR7/CXCR4 bispecific constructs (as well as other bispecific constructs comprising at least one amino acid sequence of the invention) may also be suitably linked (again, chemically or via one or more suitable linkers or spacers) to a toxin or to a (cyto)toxic residue, moiety or payload (as further described herein). Again, such (cyto) toxic bispecfic polypeptides of the invention will either not be half-life extended or will have only a limited and/or tightly controlled half-life extension.

The invention in its broadest sense also comprises derivatives of the amino acid sequences (e.g., Nanobodies) of the invention and of the polypeptides of the invention. Such derivatives can generally be obtained by modification, and in particular by chemical and/or biological (e.g. enzymatical) modification, of the amino acid sequences (e.g., Nanobodies) of the invention and polypeptides of the invention and/or of one or more of the amino acid residues that form the Nanobodies of the invention.

Examples of such modifications, as well as examples of amino acid residues within the amino acid sequences (e.g., Nanobodies) of the invention and polypeptides that can be modified in such a manner (i.e., either on the protein backbone but preferably on a side chain), methods and techniques that can be used to introduce such modifications and the potential uses and advantages of such modifications will be clear to the skilled person.

For example, such a modification may involve the introduction (e.g., by covalent linking or in another suitable manner) of one or more functional groups, residues or moieties into or onto the amino acid sequences (e.g., Nanobodies) of the invention and polypeptides of the invention, and in particular of one or more functional groups, residues or moieties that confer one or more desired properties or functionalities to the Nanobody of the invention. Example of such functional groups will be clear to the skilled person.

For example, such modification may comprise the introduction (e.g., by covalent binding or in any other suitable manner) of one or more functional groups that increase the half-life, the solubility and/or the absorption of the Nanobody of the invention, that reduce the immunogenicity and/or the toxicity of the Nanobody of the invention, that eliminate or attenuate any undesirable side effects of the Nanobody of the invention, and/or that confer other advantageous properties to and/or reduce the undesired properties of the Nanobodies and/or polypeptides of the invention; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and single domain antibodies), for which reference is for example made to Remington's Pharmaceutical Sciences, 16th ed., Mack Publishing Co., Easton, Pa. (1980). Such functional groups may for example be linked directly (for example covalently) to a Nanobody of the invention, or optionally via a suitable linker or spacer, as will again be clear to the skilled person.

One of the most widely used techniques for increasing the half-life and/or reducing the immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, Nat. Biotechnol., 54, 531-545 (2002); by Veronese and Harris, Adv. Drug Deliv. Rev. 54, 453-456 (2003), by Harris and Chess, Nat. Rev. Drug. Discov., 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., Protein Engineering, 16, 10, 761-770 (2003). For example, for this purpose, PEG may be attached to a cysteine residue that naturally occurs in a Nanobody of the invention, a Nanobody of the invention may be modified so as to suitably introduce one or more cysteine residues for attachment of PEG, or an amino acid sequence comprising one or more cysteine residues for attachment of PEG may be fused to the N- and/or C-terminus of a Nanobody of the invention, all using techniques of protein engineering known per se to the skilled person.

Preferably, for the Nanobodies and proteins of the invention, a PEG is used with a molecular weight of more than 5000, such as more than 10,000 and less than 200,000, such as less than 100,000; for example in the range of 20,000-80,000.

Another, usually less preferred modification comprises N-linked or O-linked glycosylation, usually as part of co-translational and/or post-translational modification, depending on the host cell used for expressing the Nanobody or polypeptide of the invention.

Yet another modification may comprise the introduction of one or more detectable labels or other signal-generating groups or moieties, depending on the intended use of the labelled Nanobody. Suitable labels and techniques for attaching, using and detecting them will be clear to the skilled person, and for example include, but are not limited to, the fluorescent labels, phosphorescent labels, chemiluminescent labels, bioluminescent labels, radio-isotopes, metals, metal chelates, metallic cations, chromophores and enzymes, such as those mentioned on page 109 of WO 08/020,079. Other suitable labels will be clear to the skilled person, and for example include moieties that can be detected using NMR or ESR spectroscopy.

Such labelled Nanobodies and polypeptides of the invention may for example be used for in vitro, in vivo or in situ assays (including immunoassays known per se such as ELISA, RIA, EIA and other "sandwich assays", etc.) as well as in vivo diagnostic and imaging purposes, depending on the choice of the specific label.

As will be clear to the skilled person, another modification may involve the introduction of a chelating group, for example to chelate one of the metals or metallic cations referred to above. Suitable chelating groups for example include, without limitation, diethyl-enetriaminepentaacetic acid (DTPA) or ethylenediaminetetraacetic acid (EDTA).

Yet another modification may comprise the introduction of a functional group that is one part of a specific binding pair, such as the biotin-(strept)avidin binding pair. Such a functional group may be used to link the Nanobody of the invention to another protein, polypeptide or chemical compound that is bound to the other half of the binding pair, i.e., through formation of the binding pair. For example, a Nanobody of the invention may be conjugated to biotin, and linked to another protein, polypeptide, compound or carrier conjugated to avidin or streptavidin. For example, such a conjugated Nanobody may be used as a reporter, for example in a diagnostic system where a detectable signal-producing agent is conjugated to avidin or streptavidin. Such binding pairs may for example also be used to bind the Nanobody of the invention to a carrier, including carriers suitable for pharmaceutical purposes. One non-limiting example are the liposomal formulations described by Cao and Suresh, Journal of Drug Targetting, 8, 4, 257 (2000). Such binding pairs may also be used to link a therapeutically active agent to the Nanobody of the invention.

Other potential chemical and enzymatical modifications will be clear to the skilled person. Such modifications may also be introduced for research purposes (e.g., to study function-activity relationships). Reference is for example made to Lundblad and Bradshaw, Biotechnol. Appl. Biochem., 26, 143-151 (1997).

The immunoglobulin single variable domains and polypeptides of the invention as such preferably essentially consist of a single amino acid chain that is not linked via disulphide bridges to any other amino acid sequence or chain (but that may or may not contain one or more intramolecular disulphide bridges. For example, it is known that agent of the invention—as described herein—may sometimes contain a disulphide bridge between CDR3 and CDR1 or FR2). However, it should be noted that one or more immunoglobulin single variable domains of the invention may be linked to each other and/or to other immunoglobulin single variable domains (e.g., via disulphide bridges) to provide peptide constructs that may also be useful in the invention (for example Fab' fragments, F(ab')$_2$ fragments, ScFv constructs, "diabodies" and other multispecific constructs. Reference is for example made to the review by Holliger and Hudson, Nat. Biotechnol. 2005 September; 23(9):1126-36).

Generally, when an amino acid sequence of the invention (or a compound, construct or polypeptide comprising the same) is intended for administration to a subject (for example for therapeutic and/or diagnostic purposes as described herein), it is preferably either an amino acid sequence that does not occur naturally in said subject; or, when it does occur naturally in said subject, is in essentially isolated form (as defined herein).

It will also be clear to the skilled person that for pharmaceutical use, the immunoglobulin single variable domains of the invention (as well as compounds, constructs and polypeptides comprising the same) are preferably directed against human CXCR7 and in particular human CXCR7 (SEQ ID NO: 1); whereas for veterinary purposes, the immunoglobulin single variable domains and polypeptides of the invention are preferably directed against CXCR7 from the species to be treated, or at least cross-reactive with CXCR7 from the species to be treated.

Furthermore, an amino acid sequence of the invention may optionally, and in addition to the at least one binding site for binding against CXCR7 and in particular human CXCR7 (SEQ ID NO: 1), contain one or more further binding sites for binding against other antigens, proteins or targets.

The efficacy of the immunoglobulin single variable domains and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include ligand displacement assays (Burns et al, J. Exp. Med. 2006 4; 203(9):2201-13), beta arrestin recruitment assays (Zabel et al., J. Immunol. 2009 1; 183(5):3204-11), dimerization assays (Luker et al, Faseb J. 2009 23(3): 823-34), signaling assays (Wang et al, J Immunol. 2009 Sep. 1; 183(5):3204-11) proliferation assays (Wang et al, J. Immunol. 2009 Sep. 1; 183(5):3204-11; Odemis et al., J Cell Sign. 2010 Apr. 1; 123(Pt 7): 1081-8), survival assays (Burns et al, J. Exp. Med. 2006 4; 203(9):2201-13), cell adhesion assays (Burns et al, J. Exp. Med. 2006 4; 203(9): 2201-13) and transendothelial migration assays (Mazzinghi et al, J. Exp. Med. 2008 Feb. 18; 205(2):479-90), endothelial cell sprouting assays (Wang et al, J. Immunol. 2009 Sep. 1; 183(5):3204-11), myogenic differentiation (Melchionna et al., Muscle Nerve, 2010 Feb. 11) and in vivo xenograft models (Burns et al, J. Exp. Med. 2006 4; 203(9):2201-13), collagen induced arthritis models (Hegen et al, Ann Rheum Dis. 2008 November; 67(11):1505-15) and experimental autoimmune encephalomyelitis models (Wekerle, Ann Rheum Dis. 2008 December; 67 Suppl 3:iii56-60) as well as the assays and animal models used in the experimental part below and in the prior art cited herein.

Also, according to the invention, immunoglobulin single variable domains and polypeptides that are directed against CXCR7 from a first species of warm-blooded animal may or may not show cross-reactivity with CXCR7 from one or more other species of warm-blooded animal. For example, immunoglobulin single variable domains and polypeptides directed against human CXCR7 and in particular human CXCR7 (SEQ ID NO: 1) may or may not show cross reactivity with CXCR7 from one or more other species of primates (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*)) and/or with CXCR7 from one or more species of animals that are often used in animal models for diseases (for example mouse, rat, rabbit, pig or dog), and in particular in animal models for diseases and disorders associated with CXCR7 and in particular human CXCR7 (SEQ ID NO: 1) (such as the species and animal models mentioned herein). In this respect, it will be clear to the skilled person that such cross-reactivity, when present, may have advantages from a drug development point of view, since it allows the immunoglobulin single variable domains and polypeptides against human CXCR7 and in particular human CXCR7 (SEQ ID NO: 1) to be tested in such disease models (see e.g., Example 12).

More generally, immunoglobulin single variable domains and polypeptides of the invention that are cross-reactive with CXCR7 from multiple species of mammal will usually be advantageous for use in veterinary applications, since it will allow the same amino acid sequence or polypeptide to be used across multiple species. Thus, it is also encompassed within the scope of the invention that immunoglobulin single variable domains and polypeptides directed against CXCR7 from one species of animal (such as immunoglobulin single variable domains and polypeptides against human CXCR7 (SEQ ID NO: 1)) can be used in the treatment of another species of animal, as long as the use of the immunoglobulin single variable domains and/or polypeptides provide the desired effects in the species to be treated.

The present invention is in its broadest sense also not particularly limited to or defined by a specific antigenic determinant, epitope, part, domain, subunit or confirmation (where applicable) of CXCR7 and in particular human CXCR7 (SEQ ID NO: 1) against which the immunoglobulin single variable domains and polypeptides of the invention are directed. For example, the immunoglobulin single variable domains and polypeptides may or may not be directed against the CXCL11/CXCL12 interaction site and/or CXCR7/CXCR7 homodimerization site and/or CXCR4/CXCR7 heterodimerization site (or heterodimerization of CXCR7 to other chemokine receptor such as e.g. CXCR3), and are as further defined herein.

As further described herein, a polypeptide of the invention may contain two or more immunoglobulin single variable domains of the invention that are directed against CXCR7 and in particular human CXCR7 (SEQ ID NO: 1). Generally, such polypeptides will bind to CXCR7 and in particular human CXCR7 (SEQ ID NO: 1) with increased avidity compared to a single amino acid sequence of the invention. Such a polypeptide may for example comprise two immunoglobulin single variable domains of the invention that are directed against the same antigenic determinant, epitope, part, domain, subunit or confirmation (where applicable) of CXCR7 and in particular human CXCR7 (SEQ ID NO: 1) (which may or may not be an interaction site); or comprise at least one "first" amino acid sequence of the invention that is directed against a first same antigenic determinant, epitope, part, domain, subunit or confirmation (where applicable) of CXCR7 and in particular human CXCR7 (SEQ ID NO: 1) (which may or may not be an interaction site), such as for instance Group 1 epitopes; and at least one "second" amino acid sequence of the invention that is directed against a second antigenic determinant, epitope, part, domain, subunit or confirmation (where applicable) different from the first (and which again may or may not be an interaction site), such as for instance Group 2 epitopes. Preferably, in such "biparatopic" polypeptides of the invention, at least one amino acid sequence of the invention is directed against an interaction site (as defined herein), although the invention in its broadest sense is not limited thereto. For instance, polypeptides of the invention may be formatted e.g., in a biparatopic way such as to combine monovalent building blocks directed against different epitopes as characterized in the experimental part (see Examples 9 to 17). Although the binding constants, e.g., association and dissociation constants, of individual immunoglobulin single variable domains of a "bivalent" polypeptide are wholly favourable over the binding constants of the individual immunoglobulin single variable domains of a "biparatopic" polypeptide, the present invention demonstrates completely unexpectedly that a "biparatopic" polypeptide of the invention is more effective in biological assays, e.g., β-arrestin assay, than "bivalent" polypeptides.

Also, when the target is part of a binding pair (for example, a receptor-ligand binding pair), the immunoglobulin single variable domains and polypeptides may be such that they compete with the cognate binding partners, e.g., CXCL11 (also referred to as I-TAC) and/or CXCL12 (also referred to as SDF-1), for binding to CXCR7, and/or such that they (fully or partially) neutralize binding of the binding partner to the target.

It is also expected that the immunoglobulin single variable domains and polypeptides of the invention will generally bind to all naturally occurring or synthetic analogs, variants, mutants, alleles, parts and fragments of CXCR7 and in particular human CXCR7 (SEQ ID NO: 1); or at least to those analogs, variants, mutants, alleles, parts and fragments of CXCR7 and in particular human CXCR7 (SEQ ID NO: 1) that contain one or more antigenic determinants or epitopes that are essentially the same as the antigenic determinant(s) or epitope(s) to which the immunoglobulin single variable domains and polypeptides of the invention bind to CXCR7 and in particular to human CXCR7 (SEQ ID NO: 1). Again, in such a case, the immunoglobulin single variable domains and polypeptides of the invention may bind to such analogs, variants, mutants, alleles, parts and fragments with an affinity and/or specificity that are the same as, or that are different from (i.e., higher than or lower than), the affinity and specificity with which the immunoglobulin single variable domains of the invention bind to (wild-type) CXCR7.

As CXCR7 and in particular human CXCR7 (SEQ ID NO: 1) exists in a monomeric form and in one or more multimeric forms, e.g., in homodimeric as well in heterodimeric form with CXCR4, e.g., human CXCR4 (R M Maksym et al., supra; K E Luker et al. supra), it is within the scope of the invention that the immunoglobulin single variable domains and polypeptides of the invention i) only bind to CXCR7 and in particular human CXCR7 (SEQ ID NO: 1) in monomeric form, ii) only bind to CXCR7 and in particular human CXCR7 (SEQ ID NO: 1) in multimeric/dimeric (homo- and/or heterodimeric) form, or iii) bind to both the monomeric and the multimeric form. In a preferred aspect of the invention, the polypeptides of the invention prevent formation of homodimeric human CXCR7 complexes and/or heterodimeric human CXCR4/CXCR7 complexes. In another preferred aspect of the invention, the polypeptides of the invention do not induce (even at higher concentration such as 10 nM or less, 50 nM or less, 100 nM or less, or 500 nM or less) formation of homodimeric human CXCR7 complexes and/or heterodimeric human CXCR4/CXCR7 complexes. Again, in such a case, the polypeptides of the invention may bind to the monomeric form with an affinity and/or specificity that are the same as, or that are different from (i.e., higher than or lower than), the affinity and specificity with which the immunoglobulin single variable domains of the invention bind to the multimeric form.

Also, when CXCR7 and in particular human CXCR7 (SEQ ID NO: 1) can associate with other proteins or polypeptides to form protein complexes (e.g., with CXCL12/SDF-1 or CXCL11/1-TAC), it is within the scope of the invention that the immunoglobulin single variable domains and polypeptides of the invention bind to CXCR7 and in particular human CXCR7 (SEQ ID NO: 1) in its non-associated state (and e.g. prevent the ligand binding), bind to CXCR7 and in particular human CXCR7 (SEQ ID NO: 1) in its associated state, or bind to both (preferably to the non-associated state). In all these cases, the immunoglobulin single variable domains and polypeptides of the invention may bind to such associated protein complexes with an affinity and/or specificity that may be the same as or different from (i.e., higher than or lower than) the affinity and/or specificity with which the immunoglobulin single variable domains and polypeptides of the invention bind to CXCR7 and in particular human CXCR7 (SEQ ID NO: 1) in its non-associated state.

Also, as will be clear to the skilled person, proteins or polypeptides that contain two or more immunoglobulin single variable domains directed against CXCR7 and in particular human CXCR7 (SEQ ID NO: 1) may bind with higher avidity to CXCR7 and in particular human CXCR7 (SEQ ID NO: 1) than the corresponding monomeric amino acid sequence(s). For example, and without limitation, proteins or polypeptides that contain two or more immunoglobulin single variable domains directed against different epitopes of CXCR7 and in particular human CXCR7 (SEQ ID NO: 1) may (and usually will) bind with higher avidity than each of the different monomers, and proteins or polypeptides that contain two or more immunoglobulin single variable domains directed against CXCR7 and in particular human CXCR7 (SEQ ID NO: 1) may (and usually will) bind also with higher avidity to a multimer (e.g. homodimer, heterodimer with CXCR4) of CXCR7 and in particular to a multimer (e.g. homodimer, heterodimer with human CXCR4) of human CXCR7 (SEQ ID NO: 1).

Generally, immunoglobulin single variable domains and polypeptides of the invention will at least bind to those forms of CXCR7 and in particular human CXCR7 (SEQ ID NO: 1) (including monomeric, multimeric, associated and different conformational forms) that are the most relevant from a biological and/or therapeutic point of view, as will be clear to the skilled person.

It is also within the scope of the invention to use parts, fragments, analogs, mutants, variants, alleles and/or derivatives of the immunoglobulin single variable domains and polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against CXCR7 and in particular human CXCR7 (SEQ ID NO: 1); and more preferably will be capable of specific binding to CXCR7 and in particular human CXCR7 (SEQ ID NO: 1), and even more preferably capable of binding to CXCR7 and in particular human CXCR7 (SEQ ID NO: 1) with an EC50 value, average Ki, $IC_{50}$ value concerning binding, migration, displacing and/or proliferation blocking and/or other measures for potency, as further described herein, e.g., in the experimental part) that is as defined herein and such parts, fragments, analogs, mutants, variants, alleles and/or derivatives may be more potent, more stable, more soluble and may have the same epitope. Some non-limiting examples of such parts, fragments, analogs, mutants, variants, alleles, derivatives, proteins and/or polypeptides will become clear from the further description herein. Additional fragments or polypeptides of the invention may also be provided by suitably combining (i.e. by linking or genetic fusion) one or more (smaller) parts or fragments as described herein.

For a general description of immunoglobulin single variable domains, reference is made to the further description below, as well as to the prior art cited herein. In this respect, it should however be noted that this description and the prior art mainly describes immunoglobulin single variable domains of the so-called "$V_H3$ class" (i.e., immunoglobulin single variable domains with a high degree of sequence homology to human germline sequences of the $V_H3$ class, such as DP-47, DP-51 or DP-29), which form a preferred aspect of this invention. It should however be noted that the invention in its broadest sense generally covers any type of immunoglobulin single variable domains directed against CXCR7 and in particular human CXCR7 (SEQ ID NO: 1), and for example also covers the immunoglobulin single variable domains belonging to the so-called "$V_H4$ class" (i.e., immunoglobulin single variable domains with a high degree of sequence homology to human germline sequences of the $V_H4$ class such as DP-78), as for example described in WO 07/118,670.

Generally, immunoglobulin single variable domains (in particular $V_{HH}$ sequences and sequence optimized immunoglobulin single variable domains) can in particular be characterized by the presence of one or more "Hallmark residues" (as described herein) in one or more of the framework sequences (again as further described herein).

Thus, generally, an immunoglobulin single variable domain can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively.

In a preferred aspect, the invention provides polypeptides comprising at least an immunoglobulin single variable domain that is an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) at least one of the amino acid residues at positions 11, 37, 44, 45, 47, 83, 84, 103, 104 and 108 according to the Kabat numbering are chosen from the Hallmark residues mentioned in Table A-1 below; and/or in which:

ii) said amino acid sequence has at least 80%, more preferably 90%, even more preferably 95% amino acid identity with at least one of the immunoglobulin single variable domains as shown in WO 2009/138519 (see SEQ ID NOs: 1 to 125 in WO 2009/138519), in which for the purposes of determining the degree of amino acid identity, the amino acid residues that form the CDR sequences (indicated with X in the sequences) are disregarded; and/or in which:

iii) the CDR sequences are generally as further defined herein (e.g. the CDR1, CDR2 and CDR3 in a combination as provided in Table B-2, note that the CDR definitions are calculated according to the Kabat numbering system); and/or in which:

iv) the FR sequences are generally as further defined herein, such as, for instance, the FR1, FR2, FR3 and FR4 in a combination as provided in Table B-2, and/or FR1, FR2, FR3 and FR4 has at least 80%, more preferably 90%, even more preferably 95% amino acid identity with at least one of FR1, FR2, FR3 and FR4, respectively, of the FRs as provided in Table B-2 (wherein the FR definitions are calculated according to the Kabat numbering system).

TABLE A-1

Hallmark Residues in VHHs

| Position | Human V$_H$3 | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | F$^{(1)}$, Y, V, L, A, H, S, I, W, C, N, G, D, T, P, preferably F$^{(1)}$ or Y |
| 44$^{(8)}$ | G | E$^{(3)}$, Q$^{(3)}$, G$^{(2)}$, D, A, K, R, L, P, S, V, H, T, N, W, M, I; preferably G$^{(2)}$, E$^{(3)}$ or Q$^{(3)}$; most preferably G$^{(2)}$ or Q$^{(3)}$. |
| 45$^{(8)}$ | L | L$^{(2)}$, R$^{(3)}$, P, H, F, G, Q, S, E, T, Y, C, I, D, V; preferably L$^{(2)}$ or R$^{(3)}$ |
| 47$^{(8)}$ | W, Y | F$^{(1)}$, L$^{(1)}$ or W$^{(2)}$ G, I, S, A, V, M, R, Y, E, P, T, C, H, K, Q, N, D; preferably W$^{(2)}$, L$^{(1)}$ or F$^{(1)}$ |
| 83 | R or K; usually R | R, K$^{(5)}$, T, E$^{(5)}$, Q, N, S, I, V, G, M, L, A, D, Y, H; preferably K or R; most preferably K |
| 84 | A, T, D; predominantly A | P$^{(5)}$, S, H, L, A, V, I, T, F, D, R, Y, N, Q, G, E; preferably P |
| 103 | W | W$^{(4)}$, R$^{(6)}$, G, S, K, A, M, Y, L, F, T, N, V, Q, P$^{(6)}$, E, C; preferably W |
| 104 | G | G, A, S, T, D, P, N, E, C, L; preferably G |
| 108 | L, M or T; predominantly L | Q, L$^{(7)}$, R, P, E, K, S, T, M, A, H; preferably Q or L$^{(7)}$ |

$^{(1)}$In particular, but not exclusively, in combination with KERE or KQRE at positions 43-46.
$^{(2)}$Usually as GLEW at positions 44-47.
$^{(3)}$Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREL or QQREF), KGRE (for example KGREG), KDRE (for example KDREV) are possible. Some other possible, but less preferred sequences include for example DECKL and NVCEL.
$^{(4)}$With both GLEW at positions 44-47 and KERE or KQRE at positions 43-46.
$^{(5)}$Often as KP or EP at positions 83-84 of naturally occurring V$_{HH}$ domains.
$^{(6)}$In particular, but not exclusively, in combination with GLEW at positions 44-47.
$^{(7)}$With the proviso that when positions 44-47 are GLEW, position 108 is always Q in (non-humanized) V$_{HH}$ sequences that also contain a W at 103.
$^{(8)}$The GLEW group also contains GLEW-like sequences at positions 44-47, such as for example GVEW, EPEW, GLER, DQEW, DLEW, GIEW, ELEW, GPEW, EWLP, GPER, GLER and ELEW.

Again, such immunoglobulin single variable domains may be derived in any suitable manner and from any suitable source, and may for example be naturally occurring V$_{HH}$ sequences (i.e., from a suitable species of Camelid, e.g., llama) or synthetic or semi-synthetic VHs or VLs (e.g., from human). Such immunoglobulin single variable domains may include "humanized" or otherwise "sequence optimized" VHHs, "camelized" immunoglobulin sequences (and in particular camelized heavy chain variable domain sequences, i.e., camelized VHs), as well as human VHs, human VLs, camelid VHHs that have been altered by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein.

In a further preferred aspect, the invention provides polypeptides comprising one immunoglobulin single variable domain with amino acid sequence selected from the group consisting of amino acid sequences with SEQ ID NOs: 39 to 43 and 91 as well as 99-102 (see Table B-3) and one immunoglobulin single variable domain with amino acid sequence selected from the group consisting of moieties providing an increased half-life (see below).

In a further preferred aspect, the invention provides polypeptides comprising at least one immunoglobulin single variable domain with amino acid sequence selected from the group consisting of amino acid sequences that essentially consist of 4 framework regions (FR1 to FR4, respectively) and 3 complementarity determining regions (CDR1 to CDR3, respectively), in which the CDR sequences of said amino acid sequences have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains of SEQ ID NOs: 39 to 43 and 91 as well as 99-102 (see Tables B-2 and B-3). This degree of amino acid identity can for example be determined by determining the degree of amino acid identity (in a manner described herein) between said amino acid sequence and one or more of the sequences of SEQ ID NOs: 39 to 43 and 91 as well as 99-102 (see Tables B-2 and B-3), in which the amino acid residues that form the framework regions are disregarded. Such polypeptides and/or immunoglobulin single variable domains of the invention may further provide the following:

1. polypeptides comprising at least one immunoglobulin single variable domain that is directed against (as defined herein) CXCR7 and in particular human CXCR7 (SEQ ID NO: 1) and that has at least 80%, preferably at least 85%, such as 90% or 95% or more sequence identity with at least one of the immunoglobulin single variable domains of SEQ ID NOs: 39 to 43 and 91 as well as 99-102 (see Table B-3);
2. polypeptides comprising at least one immunoglobulin single variable domain that is directed against (as defined herein) CXCR7 and in particular human CXCR7 (SEQ ID NO: 1) and that cross-block (as defined herein) the binding of at least one of the immunoglobulin single variable domains of SEQ ID NOs: 39 to 43 and 91 as well as 99-102 (see Table B-3) to CXCR7 and in particular human CXCR7 (SEQ ID NO: 1) and/or that compete with at least one of the immunoglobulin single variable domains of SEQ ID NOs: 39 to 43 and 91 as well as 99-102 (see Table B-3) for binding to CXCR7 and in particular human CXCR7 (SEQ ID NO: 1); and
3. which immunoglobulin single variable domains may be as further described herein; as well as polypeptides of the invention that comprise one or more of such immunoglobulin single variable domains (which may be as further described herein, and may for example be bispecific (e.g., also bind to serum albumin) and/or biparatopic polypeptides as described herein), and nucleic acid sequences that encode such immunoglobulin single variable domains and polypeptides. Such immunoglobulin single variable domains and polypeptides do not include any naturally occurring ligands.

The polypeptides of the invention comprise or essentially consist of at least one immunoglobulin single variable domain of the invention. Some preferred, but non-limiting examples of immunoglobulin single variable domains of the invention are given in SEQ ID NOs: 39 to 43 and 91 as well as 99-102 (see Table B-3).

1.2. Serum Albumin Binding Building Blocks or Other Building Blocks Increasing Half-Life In another aspect, the invention relates to a compound or construct, and in particular to a protein or polypeptide (also referred to herein as a "compound of the invention" or "polypeptide of the invention", respectively) that comprises or essentially consists of one or more (preferably one) immunoglobulin single variable domains directed to human CXCR7 (or suitable fragments thereof), and optionally further comprises one or more other groups, residues, moieties or binding units. As will become clear to the skilled person from the further disclosure herein, such further groups, residues, moieties, binding units or immunoglobulin single variable domains may or may not provide further functionality to the amino acid sequence of the invention (and/or to the compound or construct in which it is present) and may or may not modify the properties of the amino acid sequence of the invention.

As will be clear from the further description above and herein, this means that the immunoglobulin single variable domains of the invention can be used as "building blocks" to form polypeptides of the invention, i.e. by suitably combining them with other groups, residues, moieties or binding units, in order to form compounds or constructs as described herein (such as, without limitations, the biparatopic, bi/multivalent and bi/multispecific polypeptides of the invention described herein) which combine within one molecule one or more desired properties or biological functions.

The compounds or polypeptides of the invention can generally be prepared by a method which comprises at least one step of suitably linking the one or more immunoglobulin single variable domains of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

The process of designing/selecting and/or preparing a compound or polypeptide of the invention, starting from an amino acid sequence of the invention, is also referred to herein as "formatting" said amino acid sequence of the invention; and an amino acid of the invention that is made part of a compound or polypeptide of the invention is said to be "formatted" or to be "in the format of" said compound or polypeptide of the invention. Examples of ways in which an amino acid sequence of the invention can be formatted and examples of such formats will be clear to the skilled person based on the disclosure herein; and such formatted immunoglobulin single variable domains form a further aspect of the invention.

For example, such further groups, residues, moieties or binding units may be one or more additional immunoglobulin single variable domains, such that the compound or construct is a (fusion) protein or (fusion) polypeptide. In a preferred but non-limiting aspect, said one or more other groups, residues, moieties or binding units are immunoglobulin sequences. Even more preferably, said one or more other groups, residues, moieties or binding units are chosen from the group consisting of domain antibodies, immunoglobulin single variable domains that are suitable for use as a domain antibody, single domain antibodies, immunoglobulin single variable domains that are suitable for use as a single domain antibody, "dAb's", immunoglobulin single variable domains that are suitable for use as a dAb, or Nanobodies. Alternatively, such groups, residues, moieties or binding units may for example be chemical groups, residues, moieties, which may or may not by themselves be biologically and/or pharmacologically active. For example, and without limitation, such groups may be linked to the one or more immunoglobulin single variable domains of the invention so as to provide a "derivative" of an amino acid sequence or polypeptide of the invention, as further described herein.

Also within the scope of the present invention are compounds or constructs, that comprises or essentially consists of one or more derivatives as described herein, and optionally further comprises one or more other groups, residues, moieties or binding units, optionally linked via one or more linkers. Preferably, said one or more other groups, residues, moieties or binding units are immunoglobulin single variable domains. In the compounds or constructs described above, the one or more immunoglobulin single variable domains of the invention and the one or more groups, residues, moieties or binding units may be linked directly to each other and/or via one or more suitable linkers or spacers. For example, when the one or more groups, residues, moieties or binding units are immunoglobulin single variable domains, the linkers may also be immunoglobulin single variable domains, so that the resulting compound or construct is a fusion (protein) or fusion (polypeptide).

In one specific, but non-limiting aspect of the invention, which will be further described herein, the polypeptides of the invention have an increased half-life in serum (as further described herein) compared to the immunoglobulin single variable domain from which they have been derived. For example, an immunoglobulin single variable domain of the invention may be linked (chemically or otherwise) to one or more groups or moieties that extend the half-life (such as PEG), so as to provide a derivative of an amino acid sequence of the invention with increased half-life.

In one specific aspect of the invention, a compound of the invention or a polypeptide of the invention may have an increased half-life, compared to the corresponding amino acid sequence of the invention. Some preferred, but non-limiting examples of such compounds and polypeptides will become clear to the skilled person based on the further disclosure herein, and for example comprise immunoglobulin single variable domains or polypeptides of the invention that have been chemically modified to increase the half-life thereof (for example, by means of pegylation); immunoglobulin single variable domains of the invention that comprise at least one additional binding site for binding to a serum protein (such as serum albumin); or polypeptides of the invention that comprise at least one amino acid sequence of the invention that is linked to at least one moiety (and in particular at least one amino acid sequence) that increases the half-life of the amino acid sequence of the invention. Examples of polypeptides of the invention that comprise such half-life extending moieties or immunoglobulin single variable domains will become clear to the skilled person based on the further disclosure herein; and for example include, without limitation, polypeptides in which the one or more immunoglobulin single variable domains of the invention are suitably linked to one or more serum proteins or fragments thereof (such as (human) serum albumin or suitable fragments thereof) or to one or more binding units that can bind to serum proteins (such as, for example, domain antibodies, immunoglobulin single variable domains that are suitable for use as a domain antibody, single domain antibodies, immunoglobulin single variable domains that are suitable for use as a single domain antibody, "dAb's", immunoglobulin single variable domains that are suitable for use as a dAb, or Nanobodies that can bind to serum proteins such as serum albumin (such as human serum albumin), serum immunoglobulins such as IgG, or transferrin; reference is made to the further description and references mentioned herein); polypeptides in which an amino acid sequence of the invention is linked to an Fc portion (such as a human Fc) or a suitable part or fragment thereof; or polypeptides in which the one or more immunoglobulin single variable domains of the invention are suitable linked to one or more small proteins or peptides that can bind to serum proteins (such as, without limitation, the proteins and peptides described in WO 91/01743, WO 01/45746, WO 02/076489, WO2008/068280, WO2009/127691).

Generally, the compounds or polypeptides of the invention with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the compounds or polypeptides of the invention with increased half-life may have a half-life e.g., in humans that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such compounds or polypeptides of the invention have a serum half-life e.g., in humans that is increased with more than 1 hours, preferably more than 2 hours, more preferably more than 6 hours, such as more than 12 hours, or even more than 24, 48 or 72 hours, compared to the corresponding amino acid sequence of the invention per se.

In another preferred, but non-limiting aspect of the invention, such compounds or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least 11 days (such as about 11 to 16 days), more preferably at least about 12 days (such as about 12 to 18 days or more), or more than 14 days (such as about 14 to 19 days).

In a particular preferred but non-limiting aspect of the invention, the invention provides a polypeptide of the invention comprising i) one CXCR7 binding immunoglobulin single variable domain as described herein; and ii) one or more (preferably one) serum albumin binding immunoglobulin single variable domain as described herein.

In a further preferred aspect, the invention provides a polypeptide of the invention comprising i) one or more CXCR7 binding immunoglobulin single variable domain as described herein; and ii) one or more (preferably one) serum albumin binding immunoglobulin single variable domain of SEQ ID NO: 2 (Table B-1).

In a further preferred aspect, the invention provides a polypeptide of the invention comprising i) one or more CXCR7 binding immunoglobulin single variable domain as described herein; and ii) one or more (preferably one) serum albumin binding immunoglobulin single variable domain with CDRs (defined according to the Kabat numbering) of SEQ ID NO: 2 (Table B-2, B-1).

Thus, for example, further reference (and thus incorporated by reference) is made in particular to the experimental part and further description of WO2008/068280, wherein further details on SEQ ID NO: 2 is made and e.g., the half-life of a immunoglobulin single variable domain construct containing said sequence in rhesus monkeys is disclosed.

Generally, proteins or polypeptides that comprise or essentially consist of a single immunoglobulin single variable domain will be referred to herein as "monovalent" proteins or polypeptides or as "monovalent constructs". Proteins and polypeptides that comprise or essentially consist of two or more immunoglobulin single variable domains (such as at least two immunoglobulin single variable domains of the invention or at least one immunoglobulin single variable domain of the invention and at least one other immunoglobulin single variable domain) will be referred to herein as "multivalent" proteins or polypeptides or as "multivalent constructs", and these may provide certain advantages compared to the corresponding monovalent immunoglobulin single variable domains of the invention. Some non-limiting examples of such multivalent constructs will become clear from the further description herein.

According to another specific, but non-limiting aspect, a polypeptide of the invention comprises or essentially consists of at least one immunoglobulin single variable domain of the invention and at least one other binding unit (i.e. directed against another epitope, antigen, target, protein or polypeptide), which is preferably also a immunoglobulin single variable domain. Such proteins or polypeptides are also referred to herein as "multispecific" proteins or polypeptides or as "multispecific constructs", and these may comprise of two immunoglobulin single variable domains of the invention, such as one immunoglobulin single variable domain directed against CXCR7 and one immunoglobulin single variable domain against serum albumin. Such multispecific constructs will be clear to the skilled person based on the disclosure herein; some preferred, but non-limiting examples of such multispecific immunoglobulin single variable domains are the constructs of SEQ ID NOs: 44 to 48, 80-81, 83-85 and 88-89 as well as 131-140 (see Table B-4), as well as clones 009, 013, 018-029, 031-038, 044, 046, 048-053, 055-058, 060, 061, 063, 065, 068, 069, 072, 081-086 and 093 (Tables B-12 to B-14).

According to yet another specific, but non-limiting aspect, a polypeptide of the invention comprises or essentially consists of at least one immunoglobulin single variable domain of the invention, optionally one or more further immunoglobulin single variable domains, and at least one other amino acid sequence (such as a protein or polypeptide) that confers at least one desired property to the immunoglobulin single variable domain of the invention and/or to the resulting fusion protein. Again, such fusion proteins may provide certain advantages compared to the corresponding monovalent immunoglobulin single variable domains of the invention such as e.g. may provide an increased half-life.

In the above constructs, the one or more immunoglobulin single variable domains and/or other immunoglobulin single variable domains may be directly linked to each other and/or suitably linked to each other via one or more linker sequences. Some suitable but non-limiting examples of such linkers will become clear from the further description herein.

In one embodiment, the linker sequence joining the immunoglobulin single variable domains are SEQ ID NOs: 49 to 58—see Table B-5, or a combination of both, or as known in the art.

According to yet another specific, but non-limiting aspect, a polypeptide of the invention may for example be chosen from the group consisting of immunoglobulin single variable domains that have more than 80%, preferably more than 90%, more preferably more than 95%, such as 99% or more "sequence identity" (as defined herein) with one or more of the immunoglobulin single variable domains of SEQ ID NOs: 39 to 43 and 91 as well as 99-102 (see Table B-3), in which the polypeptides are preferably as further defined herein, i.e., in the preferred format of one immunoglobulin single variable domain directed against CXCR7 and one immunoglobulin singe variable domain directed against serum albumin.

According to yet another specific, but non-limiting aspect, a polypeptide of the invention may for example be chosen from the group consisting of polypeptides that have more than 80%, preferably more than 90%, more preferably more than 95%, such as 99% or more "sequence identity" (as defined herein) with one or more of the polypeptides of SEQ ID NOs: 44 to 48 (see Table B-4). Some illustrative non-limiting examples of biparatopic and bispecific polypeptides of the invention are given in SEQ ID NOs: 78 to 89 as well as SEQ ID NOs: 131-140, or clones 009, 013, 018-029, 031-038, 044, 046, 048-053, 055-058, 060, 061, 063, 065, 068, 069, 072, 081-086 and 093 (Tables B-12 to B-14).

1.3. Compositions of the Invention

Generally, for pharmaceutical use, the polypeptides of the invention may be formulated as a pharmaceutical preparation or composition comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc. wherein which the parenteral administration is preferred. Such suitable administration forms—which may be solid, semi-solid or liquid, depending on the manner of administration—as well as methods and carriers for use in the preparation thereof, will be clear to the skilled person, and are further described herein. Such a pharmaceutical preparation or composition will generally be referred to herein as a "pharmaceutical composition". A pharmaceutical preparation or composition for use in a non-human organism will generally be referred to herein as a "veterinary composition".

Thus, in a further aspect, the invention relates to a pharmaceutical composition that contains at least one amino acid of the invention, at least one polypeptide of the invention or at least one polypeptide of the invention and at least one suitable carrier, diluent or excipient (i.e., suitable for pharmaceutical use), and optionally one or more further active substances.

Generally, the polypeptides of the invention can be formulated and administered in any suitable manner known per se. Reference is for example made to the general background art cited above (and in particular to WO 04/041862, WO 04/041863, WO 04/041865, WO 04/041867 and WO 08/020,079) as well as to the standard handbooks, such as Remington's Pharmaceutical Sciences, 18th Ed., Mack Publishing Company, USA (1990), Remington, the Science and Practice of Pharmacy, 21th Edition, Lippincott Williams and Wilkins (2005); or the Handbook of Therapeutic Antibodies (S. Dubel, Ed.), Wiley, Weinheim, 2007 (see for example pages 252-255).

The polypeptides of the invention may be formulated and administered in any manner known per se for conventional antibodies and antibody fragments (including ScFv's and diabodies) and other pharmaceutically active proteins. Such formulations and methods for preparing the same will be clear to the skilled person, and for example include preparations suitable for parenteral administration (for example intravenous, intraperitoneal, subcutaneous, intramuscular, intraluminal, intra-arterial or intrathecal administration) or for topical (i.e., transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020,079. In one embodiment, the preparation is an aqueous solution or suspension.

The polypeptides of the invention can be administered using gene therapy methods of delivery. See, e.g., U.S. Pat. No. 5,399,346, which is incorporated by reference for its gene therapy delivery methods. Using a gene therapy method of delivery, primary cells transfected with the gene encoding an amino acid sequence, polypeptide of the invention can additionally be transfected with tissue specific promoters to target specific organs, tissue, grafts, tumors, or cells and can additionally be transfected with signal and stabilization sequences for subcellularly localized expression.

Thus, the polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the polypeptide of the invention. Their percentage in the compositions and preparations may, of course, be varied and may conveniently be between about 2 to about 60% of the weight of a given unit dosage form. The amount of the polypeptide of the invention in such therapeutically useful compositions is such that an effective dosage level will be obtained.

For local administration at the site of tumor resection, the polypeptides of the invention may be used in biodegradable polymeric drug delivery systems, slow release poly(lactic-co-glycolic acid formulations and the like (Hart et al., Cochrane Database Syst Rev. 2008 Jul. 16; (3): CD007294).

In a further preferred aspect of the invention, the polypeptides of the invention, such as a polypeptide consisting essentially of one monovalent anti-human CXCR7 immunoglobulin single variable domain and of one monovalent anti-human serum albumin immunoglobulin single variable domain linked by a GS linker, may have a beneficial distribution and kinetics profile in solid tumors compared to conventional antibodies such as e.g., IgG.

The tablets, troches, pills, capsules, and the like may also contain binders, excipients, disintegrating agents, lubricants and sweetening or flavoring agents, for example those mentioned on pages 143-144 of WO 08/020,079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptides of the invention, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The polypeptides of the invention may also be administered intravenously or intraperitoneally by infusion or injection. Particular examples are as further described on pages 144 and 145 of WO 08/020,079.

For topical administration, the polypeptides of the invention may be applied in pure form, i.e., when they are liquids. However, it will generally be desirable to administer them to the skin as compositions or formulations, in combination with a dermatologically acceptable carrier, which may be a solid or a liquid. Particular examples are as further described on page 145 of WO 08/020,079.

Generally, the concentration of the polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the polypeptides of the invention required for use in treatment will vary not only with the particular polypeptide selected but also with the route of administration, the nature of the condition being treated and the age and condition of the patient and will be ultimately at the discretion of the attendant physician or clinician. Also the dosage of the polypeptides of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed. 4), Mack Publishing Co., Easton, Pa. The dosage can also be adjusted by the individual physician in the event of any complication.

In another aspect, the invention relates to a method for the prevention and/or treatment of at least one diseases and disorders associated with CXCR7, said method comprising administering, to a subject in need thereof, a pharmaceutically active amount of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention relates to a method for the prevention and/or treatment of at least one disease or disorder that is associated with CXCR7, with its biological or pharmacological activity, and/or with the biological pathways or signaling in which CXCR7 is involved, said method comprising administering, to a subject in need thereof, a pharmaceutically active amount of an amino acid sequence of the invention, of a Polypeptide of the invention, of a polypeptide of the invention, and/or of a pharmaceutical composition comprising the same. In one embodiment, the invention relates to a method for the prevention and/or treatment of at least one disease or disorder that can be treated by modulating CXCR7, its biological or pharmacological activity, and/or the biological pathways or signaling in which CXCR7 is involved, said method comprising administering, to a subject in need thereof, a pharmaceutically active amount of a polypeptide of the invention, and/or of a pharmaceutical composition comprising the same. In one embodiment, said pharmaceutically effective amount may be an amount that is sufficient to modulate CXCR7, its biological or pharmacological activity, and/or the biological pathways or signaling in which CXCR7 is involved; and/or an amount that provides a level of the polypeptide of the invention in the circulation that is sufficient to modulate CXCR7, its biological or pharmacological activity, and/or the biological pathways or signaling in which CXCR7 is involved.

In one embodiment the invention relates to a method for the prevention and/or treatment of at least one disease or disorder that can be prevented and/or treated by administering a polypeptide of the invention, or a nucleotide construct of the invention encoding the same, and/or of a pharmaceutical composition comprising the same, to a patient. In one embodiment, the method comprises administering a pharmaceutically active amount of a polypeptide of the invention, or a nucleotide construct of the invention encoding the same, and/or of a pharmaceutical composition comprising the same to a subject in need thereof.

In one embodiment the invention relates to a method for the prevention and/or treatment of at least one disease or disorder that can be prevented and/or treated by inhibiting binding of CXCL12 and/or CXCL11 to CXCR7 in specific cells or in a specific tissue of a subject to be treated (and in particular, by inhibiting binding of CXCL12 and/or CXCL11 to CXCR7 in cancer cells or in a tumor present in the subject to be treated), said method comprising administering a pharmaceutically active amount of a polypeptide of the invention, or a nucleotide construct of the invention encoding the same, and/or of a pharmaceutical composition comprising the same, to a subject in need thereof.

In one embodiment, the invention relates to a method for the prevention and/or treatment of at least one disease or disorder chosen from the group consisting of the diseases and disorders listed herein, said method comprising administering, to a subject in need thereof, a polypeptide of the invention, or a nucleotide construct of the invention encoding the same, and/or of a pharmaceutical composition comprising the same.

In one embodiment, the invention relates to a method for immunotherapy, and in particular for passive immunotherapy, which method comprises administering, to a subject suffering from or at risk of the diseases and disorders mentioned herein, a pharmaceutically active amount of a polypeptide of the invention, or a nucleotide construct of the invention encoding the same, and/or of a pharmaceutical composition comprising the same.

In the above methods, the amino acid sequences, polypeptides of the invention and/or the compositions comprising the same can be administered in any suitable manner, depending on the specific pharmaceutical formulation or composition to be used. Thus, the polypeptides of the invention and/or the compositions comprising the same can for example be administered orally, intraperitoneally (e.g. intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more polypeptides of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of the diseases and disorders mentioned herein and depending on the specific disease or disorder to be treated, the potency of the specific polypeptide of the invention to be used, the specific route of administration and the specific pharmaceutical formulation or composition used, the polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g., by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

In one embodiment, a single contiguous polypeptide of the invention will be used. In one embodiment two or more polypeptides of the invention are provided in combination.

The polypeptides of the invention may be used in combination with one or more further pharmaceutically active compounds or principles, i.e., as a combined treatment regimen, which may or may not lead to a synergistic effect. Again, the clinician will be able to select such further compounds or principles, as well as a suitable combined treatment regimen, based on the factors cited above and his expert judgment.

In particular, the polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician, and generally include the cytostatic active principles usually applied for the treatment of the tumor to be treated.

Specific contemplated combinations for use with the polypeptides of the invention for oncology include, but are not limited to, e.g., CXCR4 antagonists such as e.g., AMD3100, other chemokine receptor antagonists, taxol; gemcitobine; cisplatin; cIAP inhibitors (such as inhibitors to cIAP1, cIAP2 and/or XIAP); MEK inhibitors including but not limited to, e.g., U0126, PD0325901; bRaf inhibitors including but not limited to, e.g., RAF265; and mTOR inhibitors including but not limited to, e.g., RAD001; VEGF inhibitors including but not limited to e.g. bevacizumab, sutinib and sorafenib; Her 2 inhibitors including but not limited to e.g., trastuzumab and lapatinib; PDGFR, FGFR, src, JAK, STAT and/or GSK3 inhibitors; selective estrogen receptor modulators including but not limited to tamoxifen; estrogen receptor downregulators including but not limited to fulvestrant. Specific contemplated combinations for use with the polypeptides of the invention for inflammatory conditions include, but are not limited to, e.g., interferon beta 1 alpha and beta, natalizumab; TNF alpha antagonists including but not limited to e.g., infliximab, adalimumab, certolizumab pegol, etanercept; disease-modifying antirheumatic drugs such as e.g., methotrexate glucocorticoids including but not limited to e.g. hydrocortisone; Nonsteroidal anti-inflammatory drugs including but not limited to e.g., ibuprofen, sulindac.

Other specific compounds/polypeptides that could be used in combination (therapy) with the compounds/polypeptides of the invention are the amino acid sequences and polypeptides directed against CXCR4 that are described in the international application WO 09/138,519 by Ablynx N.V., the non-prepublished U.S. application 61/358,495 by Ablynx N.V. filed on Jun. 25, 2010; the PCT application PCT/EP210/064766 by Ablynx N.V. filed on Oct. 4, 2010; and/or the PCT application PCT/EP2011/050156 by Ablynx N.V. filed on Jan. 7, 2011.

When two or more substances or principles are to be used as part of a combined treatment regimen, they can be administered via the same route of administration or via different routes of administration, at essentially the same time or at different times (e.g., essentially simultaneously, consecutively, or according to an alternating regime). When the substances or principles are to be administered simultaneously via the same route of administration, they may be administered as different pharmaceutical formulations or compositions or part of a combined pharmaceutical formulation or composition, as will be clear to the skilled person.

Also, when two or more active substances or principles are to be used as part of a combined treatment regimen, each of the substances or principles may be administered in the same amount and according to the same regimen as used when the compound or principle is used on its own, and such combined use may or may not lead to a synergistic effect. However, when the combined use of the two or more active substances or principles leads to a synergistic effect, it may also be possible to reduce the amount of one, more or all of the substances or principles to be administered, while still achieving the desired therapeutic action. This may for example be useful for avoiding, limiting or reducing any unwanted side-effects that are associated with the use of one or more of the substances or principles when they are used in their usual amounts, while still obtaining the desired pharmaceutical or therapeutic effect.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of polypeptide of the invention in the preparation of a pharmaceutical composition for prevention and/or treatment of at least one of the diseases and disorders associated with CXCR7; and/or for use in one or more of the methods of treatment mentioned herein.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases and disorders mentioned herein.

The invention relates to the use of a polypeptide of the invention, or a nucleotide encoding the same, in the preparation of a pharmaceutical composition for the prevention and/or treatment of at least one disease or disorder that can be prevented and/or treated by administering a polypeptide of the invention, or a nucleotide encoding the same, and/or a pharmaceutical composition of the same to a patient.

More in particular, the invention relates to the use of a polypeptide of the invention, or a nucleotide encoding the same, in the preparation of a pharmaceutical composition for the prevention and/or treatment of diseases and disorders associated with CXCR7, and in particular for the prevention and treatment of one or more of the diseases and disorders listed herein.

Again, in such a pharmaceutical composition, the one or more polypeptide of the invention, or nucleotide encoding the same, and/or a pharmaceutical composition of the same, may also be suitably combined with one or more other active principles, such as those mentioned herein.

The invention also relates to a composition (such as, without limitation, a pharmaceutical composition or preparation as further described herein) for use, either in vitro (e.g., in an in vitro or cellular assay) or in vivo (e.g., in an a single cell or multicellular organism, and in particular in a mammal, and more in particular in a human being, such as in a human being that is at risk of or suffers from a disease or disorder of the invention).

In the context of the present invention, "modulating" or "to modulate" generally means reducing or inhibiting the activity of CXCR7 and in particular human CXCR7 (SEQ ID NO: 1), as measured using a suitable in vitro, cellular or in vivo assay (such as those mentioned herein). In particular, reducing or inhibiting the activity of CXCR7 and in particular human CXCR7 (SEQ ID NO: 1), as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to activity of CXCR7 and in particular human CXCR7 (SEQ ID NO: 1) in the same assay under the same conditions but without the presence of the polypeptide of the invention.

Modulating may for example involve reducing or inhibiting the binding CXCR7 to one of its substrates or ligands and/or competing with natural ligands (CXCL11 and/or CXCL12), substrate for binding to CXCR7.

1.4. Generation of the Polypeptides of the Invention

The invention further relates to methods for preparing or generating the immunoglobulin single variable domains, polypeptides, nucleic acids, host cells, products and compositions described herein. Some preferred but non-limiting examples of such methods will become clear from the further description herein.

Generally, these methods may comprise the steps of:
a) providing a set, collection or library of immunoglobulin single variable domains; and
b) screening said set, collection or library of immunoglobulin single variable domains for immunoglobulin single variable domains that can bind to and/or have affinity for CXCR7 and in particular human CXCR7 (SEQ ID NO: 1); and
c) isolating the amino acid sequence(s) that can bind to and/or have affinity for CXCR7 and in particular human CXCR7 (SEQ ID NO: 1).

In such a method, the set, collection or library of immunoglobulin single variable domains may be any suitable set, collection or library of immunoglobulin single variable domains. For example, the set, collection or library of immunoglobulin single variable domains may be a set, collection or library of immunoglobulin sequences (as described herein), such as a naïve set, collection or library of immunoglobulin sequences; a synthetic or semi-synthetic set, collection or library of immunoglobulin sequences; and/or a set, collection or library of immunoglobulin sequences that have been subjected to affinity maturation.

Also, in such a method, the set, collection or library of immunoglobulin single variable domains may be a set, collection or library of heavy or light chain variable domains (such as VL-, VH- or VHH domains). For example, the set, collection or library of immunoglobulin single variable domains may be a set, collection or library of domain antibodies or single domain antibodies, or may be a set, collection or library of immunoglobulin single variable domains that are capable of functioning as a domain antibody or single domain antibody.

In a preferred aspect of this method, the set, collection or library of immunoglobulin single variable domains may be an immune set, collection or library of immunoglobulin sequences, for example derived from a mammal that has been suitably immunized with CXCR7 and in particular human CXCR7 (SEQ ID NO: 1) or with a suitable antigenic determinant based thereon or derived therefrom, such as an antigenic part, fragment, region, domain, loop or other epitope thereof. In one particular aspect, said antigenic determinant may be an extracellular part, region, domain, loop or other extracellular epitope(s).

In the above methods, the set, collection or library of immunoglobulin single variable domains may be displayed on a phage, phagemid, ribosome or suitable micro-organism (such as yeast), such as to facilitate screening. Suitable methods, techniques and host organisms for displaying and screening (a set, collection or library of) immunoglobulin single variable domains will be clear to the person skilled in the art, for example on the basis of the further disclosure herein. Reference is also made to the review by Hoogenboom in Nature Biotechnology, 23, 9, 1105-1116 (2005).

In another aspect, the method for generating immunoglobulin single variable domains comprises at least the steps of:
a) providing a collection or sample of cells expressing immunoglobulin single variable domains;
b) screening said collection or sample of cells for cells that express an amino acid sequence that can bind to and/or have affinity for CXCR7 and in particular human CXCR7 (SEQ ID NO: 1); and
c) either (i) isolating said amino acid sequence; or (ii) isolating from said cell a nucleic acid sequence that encodes said amino acid sequence, followed by expressing said amino acid sequence.

In another aspect, the method for generating an amino acid sequence directed against CXCR7 and in particular human CXCR7 (SEQ ID NO: 1) may comprise at least the steps of:
a) providing a set, collection or library of nucleic acid sequences encoding immunoglobulin single variable domains;
b) screening said set, collection or library of nucleic acid sequences for nucleic acid sequences that encode an amino acid sequence that can bind to and/or has affinity for CXCR7 and in particular human CXCR7 (SEQ ID NO: 1); and
c) isolating said nucleic acid sequence, followed by expressing said amino acid sequence.

In such a method, the set, collection or library of nucleic acid sequences encoding immunoglobulin single variable domains may for example be a set, collection or library of nucleic acid sequences encoding a naïve set, collection or library of immunoglobulin sequences; a set, collection or library of nucleic acid sequences encoding a synthetic or semi-synthetic set, collection or library of immunoglobulin sequences; and/or a set, collection or library of nucleic acid sequences encoding a set, collection or library of immunoglobulin sequences that have been subjected to affinity maturation.

In another aspect, the method for generating an amino acid sequence directed against CXCR7 and in particular human CXCR7 (SEQ ID NO: 1) may comprise at least the steps of:

a) providing a set, collection or library of nucleic acid sequences encoding immunoglobulin single variable domains;
b) screening said set, collection or library of nucleic acid sequences for nucleic acid sequences that encode an amino acid sequence that can bind to and/or has affinity for CXCR7 and in particular human CXCR7 (SEQ ID NO: 1) and that is cross-blocked or is cross blocking a immunoglobulin single variable domain or polypeptide of the invention, e.g., SEQ ID NOs: 39 to 43, 91 or 99-102 (Table B-3); and
c) isolating said nucleic acid sequence, followed by expressing said amino acid sequence.

The invention also relates to immunoglobulin single variable domains that are obtained by the above methods, or alternatively by a method that comprises the one of the above methods and in addition at least the steps of determining the nucleotide sequence or amino acid sequence of said immunoglobulin sequence; and of expressing or synthesizing said amino acid sequence in a manner known per se, such as by expression in a suitable host cell or host organism or by chemical synthesis.

Also, following the steps above, one or more immunoglobulin single variable domains of the invention may be suitably humanized, camelized or otherwise sequence optimized (e.g. sequence optimized for manufacturability, stability and/or solubility); and/or the amino acid sequence(s) thus obtained may be linked to each other or to one or more other suitable immunoglobulin single variable domains (optionally via one or more suitable linkers) so as to provide a polypeptide of the invention. Also, a nucleic acid sequence encoding an amino acid sequence of the invention may be suitably humanized, camelized or otherwise sequence optimized (e.g., sequence optimized for manufacturability, stability and/or solubility) and suitably expressed; and/or one or more nucleic acid sequences encoding an amino acid sequence of the invention may be linked to each other or to one or more nucleic acid sequences that encode other suitable immunoglobulin single variable domains (optionally via nucleotide sequences that encode one or more suitable linkers), after which the nucleotide sequence thus obtained may be suitably expressed so as to provide a polypeptide of the invention.

The invention further relates to applications and uses of the immunoglobulin single variable domains, compounds, constructs, polypeptides, nucleic acids, host cells, products and compositions described herein, as well as to methods for the diagnosis, prevention and/or treatment for diseases and disorders associated with CXCR7 and in particular human CXCR7 (SEQ ID NO: 1). Some preferred but non-limiting applications and uses will become clear from the further description herein.

The invention also relates to the immunoglobulin single variable domains, compounds, constructs, polypeptides, nucleic acids, host cells, products and compositions described herein for use in therapy.

In particular, the invention also relates to the immunoglobulin single variable domains, compounds, constructs, polypeptides, nucleic acids, host cells, products and compositions described herein for use in therapy of a disease or disorder that can be prevented or treated by administering, to a subject in need thereof, of (a pharmaceutically effective amount of) an amino acid sequence, compound, construct or polypeptide as described herein.

More in particular, the invention relates to the immunoglobulin single variable domains, compounds, constructs, polypeptides, nucleic acids, host cells, products and compositions described herein for use in therapy of cancer.

1.5. Variants of Polypeptides and Immunoglobulin Single Variable Domains of the Invention Polypeptides of the invention and immunoglobulin single variable domains (that form part of the polypeptides of the invention) may be altered in order to further improve potency or other desired properties.

Generally, an immunoglobulin single variable domain can be defined as a polypeptide with the formula 1:

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively.

Some particularly preferred, but non-limiting combinations of CDR sequences, as well as preferred combinations of CDR sequences and framework sequences, are mentioned in Table B-2, which lists the CDR sequences and framework sequences that are present in a number of preferred (but non-limiting) Immunoglobulin single variable domains of the invention. As will be clear to the skilled person, a combination of CDR1, CDR2 and CDR3 sequences that occur in the same clone (i.e. CDR1, CDR2 and CDR3 sequences that are mentioned on the same line or row in Table B-2) will usually be preferred (although the invention in its broadest sense is not limited thereto, and also comprises other suitable combinations of the CDR sequences mentioned in Table B-2). Also, a combination of CDR sequences and framework sequences that occur in the same clone (i.e., CDR sequences and framework sequences that are mentioned on the same line or row in Table B-2) will usually be preferred (although the invention in its broadest sense is not limited thereto, and also comprises other suitable combinations of the CDR sequences and framework sequences mentioned in Table B-2, as well as combinations of such CDR sequences and other suitable framework sequences, e.g., as further described herein).

Also, in the immunoglobulin single variable domains of the invention that comprise the combinations of CDR's mentioned in Table B-2, each CDR can be replaced by a CDR chosen from the group consisting of immunoglobulin single variable domains that have at least 80%, preferably at least 90%, more preferably at least 95%, even more preferably at least 99% sequence identity (as defined herein) with the mentioned CDR's; in which:

i) any amino acid substitution in such a CDR is preferably, and compared to the corresponding CDR sequence mentioned in Table B-2, a conservative amino acid substitution (as defined herein); and/or ii) any such CDR sequence preferably only contains amino acid substitutions, and no amino acid deletions or insertions, compared to the corresponding CDR sequence mentioned in Table B-2; and/or iii) any such CDR sequence is a CDR that is derived by means of a technique for affinity maturation known per se, and in particular starting from the corresponding CDR sequence mentioned in Table B-2.

However, as will be clear to the skilled person, the (combinations of) CDR sequences, as well as (the combinations of) CDR sequences and framework sequences mentioned in Table B-2 will generally be preferred.

Thus, in the immunoglobulin single variable domains of the invention, at least one of the CDR1, CDR2 and CDR3 sequences present is suitably chosen from the group consisting of the CDR1, CDR2 and CDR3 sequences, respectively, listed in Table B-2; or from the group of CDR1, CDR2 and CDR3 sequences, respectively, that have at least 80%, preferably at least 90%, more preferably at least 95%, even more preferably at least 99% "sequence identity" (as defined herein) with at least one of the CDR1, CDR2 and CDR3 sequences, respectively, listed in Table B-2; and/or from the group consisting of the CDR1, CDR2 and CDR3 sequences, respectively, that have 3, 2 or only 1 "amino acid difference(s)" (as defined herein) with at least one of the CDR1, CDR2 and CDR3 sequences, respectively, listed in Table B-2.

In this context, by "suitably chosen" is meant that, as applicable, a CDR1 sequence is chosen from suitable CDR1 sequences (i.e. as defined herein), a CDR2 sequence is chosen from suitable CDR2 sequences (i.e. as defined herein), and a CDR3 sequence is chosen from suitable CDR3 sequence (i.e. as defined herein), respectively. More in particular, the CDR sequences are preferably chosen such that the Nanobodies of the invention bind to CXCR7 and in particular human CXCR7 (SEQ ID NO: 1) with an affinity (suitably measured and/or expressed as a EC50 value, or alternatively as an $IC_{50}$ value, as further described herein in various in vitro and/or in vivo potency or other assays) that is as defined herein.

In particular, in the immunoglobulin single variable domains of the invention, at least the CDR3 sequence present is suitably chosen from the group consisting of the CDR3 sequences listed in Table B-2 or from the group of CDR3 sequences that have at least 80%, preferably at least 90%, more preferably at least 95%, even more preferably at least 99% sequence identity with at least one of the CDR3 sequences listed in Table B-2; and/or from the group consisting of the CDR3 sequences that have 3, 2 or only 1 amino acid difference(s) with at least one of the CDR3 sequences listed in Table B-2.

Preferably, in the immunoglobulin single variable domains of the invention, at least two of the CDR1, CDR2 and CDR3 sequences present are suitably chosen from the group consisting of the CDR1, CDR2 and CDR3 sequences, respectively, listed in Table B-2 or from the group consisting of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table B-2; and/or from the group consisting of the CDR1, CDR2 and CDR3 sequences, respectively, that have 3, 2 or only 1 "amino acid difference(s)" with at least one of the CDR1, CDR2 and CDR3 sequences, respectively, listed in Table B-2.

In particular, in the immunoglobulin single variable domains of the invention, at least the CDR3 sequence present is suitably chosen from the group consisting of the CDR3 sequences listed in Table B-2 or from the group of CDR3 sequences that have at least 80%, preferably at least 90%, more preferably at least 95%, even more preferably at least 99% sequence identity with at least one of the CDR3 sequences listed in Table B-2, respectively; and at least one of the CDR1 and CDR2 sequences present is suitably chosen from the group consisting of the CDR1 and CDR2 sequences, respectively, listed in Table B-2 or from the group of CDR1 and CDR2 sequences, respectively, that have at least 80%, preferably at least 90%, more preferably at least 95%, even more preferably at least 99% sequence identity with at least one of the CDR1 and CDR2 sequences, respectively, listed in Table B-2; and/or from the group consisting of the CDR1 and CDR2 sequences, respectively, that have 3, 2 or only 1 amino acid difference(s) with at least one of the CDR1 and CDR2 sequences, respectively, listed in Table B-2.

Most preferably, in the immunoglobulin single variable domains of the invention, all three CDR1, CDR2 and CDR3 sequences present are suitably chosen from the group consisting of the CDR1, CDR2 and CDR3 sequences, respectively, listed in Table B-2 or from the group of CDR1, CDR2 and CDR3 sequences, respectively, that have at least 80%, preferably at least 90%, more preferably at least 95%, even more preferably at least 99% sequence identity with at least one of the CDR1, CDR2 and CDR3 sequences, respectively, listed in Table B-2; and/or from the group consisting of the CDR1, CDR2 and CDR3 sequences, respectively, that have 3, 2 or only 1 amino acid difference(s) with at least one of the CDR1, CDR2 and CDR3 sequences, respectively, listed in Table B-2.

Even more preferably, in the immunoglobulin single variable domains of the invention, at least one of the CDR1, CDR2 and CDR3 sequences present is suitably chosen from the group consisting of the CDR1, CDR2 and CDR3 sequences, respectively, listed in Table B-2. Preferably, in this aspect, at least one or preferably both of the other two CDR sequences present are suitably chosen from CDR sequences that have at least 80%, preferably at least 90%, more preferably at least 95%, even more preferably at least 99% sequence identity with at least one of the corresponding CDR sequences, respectively, listed in Table B-2; and/or from the group consisting of the CDR sequences that have 3, 2 or only 1 amino acid difference(s) with at least one of the corresponding sequences, respectively, listed in Table B-2.

In particular, in the immunoglobulin single variable domains of the invention, at least the CDR3 sequence present is suitably chosen from the group consisting of the CDR3 listed in Table B-2. Preferably, in this aspect, at least one and preferably both of the CDR1 and CDR2 sequences present are suitably chosen from the groups of CDR1 and CDR2 sequences, respectively, that have at least 80%, preferably at least 90%, more preferably at least 95%, even more preferably at least 99% sequence identity with the CDR1 and CDR2 sequences, respectively, listed in Table B-2; and/or from the group consisting of the CDR1 and CDR2 sequences, respectively, that have 3, 2 or only 1 amino acid difference(s) with at least one of the CDR1 and CDR2 sequences, respectively, listed in Table B-2.

Even more preferably, in the immunoglobulin single variable domains of the invention, at least two of the CDR1, CDR2 and CDR3 sequences present are suitably chosen from the group consisting of the CDR1, CDR2 and CDR3 sequences, respectively, listed in Table B-2. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table B-2; and/or from the group consisting of CDR sequences that have 3, 2 or only 1 amino acid difference(s) with at least one of the corresponding sequences listed in Table B-2.

In particular, in the immunoglobulin single variable domains of the invention, at least the CDR3 sequence is suitably chosen from the group consisting of the CDR3 sequences listed in Table B-2, and either the CDR1 sequence or the CDR2 sequence is suitably chosen from the group consisting of the CDR1 and CDR2 sequences, respectively, listed in Table B-2. Preferably, in this aspect, the remaining CDR sequence present is suitably chosen from the group of CDR sequences that have at least 80%, preferably at least 90%, more preferably at least 95%, even more preferably at least 99% sequence identity with at least one of the corresponding CDR sequences listed in Table B-2; and/or from the group consisting of CDR sequences that have 3, 2 or only 1 amino acid difference(s) with the corresponding CDR sequences listed in Table B-2.

Even more preferably, in the immunoglobulin single variable domains of the invention, all three CDR1, CDR2 and CDR3 sequences present are suitably chosen from the group consisting of the CDR1, CDR2 and CDR3 sequences, respectively, listed in Table B-2.

Also, generally, the combinations of CDR's listed in Table B-2 (i.e., those mentioned on the same line or row in Table B-2) are preferred. Thus, it is generally preferred that, when a CDR in a immunoglobulin single variable domain of the invention is a CDR sequence mentioned in Table B-2 or is suitably chosen from the group of CDR sequences that have at least 80%, preferably at least 90%, more preferably at least 95%, even more preferably at least 99% sequence identity with a CDR sequence listed in Table B-2; and/or from the group consisting of CDR sequences that have 3, 2 or only 1 amino acid difference(s) with a CDR sequence listed in Table B-2, that at least one and preferably both of the other CDR's are suitably chosen from the CDR sequences that belong to the same combination in Table B-2 (i.e., mentioned on the same line or row in Table B-2) or are suitably chosen from the group of CDR sequences that have at least 80%, preferably at least 90%, more preferably at least 95%, even more preferably at least 99% sequence identity with the CDR sequence(s) belonging to the same combination and/or from the group consisting of CDR sequences that have 3, 2 or only 1 amino acid difference(s) with the CDR sequence(s) belonging to the same combination. The other preferences indicated in the above paragraphs also apply to the combinations of CDR's mentioned in Table B-2.

Thus, by means of non-limiting examples, a polypeptide of the invention can for example comprise a CDR1 sequence that has more than 80% sequence identity with one of the CDR1 sequences mentioned in Table B-2, a CDR2 sequence that has 3, 2 or 1 amino acid difference with one of the CDR2 sequences mentioned in Table B-2 (but belonging to a different combination), and a CDR3 sequence.

Some preferred immunoglobulin single variable domains of the invention may for example comprise: (1) a CDR1 sequence that has more than 80% sequence identity with one of the CDR1 sequences mentioned in Table B-2; a CDR2 sequence that has 3, 2 or 1 amino acid difference with one of the CDR2 sequences mentioned in Table B-2 (but belonging to a different combination); and a CDR3 sequence that has more than 80% sequence identity with one of the CDR3 sequences mentioned in Table B-2 (but belonging to a different combination); or (2) a CDR1 sequence that has more than 80% sequence identity with one of the CDR1 sequences mentioned in Table B-2; a CDR2 sequence, and one of the CDR3 sequences listed in Table B-2; or (3) a CDR1 sequence; a CDR2 sequence that has more than 80% sequence identity with one of the CDR2 sequence listed in Table B-2; and a CDR3 sequence that has 3, 2 or 1 amino acid differences with the CDR3 sequence mentioned in Table B-2 that belongs to the same combination as the CDR2 sequence.

Some particularly preferred immunoglobulin single variable domains of the invention may for example comprise: (1) a CDR1 sequence that has more than 80% sequence identity with one of the CDR1 sequences mentioned in Table B-2; a CDR2 sequence that has 3, 2 or 1 amino acid difference with the CDR2 sequence mentioned in Table B-2 that belongs to the same combination; and a CDR3 sequence that has more than 80% sequence identity with the CDR3 sequence mentioned in Table B-2 that belongs to the same combination; (2) a CDR1 sequence; a CDR2 listed in Table B-2 and a CDR3 sequence listed in Table B-2 (in which the CDR2 sequence and CDR3 sequence may belong to different combinations).

Some even more preferred immunoglobulin single variable domains of the invention may for example comprise: (1) a CDR1 sequence that has more than 80% sequence identity with one of the CDR1 sequences mentioned in Table B-2; the CDR2 sequence listed in Table B-2 that belongs to the same combination; and a CDR3 sequence mentioned in Table B-2 that belongs to a different combination; or (2) a CDR1 sequence mentioned in Table B-2; a CDR2 sequence that has 3, 2 or 1 amino acid differences with the CDR2 sequence mentioned in Table B-2 that belongs to the same combination; and a CDR3 sequence that has more than 80% sequence identity with the CDR3 sequence listed in Table B-2 that belongs to the same or a different combination.

Particularly preferred immunoglobulin single variable domains of the invention may for example comprise a CDR1 sequence mentioned in Table B-2, a CDR2 sequence that has more than 80% sequence identity with the CDR2 sequence mentioned in Table B-2 that belongs to the same combination; and the CDR3 sequence mentioned in Table B-2 that belongs to the same combination. In the most preferred immunoglobulin single variable domains of the invention, the CDR1, CDR2 and CDR3 sequences present are suitably chosen from one of the combinations of CDR1, CDR2 and CDR3 sequences, respectively, listed in Table B-2.

According to another preferred, but non-limiting aspect of the invention (a) CDR1 has a length of between 1 and 12 amino acid residues, and usually between 2 and 9 amino acid residues, such as 5, 6 or 7 amino acid residues; and/or (b) CDR2 has a length of between 13 and 24 amino acid residues, and usually between 15 and 21 amino acid residues, such as 16 and 17 amino acid residues; and/or (c) CDR3 has a length of between 2 and 35 amino acid residues, and usually between 3 and 30 amino acid residues, such as between 6 and 23 amino acid residues.

In another preferred, but non-limiting aspect, the invention relates to a immunoglobulin single variable domain in which the CDR sequences (as defined herein) have more than 80%, preferably more than 90%, more preferably more than 95%, such as 99% or more sequence identity (as defined herein) with the CDR sequences of at least one of the immunoglobulin single variable domains of SEQ ID NOs: 39 to 43 or 91 as well as 99-102 (see Table B-3).

Another preferred, but non-limiting aspect of the invention relates to humanized variants of the immunoglobulin single variable domains of SEQ ID NOs: 39 to 43 and 91 as well as 99-102 (see Table B-3), that comprise, compared to the corresponding native $V_{HH}$ sequence, at least one humanizing substitution (as defined herein), and in particular at least one humanizing substitution in at least one of its framework sequences (as defined herein).

It will be clear to the skilled person that the immunoglobulin single variable domains that are mentioned herein as "preferred" (or "more preferred", "even more preferred", etc.) are also preferred (or more preferred, or even more preferred, etc.) for use in the polypeptides described herein. Thus, polypeptides that comprise or essentially consist of one or more "preferred" immunoglobulin single variable domains of the invention will generally be preferred, and polypeptides that comprise or essentially consist of one or more "more preferred" immunoglobulin single variable domains of the invention will generally be more preferred, etc.

1.6. Nucleotides, Host Cells of the Invention

Another aspect of this invention relates to a nucleic acid that encodes an amino acid sequence of the invention (such as an immunoglobulin single variable domain of the invention) or a polypeptide of the invention comprising the same. Again, as generally described herein for the nucleic acids of the invention, such a nucleic acid may be in the form of a genetic construct, as defined herein. Specific embodiments of this aspect of the invention are provided in Table B-6, SEQ ID NOs: 59 to 63 and 73 to 77.

In another preferred, but non-limiting aspect, the invention relates to nucleic acid sequences of immunoglobulin single variable domain in which the sequences (as defined herein) have more than 80%, preferably more than 90%, more preferably more than 95%, such as 99% or more sequence identity (as defined herein) with the sequences of at least one of nucleic acid sequence of the immunoglobulin single variable domains of SEQ ID NOs: 59 to 63 and 73 to 77 (see Table B-6).

In another aspect, the invention relates to nucleic acid sequences that comprise the nucleic acid sequences of immunoglobulin single variable domain in which the sequences (as defined herein) have more than 80%, preferably more than 90%, more preferably more than 95%, such as 99% or more sequence identity (as defined herein) with the sequences of at least one of nucleic acid sequence of the immunoglobulin single variable domains of SEQ ID NOs: 59 to 63 and 73 to 77 (see Table B-6).

In another aspect, the invention relates to host or host cell that expresses or that is capable of expressing an amino acid sequence (such as an immunoglobulin single variable domain) of the invention and/or a polypeptide of the invention comprising the same; and/or that contains a nucleic acid of the invention. Some preferred but non-limiting examples of such hosts or host cells will become clear from the further description herein.

As will be clear to the skilled person, one particularly useful method for preparing a polypeptide of the invention generally comprises the steps of:
i) the expression, in a suitable host cell or host organism (also referred to herein as a "host of the invention") or in another suitable expression system of a nucleic acid that encodes said amino acid sequence, polypeptide of the invention (also referred to herein as a "nucleic acid of the invention"), optionally followed by:
ii) isolating and/or purifying the polypeptide of the invention thus obtained.

In particular, such a method may comprise the steps of:
i) cultivating and/or maintaining a host of the invention under conditions that are such that said host of the invention expresses and/or produces at least one polypeptide of the invention; optionally followed by:
ii) isolating and/or purifying the polypeptide of the invention thus obtained.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated from, as defined herein.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information on the immunoglobulin single variable domains for the polypeptides of the invention given herein, and/or can be isolated from a suitable natural source. To provide analogs, nucleotide sequences encoding naturally occurring $V_{HH}$ domains can for example be subjected to site-directed mutagenesis, so at to provide a nucleic acid of the invention encoding said analog. Also, as will be clear to the skilled person, to prepare a nucleic acid of the invention, also several nucleotide sequences, such as at least one nucleotide sequence encoding a polypeptide of the invention and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers, using for example a sequence of a naturally occurring form of CXCR7 and in particular human CXCR7 (SEQ ID NO: 1) as a template. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art and as described on pages 131-134 of WO 08/020,079 (incorporated herein by reference). Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e., a vector that can provide for expression in vitro and/or in vivo (e.g., in a suitable host cell, host organism and/or expression system).

In a preferred but non-limiting aspect, a genetic construct of the invention comprises
i) at least one nucleic acid of the invention; operably connected to
ii) one or more regulatory elements, such as a promoter and optionally a suitable terminator; and, optionally,
iii) one or more further elements of genetic constructs known per se;
in which the terms "operably connected" and "operably linked" have the meaning given on pages 131-134 of WO 08/020,079; and in which the "regulatory elements", "promoter", "terminator" and "further elements" are as described on pages 131-134 of WO 08/020,079; and in which the genetic constructs may further be as described on pages 131-134 of WO 08/020,079.

The nucleic acids of the invention and/or the genetic constructs of the invention may be used to transform a host cell or host organism, i.e., for expression and/or production of the polypeptide of the invention. Suitable hosts or host cells will be clear to the skilled person, and may for example be any suitable fungal, prokaryotic or eukaryotic cell or cell line or any suitable fungal, prokaryotic or eukaryotic organism, for example those described on pages 134 and 135 of WO 08/020,079; as well as all other hosts or host cells known per se for the expression and production of antibodies and antibody fragments (including but not limited to (single) domain antibodies and ScFv fragments), which will be clear to the skilled person. Reference is also made to the general background art cited hereinabove, as well as to for example WO 94/29457; WO 96/34103; WO 99/42077.

The immunoglobulin single variable domains, and polypeptides of the invention can for example also be produced in the milk of transgenic mammals, for example in the milk of rabbits, cows, goats or sheep (see for example U.S. Pat. No. 6,741,957, U.S. Pat. No. 6,304,489 and U.S. Pat. No. 6,849,992 for general techniques for introducing transgenes into mammals), in plants or parts of plants including but not limited to their leaves, flowers, fruits, seed, roots or turbers (for example in tobacco, maize, soybean or alfalfa) or in for example pupae of the silkworm Bombix mori.

Furthermore, the immunoglobulin single variable domains, and polypeptides of the invention can also be expressed and/or produced in cell-free expression systems, and suitable examples of such systems will be clear to the skilled person. Some preferred, but non-limiting examples include expression in the wheat germ system; in rabbit reticulocyte lysates; or in the E. coli Zubay system.

As mentioned above, one of the advantages of the use of immunoglobulin single variable domains is that the polypeptides based thereon can be prepared through expression in a suitable bacterial system, and suitable bacterial expression systems, vectors, host cells, regulatory elements, etc., will be clear to the skilled person, for example from the references cited above. It should however be noted that the invention in its broadest sense is not limited to expression in bacterial systems.

Preferably, in the invention, an (in vivo or in vitro) expression system, such as a bacterial expression system, is used that provides the polypeptides of the invention in a form that is suitable for pharmaceutical use, and such expression systems will again be clear to the skilled person. As also will be clear to the skilled person, polypeptides of the invention suitable for pharmaceutical use can be prepared using techniques for peptide synthesis.

For production on industrial scale, preferred heterologous hosts for the (industrial) production of immunoglobulin single variable domains or immunoglobulin single variable domain-containing protein therapeutics include strains of *E. coli, Pichia pastoris, S. cerevisiae* that are suitable for large scale expression/production/fermentation, and in particular for large scale pharmaceutical (i.e., GMP grade) expression/production/fermentation. Suitable examples of such strains will be clear to the skilled person. Such strains and production/expression systems are also made available by companies such as Richter Helm (Hamburg, Germany) or CMC Biologics (Soeborg, Denmark).

Alternatively, mammalian cell lines, in particular Chinese hamster ovary (CHO) cells, can be used for large scale expression/production/fermentation, and in particular for large scale pharmaceutical expression/production/fermentation. Again, such expression/production systems are also made available by some of the companies mentioned above.

The choice of the specific expression system would depend in part on the requirement for certain post-translational modifications, more specifically glycosylation. The production of a immunoglobulin single variable domain-containing recombinant protein for which glycosylation is desired or required would necessitate the use of mammalian expression hosts that have the ability to glycosylate the expressed protein. In this respect, it will be clear to the skilled person that the glycosylation pattern obtained (i.e., the nature of the saccharide, number and position of residues attached) will depend on the cell or cell line that is used for the expression. Preferably, either a human cell or cell line is used (i.e., leading to a protein that essentially has a human glycosylation pattern) or another mammalian cell line is used that can provide a glycosylation pattern that is essentially and/or functionally the same as human glycosylation or at least mimics human glycosylation. Generally, prokaryotic hosts such as *E. coli* do not have the ability to glycosylate proteins, and the use of lower eukaryotes such as yeast usually leads to a glycosylation pattern that differs from human glycosylation. Nevertheless, it should be understood that all the foregoing host cells and expression systems can be used in the invention, depending on the desired polypeptide to be obtained.

Thus, according to one non-limiting aspect of the invention, the polypeptide of the invention is glycosylated. According to another non-limiting aspect of the invention, the polypeptide of the invention is non-glycosylated.

According to one preferred, but non-limiting aspect of the invention, the polypeptide of the invention is produced in a bacterial cell, in particular a bacterial cell suitable for large scale pharmaceutical production, such as cells of the strains mentioned above.

According to another preferred, but non-limiting aspect of the invention, the polypeptide of the invention is produced in a yeast cell, in particular a yeast cell suitable for large scale pharmaceutical production, such as cells of the species mentioned above.

According to yet another preferred, but non-limiting aspect of the invention, the polypeptide of the invention is produced in a mammalian cell, in particular in a human cell or in a cell of a human cell line, and more in particular in a human cell or in a cell of a human cell line that is suitable for large scale pharmaceutical production, such as the cell lines mentioned hereinabove.

As further described on pages 138 and 139 of WO 08/020,079, when expression in a host cell is used to produce the immunoglobulin single variable domains, and the polypeptides of the invention, the immunoglobulin single variable domains, and polypeptides of the invention can be produced either intracellullarly (e.g., in the cytosol, in the periplasma or in inclusion bodies) and then isolated from the host cells and optionally further purified; or can be produced extracellularly (e.g., in the medium in which the host cells are cultured) and then isolated from the culture medium and optionally further purified. Thus, according to one non-limiting aspect of the invention, the polypeptide of the invention is an amino acid sequence, polypeptide that has been produced intracellularly and that has been isolated from the host cell, and in particular from a bacterial cell or from an inclusion body in a bacterial cell. According to another non-limiting aspect of the invention, the amino acid sequence, or polypeptide of the invention is an amino acid sequence, or polypeptide that has been produced extracellularly, and that has been isolated from the medium in which the host cell is cultivated.

Some preferred, but non-limiting promoters for use with these host cells include those mentioned on pages 139 and 140 of WO 08/020,079.

Some preferred, but non-limiting secretory sequences for use with these host cells include those mentioned on page 140 of WO 08/020,079.

Suitable techniques for transforming a host or host cell of the invention will be clear to the skilled person and may depend on the intended host cell/host organism and the genetic construct to be used. Reference is again made to the handbooks and patent applications mentioned above.

After transformation, a step for detecting and selecting those host cells or host organisms that have been successfully transformed with the nucleotide sequence/genetic construct of the invention may be performed. This may for instance be a selection step based on a selectable marker present in the genetic construct of the invention or a step involving the detection of the amino acid sequence of the invention, e.g., using specific antibodies.

The transformed host cell (which may be in the form or a stable cell line) or host organisms (which may be in the form of a stable mutant line or strain) form further aspects of the present invention.

Preferably, these host cells or host organisms are such that they express, or are (at least) capable of expressing (e.g., under suitable conditions), a polypeptide of the invention (and in case of a host organism: in at least one cell, part, tissue or organ thereof). The invention also includes further generations, progeny and/or offspring of the host cell or host organism of the invention that may for instance be obtained by cell division or by sexual or asexual reproduction.

To produce/obtain expression of the immunoglobulin single variable domains of the invention, the transformed host cell or transformed host organism may generally be kept, maintained and/or cultured under conditions such that the (desired) amino acid sequence, or polypeptide of the invention is expressed/produced. Suitable conditions will be clear to the skilled person and will usually depend upon the host cell/host organism used, as well as on the regulatory elements that control the expression of the (relevant) nucleotide sequence of the invention. Again, reference is made to the handbooks and patent applications mentioned above in the paragraphs on the genetic constructs of the invention.

Generally, suitable conditions may include the use of a suitable medium, the presence of a suitable source of food and/or suitable nutrients, the use of a suitable temperature, and optionally the presence of a suitable inducing factor or compound (e.g., when the nucleotide sequences of the invention are under the control of an inducible promoter); all of which may be selected by the skilled person. Again, under such conditions, the immunoglobulin single variable domains of the invention may be expressed in a constitutive manner, in a transient manner, or only when suitably induced.

It will also be clear to the skilled person that the amino acid sequence, or polypeptide of the invention may (first) be generated in an immature form (as mentioned above), which may then be subjected to post-translational modification, depending on the host cell/host organism used. Also, the amino acid sequence, or polypeptide of the invention may be glycosylated, again depending on the host cell/host organism used.

The amino acid sequence, or polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g., using a specific, cleavable amino acid sequence fused with the amino acid sequence, or polypeptide of the invention) and/or preparative immunological techniques (i.e. using antibodies against the amino acid sequence to be isolated).

The entire contents of all of the references (including literature references, issued patents, published patent applications, and co-pending patent applications) cited throughout this application are hereby expressly incorporated by reference, in particular for the teaching that is referenced hereinabove.

1.7 Modulators of CXCR7

A number of different screening protocols can be utilized to identify agents that modulate the level of activity or function of CXCR7 in cells, particularly in mammalian cells, and especially in human cells. In general terms, the screening methods involve screening an agent or a plurality of agents to identify one or more agents that interacts with (human) CXCR7 (SEQ ID NO:1), for example, by binding to a CXCR7 or a fragment thereof and preventing the polypeptides or ISVDs of the invention, such as, for instance, comprising any one of SEQ ID NOs: 39-48, 78-89, 91, 99-102 or 132-140, from binding to CXCR7 (SEQ ID NO: 1). In some embodiments, an agent binds CXCR7 with at least about 1.5, 2, 3, 4, 5, 10, 20, 50, 100, 300, 500, or 1000 times the affinity of the agent for another protein. In some embodiments, the fragment of CXCR7 comprising the epitopes described herein (and optionally comprising further non-CXCR7 amino acids at the N and/or C termini) is no more than, e.g., 300, 250, 200, 150, 100, 50, 40, 30, 20 or fewer amino acids. In some embodiments, the CXCR7 fragment is any fragment having less than all of the amino acids in the full length CXCR7 polypeptide.

In some embodiments, CXCR7 modulators are identified by screening for molecules that compete with the polypeptide or ISVD of the invention from binding to a CXCR7 polypeptide, or fragment thereof. Those of skill in the art will recognize that there are a number of ways to perform competition analyses, for instance, such as disclosed herein. In some embodiments, samples with CXCR7 are pre-incubated with a labeled polypeptides or ISVDs of the invention, such as, for instance, comprising any one of SEQ ID NOs: 39-48, 78-89, 91, 99-102 or 132-140 and then contacted with a potential competitor molecule. Alteration (e.g., a decrease) of the quantity of polypeptide or ISVD bound to CXCR7 in the presence of a test compound indicates that the test compound is a potential CXCR7 modulator.

1.8 Kits for Use in Diagnostic and/or Prognostic Applications

For use in the diagnostic, research, and therapeutic applications suggested above, kits are also provided by the invention. In the diagnostic and research applications such kits may include any or all of the following: assay reagents, buffers, and the anti-CXCR7 polypeptides or ISVDs of the invention. A therapeutic product may include sterile saline or another pharmaceutically acceptable emulsion and suspension base.

In addition, the kits may include instructional materials containing directions (i.e., protocols) for the practice of the methods of this invention. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

The invention will now be further described by means of the following non-limiting preferred aspects, figures and examples:

Preferred Non-limiting Aspects:

Aspect A-1: An immunoglobulin single variable domain that is directed against and/or that can specifically bind to CXCR7 and in particular human CXCR7 (SEQ ID NO: 1).

Aspect A-2: An immunoglobulin single variable domain according to aspect A-1, that is in essentially isolated form.

Aspect A-3: An immunoglobulin single variable domain according to aspect A-1 or A-2, for administration to a subject, wherein said immunoglobulin single variable domain does not naturally occur in said subject.

Aspect A-4: An immunoglobulin single variable domain that can specifically bind to CXCR7 and in particular human CXCR7 (SEQ ID NO: 1) with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter. Such an immunoglobulin single variable domain may in particular be an immunoglobulin single variable domain according to any of the preceding aspects.

Aspect A-5: An immunoglobulin single variable domain that can specifically bind to CXCR7 and in particular human CXCR7 (SEQ ID NO: 1) with a rate of association ($k_{on}$-rate) of between $10^2$ $M^{-1}$ $s^{-1}$ to about $10^7$ $M^{-1}$ $s^{-1}$, preferably between $10^3$ $M^{-1}$ $s^{-1}$ and $10^7$ $M^{-1}$ $s^{-1}$, more preferably between $10^4$ $M^{-1}$ $s^{-1}$ and $10^7$ $M^{-1}$ $s^{-1}$, such as between $10^5$ $M^{-1}$ $s^{-1}$ and $10^7$ $M^{-1}$ $s^{-1}$. Such an immunoglobulin single variable domain may in particular be an immunoglobulin single variable domain according to any of the preceding aspects.

Aspect A-6: An immunoglobulin single variable domain that can specifically bind to CXCR7 and in particular human CXCR7 (SEQ ID NO: 1) with a rate of dissociation ($k_{off}$ rate) between 1 $s^{-1}$ and $10^{-6}$ $s^{-1}$, preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$. Such an immunoglobulin single variable domain may in particular be an immunoglobulin single variable domain according to any of the preceding aspects.

Aspect A-7: An immunoglobulin single variable domain that can specifically bind to CXCR7 and in particular human CXCR7 (SEQ ID NO: 1) with an affinity less than 500 nM, preferably less than 200 nM, more preferably less than 10 nM, such as less than 500 pM. Such an immunoglobulin single variable domain may in particular be an immunoglobulin single variable domain according to any of the preceding aspects.

Aspect A-8: An immunoglobulin single variable domain that can specifically displace SDF-1 and/or I-TAC (CXCL11 and/or CXCL12) on CXCR7 and in particular on human CXCR7 (SEQ ID NO: 1) with an average Ki of less than 500 nM, preferably less than 200 nM, more preferably less than 10 nM, such as less than 1 nM and an average SDF-1 and/or I-TAC displacement of 50% or more, more preferably of 75% or more, even more preferably of 80% or more. Such an average Ki and/or average displacement value may be determined e.g. in an assay as described in Example 9 or 10.

Aspect A-9: An immunoglobulin single variable domain that can specifically displace SDF-1 and/or I-TAC (CXCL11 and/or CXCL12) on CXCR7 and in particular on human CXCR7 (SEQ ID NO: 1) with an average Ki of less than 20 nM and an average SDF-1 and/or I-TAC displacement of 70% or more. Such an average Ki and/or average displacement value may be determined e.g. in an assay as described in Example 9 or 10.

Aspect A-10: An immunoglobulin single variable domain according to any of the preceding aspects, that essentially consists of 4 framework regions (FR1 to FR4 respectively) and 3 complementarity determining regions (CDR1 to CDR3 respectively).

Aspect A-11: An immunoglobulin single variable domain according to any of the preceding aspects, that is an immunoglobulin sequence.

Aspect A-12: An immunoglobulin single variable domain according to any of the preceding aspects, that is a naturally occurring immunoglobulin sequence (from any suitable species) or a synthetic or semi-synthetic immunoglobulin sequence.

Aspect A-13: An immunoglobulin single variable domain according to any of the preceding aspects that is a humanized immunoglobulin sequence, a camelized immunoglobulin sequence or an immunoglobulin sequence that has been obtained by techniques such as affinity maturation.

Aspect A-14: An immunoglobulin single variable domain according to any of the preceding aspects, that essentially consists of a light chain variable domain sequence (e.g., a VL-sequence); or of a heavy chain variable domain sequence (e.g., a VH-sequence).

Aspect A-15: An immunoglobulin single variable domain according to any of the preceding aspects, that essentially consists of a heavy chain variable domain sequence that is derived from a conventional four-chain antibody or that essentially consist of a heavy chain variable domain sequence that is derived from heavy chain antibody.

Aspect A-16: An immunoglobulin single variable domain according to any of the preceding aspects, that essentially consists of a domain antibody (or an immunoglobulin single variable domain that is suitable for use as a domain antibody), of a single domain antibody (or an immunoglobulin single variable domain that is suitable for use as a single domain antibody), of a "dAb" (or an immunoglobulin single variable domain that is suitable for use as a dAb) or of a Nanobody (including but not limited to a VHH sequence).

Aspect A-17: An immunoglobulin single variable domain according to any of the preceding aspects, that essentially consists of a Nanobody.

Aspect A-18: An immunoglobulin single variable domain according to any of the preceding aspects, that essentially consists of a Nanobody that
i) has at least 80% amino acid identity with at least one of the immunoglobulin single variable domains of SEQ ID NOs: 1 to 22 of WO 2009/138519, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table A-1.

Aspect A-19: An immunoglobulin single variable domain according to any of the preceding aspects, that essentially consists of an immunoglobulin single variable domain that
i) has at least 80% amino acid identity with at least one of the immunoglobulin single variable domains of SEQ ID NOs: 39 to 43, 91 or 99-102, in which for the purposes of determining the degree of amino acid identity, the amino acid residues that form the CDR sequences are disregarded;
and in which:
ii) preferably one or more of the amino acid residues at positions 11, 37, 44, 45, 47, 83, 84, 103, 104 and 108 according to the Kabat numbering are chosen from the Hallmark residues mentioned in Table A-1.

Aspect A-20: An immunoglobulin single variable domain according to any of the preceding aspects, that essentially consists of a polypeptide that comprises of
i) a first immunoglobulin single variable domain that has at least 80% amino acid identity with an immunoglobulin single variable domain selected from the group of immunoglobulin single variable domain having SEQ ID NOs: 39 to 43 91 or 99-102, in which for the purposes of determining the degree of amino acid identity, the amino acid residues that form the CDR sequences are disregarded; and that comprises of
ii) a second immunoglobulin single variable domain that has at least 80% amino acid identity with the immunoglobulin single variable domain having SEQ ID NO: 2, in which for the purposes of determining the degree of amino acid identity, the amino acid residues that form the CDR sequences are disregarded; and, optionally, comprises
iii) a linker.

Aspect A-21: An immunoglobulin single variable domain according to any of the preceding aspects, that essentially consists of a humanized or otherwise sequence optimized immunoglobulin single variable domain.

Aspect A-22: An immunoglobulin single variable domain according to any of the preceding aspects, that, in addition to the at least one binding site for binding against CXCR7 and in particular human CXCR7 (SEQ ID NO: 1), contains one or more further binding sites for binding against other antigens, proteins or targets.

CDR-Based Aspects

Aspect B-1: An immunoglobulin single variable domain that is directed against and/or that can specifically bind CXCR7 and in particular human CXCR7 (SEQ ID NO: 1), and that comprises one or more (preferably one) stretches of amino acid residues chosen from the group consisting of:
a) the immunoglobulin single variable domains of SEQ ID NOs: 9 to 13, 93 or 107-110;

b) immunoglobulin single variable domains that have at least 80% amino acid identity with at least one of the immunoglobulin single variable domains of SEQ ID NOs 9 to 13, 93 or 107-110;
c) immunoglobulin single variable domains that have 3, 2, or 1 amino acid difference with at least one of the immunoglobulin single variable domains of SEQ ID NOs: 9 to 13, 93 or 107-110;
d) the immunoglobulin single variable domains of SEQ ID NOs: 19 to 23, 95, or 115-118;
e) immunoglobulin single variable domains that have at least 80% amino acid identity with at least one of the immunoglobulin single variable domains of SEQ ID NOs: 19 to 23, 95, or 115-118;
f) immunoglobulin single variable domains that have 3, 2, or 1 amino acid difference with at least one of the immunoglobulin single variable domains of SEQ ID NOs: 19 to 23, 95, or 115-118;
g) the immunoglobulin single variable domains of SEQ ID NOs: 29 to 33, 97 or 123-126;
h) immunoglobulin single variable domains that have at least 80% amino acid identity with at least one of the immunoglobulin single variable domains of SEQ ID NOs: 29 to 33, 97 or 123-126;
i) immunoglobulin single variable domains that have 3, 2, or 1 amino acid difference with at least one of the immunoglobulin single variable domains of SEQ ID NOs: 29 to 33, 97 or 123-126;
or any suitable combination thereof.

Such an immunoglobulin single variable domain may in particular be VHH or sequence optimized VHH such as humanized, stabilized and/or solubilized VHH.

Aspect B-2: An immunoglobulin single variable domain according to aspect B-1, in which at least one of said stretches of amino acid residues forms part of the antigen binding site for binding against CXCR7 and in particular human CXCR7 (SEQ ID NO: 1).

Aspect B-3: An immunoglobulin single variable domain sequence that is directed against and/or that can specifically bind CXCR7 and in particular human CXCR7 (SEQ ID NO: 1) and that comprises two or more stretches of amino acid residues chosen from the group consisting of:
a) the immunoglobulin single variable domains of SEQ ID NOs: 9 to 13, 93 or 107-110;
b) immunoglobulin single variable domains that have at least 80% amino acid identity with at least one of the immunoglobulin single variable domains of SEQ ID NOs: 9 to 13, 93 or 107-110;
c) immunoglobulin single variable domains that have 3, 2, or 1 amino acid difference with at least one of the immunoglobulin single variable domains of SEQ ID NOs: 9 to 13, 93 or 107-110;
d) the immunoglobulin single variable domains of SEQ ID NOs: 19 to 23, 95, or 115-118;
e) immunoglobulin single variable domains that have at least 80% amino acid identity with at least one of the immunoglobulin single variable domains of SEQ ID NOs: 19 to 23, 95, or 115-118;
f) immunoglobulin single variable domains that have 3, 2, or 1 amino acid difference with at least one of the immunoglobulin single variable domains of SEQ ID NOs: 19 to 23, 95, or 115-118;
g) the immunoglobulin single variable domains of SEQ ID NOs: 29 to 33, 97 or 123-126;
h) immunoglobulin single variable domains that have at least 80% amino acid identity with at least one of the immunoglobulin single variable domains of SEQ ID NOs: 29 to 33, 97 or 123-126;
i) immunoglobulin single variable domains that have 3, 2, or 1 amino acid difference with at least one of the immunoglobulin single variable domains of SEQ ID NOs: 29 to 33, 97 or 123-126;

such that (i) when the first stretch of amino acid residues corresponds to one of the immunoglobulin single variable domains according to a), b) or c), the second stretch of amino acid residues corresponds to one of the immunoglobulin single variable domains according to d), e), f), g), h) or i); (ii) when the first stretch of amino acid residues corresponds to one of the immunoglobulin single variable domains according to d), e) or f), the second stretch of amino acid residues corresponds to one of the immunoglobulin single variable domains according to a), b), c), g), h) or i); or (iii) when the first stretch of amino acid residues corresponds to one of the immunoglobulin single variable domains according to g), h) or i), the second stretch of amino acid residues corresponds to one of the immunoglobulin single variable domains according to a), b), c), d), e) or f).

Such an immunoglobulin single variable domain may in particular be VHH or sequence optimized VHH such as humanized, stabilized and/or solubilized VHH.

Aspect B-4: An immunoglobulin single variable domain according to aspect B-3, in which the at least two stretches of amino acid residues forms part of the antigen binding site for binding against CXCR7 and in particular human CXCR7 (SEQ ID NO: 1).

Aspect B-5: An immunoglobulin single variable domain sequence that is directed against and/or that can specifically bind CXCR7 and in particular human CXCR7 (SEQ ID NO: 1) and that comprises three or more stretches of amino acid residues, in which the first stretch of amino acid residues is chosen from the group consisting of:
a) the immunoglobulin single variable domains of SEQ ID NOs: 9 to 13, 93 or 107-110;
b) immunoglobulin single variable domains that have at least 80% amino acid identity with at least one of the immunoglobulin single variable domains of SEQ ID NOs: 9 to 13, 93 or 107-110;
c) immunoglobulin single variable domains that have 3, 2, or 1 amino acid difference with at least one of the immunoglobulin single variable domains of SEQ ID NOs: 9 to 13, 93 or 107-110;

the second stretch of amino acid residues is chosen from the group consisting of:
d) the immunoglobulin single variable domain of SEQ ID NOs: 19 to 23, 95, or 115-118;
e) immunoglobulin single variable domains that have at least 80% amino acid identity with at least one of the immunoglobulin single variable domains of SEQ ID NOs: 19 to 23, 95, or 115-118;
f) immunoglobulin single variable domains that have 3, 2, or 1 amino acid difference with at least one of the immunoglobulin single variable domains of SEQ ID NOs: 19 to 23, 95, or 115-118;

and the third stretch of amino acid residues is chosen from the group consisting of:
g) the immunoglobulin single variable domains of SEQ ID NOs: 29 to 33, 97 or 123-126;
h) immunoglobulin single variable domains that have at least 80% amino acid identity with at least one of the immunoglobulin single variable domains of SEQ ID NOs: 29 to 33, 97 or 123-126;

i) immunoglobulin single variable domains that have 3, 2, or 1 amino acid difference with at least one of the immunoglobulin single variable domains of SEQ ID NOs: 29 to 33, 97 or 123-126.

Such an immunoglobulin single variable domain may in particular be VHH or sequence optimized VHH such as humanized, stabilized and/or solubilized VHH.

Aspect B-6: An immunoglobulin single variable domain according to aspect B-5, in which the at least three stretches of amino acid residues forms part of the antigen binding site for binding against CXCR7 and in particular human CXCR7 (SEQ ID NO: 1).

Aspect B-7: An immunoglobulin single variable domain that is directed against and/or that can specifically bind CXCR7 and in particular human CXCR7 (SEQ ID NO: 1) in which the CDR sequences of said immunoglobulin single variable domain have at least 70% amino acid identity, preferably at least 80% amino acid identity, more preferably at least 90% amino acid identity, such as 95% amino acid identity or more or even essentially 100% amino acid identity with the CDR sequences of at least one of the immunoglobulin single variable domains of SEQ ID NOs: 39 to 43, 91 or 99-102. The CDR sequences are preferentially determined via Kabat as defined herein. Such an immunoglobulin single variable domain may in particular be VHH or sequence optimized VHH such as humanized, stabilized and/or solubilized VHH.

Aspect C-1: An immunoglobulin single variable domain or polypeptide that is directed against CXCR7 and in particular human CXCR7 (SEQ ID NO: 1) and that cross-blocks the binding of at least one of the immunoglobulin single variable domains of SEQ ID NOs: 39 to 43, 91 or 99-102, or polypeptides of SEQ ID NOs: 44 to 48, 78-89 or 131-140 to CXCR7 and in particular human CXCR7 (SEQ ID NO: 1). Such an immunoglobulin single variable domain may in particular be an immunoglobulin single variable domain according to any of the aspects A-1 to A-22 and/or according to aspects B-1 to B-7. Also, preferably, such an immunoglobulin single variable domain is able to specifically bind to CXCR7 and in particular human CXCR7 (SEQ ID NO: 1).

Aspect C-2: An immunoglobulin single variable domain or polypeptide, such as an antibody or fragment thereof, that is directed against CXCR7 and in particular human CXCR7 (SEQ ID NO: 1) and that is cross-blocked from binding to CXCR7 and in particular human CXCR7 (SEQ ID NO: 1) by at least one of the immunoglobulin single variable domains of SEQ ID NOs: 39 to 43, 91 or 99-102, or polypeptides of SEQ ID NOs: 44 to 48, 78-89 or 131-140. Such an immunoglobulin single variable domain may in particular be an immunoglobulin single variable domain according to any of the aspects A-1 to A-22 and/or according to aspects B-1 to B-7. Also, preferably, such an immunoglobulin single variable domain is able to specifically bind to CXCR7 and in particular human CXCR7 (SEQ ID NO: 1).

Aspect C-3: An immunoglobulin single variable domain or polypeptide according to any of aspects C-1 or C-2, wherein the ability of said immunoglobulin single variable domain to cross-block or to be cross-blocked is detected in a displacement assay (e.g., as described in Examples 9 and/or 10 below).

Aspect C-4: An immunoglobulin single variable domain or polypeptide according to any of aspects C-1 to C-3 wherein the ability of said immunoglobulin single variable domain to cross-block or to be cross-blocked is detected in an ELISA assay.

Aspect D-1: An immunoglobulin single variable domain according to any of aspects B-1 to B-7 or C-1 to C-7, that is in essentially isolated form.

Aspect D-2: An immunoglobulin single variable domain according to any of aspects B-1 to B-7, C-1 to C-7, and/or D1 for administration to a subject, wherein said immunoglobulin single variable domain does not naturally occur in said subject.

Aspect D-3: An immunoglobulin single variable domain according to any of aspects B-1 to B-7, C-1 to C-7, and/or D1 to D-2 that can specifically bind to CXCR7 and in particular human CXCR7 (SEQ ID NO: 1) with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter.

Aspect D-4: An immunoglobulin single variable domain according to any of aspects B-1 to B-7, C-1 to C-7, and/or D-1 to D-3 that can specifically bind to CXCR7 and in particular human CXCR7 (SEQ ID NO: 1) with a rate of association ($k_{on}$-rate) of between $10^2$ $M^{-1}$ $s^{-1}$ to about $10^7$ $M^{-1}$ $s^{-1}$, preferably between $10^3$ $M^{-1}$ $s^{-1}$ and $10^7$ $M^{-1}$ $s^{-1}$, more preferably between $10^4$ $M^{-1}$ $s^{-1}$ and $10^7$ $M^{-1}$ $s^{-1}$, such as between $10^5$ $M^{-1}$ $s^{-1}$ and $10^7$ $M^{-1}$ $s^{-1}$.

Aspect D-5: An immunoglobulin single variable domain according to any of aspects B-1 to B-7, C-1 to C-7, and/or D-1 to D-4 that can specifically bind to CXCR7 and in particular human CXCR7 (SEQ ID NO: 1) with a rate of dissociation ($k_{off}$-rate) between 1 $s^{-1}$ and $10^{-6}$ $s^{-1}$ preferably between $10^{-2}$ $s^{-1}$ and $10^{-6}$ $s^{-1}$, more preferably between $10^{-3}$ $s^{-1}$ and $10^{-6}$ $s^{-1}$, such as between $10^{-4}$ $s^{-1}$ and $10^{-6}$ $s^{-1}$.

Aspect D-6: An immunoglobulin single variable domain according to any of aspects B-1 to B-7, C-1 to C-7, and/or D-1 to D-5 that can specifically bind to CXCR7 and in particular human CXCR7 (SEQ ID NO: 1) with an affinity less than 500 nM, preferably less than 200 nM, more preferably less than 10 nM, such as less than 500 pM.

The immunoglobulin single variable domains according to aspects D-1 to D-6 may in particular be an immunoglobulin single variable domain according to any of the aspects A-1 to A-22.

Aspect E-1: An immunoglobulin single variable domain according to any of aspects B-1 to B-7, C-1 to C-7 and/or D1 to D-6, that is a naturally occurring immunoglobulin single variable domain (from any suitable species) or a synthetic or semi-synthetic immunoglobulin single variable domain.

Aspect E-2: An immunoglobulin single variable domain according to any of aspects B-1 to B-7, C-1 to C-7, D1 to D-6, and/or E-1 that is sequence optimized Aspect E-3: An immunoglobulin single variable domain according to any of aspects B-1 to B-7, C-1 to C-7, D1 to D-6, and/or D-1 or D-2 that is stabilized.

Aspect E-4: An immunoglobulin single variable domain according to any of aspects B-1 to B-7, C-1 to C-7, D1 to D-6, and/or E-1 to E-3, that is a naturally occurring immunoglobulin sequence (from any suitable species) or a synthetic or semi-synthetic immunoglobulin sequence.

Aspect E-5: An immunoglobulin single variable domain according to any of aspects B-1 to B-7, C-1 to C-7, D1 to D-6, and/or E-1 to E-4 that is a humanized immunoglobulin sequence, a camelized immunoglobulin sequence or an immunoglobulin sequence that has been obtained by techniques such as affinity maturation.

Aspect E-6: An immunoglobulin single variable domain according to any of aspects B-1 to B-7, C-1 to C-7, D1 to D-6, and/or E-1 to E-5 that essentially consists of a light chain variable domain sequence (e.g., a $V_L$-sequence); or of a heavy chain variable domain sequence (e.g., a $V_H$-sequence).

Aspect E-7: An immunoglobulin single variable domain according to any of aspects B-1 to B-7, C-1 to C-7, D1 to D-6, and/or E-1 to E-6, that essentially consists of a heavy chain variable domain sequence that is derived from a conventional four-chain antibody or that essentially consist of a heavy chain variable domain sequence that is derived from heavy chain antibody.

Aspect E-8: An immunoglobulin single variable domain according to any of aspects B-1 to B-7, C-1 to C-7, D1 to D-6, and/or E-1 to E-7, that essentially consists of a domain antibody (or an immunoglobulin single variable domain that is suitable for use as a domain antibody), of a single domain antibody (or an immunoglobulin single variable domain that is suitable for use as a single domain antibody), of a "dAb" (or an immunoglobulin single variable domain that is suitable for use as a dAb) or of a Nanobody (including but not limited to a $V_{HH}$ sequence).

Aspect E-9: An immunoglobulin single variable domain according to any of aspects B-1 to B-7, C-1 to C-7, D1 to D-6, and/or E-1 to E-8 that essentially consists of a Nanobody.

Aspect E-10: An immunoglobulin single variable domain according to any of aspects B-1 to B-7, C-1 to C-7, D1 to D-6, and/or E-1 to E-9 that essentially consists of a immunoglobulin single variable domain that
  i) has at least 80% amino acid identity with at least one of the immunoglobulin single variable domains described herein, in which for the purposes of determining the degree of amino acid identity, the amino acid residues that form the CDR sequences are disregarded;
  and in which:
  ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect E-11: An immunoglobulin single variable domain according to any of aspects B-1 to B-7, C-1 to C-7, D1 to D-6, and/or E-1 to E-10, that essentially consists of an immunoglobulin single variable domain that
  i) has at least 80% amino acid identity with at least one of the An immunoglobulin single variable domains of SEQ ID NOs: 39 to 43, 91 or 99-102, in which for the purposes of determining the degree of amino acid identity, the amino acid residues that form the CDR sequences are disregarded;
  and in which:
  ii) preferably one or more of the amino acid residues at positions 11, 37, 44, 45, 47, 83, 84, 103, 104 and 108 according to the Kabat numbering are chosen from the Hallmark residues mentioned in Table B-2.

Aspect E-12: An immunoglobulin single variable domain according to any of aspects B-1 to B-7, C-1 to C-7, D1 to D-6, and/or E-1 to E-11 that essentially consists of a humanized immunoglobulin single variable domain.

Aspect E-13: An immunoglobulin single variable domain according to any of the aspects B-1 to B-7, C-1 to C-7, D1 to D-6, and/or E-1 to E-11, that in addition to the at least one binding site for binding formed by the CDR sequences, contains one or more further binding sites for binding against other antigens, proteins or targets.

The immunoglobulin single variable domains according to aspects E-1 to E-13 may in particular be an immunoglobulin single variable domain according to any of the aspects A-1 to A-22.

Polypeptides

Aspect K-1: Polypeptide that comprises of one or more immunoglobulin single variable domains according to any of aspects A-1 to A-22, B-1 to B-7, C-1 to C-4, D-1 to D-6, and/or E-1 to E-13, and optionally further comprises one or more peptidic linkers.

Aspect K-2: Polypeptide according to aspect K-1, which additionally comprises one or more (preferably one) immunoglobulin single variable domain directed against serum albumin.

Aspect K-3: Polypeptide according to any of aspects K-1 or K-2, in which said immunoglobulin single variable domain directed against serum albumin is directed against human serum albumin.

Aspect K-4: Polypeptide according to any of aspects K-1 to K-3, in which said one or more immunoglobulin single variable domain directed against serum albumin is an immunoglobulin single variable domain with SEQ ID NO: 2.

Aspect K-5: Polypeptide that comprises of one or more immunoglobulin single variable domains according to any of aspects A-1 to A-22, B-1 to B-7, C-1 to C-4, D-1 to D-6, and/or E-1 to E-13, one or more cytotoxic payloads, and optionally further comprises one or more peptidic linkers.

Aspect K-6: Polypeptide that comprises or essentially consists of one or more immunoglobulin single variable domains according to any of aspects A-1 to A-22, B-1 to B-7, C-1 to C-4, D-1 to D-6, and/or E-1 to E-13, one or more (and preferably one) immunoglobulin single variable domains (preferably Nanobody) directed against CXCR4 and optionally further comprises one or more peptidic linkers.

Aspect K-7: Polypeptide that comprises or essentially consists of at least one (preferably one) immunoglobulin single variable domain (preferably Nanobody) directed against (human) CXCR7 and at least one (cyto)toxic group, moiety or payload (optionally linked chemically or via one or more suitable linkers or spacers).

Aspect K-8: Polypeptide that comprises or essentially consists of at least one (preferably one) immunoglobulin single variable domain (preferably Nanobody) directed against (human) CXCR7, at least one (preferably one) immunoglobulin single variable domain (preferably Nanobody) directed against (human) CXCR4 and at least one (cyto)toxic group, moiety or payload (optionally linked chemically or via one or more suitable linkers or spacers).

Aspect K-9: Polypeptide that comprises or essentially consists of at least one (preferably one) immunoglobulin single variable domain (preferably Nanobody) directed against (human) CXCR7 and at least one (preferably one) immunoglobulin single variable domain (preferably Nanobody) directed against (human) CXCR4 (optionally linked chemically or via one or more suitable linkers or spacers).

Aspect K-10: Polypeptide that comprises or essentially consists of at least one (preferably one) immunoglobulin single variable domain (preferably Nanobody) directed against (human) CXCR7, at least one (preferably one) immunoglobulin single variable domain (preferably Nanobody) directed against (human) CXCR4, and a peptide or immunoglobulin single variable domain (preferably Nanobody) directed against (human) serum albumin (optionally linked chemically or via one or more suitable linkers or spacers).

Aspect K-11: Polypeptide that comprises or essentially consists of two immunoglobulin single variable domains (preferably Nanobody) directed against (human) CXCR7, which are the same (optionally linked chemically or via one or more suitable linkers or spacers).

Aspect K-12: Polypeptide that comprises or essentially consists of two immunoglobulin single variable domains (preferably Nanobody) directed against (human) CXCR7, which are different from each other (optionally linked chemically or via one or more suitable linkers or spacers).

Aspect K-13: Polypeptide that comprises or essentially consists of two immunoglobulin single variable domains (preferably Nanobody) directed against (human) CXCR7, which are the same, and a peptide or immunoglobulin single variable domain (preferably Nanobody) directed against (human) serum albumin (optionally linked chemically or via one or more suitable linkers or spacers).

Aspect K-14: Polypeptide that comprises or essentially consists of two immunoglobulin single variable domains (preferably Nanobody) directed against (human) CXCR7, which are different from each other, and a peptide or immunoglobulin single variable domain (preferably Nanobody) directed against (human) serum albumin (optionally linked chemically or via one or more suitable linkers or spacers).

Nucleic acids

Aspect M-1: Nucleic acid or nucleotide sequence, that encodes an immunoglobulin single variable domain according to any of aspects A-1 to A-22, B-1 to B-7, C-1 to C-4, D-1 to D-6, E-1 to E-13, a polypeptide according to any of aspects K-1 to K-4.

Aspect M-2: Nucleic acid or nucleotide sequence with SEQ ID NOs: 59-63, 73-77 or 99 (Table B-6).

Host cells

Aspect N-1: Host or host cell that expresses, or that under suitable circumstances is capable of expressing, an immunoglobulin single variable domain according to any of aspects A-1 to A-22, B-1 to B-7, C-1 to C-4, D-1 to D-6, E-1 to E-13, a polypeptide according to any of aspects K-1 to K-4; and/or that comprises a nucleic acid or nucleotide sequence according to aspect M-1 or M-2.

Compositions

Aspect O-1: Composition comprising at least one immunoglobulin single variable domain according to any of aspects A-1 to A-22, B-1 to B-7, C-1 to C-4, D-1 to D-6, E-1 to E-13, or at least one polypeptide according to any of aspects K-1 to K-4, or nucleic acid or nucleotide sequence according to aspects M-1 or M-2.

Aspect O-2: Composition according to aspect O-1, which is a pharmaceutical composition.

Aspect O-3: Composition according to aspect O-2, which is a pharmaceutical composition, that further comprises at least one pharmaceutically acceptable carrier, diluent or excipient and/or adjuvant, and that optionally comprises one or more further pharmaceutically active polypeptides and/or compounds.

Making of an Agent and Composition of the Invention

Aspect P-1: Method for producing an immunoglobulin single variable domain according to any of aspects A-1 to A-22, B-1 to B-7, C-1 to C-4, D-1 to D-6, E-1 to E-13, a polypeptide according to any of aspects K-1 to K-4, said method at least comprising the steps of:
a) expressing, in a suitable host cell or host organism or in another suitable expression system, a nucleic acid or nucleotide sequence according to aspect M-1, or aspect M-2;
optionally followed by:
b) isolating and/or purifying the immunoglobulin single variable domain according to any of aspects A-1 to A-22, B-1 to B-7, C-1 to C-4, D-1 to D-6, E-1 to E-13, a polypeptide according to any of aspects K-1 to K-4.

Aspect P-2: Method for producing an immunoglobulin single variable domain according to any of aspects A-1 to A-22, B-1 to B-7, C-1 to C-4, D-1 to D-6, E-1 to E-13, a polypeptide according to any of aspects K-1 to K-4, said method at least comprising the steps of:
a) cultivating and/or maintaining a host or host cell according to aspect N-1 under conditions that are such that said host or host cell expresses and/or produces at least one immunoglobulin single variable domain according to any of aspects A-1 to A-22, B-1 to B-7, C-1 to C-4, D-1 to D-6, E-1 to E-13, a polypeptide according to any of aspects K-1 to K-4;
optionally followed by:
b) isolating and/or purifying the immunoglobulin single variable domain according to any of aspects A-1 to A-22, B-1 to B-7, C-1 to C-4, D-1 to D-6, E-1 to E-13, a polypeptide according to any of aspects K-1 to K-4.

Method of Screening

Aspect Q-1: Method for screening immunoglobulin single variable domains directed against CXCR7 and in particular human CXCR7 (SEQ ID NO: 1) that comprises at least the steps of:
a) providing a set, collection or library of nucleic acid sequences encoding immunoglobulin single variable domains;
b) screening said set, collection or library of nucleic acid sequences for nucleic acid sequences that encode an immunoglobulin single variable domain that can bind to and/or has affinity for CXCR7 and in particular human CXCR7 (SEQ ID NO: 1) and that is cross-blocked or is cross blocking a Nanobody of the invention, e.g., SEQ ID NO: 39 to 43, 91 or 99-102 (Table-B-3), or a polypeptide or construct of the invention, e.g., SEQ ID NO: 44 to 48, 78-89 or 131-140 (see Table B-4); and
c) isolating said nucleic acid sequence, followed by expressing said immunoglobulin single variable domain.

Use of Agents of the Invention

Aspect R-1: Method for the prevention and/or treatment of cancer and of inflammatory diseases (such as e.g., mentioned herein), said method comprising administering, to a subject in need thereof, a pharmaceutically active amount of at least one immunoglobulin single variable domain according to any of aspects A-1 to A-22, B-1 to B-7, C-1 to C-4, D-1 to D-6, E-1 to E-13, a polypeptide according to any of aspects K-1 to K-4; or composition according to aspect O-2 or O3.

Aspect R-2: Method for the prevention and/or treatment of at least one disease or disorder that is associated with CXCR7 and in particular human CXCR7 (SEQ ID NO: 1), such as for instance angiogenesis, and in particular in head and neck cancers, with its biological or pharmacological activity, and/or with the biological pathways or signalling in which CXCR7 and in particular human CXCR7 (SEQ ID NO: 1) is involved, said method comprising administering, to a subject in need thereof, a pharmaceutically active amount of at least one immunoglobulin single variable domain according to any of aspects A-1 to A-22, B-1 to B-7, C-1 to C-4, D-1 to D-6, E-1 to E-13, a polypeptide according to any of aspects K-1 to K-4; or composition according to aspect O-2 or O-3.

Aspect R-3: Method for the prevention and/or treatment of at least one disease or disorder that can be prevented and/or treated by administering, to a subject in need thereof, at least one immunoglobulin single variable domain according to any of aspects A-1 to A-22, B-1 to B-7, C-1 to C-4, D-1 to D-6, E-1 to E-13, a polypeptide according to any of aspects K-1 to K-4; or composition according to aspect O-2 or O-3, said method comprising administering, to a subject in need thereof, a pharmaceutically active amount of at least one at least one immunoglobulin single variable domain according to any of aspects A-1 to A-22, B-1 to B-7, C-1 to C-4, D-1 to D-6, E-1 to E-13, a polypeptide according to any of aspects K-1 to K-4; or composition according to aspect O-2 or O-3.

Aspect R-4: Method for immunotherapy, said method comprising administering, to a subject in need thereof, a pharmaceutically active amount of at least one immunoglobulin single variable domain according to any of aspects A-1 to A-22, B-1 to B-7, C-1 to C-4, D-1 to D-6, E-1 to E-13, a polypeptide according to any of aspects K-1 to K-4; or composition according to aspect O-2 or O-3.

Aspect R-5: An immunoglobulin single variable domain according to any of aspects A-1 to A-22, B-1 to B-7, C-1 to C-4, D-1 to D-6, E-1 to E-13, a polypeptide according to any of aspects K-1 to K-4, a pharmaceutical composition according to aspect O-2 or O-3 for use in one or more of the methods according to aspects R-1 to R-3.

Aspect R-6: A polypeptide according to any of aspects K-1 to K-4, for the diagnosis, prevention and/or treatment of cancer.

Further aspects:

1. A construct comprising at least one immunoglobulin single variable domain (ISVD) that binds to and/or recognizes amino acid residue M33, and optionally amino acid residue V32 and/or amino acid residue M37 in CXCR7 (SEQ ID NO: 1) and at least one ISVD that binds to and/or recognizes amino acid residue WF19, and optionally S23 and/or D25 of CXCR7 (SEQ ID NO: 1).
2. The construct according to aspect 1 for use as a medicament to reduce tumour growth and/or to treat cancer, preferably head and neck cancer or GBM.
3. An immunoglobulin single variable domain that can specifically displace SDF-1 and I-TAC on human CXCR7 (SEQ ID NO: 1) with an average Ki of less than 100 nM and an average SDF-1 and I-TAC displacement of 50% or more.
4. An immunoglobulin single variable domain that can specifically displace SDF-1 on human CXCR7 (SEQ ID NO: 1) with an average Ki of less than 100 nM and an average SDF-1 displacement of 50% or more.
5. An immunoglobulin single variable domain that can specifically displace I-TAC on human CXCR7 (SEQ ID NO: 1) with an average Ki of less than 100 nM and an average I-TAC displacement of 50% or more.
6. The immunoglobulin single variable domain of any of aspects 3-5, wherein the average Ki is 50 nM or less.
7. The immunoglobulin single variable domain of any of aspects 3-5, wherein the average Ki is 10 nM or less.
8. The immunoglobulin single variable domain of any of aspects 3-7, wherein the average SDF-1 or I-TAC displacement is 80% or more.
9. An immunoglobulin single variable domain that can bind human CXCR7 (SEQ ID NO: 1) with a Kd of less than 50 nM.
10. An immunoglobulin single variable domain that binds to and/or recognizes amino acid residue M33, and optionally amino acid residue V32 and/or amino acid residue M37 in CXCR7 (SEQ ID NO: 1).
11. An immunoglobulin single variable domain that binds to and/or recognizes amino acid residue WF19, and optionally S23 and/or D25 of CXCR7 (SEQ ID NO: 1).
12. The immunoglobulin single variable domain according to aspect 10 or 11 for use as a medicament to reduce tumour growth and/or to treat cancer, preferably head and neck cancer or GBM.
13. The immunoglobulin single variable domain of any of aspects 3-12, wherein the immunoglobulin single variable domain comprises an amino acid sequence with the formula 1

FR1-CDR1-FR2-CDR2FR3-CDR3-FR4 (1);

wherein FR1 to FR4 refer to framework regions 1 to 4 and are framework regions of an immunoglobulin single variable domain; and
wherein CDR1 is chosen from the group consisting of:
a) the immunoglobulin single variable domain of SEQ ID NO: 9,
b) immunoglobulin single variable domains that have at least 80% amino acid identity with the immunoglobulin single variable domain of SEQ ID NO: 9,
c) immunoglobulin single variable domains that have 3, 2, or 1 amino acid difference with the immunoglobulin single variable domain of SEQ ID NO: 9,
and wherein CDR2 is chosen from the group consisting of:
d) the immunoglobulin single variable domain of SEQ ID NO: 19;
e) immunoglobulin single variable domains that have at least 80% amino acid identity with the immunoglobulin single variable domain of SEQ ID NO: 19;
f) immunoglobulin single variable domains that have 3, 2, or 1 amino acid difference with the immunoglobulin single variable domain of SEQ ID NO: 19;
and wherein CDR3 is chosen from the group consisting of:
g) the immunoglobulin single variable domain of SEQ ID NO: 29;
h) immunoglobulin single variable domains that have at least 80% amino acid identity with the immunoglobulin single variable domain of SEQ ID NO: 29;
i) immunoglobulin single variable domains that have 3, 2, or 1 amino acid difference with the immunoglobulin single variable domain of SEQ ID NO: 29.
14. The immunoglobulin single variable domain of any of aspects 3-12, wherein the immunoglobulin single variable domain comprises an amino acid sequence with the formula 1

FR1-CDR1-FR2-CDR2FR3-CDR3-FR4 (1);

wherein FR1 to FR4 refer to framework regions 1 to 4 and are framework regions of an immunoglobulin single variable domain; and
wherein CDR1 is chosen from the group consisting of:
a) the immunoglobulin single variable domain of SEQ ID NO: 10,
b) immunoglobulin single variable domains that have at least 80% amino acid identity with the immunoglobulin single variable domain of SEQ ID NO: 10,
c) immunoglobulin single variable domains that have 3, 2, or 1 amino acid difference with the immunoglobulin single variable domain of SEQ ID NO: 10, and wherein CDR2 is chosen from the group consisting of:
   d) the immunoglobulin single variable domain of SEQ ID NO: 20;
   e) immunoglobulin single variable domains that have at least 80% amino acid identity with the immunoglobulin single variable domain of SEQ ID NO: 20;
   f) immunoglobulin single variable domains that have 3, 2, or 1 amino acid difference with the immunoglobulin single variable domain of SEQ ID NO: 20;
and wherein CDR3 is chosen from the group consisting of:
   g) the immunoglobulin single variable domain of SEQ ID NO: 30;
   h) immunoglobulin single variable domains that have at least 80% amino acid identity with the immunoglobulin single variable domain of SEQ ID NO: 30;
   i) immunoglobulin single variable domains that have 3, 2, or 1 amino acid difference with the immunoglobulin single variable domain of SEQ ID NO: 30.

15. The immunoglobulin single variable domain of any of aspects 3-12, wherein the immunoglobulin single variable domain comprises an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain; and
wherein CDR1 is chosen from the group consisting of:
   a) the immunoglobulin single variable domain of SEQ ID NO: 11,
   b) immunoglobulin single variable domains that have at least 80% amino acid identity with the immunoglobulin single variable domain of SEQ ID NO: 11,
   c) immunoglobulin single variable domains that have 3, 2, or 1 amino acid difference with the immunoglobulin single variable domain of SEQ ID NO: 11,
and wherein CDR2 is chosen from the group consisting of:
   d) the immunoglobulin single variable domain of SEQ ID NO: 21;
   e) immunoglobulin single variable domains that have at least 80% amino acid identity with the immunoglobulin single variable domain of SEQ ID NO: 21;
   f) immunoglobulin single variable domains that have 3, 2, or 1 amino acid difference with the immunoglobulin single variable domain of SEQ ID NO: 21;
and wherein CDR3 is chosen from the group consisting of:
   g) the immunoglobulin single variable domain of SEQ ID NO: 31;
   h) immunoglobulin single variable domains that have at least 80% amino acid identity with the immunoglobulin single variable domain of SEQ ID NO: 31;
   i) immunoglobulin single variable domains that have 3, 2, or 1 amino acid difference with the immunoglobulin single variable domain of SEQ ID NO: 31.

16. The immunoglobulin single variable domain of any of aspects 3-12, wherein the immunoglobulin single variable domain comprises an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain; and
wherein CDR1 is chosen from the group consisting of:
   a) the immunoglobulin single variable domain of SEQ ID NO: 12,
   b) immunoglobulin single variable domains that have at least 80% amino acid identity with the immunoglobulin single variable domain of SEQ ID NO: 12,
   c) immunoglobulin single variable domains that have 3, 2, or 1 amino acid difference with the immunoglobulin single variable domain of SEQ ID NO: 12,
and wherein CDR2 is chosen from the group consisting of:
   d) the immunoglobulin single variable domain of SEQ ID NO: 22;
   e) immunoglobulin single variable domains that have at least 80% amino acid identity with the immunoglobulin single variable domain of SEQ ID NO: 22;
   f) immunoglobulin single variable domains that have 3, 2, or 1 amino acid difference with the immunoglobulin single variable domain of SEQ ID NO: 22;
and wherein CDR3 is chosen from the group consisting of:
   g) the immunoglobulin single variable domain of SEQ ID NO: 32;
   h) immunoglobulin single variable domains that have at least 80% amino acid identity with the immunoglobulin single variable domain of SEQ ID NO: 32;
   i) immunoglobulin single variable domains that have 3, 2, or 1 amino acid difference with the immunoglobulin single variable domain of SEQ ID NO: 32.

17. The immunoglobulin single variable domain of any of aspects 3-12, wherein the immunoglobulin single variable domain comprises an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain; and
wherein CDR1 is chosen from the group consisting of:
   a) the immunoglobulin single variable domain of SEQ ID NO: 13,
   b) immunoglobulin single variable domains that have at least 80% amino acid identity with the immunoglobulin single variable domain of SEQ ID NO: 13,
   c) immunoglobulin single variable domains that have 3, 2, or 1 amino acid difference with the immunoglobulin single variable domain of SEQ ID NO: 13,
and wherein CDR2 is chosen from the group consisting of:
   d) the immunoglobulin single variable domain of SEQ ID NO: 23;
   e) immunoglobulin single variable domains that have at least 80% amino acid identity with the immunoglobulin single variable domain of SEQ ID NO: 23;
   f) immunoglobulin single variable domains that have 3, 2, or 1 amino acid difference with the immunoglobulin single variable domain of SEQ ID NO: 23;
and wherein CDR3 is chosen from the group consisting of:
   g) the immunoglobulin single variable domain of SEQ ID NO: 33;
   h) immunoglobulin single variable domains that have at least 80% amino acid identity with the immunoglobulin single variable domain of SEQ ID NO: 33;
   i) immunoglobulin single variable domains that have 3, 2, or 1 amino acid difference with the immunoglobulin single variable domain of SEQ ID NO: 33.

18. The immunoglobulin single variable domain of any of aspects 3-12, wherein the immunoglobulin single variable domain comprises an amino acid sequence with the formula 1

FR1-CDR1-FR2-CDR2FR3-CDR3-FR4 (1);

wherein FR1 to FR4 refer to framework regions 1 to 4 and are framework regions of an immunoglobulin single variable domain; and wherein CDR1 is chosen from the group consisting of:
  a) the immunoglobulin single variable domain of SEQ ID NO: 93,
  b) immunoglobulin single variable domains that have at least 80% amino acid identity with the immunoglobulin single variable domain of SEQ ID NO: 93,
  c) immunoglobulin single variable domains that have 3, 2, or 1 amino acid difference with the immunoglobulin single variable domain of SEQ ID NO: 93;
and wherein CDR2 is chosen from the group consisting of:
  d) the immunoglobulin single variable domain of SEQ ID NO: 95;
  e) immunoglobulin single variable domains that have at least 80% amino acid identity with the immunoglobulin single variable domain of SEQ ID NO: 95;
  f) immunoglobulin single variable domains that have 3, 2, or 1 amino acid difference with the immunoglobulin single variable domain of SEQ ID NO: 95;
and wherein CDR3 is chosen from the group consisting of:
  g) the immunoglobulin single variable domain of SEQ ID NO: 97;
  h) immunoglobulin single variable domains that have at least 80% amino acid identity with the immunoglobulin single variable domain of SEQ ID NO: 97;
  i) immunoglobulin single variable domains that have 3, 2, or 1 amino acid difference with the immunoglobulin single variable domain of SEQ ID NO: 97.

19. The immunoglobulin single variable domain of any of aspects 3-12, wherein the immunoglobulin single variable domain comprises an amino acid sequence with the formula 1

FR1-CDR1-FR2-CDR2FR3-CDR3-FR4 (1);

wherein FR1 to FR4 refer to framework regions 1 to 4 and are framework regions of an immunoglobulin single variable domain; and
wherein CDR1 is chosen from the group consisting of:
  a) the immunoglobulin single variable domain of SEQ ID NO: 107,
  b) immunoglobulin single variable domains that have at least 80% amino acid identity with the immunoglobulin single variable domain of SEQ ID NO: 107,
  c) immunoglobulin single variable domains that have 3, 2, or 1 amino acid difference with the immunoglobulin single variable domain of SEQ ID NO: 107,
and wherein CDR2 is chosen from the group consisting of:
  d) the immunoglobulin single variable domain of SEQ ID NO: 115;
  e) immunoglobulin single variable domains that have at least 80% amino acid identity with the immunoglobulin single variable domain of SEQ ID NO: 115;
  f) immunoglobulin single variable domains that have 3, 2, or 1 amino acid difference with the immunoglobulin single variable domain of SEQ ID NO: 115;
and wherein CDR3 is chosen from the group consisting of:
  g) the immunoglobulin single variable domain of SEQ ID NO: 123;
  h) immunoglobulin single variable domains that have at least 80% amino acid identity with the immunoglobulin single variable domain of SEQ ID NO: 123;
  i) immunoglobulin single variable domains that have 3, 2, or 1 amino acid difference with the immunoglobulin single variable domain of SEQ ID NO: 123.

20. The immunoglobulin single variable domain of any of aspects 3-12, wherein the immunoglobulin single variable domain comprises an amino acid sequence with the formula 1

FR1-CDR1-FR2-CDR2FR3-CDR3-FR4 (1);

wherein FR1 to FR4 refer to framework regions 1 to 4 and are framework regions of an immunoglobulin single variable domain; and
wherein CDR1 is chosen from the group consisting of:
  a) the immunoglobulin single variable domain of SEQ ID NO: 108,
  b) immunoglobulin single variable domains that have at least 80% amino acid identity with the immunoglobulin single variable domain of SEQ ID NO: 108,
  c) immunoglobulin single variable domains that have 3, 2, or 1 amino acid difference with the immunoglobulin single variable domain of SEQ ID NO: 108,
and wherein CDR2 is chosen from the group consisting of:
  d) the immunoglobulin single variable domain of SEQ ID NO: 116;
  e) immunoglobulin single variable domains that have at least 80% amino acid identity with the immunoglobulin single variable domain of SEQ ID NO: 116;
  f) immunoglobulin single variable domains that have 3, 2, or 1 amino acid difference with the immunoglobulin single variable domain of SEQ ID NO: 116;
and wherein CDR3 is chosen from the group consisting of:
  g) the immunoglobulin single variable domain of SEQ ID NO: 124;
  h) immunoglobulin single variable domains that have at least 80% amino acid identity with the immunoglobulin single variable domain of SEQ ID NO: 124;
  i) immunoglobulin single variable domains that have 3, 2, or 1 amino acid difference with the immunoglobulin single variable domain of SEQ ID NO: 124.

21. The immunoglobulin single variable domain of any of aspects 3-12, wherein the immunoglobulin single variable domain comprises an amino acid sequence with the formula 1

FR1-CDR1-FR2-CDR2FR3-CDR3-FR4 (1);

wherein FR1 to FR4 refer to framework regions 1 to 4 and are framework regions of an immunoglobulin single variable domain; and
wherein CDR1 is chosen from the group consisting of:
  a) the immunoglobulin single variable domain of SEQ ID NO: 110,
  b) immunoglobulin single variable domains that have at least 80% amino acid identity with the immunoglobulin single variable domain of SEQ ID NO: 110,
  c) immunoglobulin single variable domains that have 3, 2, or 1 amino acid difference with the immunoglobulin single variable domain of SEQ ID NO: 110, and wherein CDR2 is chosen from the group consisting of:
d) the immunoglobulin single variable domain of SEQ ID NO: 118;
e) immunoglobulin single variable domains that have at least 80% amino acid identity with the immunoglobulin single variable domain of SEQ ID NO: 118;
f) immunoglobulin single variable domains that have 3, 2, or 1 amino acid difference with the immunoglobulin single variable domain of SEQ ID NO: 118;
and wherein CDR3 is chosen from the group consisting of:
g) the immunoglobulin single variable domain of SEQ ID NO: 126;
h) immunoglobulin single variable domains that have at least 80% amino acid identity with the immunoglobulin single variable domain of SEQ ID NO: 126;
i) immunoglobulin single variable domains that have 3, 2, or 1 amino acid difference with the immunoglobulin single variable domain of SEQ ID NO: 126.

22. The immunoglobulin single variable domain according to any of aspects 1-21, wherein the framework regions (FRs) have a sequence identity of more than 80% with the FRs of SEQ ID NOs: 4 to 8, 92, 103, 104 or 106 (FR1), 14 to 18, 94, 111, 112 or 114 (FR2), 24 to 28, 96, 119, 120 or 122 (FR3), and/or 34 to 38, 98, 127, 128 or 130 (FR4).

23. A polypeptide comprising an immunoglobulin single variable domain of any of aspects 3-22.

24. The polypeptide according to aspect 23, wherein the immunoglobulin single variable domain is selected from the group consisting of immunoglobulin single variable domains that have an amino acid sequence with a sequence identity of more than 80% with the immunoglobulin single variable domains of SEQ ID NOs: 39 to 43, 91 or 99-102.

25. The polypeptide according to any of aspects 23-24 and additionally comprising at least one human serum albumin binding immunoglobulin single variable domain and optionally comprising a linker selected from the group of linkers with SEQ ID NOs: 49 to 58.

26. The polypeptide according to any of aspects 23-25 and additionally comprising ALB8 (SEQ ID NO: 2), and optionally comprising a linker selected from the group of linkers with SEQ ID NOs: 49 to 58.

27. The polypeptides according to any of aspects 23-26, wherein the polypeptide is selected from the group consisting of polypeptides that have an amino acid sequence with a sequence identity of more than 80% with the polypeptides of SEQ ID NOs: 44 to 48, 78 to 89 and 131 to 140.

28. A construct chosen from the group consisting of:
constructs comprising at least two ISVDs that bind to and/or recognize amino acid residue WF19, and optionally S23 and/or D25 of CXCR7 (SEQ ID NO: 1), wherein said at least two ISVDs can be the same or different;
constructs comprising at least two ISVDs that bind to and/or recognize amino acid residue M33, and optionally amino acid residue V32 and/or amino acid residue M37 in CXCR7 (SEQ ID NO: 1), wherein said at least two ISVDs can be the same or different;
constructs comprising at least one group 1 ISVD and at least one group 2 ISVD;
constructs comprising at least one group 1 ISVD and at least one group 3 ISVD;
constructs comprising at least one group 2 ISVD and at least one group 3 ISVD; and
constructs comprising at least one 01C10-like sequence and at least one 14G03-like sequence.

29. The construct according to aspect 28 for use as a medicament to reduce tumour growth and/or to treat cancer, preferably head and neck cancer or GBM.

30. A nucleic acid sequence encoding
i) for an immunoglobulin single variable domain according to any of aspects 3-22;
ii) for a polypeptide according to any of aspects 23-27, or
iii) for a construct according to any of aspects 1, 2, 28 or 29.

31. A pharmaceutical composition comprising
i) an immunoglobulin single variable domain according to any of aspects 3-22;
ii) a polypeptide according to any of aspects 23-27; or
iii) a construct according to any of aspects 1, 2, 28 or 29; and optionally a pharmaceutically acceptable excipient.

32. An immunoglobulin single variable domain according to any of aspects 3-22, a polypeptide according to any of aspects 23-27, or a construct according to any of aspects 1, 2, 28 or 29 for use in cancer, preferably head or neck cancer, GBM and/or inflammatory diseases.

33. An immunoglobulin single variable domain according to any of aspects 3-22, a polypeptide according to any of aspects 23-27, or a construct according to any of aspects 1, 2, 28 or 29 for use in rheumatoid arthritis.

34. An immunoglobulin single variable domain according to any of aspects 3-22, a polypeptide according to any of aspects 23-27, or a construct according to any of aspects 1, 2, 28 or 29 for use in multiple sclerosis.

35. Method for producing an immunoglobulin single variable domain according to any of aspects 3-22, a polypeptide according to any of aspects 23-27, or a construct according to any of aspects 1, 2, 28 or 29, said method at least comprising the steps of:
a) expressing, in a suitable host cell or host organism or in another suitable expression system, a nucleic acid or nucleotide sequence according to aspect 30; optionally followed by:
b) isolating and/or purifying the immunoglobulin single variable domain according to any of aspects 3-22, a polypeptide according to any of aspects 23-27, or a construct according to any of aspects 1, 2, 28 or 29.

36. An immunoglobulin single variable comprising an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain;
wherein CDR1 is the immunoglobulin single variable domain of SEQ ID NO: 9;
wherein CDR2 is the immunoglobulin single variable domain of SEQ ID NO: 19; and
wherein CDR3 is the immunoglobulin single variable domain of SEQ ID NO: 29.

37. An immunoglobulin single variable comprising an amino acid sequence with the formula 1 variable domain comprises an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain;
wherein CDR1 is the immunoglobulin single variable domain of SEQ ID NO: 10;

wherein CDR2 is the immunoglobulin single variable domain of SEQ ID NO: 20; and wherein CDR3 is the immunoglobulin single variable domain of SEQ ID NO: 30.

38. An immunoglobulin single variable comprising an amino acid sequence with the formula 1 variable domain comprises an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain;

wherein CDR1 is the immunoglobulin single variable domain of SEQ ID NO: 11;

wherein CDR2 is the immunoglobulin single variable domain of SEQ ID NO: 21; and wherein CDR3 is the immunoglobulin single variable domain of SEQ ID NO: 31.

39. An immunoglobulin single variable comprising an amino acid sequence with the formula 1 variable domain comprises an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain;

wherein CDR1 is the immunoglobulin single variable domain of SEQ ID NO: 12;

wherein CDR2 is the immunoglobulin single variable domain of SEQ ID NO: 22; and wherein CDR3 is the immunoglobulin single variable domain of SEQ ID NO: 32.

40. An immunoglobulin single variable comprising an amino acid sequence with the formula 1 variable domain comprises an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain;

wherein CDR1 is the immunoglobulin single variable domain of SEQ ID NO: 13;

wherein CDR2 is the immunoglobulin single variable domain of SEQ ID NO: 23; and wherein CDR3 is the immunoglobulin single variable domains of SEQ ID NO: 33.

41. An immunoglobulin single variable comprising an amino acid sequence with the formula 1 variable domain comprises an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain;

wherein CDR1 is the immunoglobulin single variable domain of SEQ ID NO: 93;

wherein CDR2 is the immunoglobulin single variable domain of SEQ ID NO: 95; and wherein CDR3 is the immunoglobulin single variable domain of SEQ ID NO: 97.

42. An immunoglobulin single variable comprising an amino acid sequence with the formula 1 variable domain comprises an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain;

wherein CDR1 is the immunoglobulin single variable domain of SEQ ID NO: 107;

wherein CDR2 is the immunoglobulin single variable domain of SEQ ID NO: 115; and wherein CDR3 is the immunoglobulin single variable domain of SEQ ID NO: 123.

43. An immunoglobulin single variable comprising an amino acid sequence with the formula 1 variable domain comprises an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain;

wherein CDR1 is the immunoglobulin single variable domain of SEQ ID NO: 108;

wherein CDR2 is the immunoglobulin single variable domain of SEQ ID NO: 116; and wherein CDR3 is the immunoglobulin single variable domains of SEQ ID NO: 124.

44. An immunoglobulin single variable comprising an amino acid sequence with the formula 1 variable domain comprises an amino acid sequence with the formula 1

FR1-CDR1-FR2-CDR2FR3-CDR3-FR4    (1);

wherein FR1 to FR4 refer to framework regions 1 to 4 and are framework regions of an immunoglobulin single variable domain;

wherein CDR1 is the immunoglobulin single variable domain of SEQ ID NO: 110;

wherein CDR2 is the immunoglobulin single variable domain of SEQ ID NO: 118; and wherein CDR3 is the immunoglobulin single variable domain of SEQ ID NO: 126.

The invention will now be further described by means of the following non-limiting preferred aspects, examples and figures:

The entire contents of all of the references (including literature references, issued patents, published patent applications, and co pending patent applications) cited throughout this application are hereby expressly incorporated by reference, in particular for the teaching that is referenced hereinabove.

EXPERIMENTAL PART

Sequences

TABLE B-1

Prior art sequences

| Name | SEQ ID NO: | Amino acid sequences |
|---|---|---|
| Human CXCR7 or hCXCR7 | 1 | MDLHLFDYSEPGNFSDISWPCNSSDCIVVDTVMCPNMPN KSVLLYTLSFIYIFIFVIGMIANSVVVWVNIQAKTTGYD THCYILNLAIADLWVVLTIPVWVVSLVQHNQWPMGELTC KVTHLIFSINLFGSIFFLTCMSVDRYLSITYFTNTPSSR KKMVRRVVCILVWLLAFCVSLPDTYYLKTVTSASNNETY CRSFYPEHSIKEWLIGMELVSVVLGFAVPFSIIAVFYFL LARAISASSDQEKHSSRKIIFSYVVVFLVCWLPYHVAVL LDIFSILHYIPFTCRLEHALFTALHVTQCLSLVHCCVNP VLYSFINRNYRYELMKAFIFKYSAKTGLTKLIDASRVSE TEYSALEQSTK |
| Alb8 | 2 | EVQLVESGGGLVQPGNSLRLSCAASGFTFSSFGMSWVRQ APGKGLEWVSSISGSGSDTLYADSVKGRFTISRDNAKTT LYLQMNSLRPEDTAVYYCTIGGSLSRSSQGTLVTVSS |
| Mouse CXCR7 or mCXCR7 | 3 | MDVHLFDYAEPGNYSDINWPCNSSDCIVVDTVQCPTMPN KNVLLYTLSFIYIFIFVIGMIANSVVVWVNIQAKTTGYD THCYILNLAIADLWVVITIPVWVVSLVQHNQWPMGELTC KITHLIFSINLFGSIFFLACMSVDRYLSITYFTGTSSYK KKMVRRVVCILVWLLAFFVSLPDTYYLKTVTSASNNETY CRSFYPEHSIKEWLIGMELVSVILGFAVPFTIIAIFYFL LARAMSASGDQEKHSSRKIIFSYVVVFLVCWLPYHFVVL LDIFSILHYIPFTCQLENVLFTALHVTQCLSLVHCCVNP VLYSFINRNYRYELMKAFIFKYSAKTGLTKLIDASRVSE TEYSALEQNTK |
| Tag-1 | 71 | AAAHHHHHHGAAEQKLISEEDLNGAA |
| Tag-2 | 72 | AAAEQKLISEEDLNGAAHHHHHH |
| Tag-3 | 105 | GAAEQKLISEEDLNGAAHHHHHH |
| Cynomolgus CXCR7 or cCXCR7 | 90 | MDLHVFDYSEPGNFSDISWPCNSSDCIVVDTVMCPNMPN KSVLLYTLAFIYIFIFVIGMIANSVVVWVNIQAKTTGYD THCYILNLAIADLWVVLTIPVWVVSLVQHNQWPMGELTC KVTHLIFSINLFGSIFFLTCMSVDRYLSITYFTNTSSSR KKMVRRVVCVLVWLLAFCVSLPDTYYLKTVTSASNNETY CRSFYPEHSIKEWLIGMELVSVVLGFAVPFSVIAVFYFL LARAISASGDQEKHSSRKIIFSYVVVFLVCWLPYHVAVL LDIFSILHYIPFTCRLEHALFTALHVTQCLSLVHCCVNP VLYSFINRNYRYELMKAFIFKYSAKTGLTKLIDASRVSE TEYSALEQSTK |

TABLE B-2

Sequences for CDRs and frameworks, plus preferred combinations as provided in for formula I, namely FR1-CDR1-FR2-CDR2-FR3-CDR3-FR4

| Clone | ID | FR1 | ID | CDR1 | ID | FR2 |
|---|---|---|---|---|---|---|
| 07B11 | 4 | EVQLVESGGNLVQAGGSLGLSCAAS VSISS | 9 | IHIMG | 14 | WYRQAPGKQRDLVA |
| 07C03 | 5 | EVQLVESGGGLVQAGESLTLSCAAS GRTLS | 10 | AYIMG | 15 | WFRQAPGKEREFVA |
| 08A05 | 6 | EVQLVESGGGLVQAGDSLRLSCAAS GLTFS | 11 | NYDMG | 16 | WFRQAPGKEREFVG |
| 08A10 | 7 | EVQLVESGGGLVQAGGSLRLSCAAS GSIFS | 12 | IAAMG | 17 | WYRQATGKQRELVA |
| 14G03 (09A04) | 8 | EVQLVESGGGLVQPGGSLRISCAAS GSIYL | 13 | INYMG | 18 | WYRQAPGKQRELVA |
| Alb8 | 64 | EVQLVESGGGLVQPGNSLRLSCAAS GFTFS | 65 | SFGMS | 66 | WVRQAPGKGLEWVS |
| 01C10 | 92 | EVQLVESGGGLVQTGASLRLSCAAS GRTFS | 93 | NYAMG | 94 | WFRQAPGKERERVA |
| 01C12 | 103 | EVQLVESGGGLVQAGASLRLSCAAS GRTFS | 107 | NYAMG | 111 | WFRQAPGKERERVA |
| 01B12 | 104 | EVQLVESGGGLVQAGASLRLSCAAS GRTFS | 108 | NYAMG | 112 | WFRQAPGKEREPVA |

TABLE B-2-continued

Sequences for CDRs and frameworks, plus preferred combinations as provided in for formula I, namely FR1-CDR1-FR2-CDR2-FR3-CDR3-FR4

| Clone | ID | FR1 | ID | CDR1 | ID | FR2 |
|---|---|---|---|---|---|---|
| 01F11 | 105 | EVQLVESGGGLVQAGASLRLSCAASGRTFS | 109 | NYAMG | 113 | WFRQAPGKEREPVA |
| 01B10 | 106 | EVQLVESGGGLVQAGASLRLSCAASGRTFG | 110 | NYAMG | 114 | WFRQAPGKEREPVA |

| Clone | ID | CDR2 | ID | FR3 |
|---|---|---|---|---|
| 07B11 | 19 | TITSGGSTAYADSVKG | 24 | RFTVSKDNAKNTVYLQMDSLKPEDTSVYYCAA |
| 07C03 | 20 | GIWSGGYTHLADSAKG | 25 | RFSISRDNAKNTVYLQMNGLKPEDTAVYYCAA |
| 08A05 | 21 | ASWWSGGAPYYSDSVKG | 26 | RFTISRDNAKNTVYLQANSLRPEDTAVYYCAA |
| 08A10 | 22 | TITDGGTTTYADSVKG | 27 | RVTISRDRSANTVYLAMNNLKPDDTAVYYCYA |
| 14G03 (09A04) | 23 | TLTSGGSTNYAGSVKG | 28 | RFAISRDNAKNTVYLQMNSLKPEDTAVYYCNI |
| Alb8 | 67 | SISGSGSDTLYADSVKG | 68 | RFTISRDNAKTTLYLQMNSLRPEDTAVYYCTI |
| 01C10 | 95 | AITPRAFTTYYADSVKG | 96 | RFTISRDNAKNTAYLQMVSLKPEDTAVYYCAA |
| 01C12 | 115 | AISPSAVTTYYADSVKG | 119 | RFTISRDNAKNTAYLQMVSLKPEDTAVYYCAA |
| 01B12 | 116 | AISPAALTTYYADFVKG | 120 | RFTISRDNAKNTAYLQMVSLKPEDTAVYYCAA |
| 01F11 | 117 | AISPAALTTYYADFVKG | 121 | RFTISRDNAKNTAYLQMVSLKPEDTAVYYCAA |
| 01B10 | 118 | AISPAAVTTYYADFVKG | 122 | RFTISRDNAKNTAYLQMVSLKPEDTAVYYCAA |

| Clone | ID | CDR3 | ID | FR4 |
|---|---|---|---|---|
| 07B11 | 29 | EVRNGVFGKWNHY | 34 | WGQGTQVTVSS |
| 07C03 | 30 | GLRGRQYSN | 35 | WGQGTQVTVSS |
| 08A05 | 31 | KRLRSFASGGSYDY | 36 | WGQGTQVTVSS |
| 08A10 | 32 | YLRYTSRVPGDNY | 37 | WGQGTQVTVSS |
| 14G03 (09A04) | 33 | GGTLYDRRRFES | 38 | WGQGTQVTVSS |
| Alb8 | 69 | GGSLSR | 70 | SSQGTLVTVSS |
| 01C10 | 97 | QLVGSGSNLGRQESYAY | 98 | WGQGTQVTVSS |
| 01C12 | 123 | QLPGRGSNLGRQASYAY | 127 | WGQGTQVTVSS |
| 01B12 | 124 | QLVGSGSNLGRQQSYAY | 128 | WGQGTQVTVSS |
| 01F11 | 125 | QLVGSGSNLGRQQSYAY | 129 | WGQGTQVTVSS |
| 01B10 | 126 | QLVGSGSNLGRQQSYAY | 130 | WGQGTQVTVSS |

(Terms: "ID" refers to the given SEQ ID NO. Preferred combination of FR and CDR sequences for each NB construct are used interchangeably through-out the application)

TABLE B-3

Amino acid sequences of immunoglobulin single variable sequences of the invention

| Name of clone | SEQ ID NO: | Amino acid sequences |
|---|---|---|
| 07B11 | 39 | EVQLVESGGNLVQAGGSLGLSCAASVSISSIHIMGWYRQAPGKQRDLVATITSGGSTAYADSVKGRFTVSKDNAKNTVYLQMDSLKPEDTSVYYCAAEVRNGVFGKWNHYWGQGTQVTVSS |
| 07C03 | 40 | EVQLVESGGGLVQAGESLTLSCAASGRTLSAYIMGWFRQAPGKEREFVAGIWSGGYTHLADSAKGRFSISRDNAKNTVYLQMNGLKPEDTAVYYCAAGLRGRQYSNWGQGTQVTVSS |
| 08A05 | 41 | EVQLVESGGGLVQAGDSLRLSCAASGLTFSNYDMGWFRQAPGKEREFVGASWWSGGAPYYSDSVKGRFSISRDNAKNTVYLQANSLRPEDTAVYYCAAKRLRSFASGGSYDYWGQGTQVTVSS |
| 08A10 | 42 | EVQLVESGGGLVQAGGSLRLSCAASGSIFSIAAMGWYRQATGKQRELVATITDGGTTTYADSVKGRVTISRDRSANTVYLAMNNLKPDDTAVYYCYAYLRYTSRVPGDNYWGQGTQVTVSS |
| 14G03 (09A04)* | 43 | EVQLVESGGGLVQPGGSLRISCAASGSIYLINYMGWYRQAPGKQRELVATLTSGGSTNYAGSVKGRFAISRDNAKNTVYLQMNSLKPEDTAVYYCNIGGTLYDRRRFESWGQGTQVTVSS |
| 01C10 | 91 | EVQLVESGGGLVQTGASLRLSCAASGRTFSNYAMGWFRQAPGKERERVAAITPRAFTTYYADSVKGRFTISRDNAKNTAYLQMVSLKPEDTAVYYCAAQLVGSGSNLGRQESYAYWGQGTQVTVSS |
| 01C12 | 99 | EVQLVESGGGLVQAGASLRLSCAASGRTFSNYAMGWFRQAPGKERERVAAISPSAVTTYYADSVKGRFTISRDNAKNTAYLQMVSLKPEDTAVYYCAAQLPGRGSNLGRQASYAYWGQGTQVTVSS |
| 01B12 | 100 | EVQLVESGGGLVQAGASLRLSCAASGRTFSNYAMGWFRQAPGKEREPVAAISPAALTTYYADFVKGRFTISRDNAKNTAYLQMVSLKPEDTAVYYCAAQLVGSGSNLGRQQSYAYWGQGTQVTVSS |
| 01F11 | 101 | EVQLVESGGGLVQAGASLRLSCAASGRTFSNYAMGWFRQAPGKEREPVAAISPAALTTYYADFVKGRFTISRDNAKNTAYLQMVSLKPEDTAVYYCAAQLVGSGSNLGRQQSYAYWGQGTQVTVSS |
| 01B10 | 102 | EVQLVESGGGLVQAGASLRLSCAASGRTFGNYAMGWFRQAPGKEREPVAAISPAAVTTYYADFVKGRFTISRDNAKNTAYLQMVSLKPEDTAVYYCAAQLVGSGSNLGRQQSYAYWGQGTQVTVSS |

*The sequences of 14G03 is identical to the sequence of 09A04; 14G03 is used interchangeably with 09A04.

TABLE B-4

| | Polypeptide sequences of the invention | |
|---|---|---|
| Name of clone | SEQ ID NO: | Amino acid sequences |
| 07B11-9GS-Alb8 | 44 | EVQLVESGGNLVQAGGSLGLSCAASVSISSIHIMGWYRQAPGKQRDLVATITSGGSTAYADSVKGRFTVSKDNAKNTVYLQMDSLKPEDTSVYYCAAEVRNGVFGKWNHYWGQGTQVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 07C03-9GS-Alb8 | 45 | EVQLVESGGGLVQAGESLTLSCAASGRTLSAYIMGWFRQAPGKEREFVAGIWSGGYTHLADSAKGRFSISRDNAKNTVYLQMNGLKPEDTAVYYCAAGLRGRQYSNWGQGTQVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 08A05-9GS-Alb8 | 46 | EVQLVESGGGLVQAGDSLRLSCAASGLTFSNYDMGWFRQAPGKEREFVGASWWSGGAPYYSDSVKGRFTISRDNAKNTVYLQANSLRPEDTAVYYCAAKRLRSFASGGSYDYWGQGTQVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 08A10-9GS-Alb8 | 47 | EVQLVESGGGLVQAGGSLRLSCAASGSIFSIAAMGWYRQATGKQRELVATITDGGTTTYADSVKGRVTISRDRSANTVYLAMNNLKPDDTAVYYCYAYLRYTSRVPGDNYWGQGTQVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 14G03-9GS-Alb8 | 48 | EVQLVESGGGLVQPGGSLRISCAASGSIYLINYMGWYRQAPGKQRELVATLTSGGSTNYAGSVKGRFAISRDNAKNTVYLQMNSLKPEDTAVYYCNIGGTLYDRRRFESWGQGTQVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSS |
| 07B11-9GS-07C03 | 78 | EVQLVESGGNLVQAGGSLGLSCAASVSISSIHIMGWYRQAPGKQRDLVATITSGGSTAYADSVKGRFTVSKDNAKNTVYLQMDSLKPEDTSVYYCAAEVRNGVFGKWNHYWGQGTQVTVSSGGGGSGGGSEVQLVESGGGLVQAGESLTLSCAASGRTLSAYIMGWFRQAPGKEREFVAGIWSGGYTHLADSAKGRFSISRDNAKNTVYLQMNGLKPEDTAVYYCAAGLRGRQYSNWGQGTQVTVSS |
| 07C03-9GS-07B11 | 79 | EVQLVESGGGLVQAGESLTLSCAASGRTLSAYIMGWFRQAPGKEREFVAGIWSGGYTHLADSAKGRFSISRDNAKNTVYLQMNGLKPEDTAVYYCAAGLRGRQYSNWGQGTQVTVSSGGGGSGGGSEVQLVESGGNLVQAGGSLGLSCAASVSISSIHIMGWYRQAPGKQRDLVATITSGGSTAYADSVKGRFTVSKDNAKNTVYLQMDSLKPEDTSVYYCAAEVRNGVFGKWNHYWGQGTQVTVSS |
| 07B11-9GS-Alb8-9GS-07C03 | 80 | EVQLVESGGNLVQAGGSLGLSCAASVSISSIHIMGWYRQAPGKQRDLVATITSGGSTAYADSVKGRFTVSKDNAKNTVYLQMDSLKPEDTSVYYCAAEVRNGVFGKWNHYWGQGTQVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSGGGGSGGGSEVQLVESGGGLVQAGESLTLSCAASGRTLSAYIMGWFRQAPGKEREFVAGIWSGGYTHLADSAKGRFSISRDNAKNTVYLQMNGLKPEDTAVYYCAAGLRGRQYSNWGQGTQVTVSS |
| 07B11-9GS-07C03-9GS-Alb8 | 81 | EVQLVESGGNLVQAGGSLGLSCAASVSISSIHIMGWYRQAPGKQRDLVATITSGGSTAYADSVKGRFTVSKDNAKNTVYLQMDSLKPEDTSVYYCAAEVRNGVFGKWNHYWGQGTQVTVSSGGGGSGGGSEVQLVESGGGLVQAGESLTLSCAASGRTLSAYIMGWFRQAPGKEREFVAGIWSGGYTHLADSAKGRFSISRDNAKNTVYLQMNGLKPEDTAVYYCAAGLRGRQY |

TABLE B-4-continued

Polypeptide sequences of the invention

| Name of clone | SEQ ID NO: | Amino acid sequences |
|---|---|---|
| | | SNWGQGTQVTVSSGGGGSGGGSEVQLVESGGGLVQPGNS
LRLSCAASGFTFSSFGMSWVRQAPGKGLEWVSSISGSGS
DTLYADSVKGRFTISRDNAKTTLYLQMNSLRPEDTAVYY
CTIGGSLSRSSQGTLVTVSS |
| 08A05-9GS-08A10 | 82 | EVQLVESGGGLVQAGDSLRLSCAASGLTFSNYDMGWFRQ
APGKEREFVGASWWSGGAPYYSDSVKGRFTISRDNAKNT
VYLQANSLRPEDTAVYYCAAKRLRSFASGGSYDYWGQGT
QVTVSSGGGGSGGGSEVQLVESGGGLVQAGGSLRLSCAA
SGSIFSIAAMGWYRQATGKQRELVATITDGGTTTYADSV
KGRVTISRDRSANTVYLAMNNLKPDDTAVYYCYAYLRYT
SRVPGDNYWGQGTQVTVSS |
| 08A10-9GS-Alb8-9GS-08A10 | 83 | EVQLVESGGGLVQAGGSLRLSCAASGSIFSIAAMGWYRQ
ATGKQRELVATITDGGTTTYADSVKGRVTISRDRSANTV
YLAMNNLKPDDTAVYYCYAYLRYTSRVPGDNYWGQGTQV
TVSSGGGGSGGGSEVQLVESGGGLVQPGNSLRLSCAASG
FTFSSFGMSWVRQAPGKGLEWVSSISGSGSDTLYADSVK
GRFTISRDNAKTTLYLQMNSLRPEDTAVYYCTIGGSLSR
SSQGTLVTVSSGGGGSGGGSEVQLVESGGGLVQAGGSLR
LSCAASGSIFSIAAMGWYRQATGKQRELVATITDGGTTT
YADSVKGRVTISRDRSANTVYLAMNNLKPDDTAVYYCYA
YLRYTSRVPGDNYWGQGTQVTVSS |
| 08A10-9GS-08A10-9GS-Alb8 | 84 | EVQLVESGGGLVQAGGSLRLSCAASGSIFSIAAMGWYRQ
ATGKQRELVATITDGGTTTYADSVKGRVTISRDRSANTV
YLAMNNLKPDDTAVYYCYAYLRYTSRVPGDNYWGQGTQV
TVSSGGGGSGGGSEVQLVESGGGLVQAGGSLRLSCAASG
SIFSIAAMGWYRQATGKQRELVATITDGGTTTYADSVKG
RVTISRDRSANTVYLAMNNLKPDDTAVYYCYAYLRYTSR
VPGDNYWGQGTQVTVSSGGGGSGGGSEVQLVESGGGLVQ
PGNSLRLSCAASGFTFSSFGMSWVRQAPGKGLEWVSSIS
GSGSDTLYADSVKGRFTISRDNAKTTLYLQMNSLRPEDT
AVYYCTIGGSLSRSSQGTLVTVSS |
| 08A05-9GS-08A10-9GS-Alb8 | 85 | EVQLVESGGGLVQAGDSLRLSCAASGLTFSNYDMGWFRQ
APGKEREFVGASWWSGGAPYYSDSVKGRFTISRDNAKNT
VYLQANSLRPEDTAVYYCAAKRLRSFASGGSYDYWGQGT
QVTVSSGGGGSGGGSEVQLVESGGGLVQAGGSLRLSCAA
SGSIFSIAAMGWYRQATGKQRELVATITDGGTTTYADSV
KGRVTISRDRSANTVYLAMNNLKPDDTAVYYCYAYLRYT
SRVPGDNYWGQGTQVTVSSGGGGSGGGSEVQLVESGGGL
VQPGNSLRLSCAASGFTFSSFGMSWVRQAPGKGLEWVSS
ISGSGSDTLYADSVKGRFTISRDNAKTTLYLQMNSLRPE
DTAVYYCTIGGSLSRSSQGTLVTVSS |
| 07B11-9GS-238D2 (238D2 is directed against CXCR4) | 86 | EVQLVESGGNLVQAGGSLGLSCAASVSISSSIHIMGWYRQ
APGKQRDLVATITSGGSTAYADSVKGRFTVSKDNAKNTV
YLQMDSLKPEDTSVYYCAAEVRNGVFGKWNHYWGQGTQV
TVSSGGGGSGGGSEVQLVESGGGLVQTGGSLRLSCAASG
FTFSSYAMSWVRQAPGKGLEWVSGIKSSGDSTRYAGSVK
GRFTISRDNAKNMLYLQMYSLKPEDTAVYYCAKSRVSRT
GLYTYDNRGQGTQVTVSS |
| 07C03-9GS-238D4 (238D4 is directed against CXCR4) | 87 | EVQLVESGGGLVQAGESLTLSCAASGRTLSAYIMGWFRQ
APGKEREFVAGIWSGGYTHLADSAKGRFSISRDNAKNTV
YLQMNGLKPEDTAVYYCAAGLRGRQYSNWGQGTQVTVSS
GGGGSGGGSEVQLMESGGGLVQAGGSLRLSCAASGRTFN
NYAMGWFRRAPGKEREFVAAITRSGVRSGVSAIYGDSVK
DRFTISRDNAKNTLYLQMNSLKPEDTAVYTCAASAIGSG
ALRRFEYDYSGQGTQVTVSS |
| 08A10-9GS-Alb8-9GS-238D2 (238D2 is directed against CXCR4) | 88 | EVQLVESGGGLVQAGGSLRLSCAASGSIFSIAAMGWYRQ
ATGKQRELVATITDGGTTTYADSVKGRVTISRDRSANTV
YLAMNNLKPDDTAVYYCYAYLRYTSRVPGDNYWGQGTQV
TVSSGGGGSGGGSEVQLVESGGGLVQPGNSLRLSCAASG
FTFSSFGMSWVRQAPGKGLEWVSSISGSGSDTLYADSVK
GRFTISRDNAKTTLYLQMNSLRPEDTAVYYCTIGGSLSR
SSQGTLVTVSSGGGGSGGGSEVQLVESGGGLVQTGGSLR |

TABLE B-4-continued

Polypeptide sequences of the invention

| Name of clone | SEQ ID NO: | Amino acid sequences |
|---|---|---|
| | | LSCAASGFTFSSYAMSWVRQAPGKGLEWVSGIKSSGDST RYAGSVKGRFTISRDNAKNMLYLQMYSLKPEDTAVYYCA KSRVSRTGLYTYDNRGQGTQVTVSS |
| 08A05-9GS-238D4-9GS-Alb8 (238D4 is directed against CXCR4) | 89 | EVQLVESGGGLVQAGDSLRLSCAASGLTFSNYDMGWFRQ APGKEREFVGASWWSGGAPYYSDSVKGRFTISRDNAKNT VYLQANSLRPEDTAVYYCAAKRLRSFASGGSYDYWGQGT QVTVSSGGGGSGGGSEVQLMESGGGLVQAGGSLRLSCAA SGRTFNNYAMGWFRRAPGKEREFVAAITRSGVRSGVSAI YGDSVKDRFTISRDNAKNTLYLQMNSLKPEDTAVYTCAA SAIGSGALRRFEYDYSGQGTQVTVSSGGGGSGGGGSEVQL VESGGGLVQPGNSLRLSCAASGFTFSSFGMSWVRQAPGK GLEWVSSISGSGSDTLYADSVKGRFTISRDNAKTTLYLQ MNSLRPEDTAVYYCTIGGSLSRSSQGTLVTVSS |
| clone 060 | 131 | EVQLVESGGGLVQAGDSLRLSCAASGLTFSNYDMGWFRQ APGKEREFVGASWWSGGAPYYSDSVKGRFTISRDNAKNT VYLQANSLRPEDTAVYYCAAKRLRSFASGGSYDYWGQGT LVTVSSGGGGSGGGGSGGGGSGGGGSGGGGSGGGGSGGG GSEVQLVESGGGLVQAGDSLRLSCAASGLTFSNYDMGWF RQAPGKEREFVGASWWSGGAPYYSDSVKGRFTISRDNAK NTVYLQANSLRPEDTAVYYCAAKRLRSFASGGSYDYWGQ GTLVTVSSGGGGSGGGSEVQLVESGGGLVQPGNSLRLSC AASGFTFSSFGMSWVRQAPGKGLEWVSSISGSGSDTLYA DSVKGRFTISRDNAKTTLYLQMNSLRPEDTAVYYCTIGG SLSRSSQGTLVTVSS |
| clone 083 | 132 | EVQLVESGGGLVQAGDSLRLSCAASGLTFSNYDMGWFRQ APGKEREFVGASWWSGGAPYYSDSVKGRFTISRDNAKNT VYLQANSLRPEDTAVYYCAAKRLRSFASGGSYDYWGQGT LVTVSSGGGGSGGGGSGGGGSGGGGSGGGGSGGGGSEVQ LVESGGGLVQPGNSLRLSCAASGFTFSSFGMSWVRQAPG KGLEWVSSISGSGSDTLYADSVKGRFTISRDNAKTTLYL QMNSLRPEDTAVYYCTIGGSLSRSSQGTLVTVSS |
| clone 085 | 133 | EVQLVESGGGLVQPGGSLRISCAASGSIYLINYMGWYRQ APGKQRELVATLTSGGSTNYAGSVKGRFAISRDNAKNTV YLQMNSLKPEDTAVYYCNIGGTLYDRRRFESWGQGTLVT VSSGGGGSGGGGSGGGGSGGGGSGGGGSGGGGSGGGGSE VQLVESGGGLVQTGASLRLSCAASGRTFSNYAMGWFRQA PGKERERVAAITPRAFTTYYADSVKGRFTISRDNAKNTA YLQMVSLKPEDTAVYYCAAQLVGSGSNLGRQESYAYWGQ GTLVTVSSGGGGSGGGGSGGGGSGGGGSGGGGSGGGGSG GGGSEVQLVESGGGLVQPGNSLRLSCAASGFTFSSFGMS WVRQAPGKGLEWVSSISGSGSDTLYADSVKGRFTISRDN AKTTLYLQMNSLRPEDTAVYYCTIGGSLSRSSQGTLVTV SS |
| clone 093 | 134 | EVQLVESGGGLVQTGASLRLSCAASGRTFSNYAMGWFRQ APGKERERVAAITPRAFTTYYADSVKGRFTISRDNAKNT AYLQMVSLKPEDTAVYYCAAQLVGSGSNLGRQESYAYWG QGTLVTVSSGGGGSGGGGSGGGGSGGGGSGGGGSGGGGS GGGGSEVQLVESGGGLVQTGASLRLSCAASGRTFSNYAM GWFRQAPGKERERVAAITPRAFTTYYADSVKGRFTISRD NAKNTAYLQMVSLKPEDTAVYYCAAQLVGSGSNLGRQES YAYWGQGTLVTVSSGGGGSGGGGSGGGGSGGGGSGGGGS GGGGSGGGGSEVQLVESGGGLVQPGNSLRLSCAASGFTF SSFGMSWVRQAPGKGLEWVSSISGSGSDTLYADSVKGRF TISRDNAKTTLYLQMNSLRPEDTAVYYCTIGGSLSRSSQ GTLVTVSS |
| clone 021 | 135 | EVQLVESGGGLVQAGGSLRLSCAASGSIFSIAAMGWYRQ ATGKQRELVATITDGGTTTYADSVKGRVTISRDRSANTV YLAMNNLKPDDTAVYYCYAYLRYTSRVPGDNYWGQGTLV TVSSGGGGSGGGGSGGGGSGGGGSGGGGSGGGGSGGGGS EVQLVESGGGLVQTGASLRLSCAASGRTFSNYAMGWFRQ APGKERERVAAITPRAFTTYYADSVKGRFTISRDNAKNT AYLQMVSLKPEDTAVYYCAAQLVGSGSNLGRQESYAYWG |

TABLE B-4-continued

Polypeptide sequences of the invention

| Name of clone | SEQ ID NO: | Amino acid sequences |
|---|---|---|
| | | QGTLVTVSSGGGGSGGGSEVQLVESGGGLVQPGNSLRLS
CAASGFTFSSFGMSWVRQAPGKGLEWVSSISGSGSDTLY
ADSVKGRFTISRDNAKTTLYLQMNSLRPEDTAVYYCTIG
GSLSRSSQGTLVTVSS |
| clone 023 | 136 | EVQLVESGGGLVQAGDSLRLSCAASGLTFSNYDMGWFRQ
APGKEREFVGASWWSGGAPYYSDSVKGRFTISRDNAKNT
VYLQANSLRPEDTAVYYCAAKRLRSFASGGSYDYWGQGT
LVTVSSGGGGSGGGGSGGGGSGGGGSGGGGSGGGGSGGG
GSEVQLVESGGGLVQTGASLRLSCAASGRTFSNYAMGWF
RQAPGKERERVAAITPRAFTTYYADSVKGRFTISRDNAK
NTAYLQMVSLKPEDTAVYYCAAQLVGSGSNLGRQESYAY
WGQGTLVTVSSGGGGSGGGSEVQLVESGGGLVQPGNSLR
LSCAASGFTFSSFGMSWVRQAPGKGLEWVSSISGSGSDT
LYADSVKGRFTISRDNAKTTLYLQMNSLRPEDTAVYYCT
IGGSLSRSSQGTLVTVSS |
| clone 038 | 137 | EVQLVESGGGLVQPGGSLRISCAASGSIYLINYMGWYRQ
APGKQRELVATLTSGGSTNYAGSVKGRFAISRDNAKNTV
YLQMNSLKPEDTAVYYCNIGGTLYDRRRFESWGQGTLVT
VSSGGGGSGGGGSGGGGSGGGGSGGGGSGGGGSGGGGSE
VQLVESGGGLVQTGASLRLSCAASGRTFSNYAMGWFRQA
PGKERERVAAITPRAFTTYYADSVKGRFTISRDNAKNTA
YLQMVSLKPEDTAVYYCAAQLVGSGSNLGRQESYAYWGQ
GTLVTVSSGGGGSGGGSEVQLVESGGGLVQPGNSLRLSC
AASGFTFSSFGMSWVRQAPGKGLEWVSSISGSGSDTLYA
DSVKGRFTISRDNAKTTLYLQMNSLRPEDTAVYYCTIGG
SLSRSSQGTLVTVSS |
| clone 049 | 138 | EVQLVESGGGLVQTGASLRLSCAASGRTFSNYAMGWFRQ
APGKERERVAAITPRAFTTYYADSVKGRFTISRDNAKNT
AYLQMVSLKPEDTAVYYCAAQLVGSGSNLGRQESYAYWG
QGTLVTVSSGGGGSGGGGSGGGGSGGGGSGGGGSGGGGS
GGGGSEVQLVESGGGLVQAGDSLRLSCAASGLTFSNYDM
GWFRQAPGKEREFVGASWWSGGAPYYSDSVKGRFTISRD
NAKNTVYLQANSLRPEDTAVYYCAAKRLRSFASGGSYDY
WGQGTLVTVSSGGGGSGGGSEVQLVESGGGLVQPGNSLR
LSCAASGFTFSSFGMSWVRQAPGKGLEWVSSISGSGSDT
LYADSVKGRFTISRDNAKTTLYLQMNSLRPEDTAVYYCT
IGGSLSRSSQGTLVTVSS |
| clone 052 | 139 | EVQLVESGGGLVQTGASLRLSCAASGRTFSNYAMGWFRQ
APGKERERVAAITPRAFTTYYADSVKGRFTISRDNAKNT
AYLQMVSLKPEDTAVYYCAAQLVGSGSNLGRQESYAYWG
QGTLVTVSSGGGGSGGGGSGGGGSGGGGSGGGGSGGGGS
GGGGSEVQLVESGGGLVQPGGSLRISCAASGSIYLINYM
GWYRQAPGKQRELVATLTSGGSTNYAGSVKGRFAISRDN
AKNTVYLQMNSLKPEDTAVYYCNIGGTLYDRRRFESWGQ
GTLVTVSSGGGGSGGGSEVQLVESGGGLVQPGNSLRLSC
AASGFTFSSFGMSWVRQAPGKGLEWVSSISGSGSDTLYA
DSVKGRFTISRDNAKTTLYLQMNSLRPEDTAVYYCTIGG
SLSRSSQGTLVTVSS |
| clone 086 | 140 | EVQLVESGGGLVQPGGSLRISCAASGSIYLINYMGWYRQ
APGKQRELVATLTSGGSTNYAGSVKGRFAISRDNAKNTV
YLQMNSLKPEDTAVYYCNIGGTLYDRRRFESWGQGTLVT
VSSGGGGSGGGGSGGGGSGGGGSGGGGSGGGGSGGGGSE
VQLVESGGGLVQAGESLTLSCAASGRTLSAYIMGWFRQA
PGKEREFVAGIWSGGYTHLADSAKGRFSISRDNAKNTVY
LQMNGLKPEDTAVYYCAAGLRGRQYSNWGQGTLVTVSSG
GGGSGGGSEVQLVESGGGLVQPGNSLRLSCAASGFTFSS
FGMSWVRQAPGKGLEWVSSISGSGSDTLYADSVKGRFTI
SRDNAKTTLYLQMNSLRPEDTAVYYCTIGGSLSRSSQGT
LVTVSS |

TABLE B-5

Linker sequences of the invention

| Name of linker | SEQ ID NO: | Amino acid sequences |
|---|---|---|
| 5GS | 49 | GGGGS |
| 6GS | 50 | SGGSGGS |
| 9GS | 51 | GGGSGGGS |
| 10GS | 52 | GGGGSGGGGS |
| 15GS | 53 | GGGGSGGGGSGGGGS |
| 18GS | 54 | GGGGSGGGGSGGGGGGGS |
| 20GS | 55 | GGGGSGGGGSGGGGSGGGGS |
| 25GS | 56 | GGGGSGGGGSGGGGSGGGGSGGGGS |
| 30GS | 57 | GGGGSGGGGSGGGGSGGGGSGGGGSGGGGS |
| 35GS | 58 | GGGGSGGGGSGGGGSGGGGSGGGGSGGGGSGGGGS |

TABLE B-6

Nucleic acid sequences of the invention

| Name of clone | SEQ ID NO: | Nucleic acid sequences |
|---|---|---|
| 07B11 | 59 | GAGGTGCAATTGGTGGAGTCTGGGGGAAACTTGGTGCAGGCTGGGGGGTCTCTGGGACTCTCCTGTGCAGCCTCTGTAAGCATCTCCAGTATCCATATCATGGGCTGGTACCGGCAGGCTCCAGGCAAACAGCGCGACTTGGTCGCTACTATTACTAGTGGTGGTAGCACAGCATATGCAGACTCCGTGAAGGGACGATTCACCGTCTCCAAAGACAACGCCAAGAACACGGTGTATCTGCAAATGGACAGCCTGAAACCTGAGGACACATCCGTCTATTACTGTGCAGCCCAGGTCAGAAATGGGGTGTTTGGAAAATGGAATCACTACTGGGGCCAGGGGACCCAGGTCACCGTCTCCTCA |
| 07C03 | 60 | GAGGTGCAATTGGTGGAGTCTGGGGGAGGATTGGTGCAGGCTGGGGAGTCTCTGACTCTCTCCTGTGCAGCCTCTGGACGCACCTTAAGTGCCTATATCATGGGCTGGTTCCGCCAGGCTCCAGGGAAGGAGCGGGAGTTTGTAGCCGGTATCTGGAGTGGTGGTTACACACACCTTGCAGACTCCGCGAAGGGCCGATTCAGCATCTCTAGAGACAACGCCAAGAACACTGTATATCTGCAAATGAACGGCCTGAAACCTGAGGACACGGCCGTCTATTACTGTGCAGCAGGTCTGAGAGGCCGCCAGTATAGTAACTGGGGCCAGGGGACCCAGGTCACCGTCTCCTCA |
| 08A05 | 61 | GAGGTGCAATTGGTGGAGTCTGGGGGAGGATTGGTGCAGGCTGGGGACTCTCTGAGACTCTCCTGTGCAGCCTCTGGACTCACTTTCAGTAACTATGACATGGGCTGGTTCCGCCAGGCTCCAGGGAAGGAGCGTGAATTTGTAGGGGCTAGTTGGTGGAGTGGTGGTGCCCCATACTATTCAGACTCCGTGAAGGGCCGATTCACCATCTCCAGAGACAACGCCAAGAACACGGTGTATCTGCAAGCGAACAGCCTGAGACCTGAGGACACGGCCGTTTATTACTGTGCAGCCAAAGGCTGCGTAGTTTCGCCTCCGGTGGGTCGTATGATTACTGGGGTCAGGGGACCCAGGTCACCGTCTCCTCA |
| 08A10 | 62 | GAGTCTGGGGGAGGCTTGGTGCAGGCTGGAGGGTCTCTGAGACTCTCCTGTGCAGCTTCTGGAAGCATCTTCAGTATCGCTGCCATGGGCTGGTACCGCCAGGCTACAGGGAAGCAGCGCGAGTTGGTCGCAACTATCACTGATGGCGGTACGACAACCTATGCAGACTCCGTGAAGGGCCGAGTCACCATCTCCAGGGACAGGTCTGCGAACACGGTGTATCTGCAATGAACAATTTGAAACCTGATGACACAGCCGTCTATTATTGTTATGCGTATCTGCGCTATACAAGCAGAGTACCTGGCGATAACTACTGGGGCCAGGGGACCCAGGTCACCGTCTCCTCA |
| 14G03 | 63 | GAGGTGCAATTGGTGGAGTCTGGGGGAGGCTTGGTGCAGCCTGGGGGGTCTCTGAGAATTTCCTGTGCAGCCTCTGGAAGCATCTACCTTATCAATTACATGGGCTGGTACCGCCAGGCTCCAGGGAAGCAGCGCGAGTTGGTCGCAACGCTTACTAGTGGTGGTAGTACCAACTATGCAGGCTCCGTGAAGGGCCGATTCGCCATCTCCAGAGACAACGCCAAGAACACGGTTTATCTGCAAATGAACAGCCTGAAACCTGAGGACACGGCCGTCTATTACTGTAATATAGGAGGAACGCTATACGACAGAAGGCGGTTTGAATCCTGGGGCCAGGGGACCCAGGTCACCGTCTCCTCAG |
| 01C10 | 99 | GAGGTGCAATTGGTGGAGTCTGGGGGAGGGTTGGTGCAGACTGGAGCCTCTCTGAGACTCTCCTGTGCAGCCTCTGGA |

TABLE B-6-continued

Nucleic acid sequences of the invention

| Name of clone | SEQ ID NO: | Nucleic acid sequences |
|---|---|---|
| | | CGCACCTTCAGTAACTATGCCATGGGCTGGTTCCGCCAG<br>GCTCCAGGGAAGGAGCGTGAGCGTGTAGCAGCTATTACA<br>CCGAGAGCATTTACCACATATTATGCAGACTCCGTGAAG<br>GGCCGATTCACCATCTCCAGAGACAACGCCAAGAACACG<br>GCGTATCTACAAATGGTCAGCCTGAAACCTGAGGACACG<br>GCCGTTTATTACTGTGCAGCTCAACTGGTTGGCAGCGGT<br>AGTAATTTAGGACGTCAGGAGTCCTATGCCTACTGGGGC<br>CAGGGGACCCAGGTCACCGTCTCCTC |
| 07B11-9GS-Alb8 | 73 | GAGGTGCAATTGGTGGAGTCTGGGGGAAACTTGGTGCAG<br>GCTGGGGGGTCTCTGGGACTCTCCTGTGCAGCCTCTGTA<br>AGCATCTCCAGTATCCATATCATGGGCTGGTACCGGCAG<br>GCTCCAGGCAAACAGCGCGACTTGGTCGCTACTATTACT<br>AGTGGTGGTAGCACAGCATATGCAGACTCCGTGAAGGGA<br>CGATTCACCGTCTCCAAAGACAACGCCAAGAACACGGTG<br>TATCTGCAAATGGACAGCCTGAAACCTGAGGACACATCC<br>GTCTATTACTGTGCAGCCGAGGTCAGAAATGGGGTGTTT<br>GGAAAATGGAATCACTACTGGGGCCAGGGGACCCAGGTC<br>ACGGTCTCCTCAGGAGGTGGCGGGTCCGGAGGCGGATCC<br>GAGGTACAGCTGGTGGAGTCTGGGGGTGGCTTGGTGCAA<br>CCGGGTAACAGTCTGCGCCTTAGCTGCGCAGCGTCTGGC<br>TTTACCTTCAGCTCCTTTGGCATGAGCTGGGTTCGCCAG<br>GCTCCGGGAAAAGGACTGGAATGGGTTTCGTCTATTAGC<br>GGCAGTGGTAGCGATACGCTCTACGCGGACTCCGTGAAG<br>GGCCGTTTCACCATCTCCCGCGATAACGCCAAAACTACA<br>CTGTATCTGCAAATGAATAGCCTGCGTCCTGAAGACACG<br>GCCGTTTATTACTGTACTATTGGTGGCTCGTTAAGCCGT<br>TCTTCACAGGGTACCCTGGTCACCGTCTCCTCA |
| 07C03-9GS-Alb8 | 74 | GAGGTGCAATTGGTGGAGTCTGGGGGAGGATTGGTGCAG<br>GCTGGGGAGTCTCTGACTCTCTCCTGTGCAGCCTCTGGA<br>CGCACCTTAAGTGCCTATATCATGGGCTGGTTCCGCCAG<br>GCTCCAGGGAAGGAGCGGGAGTTTGTAGCCGGTATCTGG<br>AGTGGTGGTTACACACACCTTGCAGACTCCGCGAAGGGC<br>CGATTCAGCATCTCTAGAGACAACGCCAAGAACACTGTA<br>TATCTGCAAATGAACGGCCTGAAACCTGAGGACACGGCC<br>GTCTATTACTGTGCAGCAGGTCTGAGAGGCCGCCAGTAT<br>AGTAACTGGGGCCAGGGGACCCAGGTCACGGTCTCCTCA<br>GGAGGTGGCGGGTCCGGAGGCGGATCCGAGGTACAGCTG<br>GTGGAGTCTGGGGGTGGCTTGGTGCAACCGGGTAACAGT<br>CTGCGCCTTAGCTGCGCAGCGTCTGGCTTTACCTTCAGC<br>TCCTTTGGCATGAGCTGGGTTCGCCAGGCTCCGGGAAAA<br>GGACTGGAATGGGTTTCGTCTATTAGCGGCAGTGGTAGC<br>GATACGCTCTACGCGGACTCCGTGAAGGGCCGTTTCACC<br>ATCTCCCGCGATAACGCCAAAACTACACTGTATCTGCAA<br>ATGAATAGCCTGCGTCCTGAAGACACGGCCGTTTATTAC<br>TGTACTATTGGTGGCTCGTTAAGCCGTTCTTCACAGGGT<br>ACCCTGGTCACCGTCTCCTCA |
| 08A05-9GS-Alb8 | 75 | GAGGTGCAATTGGTGGAGTCTGGGGGAGGATTGGTGCAG<br>GCTGGGGACTCTCTGAGACTCTCCTGTGCAGCCTCTGGA<br>CTCACTTTCAGTAACTATGACATGGGCTGGTTCCGCCAG<br>GCTCCAGGGAAGGAGCGTGAATTTGTAGGGGCTAGTTGG<br>TGGAGTGGTGGTGCCCCATACTATTCAGACTCCGTGAAG<br>GGCCGATTCACCATCTCCAGAGACAACGCCAAGAACACG<br>GTGTATCTGCAAGCGAACAGCCTGAGACCTGAGGACACG<br>GCCGTTTATTACTGTGCAGCCAAAAGGCTGCGTAGTTTC<br>GCCTCCGGTGGGTCGTATGATTACTGGGGTCAGGGGACC<br>CAGGTCACGGTCTCCTCAGGAGGTGGCGGGTCCGGAGGC<br>GGATCCGAGGTACAGCTGGTGGAGTCTGGGGGTGGCTTG<br>GTGCAACCGGGTAACAGTCTGCGCCTTAGCTGCGCAGCG<br>TCTGGCTTTACCTTCAGCTCCTTTGGCATGAGCTGGGTT<br>CGCCAGGCTCCGGGAAAAGGACTGGAATGGGTTTCGTCT<br>ATTAGCGGCAGTGGTAGCGATACGCTCTACGCGGACTCC<br>GTGAAGGGCCGTTTCACCATCTCCCGCGATAACGCCAAA<br>ACTACACTGTATCTGCAAATGAATAGCCTGCGTCCTGAA<br>GACACGGCCGTTTATTACTGTACTATTGGTGGCTCGTTA<br>AGCCGTTCTTCACAGGGTACCCTGGTCACCGTCTCCTCA |
| 08A10-9GS-Alb8 | 76 | GAGGTGCAATTGGTGGAGTCTGGGGGAGGCTTGGTGCAG<br>GCTGGAGGGTCTCTGAGACTCTCCTGTGCAGCTTCTGGA<br>AGCATCTTCAGTATCGCTGCCATGGGCTGGTACCGCCAG<br>GCTACAGGGAAGCAGCGCGAGTTGGTCGCAACTATCACT<br>GATGGCGGTACGACAACCTATGCAGACTCCGTGAAGGGC<br>CGAGTCACCATCTCCAGGGACAGGTCTGCGAACACGGTG |

TABLE B-6-continued

Nucleic acid sequences of the invention

| Name of clone | SEQ ID NO: | Nucleic acid sequences |
|---|---|---|
| | | TATCTGGCAATGAACAATTTGAAACCTGATGACACAGCC<br>GTCTATTATTGTTATGCGTATCTGCGCTATACAAGCAGA<br>GTACCTGGCGATAACTACTGGGGCCAGGGGACCCAGGTC<br>ACGGTCTCCTCAGGAGGTGGCGGGTCCGGAGGCGGATCC<br>GAGGTACAGCTGGTGGAGTCTGGGGGTGGCTTGGTGCAA<br>CCGGGTAACAGTCTGCGCCTTAGCTGCGCAGCGTCTGGC<br>TTTACCTTCAGCTCCTTTGGCATGAGCTGGGTTCGCCAG<br>GCTCCGGGAAAAGGACTGGAATGGGTTTCGTCTATTAGC<br>GGCAGTGGTAGCGATACGCTCTACGCGGACTCCGTGAAG<br>GGCCGTTTCACCATCTCCCGCGATAACGCCAAAACTACA<br>CTGTATCTGCAAATGAATAGCCTGCGTCCTGAAGACACG<br>GCCGTTTATTACTGTACTATTGGTGGCTCGTTAAGCCGT<br>TCTTCACAGGGTACCCTGGTCACCGTCTCCTCA |
| 14G03-9GS-Alb8 | 77 | GAGGTGCAATTGGTGGAGTCTGGGGGAGGCTTGGTGCAG<br>CCTGGGGGTCTCTGAGAATTTCCTGTGCAGCCTCTGGA<br>AGCATCTACCTTATCAATTACATGGGCTGGTACCGCCAG<br>GCTCCAGGGAAGCAGCGCGAGTTGGTCGCAACGCTTACT<br>AGTGGTGGTAGTACCAACTATGCAGGCTCCGTGAAGGGC<br>CGATTCGCCATCTCCAGAGACAACGCCAAGAACACGGTT<br>TATCTGCAAATGAACAGCCTGAAACCTGAGGACACGGCC<br>GTCTATTACTGTAATATAGGAGGAACGCTATACGACAGA<br>AGGCGGTTTGAATCCTGGGGCCAGGGGACCCAGGTCACG<br>GTCTCCTCAGGAGGTGGCGGGTCCGGAGGCGGATCCGAG<br>GTACAGCTGGTGGAGTCTGGGGGTGGCTTGGTGCAACCG<br>GGTAACAGTCTGCGCCTTAGCTGCGCAGCGTCTGGCTTT<br>ACCTTCAGCTCCTTTGGCATGAGCTGGGTTCGCCAGGCT<br>CCGGGAAAAGGACTGGAATGGGTTTCGTCTATTAGCGGC<br>AGTGGTAGCGATACGCTCTACGCGGACTCCGTGAAGGGC<br>CGTTTCACCATCTCCCGCGATAACGCCAAAACTACACTG<br>TATCTGCAAATGAATAGCCTGCGTCCTGAAGACACGGCC<br>GTTTATTACTGTACTATTGGTGGCTCGTTAAGCCGTTCT<br>TCACAGGGTACCCTGGTCACCGTCTCCTCA |

Example 1: Cloning

Human CXCR7 (hCXCR7), mouse CXCR7 (Open Biosystems) and cynomolgus encoding cDNA (Table B-1) were cloned into pVAX-1 (Invitrogen) and/or pcDNA3.1 (Invitrogen). Transfection of pVAX1-hCXCR7 and pcDNA3.1-human(mouse)(cyno)CXCR7 constructs in Hek293 cells resulted in CXCR7 cell surface expression as shown by FACS analysis using the human CXCR7 specific monoclonal antibody (Mab) 11G8 (R&D Systems) and a PE-labeled goat anti-mouse IgG detecting antibody (Jackson ImmunoResearch Inc.).

Example 2: Immunizations

For genetic immunization, endotoxin-free pVAX1-CXCR7 plasmid was produced, dissolved to a concentration of 2 mg/mL in 0.9% saline and stored at −20° C. Four llamas (391, 395, 396 and 397) were immunized with 2 mg pVAX1-hCXCR7 via intradermal Jet injection (Akra DermoJet France) for four times with two weeks intervals. Three weeks after the final DNA immunization, the 4 animals received a boost with camel kidney (CAKI) cells (Nguyen et al. 2001. Adv. Immunol. 79: 261-296) ($2 \times 10^7$ cells) stably expressing hCXCR7.

Three llamas (385, 387 and 404) were immunized with four injections of $2 \times 10^7$ HEK293 cells transfected with pcDNA3.1-hCXCR7 with two weeks intervals. From llamas 391, 395, 396 and 397, peripheral blood lymphocytes were collected 4 days and 10 days after the last DNA immunization and 3 days and 9 days after the cell boost. From llamas 385, 387 and 404, peripheral blood lymphocytes were collected 4 and 8 days after the final cell injection. Additionally, a biopsy of the palpable bow lymph node (LN) was collected from each llama via local surgery 3 days after the last cell boost. From all lymphocyte harboring immune tissues total RNA was extracted and used as template to prepare cDNA.

Example 3: Library Construction

Libraries were constructed from immune tissues collected from all llamas. In short, cDNA was prepared from the extracted total RNA samples (example 2) and used to amplify the cDNA repertoire via nested PCR as previously described (WO 02/085945 and WO 04/049794). The PCR products were digested with SfiI (introduced via nested PCR in the FR1 primer region) and BstEII (restriction site naturally occurring in FR4) and following gel electrophoresis, the DNA fragment of approximately 400 bps was purified from gel. The amplified cDNA repertoire was ligated into the corresponding restriction sites of SfiI-BstEII digested phage display vector (pAX50) to obtain a library after electroporation of *Escherichia coli* TG1. This display vector allows the production of phage particles, expressing the individual VHHs (hereinforth also referred to as Nanobodies) as a fusion protein with a C-terminal Myc-His6-tag (hereinforth also TAG-1 or SEQ ID NO: 71) and with the geneIII product.

Libraries were rescued by growing the bacteria to logarithmic phase ($OD_{600}$=0.5), followed by infection with helper phage to obtain recombinant phage expressing the cloned Nanobodies on tip of the phage as a pIII fusion protein. Phage was stored after filter sterilization at 4° C. for further use.

Example 4: Selections of Phage Displaying Human CXCR7 Binding Nanobodies

Phage from the above libraries were used for selections on hCXCR7 virus-like particles (VLP; Integral Molecular), intact CXCR7 expressing cells, membrane extracts from CXCR7 expressing cells and peptides.

In a first selection round, 10 units of VLPs derived from hCXCR7 transfected HEK293 cells were coated in 96-well Maxisorp plate (Nunc) and blocked with low-fat milk powder (Marvell 4% in PBS). After 2 hours of incubation with rescued phage, trypsin elution (1 mg/ml) was allowed for 15 minutes at room temperature subsequent to 20 PBS washes. Protease activity was immediately neutralized by applying 16 mM protease inhibitor ABSF. The round 1 phage outputs were rescued and a second selection round was performed on 10 or 1 units of plate-immobilized hCXCR7 VLPs. The round 2 phage outputs selected on 10 or 1 units plate immobilized hCXCR7 VLPs were infected into TG1 cells and plated on agar plates (LB+Amp+2% glucose).

Individual colonies of *E. coli* TG1 infected with the eluted phage pools obtained after selections were picked up and grown in 96-deep-well plates to produce monoclonal phage after addition of helper phage. The production of monoclonal Nanobodies was induced by the addition of isopropyl-b-D-thiogalactopyranoside (IPTG). The periplasmic fraction containing Nanobodies was then prepared by freezing-thawing of the bacterial pellet in PBS and subsequent centrifugation to remove cell fragments.

Example 5: Identification of CXCR7 Specific Nanobodies by Phage ELISA

From all round 2 selection outputs clones were screened in phage ELISA on 2 units of immobilized CXCR7 VLPs applying 10-fold dilutions of phage supernatant. After incubation with HRP-conjugated monoclonal-anti-M13 antibody (GE, Cat#363761) and several washings, phage binding was revealed using TMB substrate (Pierce). The reaction was stopped with $H_2SO_4$ and the absorbance was measured at 450 nm using Sunrise TECAN spectrophotometer (TECAN). Nanobodies, showing a minimally 2-fold increased ELISA signal on hCXCR7 VLPs over non-transfected control VLPs, were considered to be CXCR7 specific. CXCR7 specific Nanobodies were sequenced and redundant Nanobodies (identical AA sequence) were removed. This resulted in the identification of 78 unique sequences, belonging to 45 distinct Nanobody B-cell lineages. Phage ELISA data for representative clones from distinct Nanobody B-cell lineages are represented in Table B-7 and indicate that the Nanobodies do bind to human CXCR7 on VLP. Notably, all Nanobodies were derived from PBLs after cell boost, except for Nanobody 01C10 (see Example 2). Evaluated against the other CXCR7 specific Nanobodies, Nanobody 01C10 was a notorious weak binder, which in first instance was used for comparative reasons (data not shown).

TABLE B-7

CXCR7 screening results-ELISA.

| Clones with Tag-1 | CXCR7-LP 2U/ well [OD] | LP Null-LP [OD] | Fold CXCR7-LP/ Null-LP |
|---|---|---|---|
| 08A05 | 0.019 | 0.008 | 2.4 |
| 08A10 | 0.104 | 0.006 | 17.3 |
| 14G03 | 0.316 | 0.043 | 7.3 |
| 07B11 | 0.041 | 0.010 | 4.1 |
| 07C03 | 0.053 | 0.012 | 4.4 |
| 01C10 | 0.145 | 0.034 | 4.2 |

Example 6: Identification of CXCR7 Specific Nanobodies by FACS Analysis

Clones representing distinct Nanobody B-cell lineages were tested as periplasmic extracts for their binding to cell surface exposed CXCR7. In this assay, 5-fold dilutions of periplasmic extract were incubated with Hek293 hCXCR7 and Hek293 wt cells. Binding of the Nanobodies was detected using mouse anti-myc (Serotec), followed by anti-mouse IgG-PE (Jackson Immununoresearch). Binding signals of selected Nanobody clones (mcf values and ratios of binding) are represented in Table B-8 and indicate that the Nanobodies do bind to cellular human CXCR7.

TABLE B-8

CXCR7 screening results-FACS analysis.

| Clones with Tag-1 | Family | Llama | Hek-CXCR7 [MCF] | Hek wt [MCF] | Fold Hek CXCR7/ CXCR4 |
|---|---|---|---|---|---|
| 08A05 | 14 | 396 | 18621 | 310 | 60.1 |
| 08A10 | 20 | 397 | 27411 | 322 | 85.1 |
| 14G03 | 23 | 385 | 45811 | 381 | 120.2 |
| 07B11 | 34 | 395 | 42877 | 389 | 110.2 |
| 07C03 | 37 | 391 | 23359 | 319 | 73.2 |
| 01C10 | 1 | 395 | | No data | |

Example 7: Expression of CXCR7 Specific Nanobodies

Selected Nanobodies were recloned in *E. coli* expression vector pAX100 and expressed as C-terminal linked myc, His6 (hereforth also Tag-2 or SEQ ID NO: 72)-tagged proteins. Various Nanobodies were also expressed as fusion proteins comprising Alb8 (Nanobody-linker-Alb8-myc-His6) (see sequences SEQ ID NOs: 44 to 48—Table B-4) or as tagless Nanobodies. Expression was induced by IPTG and allowed to continue for 4 h at 37° C. After spinning the cell cultures, periplasmic extracts were prepared by freeze-thawing the pellets. Nanobodies were purified from these extracts using immobilized metal affinity chromatography (IMAC) and a buffer exchange to D-PBS.

Example 8: Binding FACS Analysis of CXCR7 Specific Nanobodies

Serial dilutions of purified proteins (concentration range: 400 nM-180 pM) were incubated with stable HEK-CXCR7 cells for 30 min at 4° C. and binding was detected using anti-mouse anti-myc (Serotec) and anti-mouse IgG-PE (Jackson Immunoresearch). The half maximal effective concentration (EC50) values and upper plateau levels of selected clones are depicted in Table B-9. These data confirm the screening data and underscore that the indicated Nanobodies bind to cellular human CXCR7.

TABLE B-9

Binding FACS analysis

| Clones with Tag-2 | EC50 | Plateau [mcf] |
|---|---|---|
| 08A05 | 8.9 | 28474 |
| 08A10 | 11.9 | 34896 |
| 14G03 | 10.2 | 23807 |
| 07B11 | 30.5 | 24898 |
| 07C03 | 3.3 | 33113 |
| 01C10 | No data | No data |

Example 9: Nanobodies Compete with SDF-1 for CXCR7 Binding (Displacement Assay)

In order to assess the competition capacity, Nanobodies were evaluated in SDF-1 ligand displacement assays using stable NIH3T3-hCXCR7 cells. 24 h after seeding the cells, the cells were pre-incubated for 1 h at 4° C. with a dilution series of purified monovalent Nanobodies and the corresponding C-terminal Tag-2 tagged fusion proteins to the human serum albumin binding Nanobody Alb8 (see Table B-4: SEQ ID NOs 44 to 48 wherein the polypeptides are all C-terminal tagged with Tag-2). Also reference molecules Mab 8F11 (Biolegend), Mab 11G8 (R&D) and unlabelled SDF-1 were included in the assay. Radiolabeled [$^{125}$I]-CXCL12 was diluted and added to the cells to reach a final concentration of 75 pM and cells were incubated for 3 h at 4° C. After incubation, cells were washed twice, lysed with RIPA buffer and the $^{125}$I signal was measured. Average Ki values and the percentage of displacement relative to the displacement of cold SDF-1, are shown in Table B-10. The competition of tested Nanobodies of Group 1 and Mab 8F11 is between 73 and 83%, relative to competition with unlabelled SDF-1. This level of displacement correspond to a 100% blocking of the CXCR7 protein, as the remaining SDF-1 binding is believed not to be CXCR7 mediated, but due to the SDF-1 interaction with heparin sulfate proteoglycans. Fusion to the human serum albumin-binding Nanobody Alb8 has no significant effect on Ki values.

TABLE B-10

Displacement assay

| Clones with Tag-2 | Average Ki whole 3T3 [nMs] | Average SDF-1 displacement (%) | n | SEM Ki | SEM SDF-1 displacement (%) |
|---|---|---|---|---|---|
| 08A05 | 13.6 | 77 | 8 | 2.5 | 6.4 |
| 08A05-9GS-Alb8 | 17.9 | | 1 | | |
| 08A10 | 12.1 | 75 | 8 | 1.8 | 3.3 |
| 08A10-9GS-Alb8 | 14.1 | | 1 | | |
| 14G03 | 3.0 | 73 | 6 | 0.6 | 3.3 |
| 14G03-9GS-Alb8 | 3.5 | | 1 | | |
| 07B11 | 96.1 | 75 | 2 | 1.3 | 1.5 |
| 07B11-9GS-Alb8 | 82.4 | | 1 | | |
| 07C03 | 12.2 | 78 | 2 | 6.6 | 15.0 |
| 07C03-9GS-Alb8 | 10.2 | | 1 | | |
| 01C10 | 20.7 | 31 | 3 | 10.7 | 15.5 |
| SDF-1 | 0.121 | 100 | 15 | 0.019 | 0.0 |
| Mab 11G8 | 4.4 | 24 | 3 | 2.7 | 2.0 |
| Mab 8F11 | 5.9 | 73 | 6 | 2.4 | 4.1 |

Example 10: Nanobodies Compete with SDF-1 for CXCR7 Binding (FACS Assay)

The potency of Nanobody 07C03 and Mab 8F11 (Biolegend) to compete with SDF-1 was evaluated in competition FACS with HEK-hCXCR7 cells. Cells were incubated simultaneously with 4 nM biotinylated SDF-1 (R&D) and with diluted test molecules, for 2 h at 4° C. Binding of biotinylated SDF-1 was detected using streptavidin-PE. Competition curves are depicted in FIG. 1. In this assay, Mab 8F11 and 07C03 competition is complete (>95%), relative to competition with unlabelled SDF-1, underscoring the complete inhibition of the SDF-1-CXCR7 interaction.

Example 11: Epitope Mapping

Figure 2:
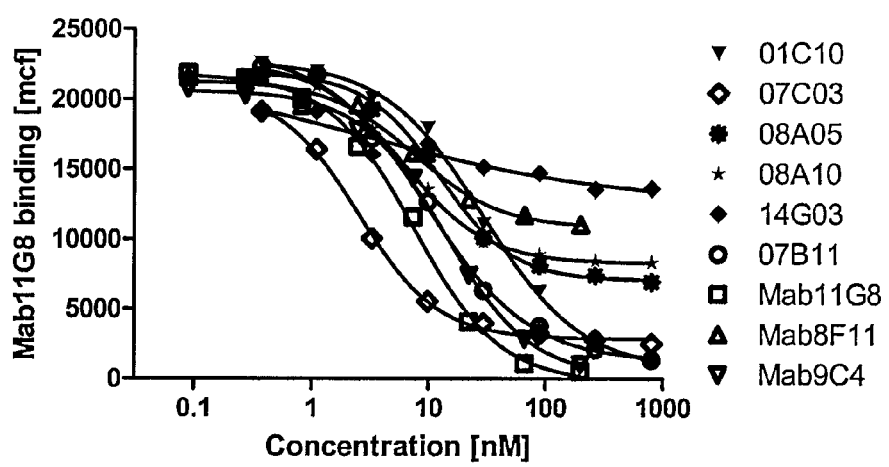
FIG. 2 shows a Mab 11G8 competition experiment using FACS.

The minimal epitope of Mab 11G8 is known to be F14SDISWP20 located at the CXCR7 N-terminus (see e.g., WO2008/048519). Cells were incubated simultaneously with 20 nM Mab 11G8 APC(R&D) and with diluted test molecules for 2 h at 4° C. Competition curves are depicted at FIG. 2. The level of competition with Mab 11G8 APC ranges from ~20 to 100%, suggesting that the respective Nanobody epitopes match to a high degree (high % of competition) with the Mab 11G8 epitope or to a low degree (low % of competition) or induce allosteric changes affecting the Mab 11G8 binding. These data indicate that the selected Nanobodies bind to divergent, but probably overlapping epitopes.

Nanobodies 08A05, 08A10, 07C03, 07B11, 01C10 and 14G03, Mab 8F11 (Biolegend), Mab 11G8 (R&D) and Mab 9C4 (MBL) were further tested for competition with Alexa647-labelled 14G03 in FACS analysis. Nanobodies 08A05, 08A10, 07C03, 07B11, Mab 8F11, Mab 11G8 and Mab 9C4 compete with 14G03 binding to CXCR7, while 01C10 does not, suggesting that 01C10 hits an epitope distinct from the epitope(s) hit by the other selected Nanobodies.

In a third approach, Nanobodies were tested for their binding to a set of 10 point mutants of CXCR7 (S9A, F14Y, 117L, S18N, W19A, S23G, D25A, V32A, M330, N36T), which yielded information on the individual Nanobody epitopes. For Nanobodies 08A05, 08A10, 07C03, 07B11 and 14G03, the epitope included residue M33, while that of 01C10 did not. The binding of 01C10 (and 07B11) was affected by the W19A mutation, while this mutation did not affect the binding of 08A05, 08A10, 07C03 and 14G03. Again, these data indicate that 01C10 hits a distinct epitope.

Example 12: Mouse/Cyno Cross-Reactivity

HEK293 cells transfected respectively with pcDNA3.1-hCXCR7 and pcDNA3.1-mCXCR7 were used to test cross-reactive binding of Nanobodies to mouse CXCR7 in FACS analysis. Cells were incubated with 32 nM Mab 11G8 (R&D), Mab 9C4 (MBL), Mab 8F11 (Biolegend) or with 800 nM Nanobody for 2 h at 4° C. Nanobody binding was detected using mouse anti-myc (Serotec) and anti-mouse IgG-PE (Jackson Immunoresearch) and Mab binding by goat anti-mouse IgG-PE (Jackson Immunoresearch). Nanobodies 08A10, 14G03, 07B11 and Mab9C4 are not cross-reactive to mouse CXCR7, Nanobodies 08A05 and 07C03 are partially cross-reactive with mouse CXCR7 and Mab 8F11, Mab 11G8 and 01C10 are cross-reactive with mouse CXCR7 (Table B-11).

Cross-reactive binding to cynomolgus CXCR7 was assessed in the same way. Nanobodies 08A10, 14G03, 07B11, 08A05, 07C03, 01C10 and Mab 9C4, Mab 8F11 and Mab 11G8 are all cross-reactive to cynomolgus CXCR7 (Table B-11).

TABLE B-11

Cross-reactivity to mouse CXCR7

| Clones with Tag-2 | Family | Llama | Mouse crossreactivity | Cyno crossreactivity |
|---|---|---|---|---|
| 01C10 | 1 | 395 | Yes | Yes |
| 08A05 | 14 | 396 | Partial | Yes |
| 08A10 | 20 | 397 | No | Yes |
| 14G03 | 23 | 385 | No | Yes |
| 07B11 | 34 | 395 | No | Yes |
| 07C03 | 37 | 391 | Partial | Yes |
| Mab 8F11 | | | Yes | Yes |
| Mab 11G8 | | | Yes | Yes |
| Mab 9C4 | | | No | Yes |

Example 13: Construction of Bivalent and Trivalent Nanobodies

Bivalent Nanobodies were constructed with one N-terminal CXCR7-specific building block (either 01C10, 14G03, 08A05, 08A10 or 07C03 but also even less potent building blocks like 08C02, 01C07, 01D04, which were not listed in the examples above) and a C-terminal human serum albumin (HSA)-specific building block (ALB8), providing the Nanobodies with an extended half-life in vivo. Trivalent Nanobodies consisted of one more CXCR7-specific building block in order to improve the potency and efficacy of the Nanobody to displace SDF-1 from the receptor. Bivalent and trivalent Nanobodies were expressed with Tag-2 extension in *Pichia*.

Example 14: Competition with SDF-1 Binding to CXCR7 of Bivalent and Trivalent Nanobodies Bivalent and trivalent Nanobodies were screened in the SDF-1 displacement assay as described in Example 9. Samples were incubated in the presence or absence of HSA to estimate the effect of HSA binding to the Nanobodies during the assay. While potencies of bivalent Nanobodies were dramatically lowered in the presence of HSA, they are much better conserved for trivalent Nanobodies (Table B-12).

TABLE B-12 competition with SDF-1 binding to CXCR7 of bivalent and trivalent Nanobodies

| Clones with Tag-3 | construct | SDF-1 Displacement in absence of HSA[Ki] | SDF-1 Displacement in presence of HSA[Ki] |
|---|---|---|---|
| 033 | 14G03-35GS-07C03-9GS-ALB8 | 0.82 | 1.74 |
| 035 | 14G03-35GS-14G03-9GS-ALB8 | 0.95 | 4.7 |
| 036 | 14G03-35GS-08C02-9GS-ALB8 | 1.34 | 6.19 |
| 032 | 14G03-35GS-08A05-9GS-ALB8 | 1.51 | 5.93 |
| 026 | 07C03-35GS-14G03-9GS-ALB8 | 1.75 | 33.03 |
| 034 | 14G03-35GS-07B11-9GS-ALB8 | 1.90 | 6.93 |
| 028 | 07C03-35GS-01C10-9GS-ALB8 | 2.2 | ND |
| 037 | 14G03-35GS-01C07-9GS-ALB8 | 2.28 | 4.48 |
| 013* | 14G03-9GS-ALB8 | 3.1 | 311 |
| 055 | 01C10-35GS-01C10-9GS-ALB8 | 3.42 | ND |
| 038 | 14G03-35GS-01C10-9GS-ALB8 | 3.47 | 5.85 |
| 052 | 01C10-35GS-14G03-9GS-ALB8 | 3.65 | 6.32 |
| 049 | 01C10-35GS-08A05-9GS-ALB8 | 3.72 | ND |

TABLE B-12-continued competition with SDF-1 binding to CXCR7 of bivalent and trivalent Nanobodies

| Clones with Tag-3 | construct | SDF-1 Displacement in absence of HSA[Ki] | SDF-1 Displacement in presence of HSA[Ki] |
|---|---|---|---|
| 018 | 08A10-35GS-14G03-9GS-ALB8 | 4.07 | ND |
| 053 | 01C10-35GS-08C02-9GS-ALB8 | 4.15 | ND |
| 048 | 01C10-35GS-08A10-9GS-ALB8 | 4.87 | ND |
| 050 | 01C10-35GS-07C03-9GS-ALB8 | 6.945 | ND |
| 025 | 07C03-35GS-07C03-9GS-ALB8 | 7.91 | ND |
| 009* | 07C03-9GS-ALB8 | 9.50 | 66.59 |
| 056 | 01D04-35GS-14G03-9GS-ALB8 | ND | 182.29 |
| Mab 8F11 | | 10.8 | |

*bears tag-2

Example 15: Inhibition of β-Arrestin Recruitment of Bivalent and Trivalent Nanobodies The PathHunter eXpress β-arrestin assay (DiscoverX) was used to assess the antagonistic effect of trivalent Nanobodies on recruitment of β-arrestin. A panel of 37 trivalent Nanobodies (clones) was screened at a 100 nM concentration in the assay. Results are ranked in Table B-13 on the basis of efficiency of inhibition. The most efficient trivalent molecules constitute combinations with 01C10, the Nanobody that hits a distinct epitope (cf. Example 11). These Nanobodies (clones) can bind in a double mode to one CXCR7 monomer.

Based on the foregoing results, the Nanobodies may be classified into 3 groups:
- Group 1: represented by 01C10, apparently hitting an epitope distinct from Group 2;
- Group 2: represented by 14G03, 08A05, 08A10 and 07C03, apparently hitting an epitope distinct from Group 1; and
- Group 3: represented by 07B11, apparently intermediary to Group 1 and Group 2.

Although Nanobodies of Group 2 (and Group 3) either monovalently or bivalently demonstrate superior binding and competition characteristics than the corresponding Nanobodies of Group 1, Nanobodies of Group 1 combined with Nanobodies of Group 2 gave wholly unexpectedly the best results in the β-arrestin recruitment assay.

TABLE B-13

Inhibition of β-arrestin recruitment of bivalent and trivalent Nanobodies

| Clones with Tag-3 | construct | % inhibition of β-arrestin recruitment |
|---|---|---|
| 038 | 14G03-35GS-01C10-9GS-ALB8 | 94.1 |
| 052 | 01C10-35GS-14G03-9GS-ALB8 | 93.7 |
| 021 | 08A10-35GS-01C10-9GS-ALB8 | 89.5 |
| 023 | 08A05-35GS-01C10-9GS-ALB8 | 92.8 |
| 049 | 01C10-35GS-08A05-9GS-ALB8 | 89.3 |
| 022 | 08A05-35GS-07C03-9GS-ALB8 | 88.9 |
| 058 | 08A10-35GS-08A05-9GS-ALB8 | 87.8 |
| 060 | 08A05-35GS-08A05-9GS-ALB8 | 86.5 |
| 032 | 14G03-35GS-08A05-9GS-ALB8 | 76.9 |
| 048 | 01C10-35GS-08A10-9GS-ALB8 | 76.6 |
| 029 | 07B11-35GS-08A05-9GS-ALB8 | 73.8 |
| 018 | 08A10-35GS-14G03-9GS-ALB8 | 68.1 |
| 044 | 01C07-35GS-08A05-9GS-ALB8 | 66.1 |
| 020 | 08A10-35GS-02C08-9GS-ALB8 | 62.1 |

TABLE B-13-continued

Inhibition of β-arrestin recruitment of bivalent and trivalent Nanobodies

| Clones with Tag-3 | construct | % inhibition of β-arrestin recruitment |
|---|---|---|
| 019 | 08A10-35GS-08C02-9GS-ALB8 | 61.6 |
| 028 | 07C03-35GS-01C10-9GS-ALB8 | 60.6 |
| 053 | 01C10-35GS-08C02-9GS-ALB8 | 58.8 |
| 061 | 08A05-35GS-02C08-9GS-ALB8 | 58.6 |
| 025 | 07C03-35GS-07C03-9GS-ALB8 | 54.5 |
| 027 | 07C03-35GS-02C08-9GS-ALB8 | 49.3 |
| 034 | 14G03-35GS-07B11-9GS-ALB8 | 43.5 |
| 050 | 01C10-35GS-07C03-9GS-ALB8 | 41.8 |
| 033 | 14G03-35GS-07C03-9GS-ALB8 | 41.2 |
| 026 | 07C03-35GS-14G03-9GS-ALB8 | 35.2 |
| 037 | 14G03-35GS-01C07-9GS-ALB8 | 34.0 |
| 065 | 02C08-35GS-08C02-9GS-ALB8 | 31.3 |
| 046 | 02C08-35GS-07B11-9GS-ALB8 | 29.6 |
| 051 | 01C10-35GS-07B11-9GS-ALB8 | 28.3 |
| 057 | 07B11-35GS-14G03-9GS-ALB8 | 26.0 |
| 063 | 01C07-35GS-08C02-9GS-ALB8 | 25.8 |
| 035 | 14G03-35GS-14G03-9GS-ALB8 | 24.9 |
| 036 | 14G03-35GS-08C02-9GS-ALB8 | 22.0 |
| 031 | 07B11-35GS-01C10-9GS-ALB8 | 4.3 |
| 055 | 01C10-35GS-01C10-9GS-ALB8 | −8.5 |
| 056 | 01D04-35GS-14G03-9GS-ALB8 | −51.3 |

Example 16: Optimization of Bivalent and Trivalent Nanobodies

Selected bivalent and trivalent Nanobodies were further characterized in the β-arrestin recruitment assay and potencies were assessed. The assay was run in the presence and absence of HSA to estimate the effect of HSA binding to the Nanobody during the assay. Longer linkers preceding the ALB8 building block were evaluated to minimize sterical interference of HSA binding to the Nanobody (Table B-14).

TABLE B-14

Optimization of bivalent and trivalent Nanobodies

| Clones with Tag-3 | construct | β-arrestin recruitment in absence of HSA [IC50] | β-arrestin recruitment in presence of HSA [IC50] |
|---|---|---|---|
| 038 | 14G03-35GS-01C10-9GS-ALB8 | 3.28 | 19.38 |
| 052 | 01C10-35GS-14G03-9GS-ALB8 | 18.3 | 86.8 |
| 055 | 01C10-35GS-01C10-9GS-ALB8 | no antagonism | no antagonism |
| 056 | 01D04-35GS-14G03-9GS-ALB8 | no antagonism | no antagonism |
| 068 | 07C03-9GS-ALB8 | 279.6 | inefficient antagonism |
| 069 | 08A05-9GS-ALB8 | 120.2 | inefficient antagonism |
| 072 | 14G03-9GS-ALB8 | inefficient antagonism | inefficient antagonism |
| 081 | 07C03-30GS-ALB8 | 296.9 | inefficient antagonism |
| 082 | 14G03-30GS-ALB8 | 578 | inefficient antagonism |
| 083 | 08A05-30GS-ALB8 | 45.46 | 179.1 |
| 084 | 14G03-35GS-01C10-35GS-ALB8 | 6.3 | 10.0 |

Example 17: Characterization of Tagless Nanobodies

Figure 8:
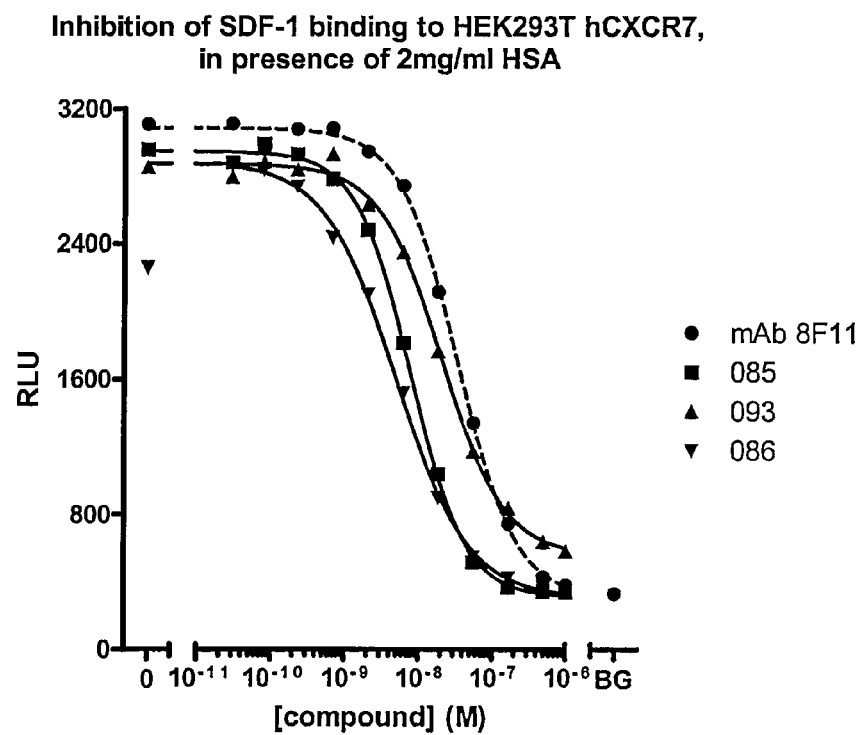
FIG. 8 shows inhibition of SDF-1 binding to HEK293T hCXCR7 in the presence of 2 mg/ml HSA.
Figure 9:
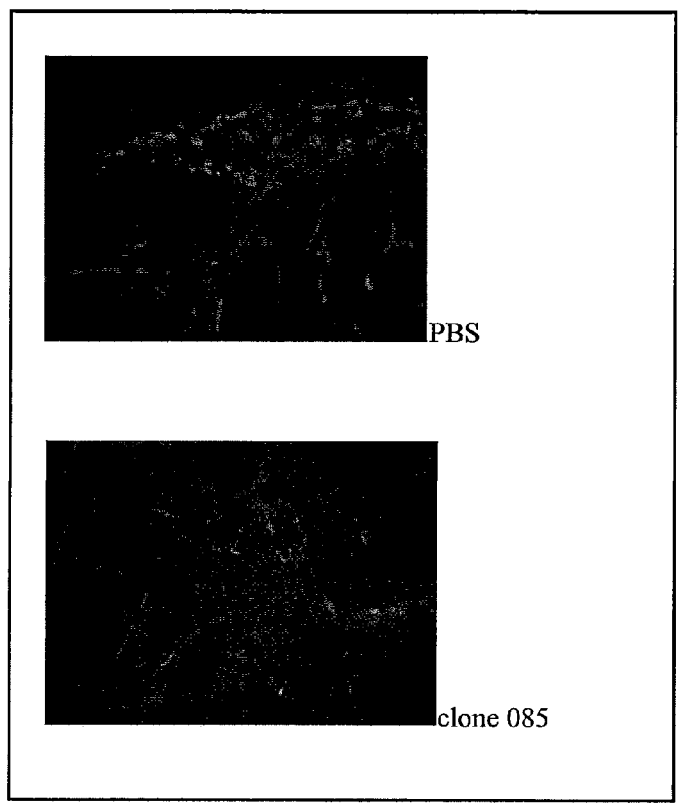
FIG. 9 shows that Nanobodies reduce in vivo xenograft growth by reducing angiogenesis. Nude mice were transplanted with 22A tumors were treated biweekly for 7 weeks with PBS, clone 060 or clone 085. Tumor growth was followed by measuring xenograft size with a caliper and was significantly slower in mice treated with clone 085 (NB4) compared to PBS or clone 060. A-B, Tumor sections from PBS- or clone 085-treated mice were stained for the endothelial cell marker CD31. The staining was quantified and significantly less CD31 staining was observed in clone 085-treated tumors compared to PBS-treated tumors ($p<0.05$ in an unpaired t-test comparison) (B).
Figure 9:
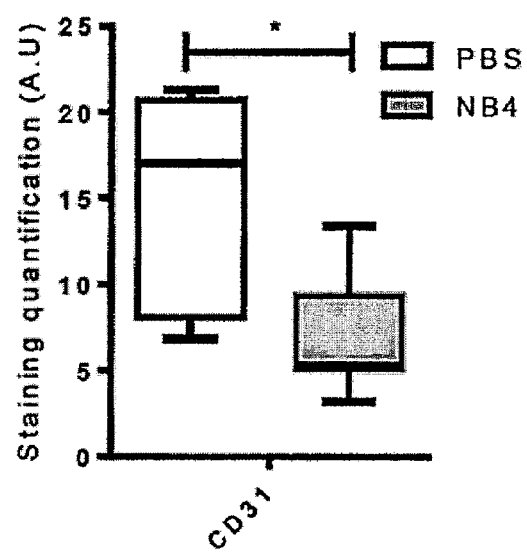

To exclude any influence of Tag-3 on Nanobody potencies, selected Nanobodies were expressed without Tag-3 and characterized in both the β-arrestin recruitment assay and in the SDF-1 competition FACS in the presence of 2 mg/ml HSA (further essentially as described in Example 10) and potencies were assessed (Table B-15 and FIG. 8). Constructs comprising "Group 2 ISVD"-"Group 2 ISVD" (represented by e.g. clone 086) and constructs comprising "Group 2 ISVD"-"Group 1 ISVD" (represented by e.g., clone 085) are more efficacious in SDF-1 displacement than constructs comprising "Group 1 ISVD"-"Group 1 ISVD" (represented by e.g., clone 093). Competition with constructs comprising "Group 1 ISVD"-"Group 1 ISVD" (represented by e.g., clone 093) is less effective.

These data corroborate the radioligand competition assays, in which the monovalent 01C10 was tested (cf. Table B-10: 31% for 01C10).

Thus, Group 2 ISVDs are excellent SDF-1 displacers.

TABLE B-15

Characterization of tagless Nanobodies

| Clones | construct | β-arrestin recruitment in absence of HSA [IC50] | β-arrestin recruitment in presence of HSA [IC50] | SDF-1 displacement FACS [IC50] |
|---|---|---|---|---|
| 085 | 14G03-35GS-01C10-35GS-ALB8 | 4.36 | 22.31 | 7.83 |
| 086 | 14G03-35GS-07C03-9GS-ALB8 | weak antagonism | no antagonism | 5.02 |
| 093 | 01C10-35GS-01C10-35GS-ALB8 | no antagonism | no antagonism | 20.6 |
| Mab 8F11 | | 12.9 | 34.8 | 34.2 |

Example 18: Immunohistochemical Analysis of CXCR7 Expression in Primary Tumor Sections Tumor sections that were analyzed for CXCR7 expression originated from human primary tumors of variable cancer types that had been passaged one time in nude mice. Paraffin embedded tumors were cut into 5 μm sections (with a Leica RM 2135 microtome), dried, dewaxed and stained with hematoxylin and eosin. Thereafter, one representative region was marked on these tumor sections so that a 1 mm diameter cone for assembling the Tissue Micro Array (TMA) could be punched out. The TMA was then prepared according to Mirlacher and Storz using a Beecher Instruments Micro Tissuearrayer (Mirlacher M. and Storz M., 2000, Gewebe-Chips für die molekulare Untersuchung von Tumoren, Labmed., 293-297). Array sections were cut using the Instrumedics Sectioning Aid System and specifically coated using "Starfrost" slides.

Immunohistochemical staining of CXCR7-expressing tissue was performed as follows: (1) paraffin was removed from the tissue, tissues were dehydrated and washed; (2) endogenous peroxidase was inactivated by addition of 3% H2O2 in distilled water; (3) the specimen was dried upon washing; (4) unspecific binding was blocked by 10% BSA in PBS; (5) the anti-human/mouse CXCR7 monoclonal antibody (Biolegend, clone Mab 8F11) or an isotype control antibody (Biolegend, IgG2b) was incubated at a concentration of 25 µg/mL and subsequently the tissue was washed; (6) the secondary antibody goat anti-mouse biotinylated IgG (JacksonlmmunoResearch) was incubated at a final concentration of 2.8 µg/mL and the tissue was washed afterwards; (7) the detection was performed with the ABC solution and peroxidase substrate of the Vectastain ABC kit (Vector), each step followed by a washing step; (8) counterstaining with hematoxylin and (9) dehydration of the tissue.

The TMA (170 tumor models) was evaluated semi-quantitatively using a Zeiss Axiovert 35 microscope. Photographs were taken with a Zeiss AxioCam MRc camera. All tumor samples were evaluated in duplicate. Staining was interpreted based on the proportion of positively-stained cells as well as on the signal intensity. Samples were grouped in the following categories: 0, no staining (antigen absent); 1, weak staining; 2, moderate staining; 3, strong staining.

FIG. 3A gives an overview of the scores assigned to the different tumor types. A high CXCR7 expression (score=3) in at least one of the two tissue patches was found in 55 out of the 170 tumors tested (=32.4%). Nine tumors did not show any CXCR7 expression (staining score=0) and for the rest of the xenograft tissues a weak or intermediate expression (scores 1 and 2) was found. Notably, the majority of colon cancer tumors (19 out of 23 or 82.6%) and gastric cancer tumors (8 out of 12 or 66.7%) displayed no or only weak staining with a score of ≤1, whereas all of the head and neck cancer tumors (7 out of 7 or 100%) tested showed a relatively high CXCR7 expression with a score of ≥2. In the other histotypes, however, CXCR7 staining was highly variable between the individual tumor models.

For some tumor samples, staining intensity was confirmed on whole tumor sections; (FIG. 3B-C), melanoma, and non-small cell lung cancer (NSCLC) displayed a strong CXCR7 protein expression (100%, 83% and 93% of tumors stained with a score of at least 2, respectively).

These data highlight a potential novel tumorigenic role of CXCR7 in head and neck cancer.

Example 19: CXCR7 Nanobodies Reduce Head and Neck Cancer Xenograft Tumour Growth In Vivo 19.1 Materials and Methods
19.1.1 Cell Lines.

Cell line UM-SCC-11B (11B) was cultured from a biopsy of a primary laryngeal cancer, after the patient got chemotherapy. Cell line UM-SCC-22A (22A) was derived from a primary squamous cell carcinoma of the oropharynx. Cell line UM-SCC-22B (22B) was derived from a metastatic squamous cell carcinoma of the oropharynx. The human head and neck squamous cell carcinoma (HNSCC) cell lines FaDu and HNX-OE have been described earlier (Hermsen et al. (1996) "Centromeric breakage as a major cause of cytogenetic abnormalities in oral squamous cell carcinoma" Genes Chromosomes Cancer 15:1-9; Ranger (1972) "A new human cell line (FaDu) from a hypopharyngeal carcinoma" Cancer 29:117-421). The HNX-OE and 93-VU-147T cell lines were established at Vrije Universiteit Amsterdam (Hermsen et al. ibid), whereas the FaDu line was obtained from Karl-Heinz Heider (Boehringer Ingelheim Austria).

19.1.2 Quantitative RT-PCR Analysis.

Total RNA was extracted from head and neck cancer cell lines and primary keratinocytes with the RNeasy kit from Qiagen according to the manufacturer protocol. Messenger (m)RNA was converted into cDNA using the BioRad iScript cDNA synthesis kit. Subsequently, mRNA expression levels were detected with SyberGreen (BioRad) using CXCR7 and β-actin-specific primers from Origene. CXCR7 expression levels were normalized against those of β-actin to allow comparison of the different cell lines.

19.1.3 Radioligand Binding.

Head and neck cancer cell lines were seeded on poly-L-lysine-coated 96-well plates and grown overnight. The following day, binding buffer (50 mM Hepes pH 7.4, 1 mM $CaCl_2$, 5 mM $MgCl_2$, 0.1 M NaCl) supplemented with 0.5% BSA was added to the cells in the absence or presence of either chemokine ($10^{-7}$ M) or CXCR7-specific Nanobody 9A4 ($10^{-6}$ M). Subsequently, radiolabelled [$^{125}$I]-CXCL12 (Perkin-Elmer) was added to reach a final concentration of 75 µM. Cells were incubated for 3 h at 4° C., washed twice with binding buffer containing 0.5 M NaCl. After harvesting the samples with lysis buffer, the remaining cell-bound radioactivity was counted.

19.1.4 Animal Experiment.

All animal experiments were conducted according to the NIH principles of laboratory animal care and Dutch national law ["Wet op de Dierproeven" (Stb 1985, 336)], approved by the Dierexperimentencommissie from the VU University Medical Center and performed in compliance with the protocol FaCh 10-01. Head and neck cancer cells 22A were injected s.c. in the flanks of 8- to 10-week old female donor nude mice (Hsd, athymic nu/nu, Harlan laboratories). Xenograft tumors were grown to a size of 200-500 $mm^3$, and were subsequently excised, cut in smaller pieces of equal size and transplanted s.c. in the flanks of recipient nude mice. When transplanted tumors properly engrafted, mice were injected i.p. bi-weekly with either PBS, or 1 mg bivalent Nanobody or 1.5 mg trivalent Nanobody.

19.1.5 Immunofluorescence 22A cells-derived xenograft sections (8 µm) were fixed in −20° C. acetone. Following blocking with 10% BSA TBS solution, primary antibodies (C1C2 polyclonal anti-CXCR7 antibody 1:25, Genetex; anti-ki67, 1:250, Abcam; anti-CD31, 1:100, BD Pharmingen) were incubated for 1 h at RT in blocking buffer. Sections were washed with PBS and incubated for 30 min at RT with goat anti-rabbit Alexa 488 or anti-rat Alexa 546 (1:500, Invitrogen). Sections were mounted with DAPI-containing Vectashield medium (Vector Labs). Fluorescence was visualised using a Nikon Eclipse TE200 microscope and processed with XM10 camera and Cell^B imaging software (Olympus). CD31 staining intensities were quantified using Image-Pro Premier (Media Cybernetics) and unpaired t-test analysis (P<0.05) was used to determine the significance with the GraphPad Prism software (San Diego, Calif.).

19.1.6 Competition FACS

Transiently transfected HEK293T-hCXCR7 cells were incubated simultaneously with 20 nM of APC-labelled monoclonal antibody 11G8 (R&D Systems) and with a dilution range of Nanobodies or monoclonal antibodies for 2 h at 4° C. using a standard FACS protocol.

19.1.7 Cell Cycle Assay 22A cells were plated on a 6-well plate (75.000 cells/well). The next day cells were synchronized in serum-free medium for 24 hours and stimulated for another 24 hours on full growth medium with or without stimuli (1 nM CXCL12, 1 µM clone 085, 10 µg/ml EGF or 10 µg/ml Erbitux). Cells were stained with propidium iodine, and cell cycle populations were determined by using the Guava EasyCyte system according to the manufacturer's recommendations (Millipore). The Guava Cell Cycle software was used to determine the cell populations in the different cell cycle phases and the P.I. was quantified from the (% S+% G2M) % GOG1 ratios as previously described (Maussang et al PNAS 2006).

19.1.8 Human Angiogenesis Antibody Array 22A cells were grown on a 12-well plate (200.000 cells/well). The next day the medium was removed and cells were incubated on serum-free medium with or without stimuli (1 nM CXCL12, 1 µM clone 085 and combination) for 48 hours. The supernatant was subsequently collected, centrifuged to remove cellular debris and used undiluted in a human angiogenesis array (RayBiotech) according to the manufacturer's instructions. Relative amounts of cytokines and chemokines involved in angiogenesis were normalized against positive controls present on the array.

19.2 Results 19.2.1 mRNA Expression of CXCR7.

Figure 4:
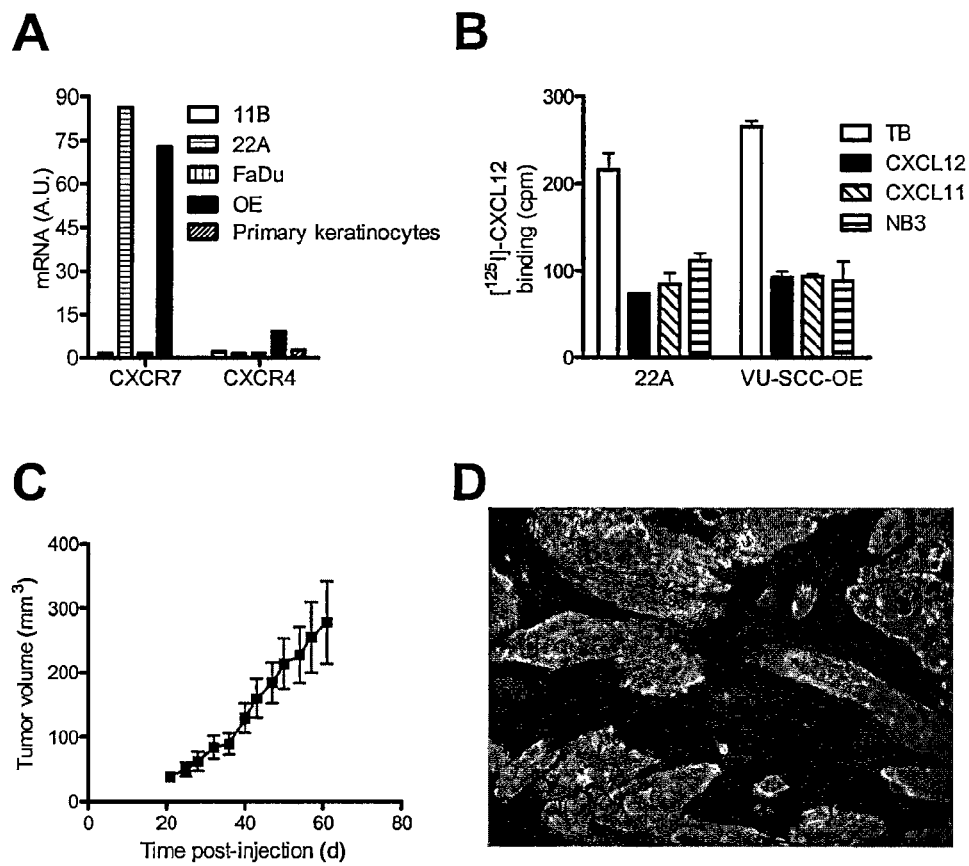
FIG. 4 shows CXCR7 expression in head and neck cancer cells. A, Human head and neck cancer cell lines and primary keratinocytes were tested for CXCR7 and CXCR4 mRNA expression by quantitative RT-PCR. Expression was related to the β-actin content. A.U., arbitrary units; OE, VU-SCC-OE. B, [$^{125}$I]-CXCL12 radioligand binding with head and neck cancer cells. Specific CXCR7 expression was confirmed using the cold chemokines CXCL12 and CXCL11 and CXCR7-specific Nanobody 09A04 (NB3). (TB, total binding) C, Growth rate of 22A cells injected s.c. in the flank of nude mice. D, immunofluorescence staining of CXCR7 protein with C1C2 polyclonal antibody on 22A-derived xenograft tumors developed in nude mice.

In order to confirm CXCR7 expression in head and neck cancer cells lines, we screened four previously described head and neck squamous cell carcinomas (HNSCC) cell lines. Quantitative RT-PCR analysis was performed on RNA extracted from 11B, 22A, FaDu and VU-SCC-OE cell lines. Two out of the four tested cell lines displayed CXCR7 mRNA expression, namely the 22A and VU-SCC-OE cell lines (FIG. 4A). Since CXCL12, highly expressed at tumor sites, is also known to bind CXCR4 we also determined CXCR4 mRNA expression levels in these cell lines. As can be seen in FIG. 4A CXCR4 mRNA levels in all four examined cell lines are low compared to CXCR7 mRNA levels. In contrast, primary keratinocytes isolated from healthy tissue do not show any expression of CXCR7 nor CXCR4 mRNA (FIG. 4A).

19.2.2 Protein Expression of CXCR7.

CXCR7 mRNA is expressed in a wide range of tissues in humans. However, mRNA expression does not always correlate with cell surface expression of the protein. Therefore, in order to further assess the presence of CXCR7 protein, protein expression of CXCR7 was confirmed in a $[^{125}I]$-CXCL12 radioligand binding assay. CXCR7-specific expression was determined by displacing the radioligand with the cold chemokines CXCL12 and CXCL11, but not CXCL10. Additionally, the monovalent Nanobody 09A04 displaced $[^{125}I]$-CXCL12 to a similar extent than CXCL11 and CXCL12 (FIG. 4B).

These data confirmed that mRNA and protein CXCR7 were expressed in 4 head and neck cancer cell lines.

19.2.3 Head and Neck Cancer Cell Line 22a as CXCR7 In Vitro and In Vivo Model System.

CXCR7-expressing cell lines were used in a xenograft model in vivo where tumour growth was measured. The 22A cell line was chosen as xenograft tumour model since nude mice s.c. injected with $2\times10^6$ cells per flank allowed for xenograft tumor formation.

At 61 days post-injection, 22A tumors reached an average size of 278±64 mm3 (FIG. 4C). At that stage, CXCR7 protein expression was investigated by immunofluorescence. A rabbit polyclonal anti-CXCR7 antibody (C1C2, GeneTex) was used instead of mouse monoclonal antibodies to avoid the use of a secondary anti-mouse antibody that might react with endogenous murine immunoglobulins. 22A xenograft sections displayed a non-homogenous expression of CXCR7, reflecting the differentiated nature of the tumor with a mixture of epithelial cells (CXCR7 positive) and stromal cells (FIG. 4D). This pattern was similar to what was observed in human biopsies (FIG. 3C).

We conclude that 22A cells grown as xenograft express CXCR7 protein.

19.2.4 Formatted CXCR7 Nanobodies Inhibit Secretion of Angiogenic Factors, but not Cell Cycle Progression.

Figure 5:
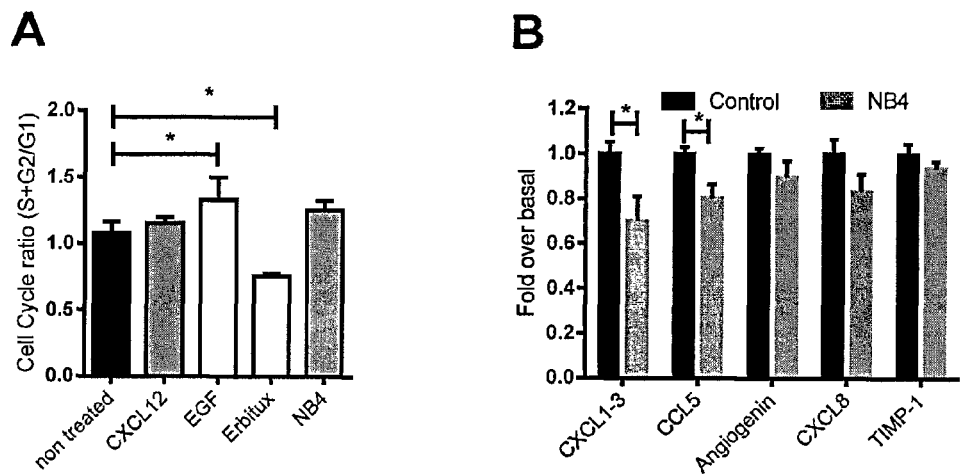
FIG. 5 shows the effect of Nanobodies on cell cycle progression of cancer cells and release of angiogenic factors. A, Cell cycle analysis of 22A cells in the absence or presence of CXCR7 (CXCL12 or clone 085 (NB4)) or EGFR (EGF or EGFR-specific monoclonal antibody Erbitux) reagents. B, Secretion of angiogenic factors from 22A cells in the absence or presence of clone 085 ($10^{-6}$ M). Only CXCL1-3, CCL5, Angiogenin CXCL8 and TIMP1 were detected in this array and were therefore quantified.

Next, we tested whether Nanobodies inhibit cell cycle progression of 22A cells, focusing solely on clone 085 (NB4) due to its enhanced affinity and potency compared to clone 060. Stimulation of 22A cells with CXCL12 ($10^{-9}$ M) did not affect cell cycle progression in a significant manner, nor did clone 085 (FIG. 5A). As a positive control, 22A cells were stimulated with epidermal growth factor (EGF) (10 µg/ml) as it was reported earlier that these cells are EGF-sensitive (Helman et al. (2010) Optical imaging predicts tumor response to anti-EGFR therapy. Cancer Biol Ther 10, 166-17132). As expected, EGF stimulation led to a significant increase in cell cycle progression. Equally, blocking endogenous EGFR signaling with the EGFR-specific monoclonal antibody Erbitux (10 µg/ml) significantly decreased cell cycle progression. Thus in contrast to EGFR, CXCR7 did not influence 22A cell cycle progression. Finally, an angiogenesis antibody array was used to determine whether Nanobody treatment would affect the secretion of angiogenic factors from 22A cells. Several angiogenic factors are endogenously secreted by 22A cells under basal conditions. Stimulation with CXCL12 ($10^{-9}$ M) did not lead to any significant changes in secretion (data not shown). Only clone 085 treatment led to a decrease of basal CXCL1-3 and CCL5 secretion, suggesting an involvement of CXCR7 in endogenous release levels of these chemokines (FIG. 5B).

19.2.5 CXCR7 Nanobodies are Able to Inhibit Tumour Growth.

Figure 6:
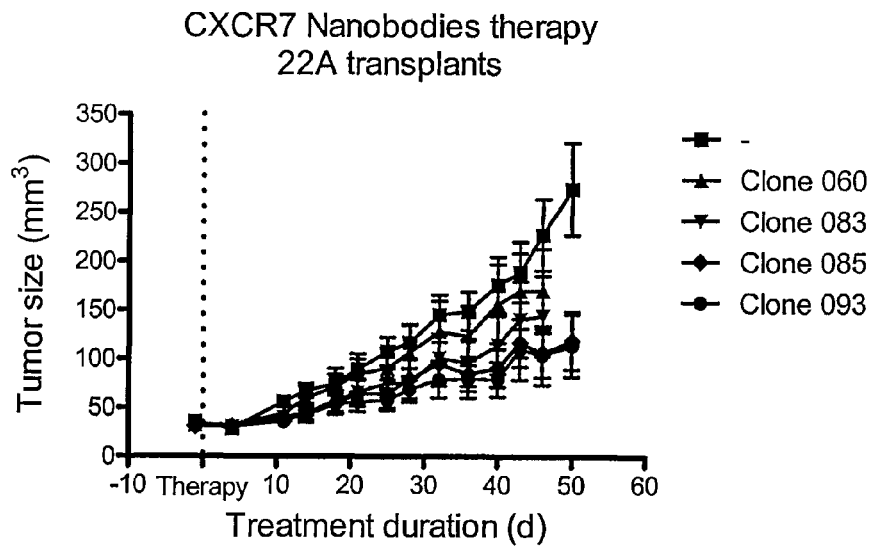
FIG. 6 shows in vivo CXCR7 Nanobody therapy with 22A transplants in nude mice: "−" negative control (PBS); polypeptide constructs clone 060, clone 083, clone 085 and clone 093.
Figure 7:
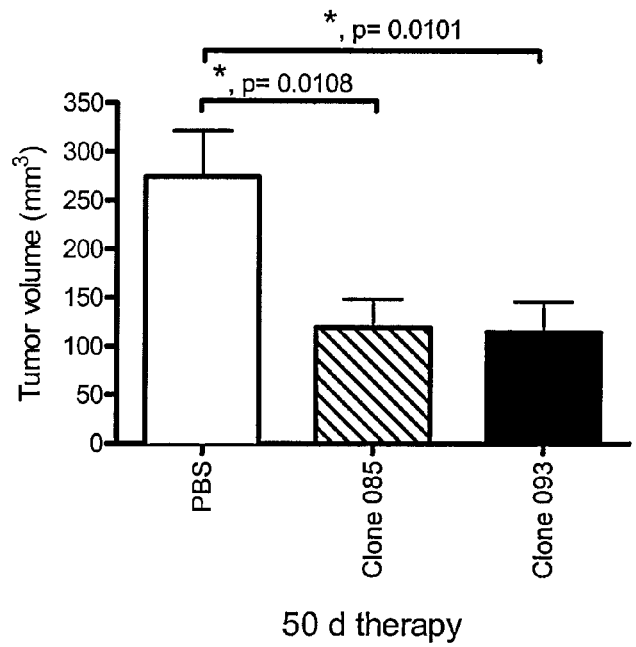
FIG. 7 shows tumour volumes after 50 days of treatment with in vivo CXCR7 Nanobody therapy with 22A transplants in nude mice: "−" negative control (PBS); polypeptide constructs clone 085 and clone 093.

Next, to ensure that mice from different groups (treated vs. non-treated) presented similar initial tumour sizes for the therapy experiment, we performed tumour transplantation. First, donor nude mice were initially injected with $2\times10^6$ 22A cells s.c. in their flanks. Tumours were grown to a size of 200-500 mm³ and subsequently extracted, cut in smaller pieces of equal size, and transplanted s.c. in recipient nude mice. When engrafted tumours started growing, mice were randomly distributed into five groups that were injected bi-weekly with 400 ul PBS without or with Nanobodies. The constructs tested for therapy were clone 060, clone 083, clone 085 and clone 093. Bivalent and trivalent Nanobodies were dosed at 1 and 1.5 mg per injection, respectively. Over a period of 50 days of therapy, the control (PBS) and clone 060 and clone 083 groups grew tumors to a similar extent (no significant different sizes) (FIG. 6). Mice treated with clone 085 and clone 093 displayed a slower tumour growth and significant smaller size compared to PBS-injected mice at the end of the therapy experiment (tumour volumes PBS=274±47 mm³, clone 085=119±30 mm³ and clone 093=114±32 mm³) (FIG. 7).

Since during the therapy period, no weight loss was observed for any Nanobody-injected animals, the tumor growth inhibitory effect of clone 085 could not be attributed to toxicity issues. To identify the in vivo mode of action of Nanobodies, tumors were stained for the angiogenesis marker CD31 (cf. FIGS. 7B-C). CD31 staining was present in the periphery of the tumor and CD31 staining pattern was strongly reduced in clone 085 treated mice compared to PBS treated mice. Quantification of the staining intensities in 10 independent tumors from both PBS- and clone 085-treated groups confirmed that CD31 is significantly decreased in mice receiving clone 085 therapy.

Thus, CXCR7 Nanobodies reduce head and neck cancer cell growth in vivo.

This study supports not only the anti-tumour efficacy of the Nanobodies, but also an excellent safety profile, a reflection of its highly targeted and specific activity profile, which is fundamentally different from many other cytotoxic drugs in development or on the market.

19.3 Discussion

Nanobodies represent a novel class of potential antibody-based therapeutics and have been successfully developed against several drug targets. Llama-derived immunoglobulin single variable domain antibodies have proven to be an excellent platform to use in cancer drug research, either as therapy or as a diagnostic tool. Therapeutic Nanobodies have been generated against cancer-specific drug targets such as the receptor tyrosine kinases EGFR/Erbb1, HER2, c-Met, VEGFR2 and more recently against the chemokine receptor CXCR4. Based on our experience with CXCR4, we identified therapeutic and high-affinity Nanobodies against the other CXCL12 receptor, i.e. CXCR7. Following in vivo whole cell and DNA immunization, [$^{125}$I]-CXCL12 radio-ligand displacement screening on whole CXCR7-expressing cells allowed us to select potent Nanobodies with affinities in the nanomolar range. In order to functionally characterize these Nanobodies, we used a β-arresting BRET recruitment assay, since CXCR7 is devoid of the classical G protein-mediated signaling. Interestingly, unlike our CXCR7-specific small molecule VUF11403, the majority of Nanobodies act as antagonists on CXCR7 and do not induce recruitment of β-arrestin. As such, the low molecular weight compound and antibody-derived therapeutics present opposite effects on CXCR7 mediated recruitment of β-arrestin.

The chemokine receptor CXCR7 is currently considered as a drug target in oncology due to its overexpression in a wide range of tumors, e.g. glioblastoma, hepatocellular carcinoma, bladder and cervical cancer. In our search for an appropriate CXCR7-expressing in vivo tumor model, we evaluated human tumor biopsies from various origins for CXCR7 expression by immunostaining with the 8F11 monoclonal antibody. Our results indicate that CXCR7 is highly expressed in melanoma, mammary and NSCLC tissue as previously described. Moreover, we show that colon and gastric tumor tissue express relatively low levels of CXCR7 compared to the other tumor tissues analyzed. Importantly, we show a high incidence of CXCR7 protein expression in head and neck tumor biopsies, in line with previous studies where CXCR7 expression was detected in oral carcinoma patient material. Several human HNSCC cells analyzed in our studies showed high expression of CXCR7, as detected by radioligand binding and anti-CXCR7 antibody staining. The selected patient-derived HNSCC 22A cell line appears a suitable model system for CXCR7, inducing tumor formation in a xenograft model, showing elevated levels of CXCR7 expression and not CXCR4 in these cells. Most importantly, we show that the CXCR7 Nanobodies represented by clone 085 reduces tumor growth in vivo. The fact that clone 060 is less able to reduce tumor growth can likely be attributed to its 10-fold lower affinity and potency to inhibit CXCL12 binding and signaling on the human CXCR7 receptor, when compared to Nanobodies represented by clone 085. We cannot exclude a potential effect of Nanobodies represented by clone 085 on mouse stromal cells due to its cross-reactivity with mouse CXCR7. However, staining of 22A-derived mouse xenograft and human biopsies seem to exclude the presence of CXCR7 protein in tumor stromal cells. Overall, the inhibitory effect of Nanobodies represented by clone 085 strengthens a potential role for CXCR7 in oncogenesis, and in particular head and neck cancer.

Cell cycle progression of 22A cells in vitro was not affected by treatment with Nanobodies represented by clone 085 or the chemokine CXCL12, ruling out a direct involvement of CXCR7 in head and neck cancer cell proliferation. This lack of involvement of CXCR7 in cellular proliferation was previously observed in other cancer types, in particular in glioma cells. In vitro, we demonstrated that inhibition of CXCR7 by Nanobodies represented by clone 085 in 22A cells reduces secretion of the angiogenic factors CXCL1-3 and CCL5. These factors are known to play an important role in angiogenesis by stimulating recruitment of e.g. endothelial cells. Expression of several chemokines and chemokine receptors in HNSCC was evaluated previously by others and these CXCL1-3 and CCL5 chemokines were expressed by a vast majority of head and neck cancer cell lines. Others have shown that CXCR7 is able to promote growth and signaling in a ligand-independent manner. In vivo, we confirmed that Nanobodies represented by clone 085 (including clone 093) reduces significantly tumor angiogenesis. Further research may be required to further dissect the precise molecular mechanisms by which clone 085 decreases angiogenesis in head and neck tumors.

In summary, using the Nanobody platform we generated Nanobodies against the oncogenic chemokine receptor CXCR7. These llama-derived single domain antibodies were functionally able to inhibit CXCL12 binding, block β-arresting recruitment to CXCR7 and decrease secretion of angiogenic factors in head and neck cancer cell line. Notably, we demonstrate for the first time the enhanced CXCR7 expression in head and neck cancer biopsies, and derived cell lines. Treatment of head and neck cancer xenografts with CXCR7 Nanobodies reduced tumor growth by inhibiting blood vessel formation. We demonstrate that CXCR7 is a novel drug target against this devastating disease.

Example 20: CXCR7 Nanobodies Reduce Xenograft Tumour Growth In Vivo

In Example 19, it has been demonstrated that CXCR7 Nanobodies are able to inhibit tumours as exemplified by head and neck cancers.

In a first phase to demonstrate in vivo that the Nanobodies are also effective in other tumours in which CXCR7 is (over)-expressed than head and neck cancers, further xenograph models can be used.

Gliomas are the most common forms of primary human brain tumors, and they are often classified into four clinical grades. The most aggressive tumors, grade 4 tumors, also known as glioblastoma multiforme (GBM), are associated with high mortality and morbidity. Survival of patients affected by GBM has remained virtually unchanged during the last decades (i.e., 6-12 months postdiagnosis) despite advances in surgery, radiation, and chemotherapy. GBM xenograph models can be used essentially as described, for instance, by Yi et al. (EGFR Gene Overexpression Retained in an Invasive Xenograft Model by Solid Orthotopic Transplantation of Human Glioblastoma Multiforme Into Nude Mice" Cancer Invest. 2011 29: 229-239).

Essentially, the xenograph set up as described in Example 19 is employed, but using xenographs derived from primary tumours, which are obtained from patients who undergo surgical treatment. Cells derived from these tumours are injected into 4-6 weeks old, congenitally athymic nude mice, female, on Balb/c nu/nu background. Mice are maintained under specific pathogen-free barrier environment. For grafting and imaging, the mice are anesthetized intraperitoneally with a 0.10 mg ketamine hydrochloride solution per gram body weight. If necessary, the tumours are excised and retransplanted into other mice, as described in Example 19.

Therapy is started with biweekly injections of 1.5 mg of either PBS, clone 060, clone 083, clone 085 and clone 093. Tumour size is measured every 4 days. The tumour size is measured by a caliper, and the tumour volume is calculated using the formula (length×width$^2$)/2. The development of the tumour volumes of the mice is followed for 30 days. At 30 days the mice are sacrificed. The tumours are weighed and fixed in 4% polyformaldehyde. The tumour sections are excised for immunohistochemical analysis.

Figure 3:
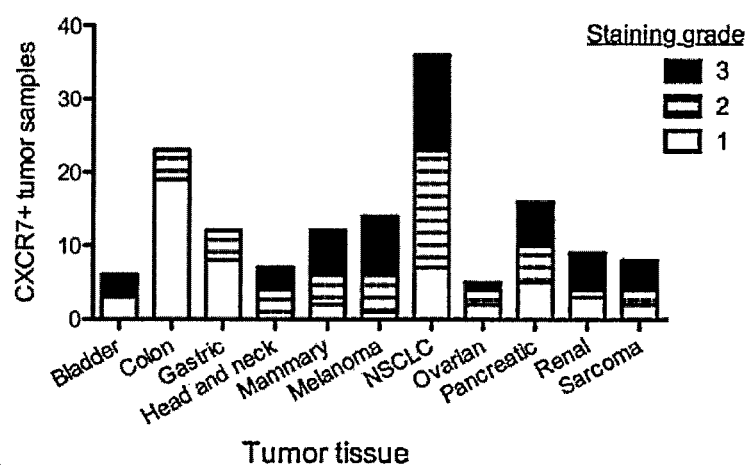
FIG. 3 shows CXCR7 expression in human tumor biopsies. A, Expression of CXCR7 protein was determined by immunohistochemistry with the monoclonal antibody 8F11 in human cancer biopsies (NSCLC, non-small cell lung cancer). Staining intensity was ranked from weak (1), to average (2) and high (3). B-C, Representative CXCR7 immunohistochemical staining in head and neck cancer biopsy in the absence (B) or presence (C) of 8F11 monoclonal anti-CXCR7 antibody.
Figure 3:
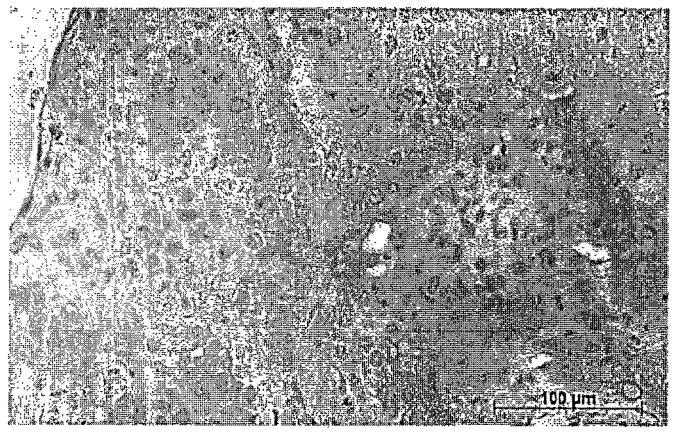
Figure 3:
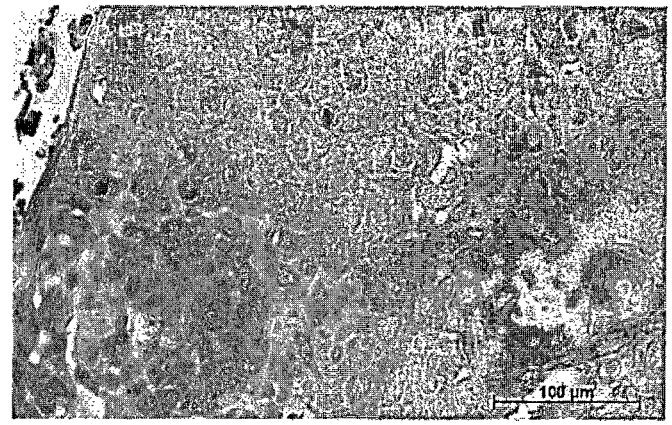

The tumours listed in FIG. 3 are tested similarly, either by xenographs of established cell lines or derived from primary tumours. Tumours having a high percentage of CXCR7 are preferred for initial testing.

Example 21: Group 1 Immunoglobulin Single Variable Domains

In view of binding, competition and/or β-arrestin results, various ISVDs were not further assessed after initial screening. However, the in vivo results of Examples 19-20 prompted us to further evaluate the presence of other family members of Group 1 ISVDs.

After reassessing the sequences, at least the following 4 Group 1 ISVDs were identified: 01C12 (SEQ ID NO: 99), 01B12 (SEQ ID NO: 100), 01F11 (SEQ ID NO: 101) and 01B10 (SEQ ID NO: 102) (Table B-3).

Example 22: CXCR7 Nanobodies Reduce Head and Neck Cancer Xenograft Tumour Growth In Vivo In Example 19 it was demonstrated that CXCR7 Nanobodies reduce head and neck cancer cell growth in vivo. In Example 19, mice received 1.5 mg of either clone 085 (Group 1 ISVD-Group 2 ISVD) or clone 093 (Group 1 ISVD-Group 1 ISVD).

In view of the binding efficacies of Group 2 ISVDs, it is expected that constructs comprising Group 1 ISVD-Group 2 ISVD (e.g. clone 085) would be more efficient than Group 1 ISVD-Group 1 ISVD (e.g. clone 093).

Accordingly, the in vivo xenograft model of Example 19 is used to test this hypothesis. Again, the mice are randomly distributed into 11 groups of 5 mice each that are injected bi-weekly with 400 ul PBS without or with the constructs. The constructs tested for therapy are clone 085 and clone 093.

The dosing is according to the following scheme:

| construct | dose/biweekly/5 mice | | | | |
|---|---|---|---|---|---|
| clone 085 | 1.5 mg | 0.75 mg | 0.375 mg | 0.17 mg | 0.085 mg |
| clone 093 | 1.5 mg | 0.75 mg | 0.375 mg | 0.17 mg | 0.085 mg |
| PBS (negative control) | — | — | — | — | — |

Tumour size is measured every 4 days. The tumour size is measured by a caliper, and the tumour volume is calculated using the formula (length×width$^2$)/2. The development of the tumour volumes of the mice is followed for 30 days. At 50 days the mice are sacrificed. The tumours are weighed and fixed in 4% polyformaldehyde. The tumour sections are excised for immunohistochemical analysis.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety, particularly for the use or subject matter referenced herein.

What is claimed is:

1. An immunoglobulin single variable domain comprising an amino acid sequence with the formula 1

FR1-CDR1-FR2-CDR2-FR3-CDR3-FR4 (1);

wherein FR1 to FR4 refer to framework regions 1 to 4 and are framework regions of an immunoglobulin single variable domain; and wherein CDR1, CDR2 and CDR3 are chosen from:

CDR1 is the amino acid sequence of SEQ ID NO: 9, CDR2 is the amino acid sequence of SEQ ID NO: 19, and CDR3 is the amino acid sequence of SEQ ID NO: 29;

or

CDR1 is the amino acid sequence of SEQ ID NO: 10, CDR2 is the amino acid sequence of SEQ ID NO: 20, and CDR3 is the amino acid sequence of SEQ ID NO: 30;

or

CDR1 is the amino acid sequence of SEQ ID NO: 11, CDR2 is the amino acid sequence of SEQ ID NO: 21, and CDR3—is the amino acid sequence of SEQ ID NO: 31;

or

CDR1 is the amino acid sequence of SEQ ID NO: 12, CDR2 is the amino acid sequence of SEQ ID NO: 22, and CDR3 is the amino acid sequence of SEQ ID NO: 32;

or

CDR1 is the amino acid sequence of SEQ ID NO: 93, CDR2 is the amino acid sequence of SEQ ID NO: 95, and CDR3 is the amino acid sequence of SEQ ID NO: 97;

or

CDR1 is the amino acid sequence of SEQ ID NO: 107, CDR2 is the amino acid sequence of SEQ ID NO: 115, and CDR3 is the amino acid sequence of SEQ ID NO: 123;

or

CDR1 is the amino acid sequence of SEQ ID NO: 108, CDR2 is the amino acid sequence of SEQ ID NO: 116, and CDR3 is the amino acid sequence of SEQ ID NO: 124;

or

CDR1 is the amino acid sequence of SEQ ID NO: 110, CDR2 is the amino acid sequence of SEQ ID NO: 118, and CDR3 is the amino acid sequence of SEQ ID NO: 126;

wherein the immunoglobulin single variable domain specifically binds to CXCR7.

2. The immunoglobulin single variable domain according to claim 1, wherein the framework regions (FRs) have a sequence identity of more than 80% with the FRs of SEQ ID NOs: 4 to 8, 92, 103, 104 or 106 (FR1), 14 to 18, 94, 111, 112 or 114 (FR2), 24 to 28, 96, 119, 120 or 122 (FR3), and/or 34 to 38, 98, 127, 128 or 130 (FR4).

3. A polypeptide comprising an immunoglobulin single variable domain according to claim 1.

4. The polypeptide according to claim 3, wherein the immunoglobulin single variable domain is selected from the group consisting of immunoglobulin single variable domains that have an amino acid sequence with a sequence identity of more than 80% with the immunoglobulin single variable domains of SEQ ID NOs: 39 to 43, 91 or 99-102.

5. The polypeptide according to claim 3 and additionally comprising at least one human serum albumin binding immunoglobulin single variable domain and optionally comprising a linker selected from the group of linkers with SEQ ID NOs: 49 to 58.

6. The polypeptide according to claim 3 and additionally comprising ALB8 (SEQ ID NO: 2), and optionally comprising a linker selected from the group of linkers with SEQ ID NOs: 49 to 58.

7. The polypeptide according to claim 3, wherein the polypeptide is selected from the group consisting of polypeptides that have an amino acid sequence with a sequence identity of more than 80% with the polypeptides of SEQ ID NOs: 44 to 48, 78 to 89 and 131 to 140.

8. A pharmaceutical composition comprising an immunoglobulin single variable domain according to claim 1 and optionally a pharmaceutically acceptable excipient.

* * * * *